(12) United States Patent
Leppert et al.

(10) Patent No.: US 9,617,316 B2
(45) Date of Patent: Apr. 11, 2017

(54) MUTANT SODIUM CHANNEL NAV1.7 AND METHODS RELATED THERETO

(71) Applicants: Mark F. Leppert, Salt Lake City, UT (US); Nanda A. Singh, Heber City, UT (US)

(72) Inventors: Mark F. Leppert, Salt Lake City, UT (US); Nanda A. Singh, Heber City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 320 days.

(21) Appl. No.: 13/967,306

(22) Filed: Aug. 14, 2013

(65) Prior Publication Data

US 2014/0165219 A1 Jun. 12, 2014

Related U.S. Application Data

(63) Continuation of application No. 13/395,651, filed as application No. PCT/US2010/048680 on Sep. 13, 2010, now abandoned.

(60) Provisional application No. 61/241,612, filed on Sep. 11, 2009.

(51) Int. Cl.
| | | |
|---|---|---|
| *C07H 21/00* | (2006.01) | |
| *C07K 14/47* | (2006.01) | |
| *C12N 15/85* | (2006.01) | |
| *C07K 14/705* | (2006.01) | |
| *C12Q 1/68* | (2006.01) | |
| *A01K 67/027* | (2006.01) | |

(52) U.S. Cl.
CPC .......... *C07K 14/47* (2013.01); *A01K 67/0275* (2013.01); *C07K 14/705* (2013.01); *C12N 15/85* (2013.01); *C12Q 1/6883* (2013.01); *C12Q 2600/106* (2013.01); *C12Q 2600/136* (2013.01); *C12Q 2600/156* (2013.01); *C12Q 2600/172* (2013.01)

(58) Field of Classification Search
CPC ................................ C12N 15/85; C07K 14/47
See application file for complete search history.

(56) References Cited

U.S. PATENT DOCUMENTS

| 6,060,271 | A | 5/2000 | Walewski et al. |
|---|---|---|---|
| 6,110,672 | A | 8/2000 | Mandel et al. |
| 6,673,549 | B1 | 1/2004 | Furness et al. |
| 7,670,771 | B2 | 3/2010 | Leppert et al. |
| 2003/0194751 | A1 | 10/2003 | Dubin et al. |
| 2004/0214195 | A1 | 10/2004 | Rouleau et al. |
| 2007/0212685 | A1 | 9/2007 | MacDonald et al. |
| 2007/0275384 | A1 | 11/2007 | Leppert et al. |

FOREIGN PATENT DOCUMENTS

| WO | WO 96/14077 | 5/1996 |
|---|---|---|
| WO | WO 00/46358 | 8/2000 |
| WO | WO 02/18637 | 3/2002 |
| WO | WO 02/50096 | 6/2002 |
| WO | WO 02/083945 | 10/2002 |

OTHER PUBLICATIONS

Meisler et al.; Sodium Channel Mutations in Epilepsy and Other Neurological Disorders; J. Clin. Invest; Aug. 2005; pp. 2010-2017; vol. 115, No. 8.

Peiffer et al.; A Locus for Febrile Seizures (FEB3) Maps to Chromosome 2q23-24; Ann. Neurol.; 1999; pp. 671-678; vol. 46, No. 4.

RPCI-23-479K6.TJ RPCI-23 Mus musculus genomic clone RPCI-23-479K6, genomic survey sequence; Database GenBank (online), Accession No. AZ123090; http://www.ncbi.nlm.nih.gov/nucgss/AZ123090; updated May 10, 2000; retrieved on Dec. 7, 2010.

Singh et al.; A Role of SCN9A in Human Epilepsies, as a Cause of Febrile Seizures and as a Potential Modifier of Dravet Syndrome, PLoS Genet; published online Sep. 18, 2009; p. e1000649; vol. 5, No. 9.

Toledo-Aral et al.; Identification of PN1, a predominant voltage-dependent sodium channel expressed principally in peripheral neurons; Proc. Natl. Acad. Sci. USA; Feb. 1997; pp. 1527-1532; vol. 94.

*Primary Examiner* — Marcia S Noble

(74) *Attorney, Agent, or Firm* — David W. Osborne; Thorpe North & Western, LLP

(57) ABSTRACT

Described are mutant $Na_v1.7$ sodium channel alpha-subunits and nucleic acid sequences encoding such mutants. Further described are methods for characterizing a nucleic acid sequence that encodes a $Na_v1.7$ sodium channel alpha-subunit, methods for determining a $Na_v1.7$ haplotype, methods for determining a subject's predisposition to a neurologic disorder associated with a sodium channel mutation, and methods of identifying a compound that modulates mutant $Na_v1.7$ sodium channels. Other materials, compositions, articles, devices, and methods relating to mutant $Na_v1.7$ sodium channels are also described herein.

4 Claims, 11 Drawing Sheets

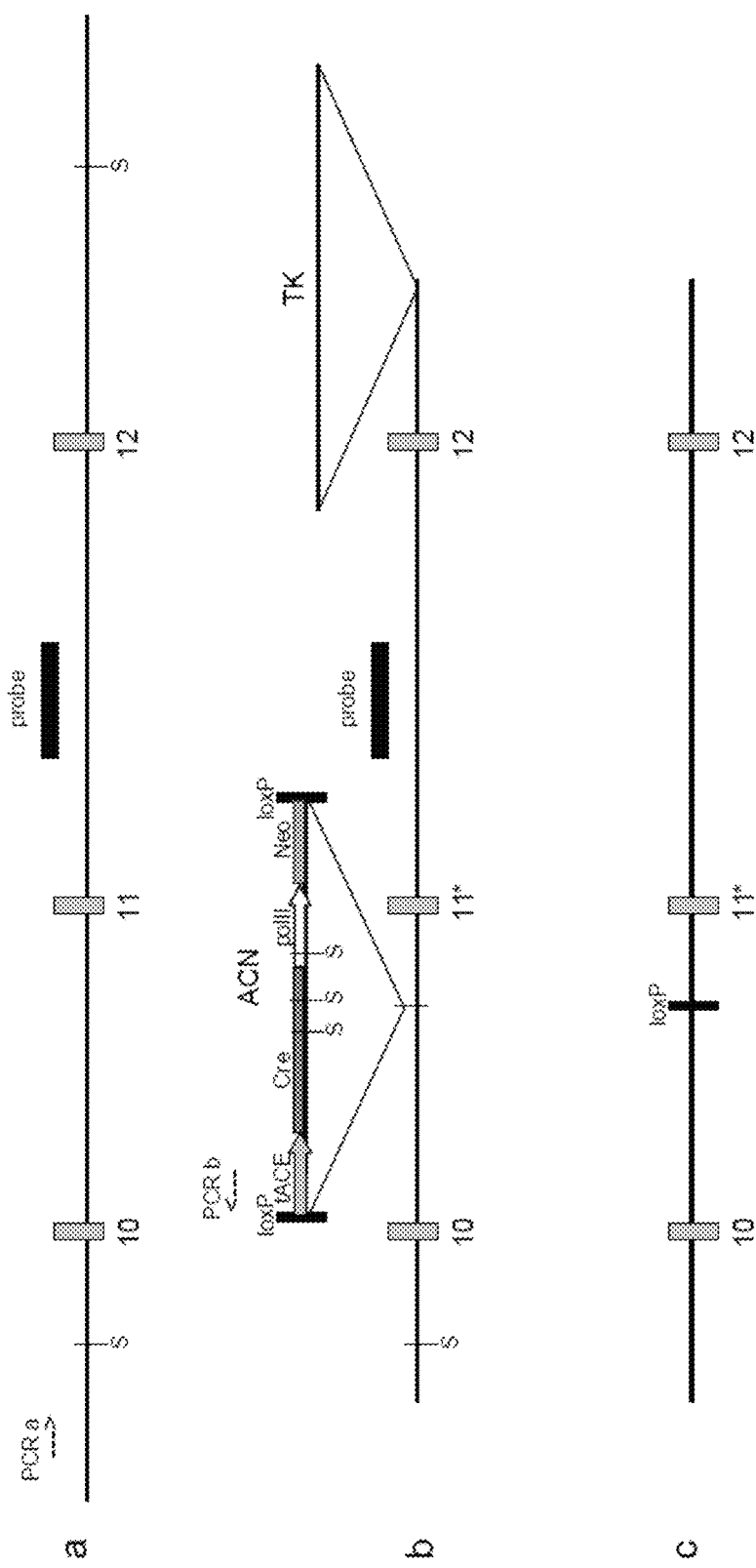
FIG. 4a-c

MUTANT SODIUM CHANNEL NAV1.7 AND METHODS RELATED THERETO

PRIORITY INFORMATION

This application is a continuation of U.S. patent application Ser. No. 13/395,651, filed Jul. 23, 2012, which is a U.S. national stage entry of PCT Application Ser. No. PCT/US2010/048680, filed Sep. 13, 2010, which claims the priority benefit of U.S. Provisional Patent Application Ser. No. 61/241,612, filed Sep. 11, 2009, each of which are incorporated herein by reference.

GOVERNMENT INTEREST

This invention was made with government support under Grant No. R01 NS032666 awarded by the National Institutes of Health. The government has certain rights in the invention.

BACKGROUND

Voltage-gated sodium channels are transmembrane proteins that mediate regenerative inward currents that are responsible for the initial depolarization of action potentials in excitable cells, such as neurons and muscle. Sodium channels are typically a complex of various subunits, the principle one being the alpha-subunit. The alpha-subunit is the pore-forming subunit, and it alone is sufficient for all known sodium channel function. However, in certain sodium channels, smaller, auxiliary subunits called beta-subunits are known to associate with the larger alpha-subunit and are believed to modulate some of the functions of the alpha-subunit. (See Kraner, et al. (1985) J Biol Chem 260:6341-6347; Tanaka, et al. (1983) J Biol Chem 258: 7519-7526; Hartshorne, et al. (1984) J Biol Chem 259:1667-1675; Catterall, (1992) Physiol Rev 72:S14-S48; Anderson, et al. (1992) Physiol Rev 72:S89-S158.) A review of sodium channels is presented in Catterall, (1995) Ann Rev Biochem 64:493-531.

The primary structures of sodium channel alpha-subunits from a variety of tissues (brain, peripheral nerve, skeletal muscle, and cardiac muscle) and organisms (jellyfish, squid, eel, rat, human) have been identified, and their amino acid sequences show individual regions which have been conserved over a long evolutionary period (see Alberts, et al., eds., "Molecular Biology of the Cell" 534-535, Garland Pub., New York, N.Y. (1994)). From these studies it is known that the alpha-subunit of a sodium channel is a large glycoprotein containing four homologous domains (labeled I-IV in FIG. 1) connected by intracellular loops. The N-terminus of the alpha-subunit extends intracellularly at domain I (i.e., DI) and the C-terminus of the alpha-subunit extends intracellularly at domain IV (i.e., DIV). In the plasma membrane, the four domains orient in such a way as to create a central pore whose structural constituents determine the selectivity and conductance properties of the sodium channel.

Each domain of the sodium channel alpha-subunit contains six transmembrane alpha-helices or segments (labeled 1-6 in FIG. 1). Five of these transmembrane segments are hydrophobic, whereas one segment is positively charged with several lysine or arginine residues. This highly charged segment is the fourth transmembrane segment in each domain. Extracellular loops connect segment 1 (i.e., S1) to segment 2 (i.e., S2) and segment 3 (i.e., S3) to segment 4 (i.e., S4). Intracellular loops connect S2 to S3 and S4 to segment 5 (i.e., S5). An extracellular re-enterant loop connects S5 to segment 6 (i.e., S6). (See Agnew, et al. (1978) Proc Natl Acad Sci USA 75:2606-2610; Agnew, et al. (1980) Biochem Biophys Res Comm 92:860-866; Catterall, (1986) Ann Rev Biochem 55:953-985; Catterall, (1992) Physiol Rev 72:S14-S48.)

Voltage-gated sodium channels can be named according to a standardized form of nomenclature outlined in Goldin, et al. (2000) Neuron 28:365-368. According to that system, voltage-gated sodium channels are grouped into one family from which nine mammalian isoforms and have been identified and expressed. These nine isoforms are given the names Nav1.1 through Nav1.9. Also, splice variants of the various isoforms are distinguished by the use of lower case letters following the numbers (e.g., "Nav1.1a").

Because of the important role sodium channels play in the transmission of action potentials in excitable cells like neurons and muscle, sodium channels have been implicated in many sensory, motor, and neurologic disorders. Accordingly, sodium channels have been the focus of much scientific research. However, while a great deal has been learned about sodium channels, there remains a need for further understanding of the functioning of sodium channels, and means to diagnose, predict, prevent, and treat diseases, disorders, and conditions that result from variations and abnormalities of sodium channels. These and other objects and advantages of the materials, compositions, articles, devices, and methods described herein, as well as additional inventive features, will be apparent from the following disclosure.

BRIEF SUMMARY

In accordance with the purpose of this invention, as embodied and broadly described herein, this invention relates to mutant $Na_v1.7$ sodium channel alpha-subunits and methods of use thereof. Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 4a-b show a schematic representation of the (a) wild-type allele, (b) targeting construct introduced into embryonic stem (ES) cells. Numbered boxes denote exons; *, N641Y missense change introduced into exon 11; PCRa and PCRb, primers used to screen ES cell DNA for homologous recombination; S and probe, denotes SspI sites and probe used in genomic Southern blot of ES cells; ACN cassette, Cre-recombinase gene (Cre) driven by the testes-specific promoter from the angiotensin-converting enzyme gene (tACE); Cre is linked to the $Neo^r$ selectable marker driven by the mouse RNA polymerase II large subunit gene (polII); the entire cassette is flanked by 34 bp loxP sites oriented in parallel. TK, HSV-TK gene for negative selection of ES cells. FIG. 4c shows that following Cre-mediated self-excision in the chimeric mouse germline, a single loxP site and the point mutation remain.

FIG. 7 shows increased corneal kindling acquisition rates of Scn9a knockin mice compared to wild-type littermate controls. Male N5F2 mice separated by genotype (n=8-15) were stimulated with corneal electrodes twice daily until four consecutive Racine Stage 4 or 5 secondarily generalized seizures were elicited.

DETAILED DESCRIPTION

Figure 1:
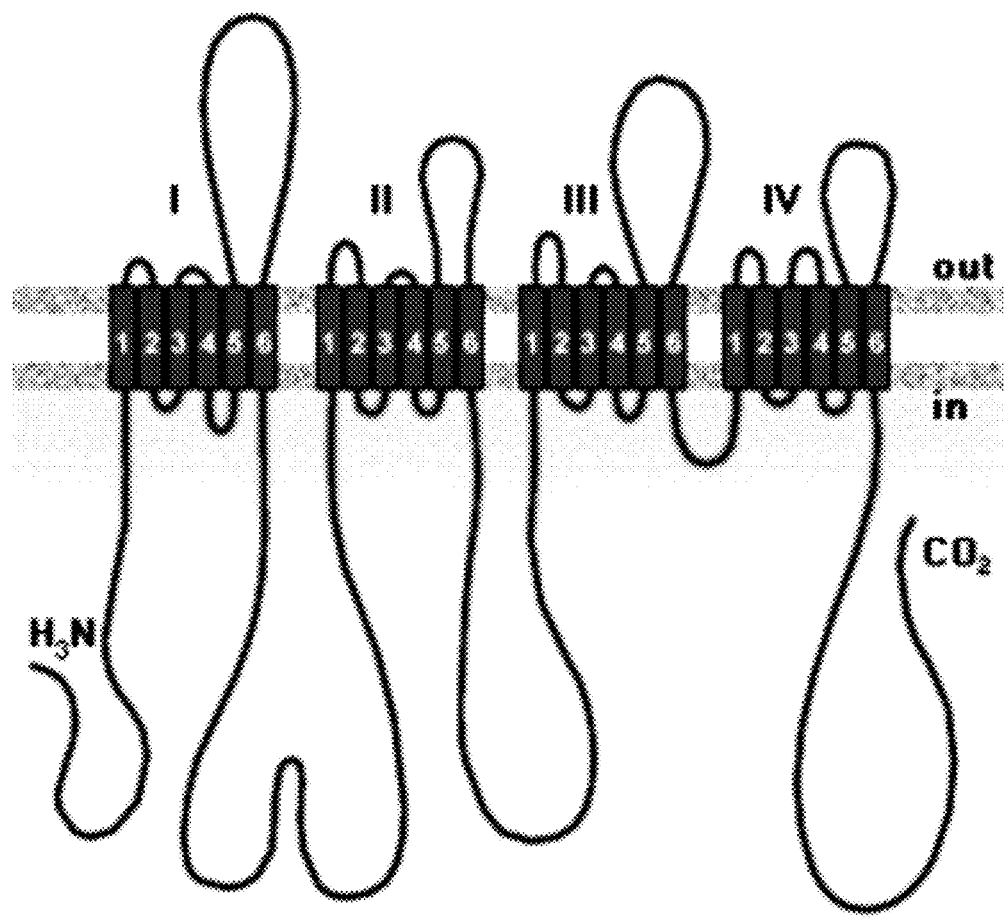
FIG. 1 is a diagram of the secondary structure of a sodium channel alpha-subunit. Not shown is the pore region in each of the four domains, which consists of an inward loop between transmembrane regions 5 and 6.

The disclosed method and compositions may be understood more readily by reference to the following detailed description of particular embodiments and the Example included therein and to the Figures and their previous and following description.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a nucleotide is disclosed and discussed and a number of modifications that can be made to a number of molecules including the nucleotide are discussed, each and every combination and permutation of nucleotide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

As used herein, a plurality of items, structural elements, compositional elements, and/or materials may be presented in a common list for convenience in explaining concepts to which they may pertain. However, these lists should be construed as though each member of the list is individually identified as a separate and unique member. Thus, no individual member of such list should be construed as a de facto equivalent of any other member of the same list solely based on their presentation in a common group without indications to the contrary.

Those skilled in the art will recognize, or be able to ascertain using no more than routine experimentation, many equivalents to the specific embodiments of the method and compositions described herein. Such equivalents are intended to be encompassed by the following claims.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

A. Methods

1. Selecting Therapy

Selecting the appropriate antiepileptic drug for newly diagnosed epilepsy patients is a difficult process, and many drugs have adverse side effects. An important goal of mutation characterization is the development of individualized treatments tailored to each patient mutation. As disclosed herein, sodium channel blockers are contraindicated for patients with neurological disorders who have mutations in SCN9A (gene that encodes $Na_v1.7$), since further reduction of the level of functional channel can worsen their condition.

Thus, disclosed herein is a method for selecting a therapy for a subject diagnosed with a neurologic disorder comprising detecting in a nucleic acid sample from the subject one or more $Na_v1.7$ mutations. In some aspects, the one or more $Na_v1.7$ mutations can comprise mutations in the nucleic acid sequence that encodes residue 228, residue 490, residue 519, residue 684, residue 699, residue 1160, or residue 1267 of the amino acid sequence of $Na_v1.7$. Thus, the one or more $Na_v1.7$ mutations can comprise mutations in the nucleic acid sequence 684, 1469, 1555, 2052, 2096, 3478, and/or 3799 of SCN9A. The one or more $Na_v1.7$ mutations can further comprise mutations in the nucleic acid sequence that encodes residue 62, residue 149, residue 641, residue 655, residue 739, or residue 1123 of the encoded amino acid sequence of $Na_v1.7$. Thus, the one or more $Na_v1.7$ mutations can further comprise mutations in the nucleic acid sequence at nucleotide position 184, 446, 1921, 1964, 2215, and/or 3369 of SCN9A.

Thus, disclosed herein is a method for selecting a therapy for a subject diagnosed with Dravet syndrome comprising detecting in a nucleic acid sample from the subject one or more $Na_v1.7$ mutations. In some aspects, the one or more $Na_v1.7$ mutations can comprise mutations in the nucleic acid sequence that encodes residue 228, residue 519, residue 684, residue 699, residue 1160, or residue 1267 of the amino acid sequence of $Na_v1.7$. Thus, the one or more $Na_v1.7$ mutations can comprise mutations in the nucleic acid sequence at nucleotides 684, 1555, 2052, 2096, 3478, or 3799 of SCN9A. In some aspects, the one or more $Na_v1.7$ mutations can comprise mutations in the nucleic acid sequence that encodes residue 655, residue 739, or residue 1123 of the amino acid sequence of $Na_v1.7$. Thus, the one or more $Na_v1.7$ mutations can comprise mutations in the nucleic acid sequence at nucleotides 1964, 2215, or 3369 of SCN9A.

As used herein, "neurological disorder" and "neurologic disorder associated with a sodium channel mutation" includes, but is not limited to, seizure disorders. "Seizure disorders" as used herein includes disorders having symptomatologies that include seizures (e.g., febrile seizures, afebrile seizures, and epileptic seizures). As used herein "epileptic seizures" includes, but is not limited to, partial (e.g., simple and complex) and generalized (e.g., absence, myoclonic, and tonic-clonic) seizures, temporal lobe epilepsy, and severe myoclonic epilepsy of infancy.

Also disclosed herein is a method for selecting a therapy for a subject diagnosed with a neurologic disorder comprising detecting in a sample from the subject $Na_v1.7$ protein comprising one or more mutations. This method can comprise, for example, the use of antibodies specific for $Na_v1.7$ protein comprising the one or more mutations. In some aspects, the antibodies can be specific for a $Na_v1.7$ mutation at amino acid residue 228, residue 490, residue 519, residue 684, residue 699, residue 1160, or residue 1267 of the amino acid sequence of $Na_v1.7$. In some aspects, the antibodies can be specific for a $Na_v1.7$ mutation at amino acid residue 62, residue 149, residue 641, residue 655, residue 739, or residue 1123 of the encoded amino acid sequence of $Na_v1.7$.

Also disclosed herein is a method for selecting a therapy for a subject diagnosed with Dravet Syndrome comprising detecting in a sample from the subject sodium channel protein comprising one or more mutations that correlates with the SMEI. This method can comprise, for example, the use of antibodies specific for $Na_v1.7$ protein comprising the mutation(s). In some aspects, the antibodies can be specific for a $Na_v1.7$ mutation at amino acid residue 228, residue 519, residue 655, residue 684, residue 699, residue 739, residue 1123, residue 1160, or residue 1267 of the amino acid sequence of $Na_v1.7$. This method can further comprise, for example, the use of antibodies specific for $Na_v1.1$ protein comprising mutation(s) that correlate with the SMEI. For example, the antibodies can be specific for a $Na_v1.1$ protein comprising mutations at amino acid residue 934, residue 982, residue 1326, or residue 892 of $Na_v1.1$.

The herein disclosed methods can further comprise detecting in the nucleic acid sample from the subject one or more $Na_v1.1$ (SCN1A gene) mutations. In some aspects, the one or more $Na_v1.1$ mutations can comprise mutations (including deletions) in the nucleic acid sequence that encodes residue 934, residue 982, residue 1326, or residue 892 of $Na_v1.1$. The one or more $Na_v1.1$ mutations can comprise nucleic acid mutations at positions c.4338+1, c.1029−1, or c.3706−2.

Also disclosed herein is a method for selecting a therapy for a subject diagnosed with a neurologic disorder comprising comparing the subject's $Na_v1.7$ haplotype with one or more reference haplotypes, a similar haplotype in the subject's $Na_v1.7$ haplotype as compared to the reference haplotype or haplotypes indicating a course of therapy. Thus, in some aspects, each haplotype can be correlated with specific therapeutic outcomes and/or preferred course of therapies to generate a database of reference haplotypes, such that one of skill in the art can compare a subject's haplotype to a reference haplotype or haplotypes and determine a preferred course of therapy. In some aspects, the reference haplotype can comprise nucleotides that encode one or more mutations in the $Na_v1.7$ sodium channel alpha-subunit. For example, the reference haplotype can comprise nucleotides that encode one or more mutations at residue 228, residue 490, residue 519, residue 684, residue 699, residue 1160, or residue 1267 of the encoded amino acid sequence of $Na_v1.7$. Thus, the reference haplotype can comprise mutations in the nucleic acid sequence at nucleotides 684, 1469, 1555, 2052, 2096, 3478, and/or 3799 of SCN9A. The reference haplotypes can further comprise nucleotides that encode one or more mutations at residue 62, residue 149, residue 641, residue 655, residue 739, or residue 1123 of the encoded amino acid sequence of $Na_v1.7$. Thus, the reference haplotype can comprise mutations in the nucleic acid sequence at nucleotides 184, 446, 1921, 1964, 2215, and/or 3369 of SCN9A.

Also disclosed herein is a method for selecting a therapy for a subject diagnosed with Dravet syndrome comprising comparing the subject's $Na_v1.7$ haplotype with one or more reference haplotypes, a similar haplotype in the subject's $Na_v1.7$ haplotype as compared to the reference haplotype or haplotypes indicating a course of therapy. Thus, in some aspects, each haplotype can be correlated with specific therapeutic outcomes and/or preferred course of therapies to generate a database of reference haplotypes, such that one of skill in the art can compare a subject's haplotype to a reference haplotype or haplotypes and determine a preferred course of therapy. In some aspects, the reference haplotype can comprise nucleotides that encode one or more mutations in the $Na_v1.7$ sodium channel alpha-subunit. For example, the reference haplotype can comprise nucleotides that encode one or more mutations at residue 228, residue 519, residue 684, residue 699, residue 1160, or residue 1267 of the encoded amino acid sequence of $Na_v1.7$. Thus, the reference haplotype can comprise mutations in the nucleic acid sequence at nucleotides 684, 1555, 2052, 2215, or 3799 of SCN9A. In another example, the reference haplotype can comprise nucleotides that encode one or more mutations at residue 655, residue 739, residue or 1123 of the encoded amino acid sequence of $Na_v1.7$. Thus, the reference haplotype can comprise mutations in the nucleic acid sequence at nucleotides 1964, 2215, or 3369 of SCN9A.

The reference haplotypes of the disclosed methods can further comprise nucleotides that encode one or more $Na_v1.1$ (SCN1A gene) mutations that correlates with SMEI. The one or more $Na_v1.1$ mutations can comprise mutations (including deletions) in the nucleic acid sequence that encodes residue 934, residue 982, residue 1326, or residue 892 of $Na_v1.1$. The one or more $Na_v1.1$ mutations can comprise nucleic acid mutations at positions c.4338+1, c.1029−1, or c.3706−2.

Since subjects will vary depending on numerous parameters including, but not limited to, race, age, weight, medical history etc., as more information is gathered on populations, the database can contain haplotype information classified by race, age, weight, medical history etc., such that one of skill in the art can assess the subject's risk of developing neurologic disorders based on information more closely associated with the subject's demographic profile. Where there is a differential distribution of a mutation by racial background or another parameter, guidelines for drug administration can be generally tailored to a particular group.

In some aspects of the disclosed methods, wherein the subject has one or more $Na_v1.7$ mutations, the selected therapy is other than a sodium channel blocker. In some aspects, wherein the subject has one or more $Na_v1.7$ mutations, the selected therapy is not a use-dependent sodium channel blocker. In some aspects, wherein the subject has one or more $Na_v1.7$ mutations, the selected therapy is any drug used to treat generalized epilepsy that lacks sodium channel blocking activity. Thus, in some aspects, wherein the subject has one or more $Na_v1.7$ mutations, the selected therapy is valproate, benzodiazepines (Guerrini et al Epilepsia 39:508-512, 1998) stiripentol (Kassai et al Epilepsia 2008 49:343), toprimate, or levetiracetam (Striano et al. Neurology 2007 69:250). In some aspects, wherein the subject has one or more $Na_v1.7$ mutations, the selected therapy is other than Lamotrigine (Guerrini et al Epilepsia 39:508-512, 1998), carbamazepine or phenyloin.

2. Determining a Predisposition

Also disclosed herein is a method for determining a subject's predisposition to a neurologic disorder comprising detecting in a nucleic acid sample from the subject one or more $Na_v1.7$ mutations that correlates with the neurologic disorder. In some aspects, the subject has a family member diagnosed with a neurological disorder and identified as having one or more $Na_v1.7$ mutations. Thus, in some aspects, the method comprises detecting in a nucleic acid sample from the subject or more $Na_v1.7$ mutations detected in the family member having the nuerological disease, thus determining a predisposition of the subject toward the same neurological disease.

The one or more $Na_v1.7$ mutations can comprise mutations in the nucleic acid sequence that encodes residue 228, residue 490, residue 519, residue 684, residue 699, residue 1160, or residue 1267 of the amino acid sequence of $Na_v1.7$. Thus, the one or more $Na_v1.7$ mutations can comprise mutations in the nucleic acid sequence 684, 1469, 1555, 2052, 2096, 3478, and/or 3799 of SCN9A. The one or more $Na_v1.7$ mutations can further comprise mutations in the nucleic acid sequence that encodes residue 62, residue 149, residue 641, residue 655, residue 739, or residue 1123 of the encoded amino acid sequence of $Na_v1.7$. Thus, the one or more $Na_v1.7$ mutations can further comprise mutations in the nucleic acid sequence at nucleotide position 184, 446, 1921, 1964, 2215, and/or 3369 of SCN9A.

Also disclosed herein is a method for determining a subject's predisposition to a neurologic disorder comprising detecing in a sample from the subject $Na_v1.7$ protein comprising one or more mutations that correlates with the neurologic disorder. This method can comprise, for example, the use of antibodies specific for $Na_v1.7$ protein comprising the mutation(s). In some aspects, the subject has a family member diagnosed with a neurological disorder and identified as having one or more $Na_v1.7$ mutations. Thus, in some aspects, the method comprises detecting in a nucleic acid sample from the subject the one or more $Na_v1.7$ mutations detected in the family member having the nuerological disease, thus determining a predisposition of the subject toward the same neurological disease.

The antibodies can therefore be specific for a $Na_v1.7$ mutation at amino acid residue 228, residue 490, residue 519, residue 684, residue 699, residue 1160, or residue 1267 of the amino acid sequence of $Na_v1.7$. Additionally, the antibodies can be specific for a $Na_v1.7$ mutation at amino acid residue 62, residue 149, residue 641, residue 655, residue 739, or residue 1123 of the encoded amino acid sequence of $Na_v1.7$.

Also disclosed herein is a method for determining a subject's predisposition to a neurologic disorder associated with a sodium channel mutation comprising comparing the subject's $Na_v1.7$ haplotype with one or more reference haplotypes that correlate with the neurologic disorder, a similar haplotype in the subject's $Na_v1.7$ haplotype as compared to the reference haplotype or haplotypes indicating a predisposition to the neurologic disorder. In some aspects, the subject has a family member diagnosed with a neurological disorder and identified as having one or more $Na_v1.7$ mutations. Thus, in some aspects, the method comprises detecting in a nucleic acid sample from the subject the $Na_v1.7$ haplotype detected in the family member having the neurological disease, thus determining a predisposition of the subject toward the same neurological disease.

Each haplotype can be correlated with specific neurologic disorders or severity of such disorders to generate a database of reference haplotypes, such that one of skill in the art can compare a subject's haplotype to a reference haplotype or haplotypes and determine whether the subject is at risk for a neurologic disorder.

The reference haplotype can comprise nucleotides that encode one or more mutations in the $Na_v1.7$ sodium channel alpha-subunit. For example, the reference haplotype can comprise nucleotides that encode one or more mutations at residue 228, residue 490, residue 519, residue 684, residue 699, residue 1160, or residue 1267 of the encoded amino acid sequence of $Na_v1.7$. Thus, the reference haplotype can comprise mutations in the nucleic acid sequence at nucleotides 684, 1469, 1555, 2052, 2096, 3478, and/or 3799 of SCN9A. The reference haplotypes can further comprise nucleotides that encode one or more mutations at residue 62, residue 149, residue 641, residue 655, residue 739, or residue 1123 of the encoded amino acid sequence of $Na_v1.7$. Thus, the reference haplotype can comprise mutations in the nucleic acid sequence at nucleotides 184, 446, 1921, 1964, 2215, and/or 3369 of SCN9A.

Disclosed herein is a method for determining a subject's predisposition to severe myoclonic epilepsy of infancy (SMEI) comprising detecting in a nucleic acid sample from the subject one or more $Na_v1.7$ mutations that correlates with SMEI. In some aspects, the subject has a family member diagnosed with SMEI and identified as having one or more $Na_v1.7$ mutations. Thus, in some aspects, the method comprises detecting in a nucleic acid sample from the subject one or more $Na_v1.7$ mutations detected in the family member having SMEI, thus determining a predisposition of the subject toward SMEI.

The one or more $Na_v1.7$ mutations can comprise mutations in the nucleic acid sequence that encodes residue 228, residue 519, residue 684, residue 699, residue 1160, or residue 1267 of the amino acid sequence of $Na_v1.7$. Thus, the one or more $Na_v1.7$ mutations can comprise mutations in the nucleic acid sequence at nucleotides 684, 1555, 2052, 2096, 3478, or 3799 of SCN9A. In another aspect, one or more $Na_v1.7$ mutations can comprise mutations in the nucleic acid sequence that encodes residue 655, residue 739, or residue 1123 of the amino acid sequence of $Na_v1.7$. Thus, the one or more $Na_v1.7$ mutations can comprise mutations in the nucleic acid sequence at 1964, 2215, or 3369 of SCN9A.

The method can further comprise detecting in the nucleic acid sample from the subject one or more $Na_v1.1$ (SCN1A gene) mutations that correlates with SMEI. The one or more $Na_v1.1$ mutations can comprise mutations (including deletions) in the nucleic acid sequence that encodes residue 934, residue 982, residue 1326, or residue 892 of $Na_v1.1$. The one or more $Na_v1.1$ mutations can comprise nucleic acid mutations at positions c.4338+1, c.1029−1, or c.3706−2.

Also disclosed herein is a method for determining a subject's predisposition to Dravet syndrome comprising detecting in a sample from the subject sodium channel protein comprising one or more mutations that correlates with the SMEI. This method can comprise, for example, the use of antibodies specific for $Na_v1.7$ protein comprising the mutation(s). In some aspects, the subject has a family member diagnosed with SMEI and identified as having one or more $Na_v1.7$ mutations. Thus, in some aspects, the method comprises detecting in a nucleic acid sample from the subject one or more $Na_v1.7$ mutations detected in the family member having SMEI, thus determining a predisposition of the subject toward SMEI.

The antibodies can therefore be specific for a $Na_v1.7$ mutation at amino acid residue 228, residue 519, residue 684, residue 699, residue 1160, or residue 1267 of the amino acid sequence of $Na_v1.7$. In another aspect, the antibodies can be specific for a $Na_v1.7$ mutation at amino acid residue 655, residue 739, or residue 1123 of the amino acid sequence of $Na_v1.7$. This method can further comprise, for example, the use of antibodies specific for $Na_v1.1$ protein comprising mutation(s) that correlate with the SMEI. For example, the antibodies can be specific for a $Na_v1.1$ protein comprising mutations at amino acid residue 934, residue 982, residue 1326, or residue 892 of $Na_v1.1$.

Also disclosed herein is a method for determining a subject's predisposition to Dravet syndrome comprising comparing the subject's $Na_v1.7$ haplotype with one or more reference haplotypes that correlate with SMEI, a similar haplotype in the subject's $Na_v1.7$ haplotype as compared to the reference haplotype or haplotypes indicating a predisposition to SMEI. In some aspects, the subject has a family member diagnosed with SMEI and identified as having one or more $Na_v1.7$ mutations. Thus, in some aspects, the method comprises detecting in a nucleic acid sample from the subject the $Na_v1.7$ haplotype detected in the family member having SMEI, thus determining a predisposition of the subject toward SMEI.

Each haplotype can be correlated with specific neurologic disorders or severity of such disorders to generate a database of reference haplotypes, such that one of skill in the art can compare a subject's haplotype to a reference haplotype or haplotypes and determine whether the subject is at risk for a neurologic disorder.

The reference haplotype can comprise nucleotides that encode one or more mutations in the $Na_v1.7$ sodium channel alpha-subunit. For example, the reference haplotype can comprise nucleotides that encode one or more mutations at residue 228, residue 519, residue 684, residue 699, residue 1160, or residue 1267 of the encoded amino acid sequence of $Na_v1.7$. Thus, the reference haplotype can comprise mutations in the nucleic acid sequence at nucleotides 684, 1555, 2052, 2096, 3478, or 3799 of SCN9A. In another example, the reference haplotype can comprise nucleotides that encode one or more mutations at residue 655, residue 739, or residue 1123 of the encoded amino acid sequence of $Na_v1.7$. Thus, the reference haplotype can comprise mutations in the nucleic acid sequence at nucleotides 1964, 2215, or 3369 of SCN9A.

The reference haplotypes can further comprise nucleotides that encode one or more $Na_v1.1$ (SCN/A gene) mutations that correlates with SMEI. The one or more $Na_v1.1$ mutations can comprise mutations (including deletions) in the nucleic acid sequence that encodes residue 934, residue 982, residue 1326, or residue 892 of $Na_v1.1$. The one or more $Na_v1.1$ mutations can comprise nucleic acid mutations at positions c.4338+1, c.1029−1, or c.3706−2.

3. Characterizing Mutant $Na_v1.7$ Nucleic Acid Sequences

It has been found that, in certain neurologic disorders, specific sites in the $Na_v1.7$ gene are mutated, i.e., the nucleotide at a specific position or at specific positions differs from that observed in the most commonly found $Na_v1.7$ gene sequence. Accordingly, disclosed herein are methods of characterizing mutant nucleic acid sequences that encode a $Na_v1.7$ sodium channel alpha-subunit and the use of such nucleic acids to diagnose and treat disease states and neurologic disorders, such as seizures.

Disclosed herein is a method of characterizing a nucleic acid sequence that encodes a $Na_v1.7$ sodium channel alpha-subunit, comprising the step of identifying mutations at one or more sites in regions of the nucleic acid sequence that encode various regions of the $Na_v1.7$ sodium channel alpha-subunit. While mutations can be present in any region of the $Na_v1.7$ nucleic acid sequence, specific regions of the nucleic acid sequence where mutations can be identified include, but are not limited to, those regions that encode an intracellular N-terminal region, an extracellular loop in domain I, an intracellular loop between domains I and II, an intracellular loop between domains II and III, an intramembrane region of domain II, an extracellular loop in domain III, or any combination thereof. Such identified nucleotides can indicate the character of the nucleic acid sequence.

The terms "mutation" and "mutant," as used herein, mean that, at one or more specific positions in a nucleic acid or amino acid sequence, a nucleotide or amino acid that differs from the most commonly found nucleotide or amino acid can be identified. A mutation includes deletions, additions, insertions, and substitutions in the nucleotide or amino acid sequence. For example, in one particular mutant $Na_v1.7$ nucleic acid sequence disclosed herein, position 184 of the nucleic acid sequence contains a substitution; that is, the most commonly found nucleotide at position 184 of the $Na_v1.7$ gene is A, whereas in the mutant $Na_v1.7$ nucleic acid sequence, the nucleotide found at position 184, i.e., the mutated site, is G. One of skill in the art can analyze position 184 and determine which of the two amino acids (A or G) is present. As another example, in one particular mutant $Na_v1.7$ sodium channel alpha-subunit disclosed herein, position 62 of the amino acid sequence contains a substitution; that is, the most commonly found amino acid at position 62 of the $Na_v1.7$ amino acid sequence is isoleucine, whereas in the mutant $Na_v1.7$ amino acid sequence, the amino acid found at position 62, i.e., the mutated site, is valine. Also, one of skill in the art can analyze position 62 of the amino acid sequence and determine which of the two amino acids (isoleucine or valine) is present. Further, as used herein, "mutant" also includes combinations of mutations at more than one position in the $Na_v1.7$ nucleic acid or amino acid sequence. Mutations may provide functional differences in the genetic sequence, through changes in the encoded polypeptide, changes in mRNA stability, binding of transcriptional and translation factors to the DNA or RNA, and the like. The mutations can also be used as single nucleotide or single amino acid mutations to detect genetic linkage to phenotypic variation in activity and expression of sodium channels.

As utilized herein, the "character" of the $Na_v1.7$ nucleic acid sequence can be the combination of nucleotides present at mutated sites that make up the $Na_v1.7$ sodium channel alpha-subunit haplotype as well as the biological activity associated with a particular mutation or combination of mutations.

In one specific aspect, a mutation can be present in the nucleic acid region encoding the intracellular N-terminus region of the $Na_v1.7$ sodium channel alpha-subunit. For example, such a mutation can be at the site that encodes amino acid residue 62. The mutated site can be at position 184 of the $Na_v1.7$ nucleic acid sequence. In one particular aspect, the mutation can encode a valine at amino acid residue 62.

In another aspect, a mutation can be present in the nucleic acid region encoding the extracellular loop of domain I of the $Na_v1.7$ sodium channel alpha-subunit. For example, such a mutation can be at the site that encodes amino acid residue 149. The mutated site can be at position 446 of the $Na_v1.7$ nucleic acid sequence. In one specific aspect, the mutation can encode a glutamine at amino acid residue 149.

In yet another aspect, mutations can be present in the nucleic acid region encoding the intracellular loop between domains I and II of the $Na_v1.7$ sodium channel alpha-subunit. For example, such mutations can be at sites that encode amino acid residue 641 and/or amino acid residue 655. The mutated sites can be at positions 1921 and/or 1964 of the $Na_v1.7$ nucleic acid sequence. In one specific aspect, the mutation can encode a tyrosine at amino acid residue 641. In another aspect, the mutation can encode an arginine at amino acid residue 655.

In a further aspect, a mutation can be present in the nucleic acid region encoding the intramembrane region of domain II of the $Na_v1.7$ sodium channel alpha-subunit. For example, such a mutation can be at the site that encodes amino acid residue 739. The mutated site can be at position 2215 of the $Na_v1.7$ nucleic acid sequence. In one specific aspect, the mutation can encode a valine at amino acid residue 739.

In still another aspect, a mutation can be present in the nucleic acid region encoding the intracellular loop between domains II and III of the $Na_v1.7$ sodium channel alpha-subunit. For example, such a mutation can be at the site that encodes amino acid residue 1123. The mutated site can be at position 3369 of the $Na_v1.7$ nucleic acid sequence. In one specific aspect, the mutation can encode a phenylalanine at amino acid residue 1123.

Mutations can also be present in more than one region of the nucleic acid sequence, such as in regions that encode an intracellular N-terminal region and an extracellular loop in domain I; an intracellular N-terminal region and an intracellular loop between domains I and II; an intracellular N-terminal region and an intracellular loop between domains II and III; an intracellular N-terminal region and an intramembrane region of domain II; an extracellular loop in domain I and an intracellular loop between domains I and II; an extracellular loop in domain I and an intracellular loop between domains II and III; an extracellular loop in domain I and an intramembrane region of domain II; an intracellular loop between domains I and II and an intracellular loop between domains II and III; an intracellular loop between domains I and II and an intramembrane region of domain II; and an intracellular loop between domains II and III and an intramembrane region of domain II.

Some of the mutations that can be identified by the methods disclosed herein include, but are not limited to, mutations at positions 184, 446, 1921, 1964, 2215, 3369, or any combination thereof, of the $Na_v1.7$ nucleic acid sequence. Any individual mutation can be analyzed at any of these positions, or combinations of mutant variants at more than one position can be identified and analyzed by the methods disclosed herein.

A number of methods are available for analyzing nucleic acids for the presence of a specific sequence. For all of the methods described herein, genomic DNA can be extracted from a sample and this sample can be from any organism and can be, but is not limited to, peripheral blood, bone marrow specimens, primary tumors, embedded tissue sections, frozen tissue sections, cell preparations, cytological preparations, exfoliate samples (e.g., sputum), fine needle aspirations, amnion cells, fresh tissue, dry tissue, and cultured cells or tissue. Such samples can be obtained directly from a subject, commercially obtained or obtained via other means. Thus, the methods described herein can be utilized to analyze a nucleic acid sample that comprises genomic DNA, amplified DNA (such as a PCR product), cDNA, cRNA, a restriction fragment or any other desired nucleic acid sample. When one performs one of the herein described methods on genomic DNA, typically the genomic DNA will be treated in a manner to reduce viscosity of the DNA and allow better contact of a primer or probe with the target region of the genomic DNA. Such reduction in viscosity can be achieved by any desired methods, which are known to the skilled artisan, such as DNase treatment or shearing of the genomic DNA, preferably lightly.

If sufficient DNA is available, genomic DNA can be used directly. Alternatively, the region of interest is cloned into a suitable vector and grown in sufficient quantity for analysis. The nucleic acid may be amplified by conventional techniques, such as the polymerase chain reaction (PCR), to provide sufficient amounts for analysis. A variety of PCR techniques are familiar to those skilled in the art. For a review of PCR technology, see the publication entitled "PCR Methods and Applications" (1991, Cold Spring Harbor Laboratory Press), which is incorporated herein by reference in its entirety for amplification methods. In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195, 4,683,202, and 4,965,188. Each of these publications is incorporated herein by reference in its entirety for PCR methods. One of skill in the art would know how to design and synthesize primers flanking any of the nucleic acid sequences disclosed herein.

For example, the disclosed method provides primers GTCCCGCCCATTGCCTGACAC (SEQ ID NO:20) and TTCTGGTCATGATATGGTTATTCAC (SEQ ID NO:21), which can be utilized to amplify the region of the $Na_v1.7$ nucleic acid sequence comprising nucleotide position 184 in order to identify a mutation at this site. The disclosed method also provides primers TGATAGATGCGTTGATGACATTGG (SEQ ID NO:22) and TTCATAAATGCAGTAACTTCCTGG (SEQ ID NO:23), which can be utilized to amplify the region of the $Na_v1.7$ nucleic acid sequence comprising nucleotide position 446 in order to identify a mutation at this site. Also, the disclosed method provides primers TGTTTCTTTTAAGTCAGTACAGAG (SEQ ID NO:24) and AGAGCCATTCACAAGACCAGAG (SEQ ID NO:25), which can be utilized to amplify the region of the $Na_v1.7$ nucleic acid sequence comprising nucleotide position 1921 in order to identify a mutation at this site. Additionally, the disclosed method provides primers ACTCAGAAAGGCAGAGAGGTG (SEQ ID NO:26) and TTGCCATGTTATCAATGTCTGTG (SEQ ID NO:27), which can be utilized to amplify the region of the $Na_v1.7$ nucleic acid sequence comprising nucleotide position 1964 in order to identify a mutation at this site. Further, the disclosed method provides primers GACTGATTTGTATCTGGTTAGGAG (SEQ ID NO:28) and GCAATGTAATTAGGAAGGTGTGAG (SEQ ID NO:29), which can be utilized to amplify the region of the $Na_v1.7$ nucleic acid sequence comprising nucleotide position 2215 in order to identify a mutation at this site. For example, the disclosed method provides primers TTTGAATGAACTCTAAATGAACTACC (SEQ ID NO:30) and TAAGTATTAGGCGTTAAGACAAACC (SEQ ID NO:31), which can be utilized to amplify the region of the $Na_v1.7$ nucleic acid sequence comprising nucleotide position 3369 in order to identify a mutation at this site. One of skill in the art would know how to design primers accordingly to amplify any region of the $Na_v1.7$ nucleic acid sequence for the purposes of identifying a mutation at any nucleotide position throughout the $Na_v1.7$ sodium channel alpha-subunit sequence. Amplification may also be used to determine whether a mutation is present by using a primer that is specific for the mutation.

Various methods are known in the art that utilize oligonucleotide ligation as a means of detecting mutations, for examples see Riley, et al. (1990) Nucleic Acids Res 18:2887-2890; and Delahunty, et al. (1996) Am J Hum Genet. 58:1239-1246, which are incorporated herein by reference in their entirety for methods of detecting mutations. Such methods include single base chain extension (SBCE), oligonucleotide ligation assay (OLA) and cleavase reaction/signal release (Invader methods, Third Wave Technologies).

LCR and Gap LCR are exponential amplification techniques. Both depend on DNA ligase to join adjacent primers annealed to a DNA molecule. In Ligase Chain Reaction (LCR), probe pairs are used which include two primary (first and second) and two secondary (third and fourth) probes, all of which are employed in molar excess to target. The first probe hybridizes to a first segment of the target strand and the second probe hybridizes to a second segment of the target strand, the first and second segments being contiguous so that the primary probes abut one another in 5'-phosphate-3'-hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes, which can be ligated to form a complementary, secondary ligated product. It is important to realize that the ligated products are functionally equivalent to either the target or its complement. By repeated cycles of hybridization and ligation, amplification of the target sequence is achieved. A method for multiplex LCR has also been described (WO 9320227, which is incorporated herein by reference in its entirety for the methods taught therein). Gap LCR (GLCR) is a version of LCR where the probes are not adjacent but are separated by 2 to 3 bases.

A method for typing single nucleotide mutations in DNA, labeled Genetic Bit Analysis (GBA), has been described in Nikiforov, et al. (1994) Nucleic Acid Res 22:4167-4175. In this method, specific fragments of genomic DNA containing the mutated site(s) are first amplified by the polymerase chain reaction (PCR) using one regular and one phosphorothioate-modified primer. The double-stranded PCR product is rendered single-stranded by treatment with the enzyme T7 gene 6 exonuclease, and captured onto individual wells of a 96 well polystyrene plate by hybridization to an immobilized oligonucleotide primer. This primer is designed to hybridize to the single-stranded target DNA immediately adjacent from the mutated site of interest. Using the Klenow fragment of E. coli DNA polymerase I or the modified T7 DNA polymerase (Sequenase), the 3' end of the capture oligonucleotide is extended by one base using a mixture of one biotin-labeled, one fluorescein-labeled, and two unlabeled dideoxynucleoside triphosphates. Antibody conjugates of alkaline phosphatase and horseradish peroxidase are then used to determine the nature of the extended base in an ELISA format. Additionally, minisequencing with immobilized primers has been utilized for detection of mutations in PCR products (see Pastinen, et al. (1997) Genome Res 7:606-614).

The effect of phosphorothioate bonds on the hydrolytic activity of the 5'-->3' double-strand-specific T7 gene 6 exonuclease is used in order to improve upon GBA. The use of phosphorothioate primers and exonuclease hydrolysis for the preparation of single-stranded PCR products and their detection by solid-phase hybridization can be used. (See Nikiforov, et al. (1994) PCR Methods and Applications 3:285-291.) Double-stranded DNA substrates containing one phosphorothioate residue at the 5' end were found to be hydrolyzed by this enzyme as efficiently as unmodified ones. The enzyme activity was, however, completely inhibited by the presence of four phosphorothioates. On the basis of these results, a method for the conversion of double-stranded PCR products into full-length, single-stranded DNA fragments was developed. In this method, one of the PCR primers contains four phosphorothioates at its 5' end, and the opposite strand primer is unmodified. Following the amplification, the double-stranded product is treated with T7 gene 6 exonuclease. The phosphorothioated strand is protected from the action of this enzyme, whereas the opposite strand is hydrolyzed. When the phosphorothioated PCR primer is 5' biotinylated, the single-stranded PCR product can be easily detected colorimetrically after hybridization to an oligonucleotide probe immobilized on a microtiter plate. A simple and efficient method for the immobilization of relatively short oligonucleotides to microtiter plates with a hydrophilic surface in the presence of salt can be used.

DNA analysis based on template hybridization (or hybridization plus enzymatic processing) to an array of surface-bound oligonucleotides is well suited for high density, parallel, low cost and automatable processing (Ives, et al. (1996) Proc SPIE-Int Soc Opt Eng 2680 (Ultrasensitive Biochemical Diagnostics) 258-269). Direct fluorescence detection of labeled DNA provides the benefits of linearity, large dynamic range, multianalyte detection, processing simplicity and safe handling at reasonable cost. The Molecular Tool Corporation has applied a proprietary enzymatic method of solid phase genotyping to DNA processing in 96-well plates and glass microscope slides. Detecting the fluor-labeled GBA dideoxynucleotides requires a detection limit of approximately 100 mols/$\mu m^2$. Commercially available plate readers detect about 1000 mols/$\mu m^2$, and an experimental setup with an argon laser and thermoelectrically-cooled CCD can detect approximately 1 order of magnitude less signal. The current limit is due to glass fluorescence. Dideoxynucleotides labeled with fluorescein, eosin, tetramethylrhodamine, Lissamine and Texas Red have been characterized, and photobleaching, quenching and indirect detection with fluorogenic substrates have been investigated.

Other amplification techniques that can be used in the context of the present invention include, but are not limited to, Q-beta amplification as described in European Patent Application No 4544610, strand displacement amplification as described in EP 684 315A and, target mediated amplification as described in PCT Publication WO 9322461, the disclosures of which are incorporated herein by reference in their entirety for the methods taught therein.

Allele specific amplification can also be utilized for biallelic markers. Discrimination between the two alleles of a biallelic marker can also be achieved by allele specific amplification, a selective strategy, whereby one of the alleles is amplified without amplification of the other allele. For allele specific amplification, at least one member of the pair of primers is sufficiently complementary with a region of a reference sequence (i.e., $Na_v1.7$) comprising the polymorphic base of a biallelic marker of the present invention to hybridize therewith. Such primers are able to discriminate between the two alleles of a biallelic marker. This can be accomplished by placing the mutated base at the 3' end of one of the amplification primers. Such allele specific primers tend to selectively prime an amplification or sequencing reaction so long as they are used with a nucleic acid sample that contains one of the two alleles present at a biallelic marker because the extension forms from the 3' end of the primer, a mismatch at or near this position has an inhibitory effect on amplification. Therefore, under appropriate amplification conditions, these primers only direct amplification on their complementary allele. Determining the precise location of the mismatch and the corresponding assay conditions are well with the ordinary skill in the art.

A detectable label may be included in an amplification reaction. Suitable labels include fluorochromes, e.g., fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE),6-carboxy-X-rhodamine (ROX), 6-carboxy-2',4', 7',4,7-hexachlorofluorescein (HEX), 5-carboxyfluorescein (5-FAM) or N,N,N',N'-tetramethyl-6-carboxyrhodamine (TAMRA), radioactive labels, e.g., 32 P, 35 S, 3 H; etc. The label may be a two stage system, where the amplified DNA is conjugated to biotin, haptens, etc. having a high affinity binding partner, e.g., avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g., amplified or cloned fragment, can be analyzed by one of a number of methods known in the art. The nucleic acid can be sequenced by dideoxy or other methods. Hybridization with the variant sequence can also be used to determine its presence, by Southern blots, dot blots, etc. The hybridization pattern of a control (reference) and variant sequence to an array of oligonucleotide probes immobilized on a solid support, as described in U.S. Pat. No. 5,445,934 and WO 95/35505, which are incorporated herein by reference in their entirety for the methods, may also be used as a means of detecting the presence of variant sequences. Single strand conformational polymorphism (SSCP) analysis, denaturing gradient gel electrophoresis (DGGE), mismatch cleavage detection, and heteroduplex analysis in gel matrices are used to detect conformational changes created by DNA sequence variation as alterations in electrophoretic mobility. Alternatively, where a mutation creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels.

The disclosed materials, compositions, and methods also provide the use of the nucleic acid sequences described herein in methods using a mobile solid support to analyze mutations. See, for example, WO 01/48244, which is incorporated herein by reference in its entirety for the methods taught therein.

The method of performing a Luminex FlowMetrix-based SNP analysis involves differential hybridization of a PCR product to two differently-colored FACS-analyzable beads. The FlowMetrix system currently consists of uniformly-sized 5 micron polystyrene-divinylbenzene beads stained in eight concentrations of two dyes (orange and red). The matrix of the two dyes in eight concentrations allows for 64 differently-colored beads that can each be differentiated by a FACScalibur suitably modified with the Luminex PC computer board. In the Luminex SNP analysis, covalently-linked to a bead is a short (approximately 18-20 bases) "target" oligodeoxynucleotide (oligo). The nucleotide positioned at the center of the target oligo encodes the polymorphic base. A pair of beads are synthesized; each bead of the pair has attached to it one of the polymorphic oligonucleotides. A PCR of the region of DNA surrounding the to-be analyzed SNP is performed to generate a PCR product. Conditions are established that allow hybridization of the PCR product preferentially to the bead on which is encoded the precise complement. In one format ("without competitor"), the PCR product itself incorporates a flourescein dye and it is the gain of the flourescein stain on the bead, as measured during the FACScalibur run, that indicates hybridization. In a second format ("with competitor,") the beads are hybridized with a competitor to the PCR product. The competitor itself in this case is labeled with flourescein. And it is the loss of the flourescein by displacement by unlabeled PCR product that indicates successful hybridization.

4. Haplotyping

Also disclosed herein is a method for determining a $Na_v1.7$ haplotype in a human subject, wherein the method comprises identifying one or more nucleotides encoding amino acid residues 228, 490, 519, 684, 699, 1160, or 1267, or any combination thereof, wherein the nucleotide or nucleotides indicate the haplotype. The disclosed method can further comprise identifying one or more nucleotides encoding amino acid residues 62, 149, 641, 655, 739, 1123, or any combination thereof, wherein the nucleotide or nucleotides indicate the haplotype.

Also disclosed is a method for determining a $Na_v1.7$ haplotype in a human subject comprising identifying one or more nucleotides present at one or more of sites 684, 1469, 1555, 2052, 2096, 3478, or 3799, in either or both copies of the $Na_v1.7$ gene (SCN9A) contained in the subject genomic nucleic acid, wherein the nucleotide present at the mutated site or sites indicates the $Na_v1.7$ haplotype. It will be recognized by one of skill in the art that numerous haplotypes are possible. The method can further comprise identifying one or more nucleotides present at one or more of sites 184, 446, 1921, 1964, 2215, or 3369, in either or both copies of the $Na_v1.7$ gene (SCN9A) contained in the subject genomic nucleic acid, wherein the nucleotide present at the mutated site or sites indicates the $Na_v1.7$ haplotype. It will be recognized by one of skill in the art that numerous haplotypes are possible.

For example, one of skill in the art could identify the nucleotide present in either or both copies of the $Na_v1.7$ gene (SCN9A) contained in the subject genomic nucleic acid that encodes for amino acid 228 in the $Na_v1.7$ sodium channel alpha-subunit sequence.

The haplotypes for this particular analysis can comprise, for example, I228M, S490N, E519K, I684M, C699Y, E1160Q, L1267V, or any combination thereof, where the number indicates a position in the $Na_v1.7$ sodium channel alpha-subunit, the first letter represents the most common amino acid found at that positions, and the last letter represents the amino acid found in the haplotype. The haplotypes for this particular analysis can further comprise I62V, P149Q, N641Y, K655R, I739V, L1123F, or any combination thereof. Similarly, one of skill in the art could identify the nucleotide in a $Na_v1.7$ nucleic acid sequence at position 684, 1469, 1555, 2052, 2096, 3478, and/or 3799, and determine the $Na_v1.7$ haplotype. One of skill in the art could further identify the nucleotide in a $Na_v1.7$ nucleic acid sequence at position 184, 446, 1921, 1964, 2215, and/or 3369, and determine the $Na_v1.7$ haplotype. Therefore, any of positions 184, 446, 684, 1469, 1555, 1921, 1964, 2052, 2096, 2215, 3369, 3478, and/or 3799 in the nucleic acid sequence or positions 62, 149, 228, 490, 519, 641, 655, 684, 699, 739, 1160, 1123, and/or 1267 in the encoded amino acid sequence can be analyzed individually or in combination to obtain the haplotypes of the disclosed subject matter.

5. Methods of Drug Screening and Delivery

The materials, compositions, articles, devices and methods disclosed herein, in one aspect, relate to a method of identifying a compound that modulates mutant $Na_v1.7$ sodium channels comprising contacting, with a test compound, a cell containing a mutant $Na_v1.7$ nucleic acid that encodes a mutant $Na_v1.7$ sodium channel; detecting $Na_v1.7$ sodium channel activity; and comparing the $Na_v1.7$ sodium channel activity in the contacted cell with the amount of $Na_v1.7$ sodium channel activity in a control cell, wherein the control cell is not contacted by the test compound, an increased or decreased $Na_v1.7$ sodium channel activity in the test cell as compared to the control cell indicating a compound that modulates mutant $Na_v1.7$ sodium channels. Detecting sodium channel activity can be accomplished by methods known in the art. For example, a suitable protocol for detecting sodium channel activity is described in Kausalia, et al. (2003) J. Neurophysiol. 10.1152/jn.00676.2003.

The mutant $Na_v1.7$ sodium channel can comprise one or more mutations at 228, residue 490, residue 519, residue 684, residue 699, residue 1160, or residue 1267 of the encoded amino acid sequence of $Na_v1.7$. The mutant $Na_v1.7$ sodium channel can further comprise one or more mutations at residue 62, residue 149, residue 641, residue 655, residue 739, or residue 1123 of the encoded amino acid sequence of $Na_v1.7$.

The cell can express the mutant channel naturally or can be genetically modified to do so. Optionally, the cell is an oocyte that expressed the mutant sodium channel. The mutant sodium channel can comprise a I228M, S490N, E519K, I684M, C699Y, E1160Q, or L1267V mutant. The mutant sodium channel can further comprise a I62V, P149Q, N641Y, K655R, I739V, or L1123F mutant. Optionally, a mutant channel can comprise one or more of the site mutations.

Optionally, channel activity is tested using intracellular or extracellular recording to assess changes in membrane potential associated with sodium ion flux. Alternatively, imaging technologies can be used to observe labeled ion flux. Expression can be assessed in *Xenopus* oocytes or mammalian cells such as CHO, HEK and tsa201. Mutations may result in errors of protein trafficking and protein interaction. As such, mutant channels can be assessed for their ability to form functional channels in the cell membrane as opposed to being retained in the endoplasmic reticulum by using labeled antibodies to the wild-type channel, or by attaching a common epitope to the channels and using a specific antibody to that epitope. Mutations that alter interactions with intracellular proteins, such as protein kinase A, protein kinase C or calmodulin kinase, or the sodium channel beta-subunits, can be identified through yeast 2-hybrid studies, co-immunoprecipitation experiments or electrophysiological experiments.

6. Method of Administration

Also, the materials, compositions, articles, devices, and methods disclosed herein, in one aspect, relate to a method of preventing or reducing the effects of neurologic disorders like febrile seizures, afebrile seizures, or epilepsy by treating a subject at risk for neurologic disorders with a composition that modulates mutant $Na_v1.7$ levels. Thus, a subject with a mutation(s) in $Na_v1.7$ sodium channel alpha-subunits, consistent with a neurologic disorder or an increased risk of a neurologic disorder, can be treated with a composition comprising a mutant $Na_v1.7$ modulator identified or manufactured using the methods taught herein.

The materials and compositions disclosed herein can be administered in vivo in a pharmaceutically acceptable carrier. By "pharmaceutically acceptable carrier" is meant a material that is not biologically or otherwise undesirable, i.e., the material may be administered to a subject, along with a modulator of $Na_v1.7$ sodium channel function identified or made by the methods taught herein, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, although topical intranasal administration or administration by inhalant is typically preferred. As used herein, "topical intranasal administration" means delivery of the compositions into the nose and nasal passages through one or both of the nares and can comprise delivery by a spraying mechanism or droplet mechanism, or through aerosolization of the composition. The latter may be effective when a large number of animals are to be treated simultaneously. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the disorder being treated, the particular nucleic acid or modulator used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner wherein the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g., (1987) Proc Natl Acad Sci USA 84:7851; (1989) Biochemistry 28:908, which are hereby incorporated by reference in their entireties for their teachings of liposome construction and administration). When liposomes are endocytosed by a target cell, for example, they can be routed to acidic endosomes which will destabilize the liposome and result in drug release.

Alternatively, the liposome membrane can be chemically modified such that an enzyme is placed as a coating on the membrane which slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release. This liposome delivery system can also be made to target B cells by incorporating into the liposome structure a ligand having an affinity for B cell-specific receptors.

Compositions including the liposomes in a pharmaceutically acceptable carrier are also contemplated.

Transdermal delivery devices have been employed for delivery of low molecular weight proteins by using lipid-based compositions (i.e., in the form of a patch) in combination with sonophoresis. However, as reported in U.S. Pat. No. 6,041,253, which is hereby incorporated by reference in its entirety for the methods taught therein, transdermal delivery can be further enhanced by the application of an electric field, for example, by ionophoresis or electroporation. Using low frequency ultrasound which induces cavitation of the lipid layers of the stratum corneum, higher transdermal fluxes, rapid control of transdermal fluxes, and drug delivery at lower ultrasound intensities can be achieved. Still further enhancement can be obtained using a combination of chemical enhancers and/or magnetic field along with the electric field and ultrasound.

Implantable or injectable protein depot compositions can also be employed, providing long-term delivery of the composition. For example, U.S. Pat. No. 6,331,311, which is hereby incorporated by reference in its entirety for protein depot compositions and uses, reports an injectable depot gel composition which includes a biocompatible polymer, a solvent that dissolves the polymer and forms a viscous gel, and an emulsifying agent in the form of a dispersed droplet phase in the viscous gel. Upon injection, such a gel composition can provide a relatively continuous rate of dispersion of the agent to be delivered, thereby avoiding an initial burst of the agent to be delivered.

The test compound and modulator taught herein can be, but is not limited to, antibodies, chemicals, small molecules, modified antisense RNAs, ions, siRNAs, receptor ligands, drugs and secreted proteins.

B. Compositions

1. Mutant $Na_v1.7$ Sodium Channel Alpha-Subunits

In one aspect, disclosed herein are mutant $Na_v1.7$ sodium channel alpha-subunits and the use of such mutant $Na_v1.7$ sodium channels to diagnose and treat disease states such as, for example, neurologic disorders associated with a sodium channel mutation. It was found that specific sites in the $Na_v1.7$ sodium channel alpha-subunit are mutated, i.e., the amino acid at a specific position or at specific positions differs from that observed in the most commonly found $Na_v1.7$ sodium channel.

In one aspect, the mutant $Na_v1.7$ sodium channel alpha-subunits described herein have one or more mutated sites. For example, in one aspect, disclosed herein is a mutant $Na_v1.7$ sodium channel alpha-subunit where the amino acid at position 62 is not isoleucine (I) as is commonly found at position 62 but, rather, valine (V) (SEQ ID NO:2). In another aspect, disclosed herein is a mutant $Na_v1.7$ sodium channel alpha-subunit where the amino acid at position 149 is not proline (P) as is commonly found at position 149 but, rather, glutamine (Q) (SEQ ID NO:3). In another aspect, disclosed herein is a mutant $Na_v1.7$ sodium channel alpha-subunit where the amino acid at position 641 is not asparagines (N) as is commonly found at position 641 but, rather, tyrosine (Y) (SEQ ID NO:4). In yet another aspect, disclosed herein is a mutant $Na_v1.7$ sodium channel alpha-subunit where the amino acid at position 655 is not lysine (K) as is commonly found at position 655 but, rather, arginine (R) (SEQ ID NO:5). In a further aspect, disclosed herein is a mutant $Na_v1.7$ sodium channel alpha-subunit where the amino acid at position 739 is not isoleucine (I) as is commonly found at position 739 but, rather, valine (V) (SEQ ID NO:6). In a still further aspect, disclosed herein is a mutant $Na_v1.7$ sodium channel alpha-subunit where the amino acid at position 1123 is not leucine (L) as is commonly found at position 1123 but, rather, phenylalanine (F) (SEQ ID NO:7).

For example, in one aspect, disclosed herein is a mutant $Na_v1.7$ sodium channel alpha-subunit where the amino acid at position 228 is not isoleucine (I) as is commonly found at position 228 but, rather, methionine (M) (SEQ ID NO:79). For example, in one aspect, disclosed herein is a mutant $Na_v1.7$ sodium channel alpha-subunit where the amino acid at position 490 is not serine (S) as is commonly found at position 490 but, rather, asparagine (N) (SEQ ID NO:80). For example, in one aspect, disclosed herein is a mutant $Na_v1.7$ sodium channel alpha-subunit where the amino acid at position 519 is not glutamic acid (E) as is commonly found at position 519 but, rather, lysine (K) (SEQ ID NO:81). For example, in one aspect, disclosed herein is a mutant $Na_v1.7$ sodium channel alpha-subunit where the amino acid at position 684 is not isoleucine (I) as is commonly found at position 684 but, rather, methionine (M) (SEQ ID NO:82). For example, in one aspect, disclosed herein is a mutant $Na_v1.7$ sodium channel alpha-subunit where the amino acid at position 699 is not cysteine (C) as is commonly found at position 699 but, rather, tyrosine (Y) (SEQ ID NO:83). For example, in one aspect, disclosed herein is a mutant $Na_v1.7$ sodium channel alpha-subunit where the amino acid at position 1160 is not glutamic acid (E) as is commonly found at position 1160 but, rather, glutamine (Q) (SEQ ID NO:84). For example, in one aspect, disclosed herein is a mutant $Na_v1.7$ sodium channel alpha-subunit where the amino acid at position 1267 is not leucine (L) as is commonly found at position 62 but, rather, valine (V) (SEQ ID NO:85).

Thus, SEQ ID NO:2 sets forth a particular sequence of a mutant 162V mutant sodium channel alpha-subunit, SEQ ID NO:3 sets forth a particular sequence of a mutant P149Q $Na_v1.7$ sodium channel alpha-subunit, SEQ ID NO:4 sets forth a particular sequence of a mutant N641Y $Na_v1.7$ sodium channel alpha-subunit, SEQ ID NO:5 sets forth a particular sequence of a mutant K655R$Na_v1.7$ sodium channel alpha-subunit, SEQ ID NO:6 sets forth a particular sequence of a mutant I739V $Na_v1.7$ sodium channel alpha-subunit, and SEQ ID NO:7 sets forth a particular sequence of a mutant L1123F $Na_v1.7$ sodium channel alpha-subunit. As a further example, SEQ ID NO:79 sets forth a particular sequence of a mutant I228M mutant sodium channel alpha-subunit, SEQ ID NO:80 sets forth a particular sequence of a mutant S490N mutant sodium channel alpha-subunit, SEQ ID NO:81 sets forth a particular sequence of a mutant E519K mutant sodium channel alpha-subunit, SEQ ID NO:82 sets forth a particular sequence of a mutant I684M mutant sodium channel alpha-subunit, SEQ ID NO:83 sets forth a particular sequence of a mutant C699Y mutant sodium channel alpha-subunit, SEQ ID NO:84 sets forth a particular sequence of a mutant E1160Q mutant sodium channel alpha-subunit, and SEQ ID NO:85 sets forth a particular sequence of a mutant L1267V mutant sodium channel alpha-subunit.

Also contemplated are variants and derivatives of the disclosed mutant $Na_v1.7$ amino acid sequences. It is understood that one way to define the variants and derivatives of the disclosed proteins herein is through defining the variants and derivatives in terms of homology/identity to specific known sequences. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

Specifically disclosed are variants of these and other proteins herein disclosed which have at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the stated sequence. Also, provided are amino acid sequences have at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence idenity to sequences set forth in SEQ ID NOs:2, 3, 4, 5, 6, 7, 86, 87, 88, 89, 90, 91, 92. Also, provided are amino acid sequences comprising the sequences set forth in SEQ ID NOs:2, 3, 4, 5, 6, 7, 86, 87, 88, 89, 90, 91, 92, or any fragment thereof wherein the sequence comprises one or more conservative amino acid substitutions.

Amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place.

Preferably, the amino acid sequence with conservative amino acid substitutions maintains sodium channel function. Examples of conservative amino acid substitutions are shown in Table 1. Those of skill in the art readily understand how to determine the homology of two proteins. For example, the homology can be calculated after aligning the two sequences so that the homology is at its highest level.

TABLE 1

Amino Acid Substitutions
Original Residue Exemplary Conservative Substitutions, others are known in the art.

| |
| --- |
| Ala ↔ ser |
| Arg ↔ lys or gln |
| Asn ↔ gln or his |
| Asp ↔ glu |
| Cys ↔ ser |
| Gln ↔ asn or lys |
| Glu ↔ asp |
| Gly ↔ pro |
| His ↔ asn or gln |
| Ile ↔ leu or val |
| Leu ↔ ile or val |
| Lys ↔ arg or gln; |
| Met ↔ leu or ile |
| Phe ↔ leu or tyr |
| Ser ↔ thr |
| Thr ↔ ser |
| Trp ↔ tyr |
| Tyr ↔ trp or phe |
| Val ↔ ile or leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

Another way of calculating homology can be performed by published algorithms. Optimal alignment of sequences for comparison may be conducted by the local homology algorithm of Smith and Waterman (1981) Adv Appl Math 2:482, by the homology alignment algorithm of Needleman and Wunsch (1970) J Mol Biol 48:443, by the search for similarity method of Pearson and Lipman, (1988) Proc Natl Acad Sci USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

Also, disclosed herein are isolated polypeptides and fragments of polypeptides comprising mutant $Na_v1.7$ sodium channel alpha-subunit amino acid sequences. For example, disclosed herein are isolated polypeptides having amino acid sequences of SEQ ID NOs:2, 3, 4, 5, 6, 7, 86, 87, 88, 89, 90, 91, and 92. In another aspect, disclosed herein are fragments of such sequences. For example, disclosed herein are isolated polypeptides having amino acid sequences of SEQ ID NOs:32, 33, 34, 35, 36, and 37.

Also, provided are fragments of at least 2, 3, 4, 5, 6, 7, 8, 9, 10, 11, 12, 13, 14, 15, 16, 17, 18, 19, 20, 25, 30 contiguous amino acid sequences corresponding to SEQ ID NOs:2, 3, 4, 5, 6, and 7. For example, provided are fragments of at least 5 contiguous amino acid sequences corresponding to SEQ ID NOs:2, 3, 4, 5, 6, and 7. For example, disclosed are isolated polypeptides having amino acid sequences PFVYG (SEQ ID NO:32), NPQDW (SEQ ID NO:33), LPYGQ (SEQ ID NO:34), IHRKR (SEQ ID NO:35), LAVTI (SEQ ID NO:36), and NPFPG (SEQ ID NO:37).

It is understood that there are numerous amino acid and peptide analogs which can be incorporated into the disclosed compositions. For example, there are numerous D amino acids or amino acids which have a different functional substituent than the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Enginerring Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—$CH$=$CH$— (cis and trans), —$COCH_2$—$CH(OH)CH_2$—, and —$CHH_2SO$—(These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—$CH H_2$—S); Hann J. Chem. Soc Perkin Trans. I 307-314 (1982) (—$CH$—$CH$—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appin, EP 45665 CA (1982): 97:39405 (1982) (—$CH(OH)CH_2$—); Holladay et al. Tetrahedron. Lett 24:4401-4404 (1983) (—$C(OH)CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together.

This can be beneficial to constrain peptides into particular conformations. (Rizo and Gierasch Ann. Rev. Biochem. 61:387 (1992), incorporated herein by reference).

2. Isolated $Na_v1.7$ Nucleic Acid Sequences

As this specification discusses various amino acid sequences it is understood that the nucleic acids that can encode those amino acid sequences are also disclosed. This would include all degenerate sequences related to a specific amino acid sequence, i.e. all nucleic acids having a sequence that encodes one particular amino acid sequence as well as all nucleic acids, including degenerate nucleic acids, encoding the disclosed variants and derivatives of the amino acid sequences. Thus, while each particular nucleic acid sequence may not be written out herein, it is understood that each and every sequence is in fact disclosed and described herein through the disclosed amino acid sequence.

For example, one of the many nucleic acid sequences that can encode the amino acid sequence of SEQ ID NO:2 is set forth in SEQ ID NO:8. Another nucleic acid sequence that encodes the amino acid sequence of SEQ ID NO:3 is set forth in SEQ ID NO:9. Another nucleic acid sequence that encodes the amino acid sequence of SEQ ID NO:4 is set forth in SEQ ID NO:10. Another nucleic acid sequence that encodes the amino acid sequence of SEQ ID NO:5 is set forth in SEQ ID NO:11. Another nucleic acid sequence that encodes the amino acid sequence of SEQ ID NO:6 is set forth in SEQ ID NO:12. Another nucleic acid sequence that encodes the amino acid sequence of SEQ ID NO:7 is set forth in SEQ ID NO:13. Another nucleic acid sequence that encodes the amino acid sequence of SEQ ID NO:79 is set forth in SEQ ID NO:86. Another nucleic acid sequence that encodes the amino acid sequence of SEQ ID NO:80 is set forth in SEQ ID NO:87. Another nucleic acid sequence that encodes the amino acid sequence of SEQ ID NO:81 is set forth in SEQ ID NO:88. Another nucleic acid sequence that encodes the amino acid sequence of SEQ ID NO:82 is set forth in SEQ ID NO:89. Another nucleic acid sequence that encodes the amino acid sequence of SEQ ID NO:83 is set forth in SEQ ID NO:90. Another nucleic acid sequence that encodes the amino acid sequence of SEQ ID NO:84 is set forth in SEQ ID NO:91. Another nucleic acid sequence that encodes the amino acid sequence of SEQ ID NO:85 is set forth in SEQ ID NO:92.

It is also understood that while no amino acid sequence indicates what particular DNA sequence encodes that protein within an organism, where particular variants of a disclosed protein are disclosed herein, the known nucleic acid sequence that encodes that amino acid sequence in the particular mutant $Na_v1.7$ sodium channel alpha-subunit from which that amino acid sequence arises is also known and herein disclosed and described.

The nucleic acid sequences disclosed herein can be isolated by methods known in the art and described herein. In one aspect, disclosed herein are isolated nucleic acids comprising nucleotide sequences encoding mutant $Na_v1.7$ sodium channel alpha-subunits.

For example, in one aspect, disclosed herein is an isolated nucleic acid sequence comprising a nucleotide sequence encoding the amino acid sequence set forth in SEQ ID NO:2. In another aspect, disclosed herein is an isolated nucleic acid sequence comprising a nucleotide sequence encoding the amino acid sequence set forth in SEQ ID NO:3. In yet another aspect, disclosed herein is an isolated nucleic acid sequence comprising a nucleotide sequence encoding the amino acid sequence set forth in SEQ ID NO:4. In a further aspect, disclosed herein is an isolated nucleic acid sequence comprising a nucleotide sequence encoding the amino acid sequence set forth in SEQ ID NO:5. In a still further aspect, disclosed herein is an isolated nucleic acid sequence comprising a nucleotide sequence encoding the amino acid sequence set forth in SEQ ID NO:6. In one aspect, disclosed herein is an isolated nucleic acid sequence comprising a nucleotide sequence encoding the amino acid sequence set forth in SEQ ID NO:7. In one aspect, disclosed herein is an isolated nucleic acid sequence comprising a nucleotide sequence encoding the amino acid sequence set forth in SEQ ID NO:79. In one aspect, disclosed herein is an isolated nucleic acid sequence comprising a nucleotide sequence encoding the amino acid sequence set forth in SEQ ID NO:80. In one aspect, disclosed herein is an isolated nucleic acid sequence comprising a nucleotide sequence encoding the amino acid sequence set forth in SEQ ID NO:81. In one aspect, disclosed herein is an isolated nucleic acid sequence comprising a nucleotide sequence encoding the amino acid sequence set forth in SEQ ID NO:82. In one aspect, disclosed herein is an isolated nucleic acid sequence comprising a nucleotide sequence encoding the amino acid sequence set forth in SEQ ID NO:83. In one aspect, disclosed herein is an isolated nucleic acid sequence comprising a nucleotide sequence encoding the amino acid sequence set forth in SEQ ID NO:84. In one aspect, disclosed herein is an isolated nucleic acid sequence comprising a nucleotide sequence encoding the amino acid sequence set forth in SEQ ID NO:85. Also disclosed herein is an isolated nucleic acid sequence comprising the nucleic acid sequence set forth in SEQ ID NO:8. Also disclosed herein is an isolated nucleic acid sequence comprising the nucleic acid sequence set forth in SEQ ID NO:9. Also disclosed herein is an isolated nucleic acid sequence comprising the nucleic acid sequence set forth in SEQ ID NO:10. Also disclosed herein is an isolated nucleic acid sequence comprising the nucleic acid sequence set forth in SEQ ID NO:11. Also disclosed herein is an isolated nucleic acid sequence comprising the nucleic acid sequence set forth in SEQ ID NO:12. Also disclosed herein is an isolated nucleic acid sequence comprising the nucleic acid sequence set forth in SEQ ID NO:13. Also disclosed herein is an isolated nucleic acid sequence comprising the nucleic acid sequence set forth in SEQ ID NO:86. Also disclosed herein is an isolated nucleic acid sequence comprising the nucleic acid sequence set forth in SEQ ID NO:87. Also disclosed herein is an isolated nucleic acid sequence comprising the nucleic acid sequence set forth in SEQ ID NO:88. Also disclosed herein is an isolated nucleic acid sequence comprising the nucleic acid sequence set forth in SEQ ID NO:89. Also disclosed herein is an isolated nucleic acid sequence comprising the nucleic acid sequence set forth in SEQ ID NO:90. Also disclosed herein is an isolated nucleic acid sequence comprising the nucleic acid sequence set forth in SEQ ID NO:91. Also disclosed herein is an isolated nucleic acid sequence comprising the nucleic acid sequence set forth in SEQ ID NO:92.

Also, disclosed herein is an isolated nucleic acid comprising a nucleotide sequence encoding at least 5 contiguous residues of the $Na_v1.7$ sodium channel alpha-subunit. For example, in one aspect, disclosed herein is an isolated nucleic acid comprising a nucleotide sequence encoding at least 5 contiguous residues of the amino acid sequence of SEQ ID NO:2, wherein one of the amino acid residues comprises a valine in a position that corresponds to position 62 in SEQ ID NO:2. In another aspect, disclosed herein is an isolated nucleic acid comprising a nucleotide sequence encoding at least 5 contiguous residues of the amino acid sequence of SEQ ID NO:3, wherein one of the amino acid residues comprises a glutamine in a position that corresponds to position 149 in SEQ ID NO:3. In yet another aspect, disclosed herein is an isolated nucleic acid comprising a nucleotide sequence encoding at least 5 contiguous residues of the amino acid sequence of SEQ ID NO:4, wherein one of the amino acid residues comprises a tyrosine in a position that corresponds to position 641 in SEQ ID NO:4. In a further aspect, disclosed herein is an isolated nucleic acid comprising a nucleotide sequence encoding at least 5 contiguous residues of the amino acid sequence of SEQ ID NO:5, wherein one of the amino acid residues comprises an arginine in a position that corresponds to position 655 in SEQ ID NO:5. In a still further aspect, disclosed herein is an isolated nucleic acid comprising a nucleotide sequence encoding at least 5 contiguous residues of the amino acid sequence of SEQ ID NO:6, wherein one of the amino acid residues comprises a valine in a position that corresponds to position 739 in SEQ ID NO:6. In one aspect, disclosed herein is an isolated nucleic acid comprising a nucleotide sequence encoding at least 5 contiguous residues of the amino acid sequence of SEQ ID NO:7, wherein one of the amino acid residues comprises a phenylalanine in a position that corresponds to position 1123 in SEQ ID NO:7. In one aspect, disclosed herein is an isolated nucleic acid comprising a nucleotide sequence encoding at least 5 contiguous residues of the amino acid sequence of SEQ ID NO:79, wherein one of the amino acid residues comprises a methionine in a position that corresponds to position 228 in SEQ ID NO:79. In one aspect, disclosed herein is an isolated nucleic acid comprising a nucleotide sequence encoding at least 5 contiguous residues of the amino acid sequence of SEQ ID NO:80, wherein one of the amino acid residues comprises an asparagine in a position that corresponds to position 490 in SEQ ID NO:80. In one aspect, disclosed herein is an isolated nucleic acid comprising a nucleotide sequence encoding at least 5 contiguous residues of the amino acid sequence of SEQ ID NO:81, wherein one of the amino acid residues comprises a lysine in a position that corresponds to position 519 in SEQ ID NO:81. In one aspect, disclosed herein is an isolated nucleic acid comprising a nucleotide sequence encoding at least 5 contiguous residues of the amino acid sequence of SEQ ID NO:82, wherein one of the amino acid residues comprises a methionine in a position that corresponds to position 684 in SEQ ID NO:82. In one aspect, disclosed herein is an isolated nucleic acid comprising a nucleotide sequence encoding at least 5 contiguous residues of the amino acid sequence of SEQ ID NO:83, wherein one of the amino acid residues comprises a tyrosine in a position that corresponds to position 699 in SEQ ID NO:83. In one aspect, disclosed herein is an isolated nucleic acid comprising a nucleotide sequence encoding at least 5 contiguous residues of the amino acid sequence of SEQ ID NO:84, wherein one of the amino acid residues comprises a glutamine in a position that corresponds to position 1160 in SEQ ID NO:84. In one aspect, disclosed herein is an isolated nucleic acid comprising a nucleotide sequence encoding at least 5 contiguous residues of the amino acid sequence of SEQ ID NO:85, wherein one of the amino acid residues comprises a valine in a position that corresponds to position 1267 in SEQ ID NO:85.

3. Reference Nucleic Acid Sequences

Reference sequences of the $Na_v1.7$ gene comprising the most commonly found allele are provided herein. As utilized herein, "reference sequence" refers to a nucleic acid sequence that encodes a $Na_v1.7$ sodium channel alpha-subunit or fragment thereof comprising a specific nucleotide at a particular position(s) in the $Na_v1.7$ nucleic acid sequence. Optionally, the reference sequence comprises the most commonly found nucleotide or allele at the particular position or positions. This reference sequence can be a full-length $Na_v1.7$ nucleic acid sequence or fragments thereof. An example of a full-length human $Na_v1.7$ nucleic acid sequence is provided herein as SEQ ID NO:1.

The term "wild-type" may also be used to refer to the reference sequence comprising the most commonly found allele. It will be understood by one of skill in the art that the designation as "wild-type" is merely a convenient label for a common allele and should not be construed as conferring any particular property on that form of the sequence.

Alternatively, one of skill in the art can utilize a reference sequence or a fragment thereof comprising a nucleotide or allele that is not the most commonly found nucleotide or allele at a specific nucleotide position(s) in the $Na_v1.7$ nucleic acid sequence or can utilize a reference sequence that comprises alternative nucleotides at a specific position(s). An example of a full-length $Na_v1.7$ nucleic acid sequence that comprises such an alternative nucleotide at position 184 is provided herein as SEQ ID NO:8. Therefore, when utilizing this reference sequence or a fragment thereof, the nucleotide at position 184 can be A or G. Other examples of full-length $Na_v1.7$ reference sequences that comprise such alternative nucleotides at positions 446, 1921, 1964, 2215, and 3369 are provided herein as SEQ ID NO's:9, 10, 11, 12, and 13, respectively.

Other examples of full-length $Na_v1.7$ reference sequences that comprise such alternative nucleotides at positions 684, 1469, 1555, 2052, 2096, 3478, and 3799 are provided herein as SEQ ID NO's:86, 87, 88, 89, 90, 91, and 92, respectively. Therefore, when utilizing these reference sequences or fragments thereof, respectively, the nucleotide at position 684 can be C or G, the nucleotide at position 1469 can be G or A, the nucleotide at position 1555 can be position G or A, the nucleotide at position 2052 can be A or G, the nucleotide at position 2096 can be G or A, the nucleotide at position 3478 can be G or C, and the nucleotide at position 3799 can be C or G.

In one aspect, the reference sequence can comprise a fragment of the $Na_v1.7$ nucleic acid sequence. For example, disclosed herein is a reference sequence comprising the nucleotide sequence GCCCTTCATCTATGG (SEQ ID NO:14), corresponding to nucleotides 177 to 191 of the $Na_v1.7$ gene sequence. This reference sequence has an "A" at position 184, which is the most commonly found nucleotide at this position. Therefore, one of skill in the art can compare this reference sequence to a test sequence and determine if the most commonly found nucleotide (A) is present at position 184 of the test sequence or if another nucleotide (G) is present at position 184 of the test sequence. Also provided are nucleotide sequence corresponding to any fragment of SEQ ID NO:14 that includes the A at position 184 or the corresponding sequence with a G at position 184.

As another example, disclosed herein is a reference sequence comprising the nucleotide sequence AACCCGC-CGGACTGG (SEQ ID NO:15), corresponding to nucleotides 439 to 453 of the $Na_v1.7$ gene sequence. This reference sequence has a "C" at position 446, which is the most commonly found nucleotide at this position. Therefore, one of skill in the art can compare this reference sequence to a test sequence and determine if the most commonly found nucleotide (C) is present at position 446 of the test sequence or if another nucleotide (A) is present at position 446 of the test sequence. Also provided are nucleotide sequence corresponding to any fragment of SEQ ID NO:15 that includes the C at position 446 or the corresponding sequence with a A at position 446.

Also, disclosed herein is a reference sequence comprising the nucleotide sequence GCTCCCCAATGGACA (SEQ ID NO:16), corresponding to nucleotides 1914 to 1928 of the $Na_v1.7$ gene sequence. This reference sequence has an "A" at position 1921, which is the most commonly found nucleotide at this position. Therefore, one of skill in the art can compare this reference sequence to a test sequence and determine if the most commonly found nucleotide (A) is present at position 1921 of the test sequence or if another nucleotide (G) is present at position 1921 of the test sequence. Also provided are nucleotide sequence corresponding to any fragment of SEQ ID NO:16 that includes the A at position 1921 or the corresponding sequence with a G at position 1921.

Further, disclosed herein is a reference sequence comprising the nucleotide sequence ATACACAAGAAAAGG (SEQ ID NO:17), corresponding to nucleotides 1956 to 1971 of the $Na_v1.7$ gene sequence. This reference sequence has an "A" at position 1964, which is the most commonly found nucleotide at this position. Therefore, one of skill in the art can compare this reference sequence to a test sequence and determine if the most commonly found nucleotide (A) is present at position 1964 of the test sequence or if another nucleotide (G) is present at position 1964 of the test sequence. Also provided are nucleotide sequence corresponding to any fragment of SEQ ID NO:17 that includes the A at position 1964 or the corresponding sequence with a G at position 1964.

In yet another example, disclosed herein is a reference sequence comprising the nucleotide sequence TCTTGCAATTACCAT (SEQ ID NO:18), corresponding to nucleotides 2208 to 2222 of the $Na_v1.7$ gene sequence. This reference sequence has an "A" at position 2215, which is the most commonly found nucleotide at this position. Therefore, one of skill in the art can compare this reference sequence to a test sequence and determine if the most commonly found nucleotide (A) is present at position 2215 of the test sequence or if another nucleotide (G) is present at position 2215 of the test sequence. Also provided are nucleotide sequence corresponding to any fragment of SEQ ID NO:18 that includes the A at position 2215 or the corresponding sequence with a G at position 2215.

In still another example, disclosed herein is a reference sequence comprising the nucleotide sequence ACCCTTTGCCTGGAG (SEQ ID NO:19), corresponding to nucleotides 3362 to 3376 of the $Na_v1.7$ gene sequence. This reference sequence has a "G" at position 3369, which is the most commonly found nucleotide at this position. Therefore, one of skill in the art can compare this reference sequence to a test sequence and determine if the most commonly found nucleotide (G) is present at position 3369 of the test sequence or if another nucleotide (T) is present at position 3369 of the test sequence. Also provided are nucleotide sequence corresponding to any fragment of SEQ ID NO:19 that includes the G at position 3369 or the corresponding sequence with a T at position 3369.

In one aspect, the reference sequence can comprise a fragment of the $Na_v1.7$ nucleic acid sequence. For example, disclosed herein is a reference sequence comprising the nucleotide sequence CTGTAATCCCAGGCC (SEQ ID NO:93), corresponding to nucleotides 677 to 691 of the $Na_v1.7$ gene sequence. This reference sequence has a "C" at position 684, which is the most commonly found nucleotide at this position. Therefore, one of skill in the art can compare this reference sequence to a test sequence and determine if the most commonly found nucleotide (A) is present at position 684 of the test sequence or if another nucleotide (G) is present at position 684 of the test sequence. Also provided are nucleotide sequence corresponding to any fragment of SEQ ID NO:93 that includes the A at position 684 or the corresponding sequence with a G at position 684.

In one aspect, the reference sequence can comprise a fragment of the $Na_v1.7$ nucleic acid sequence. For example, disclosed herein is a reference sequence comprising the nucleotide sequence CTCTCCAGTGGAGAG (SEQ ID NO:94), corresponding to nucleotides 1461 to 1475 of the $Na_v1.7$ gene sequence. This reference sequence has a "G" at position 1469, which is the most commonly found nucleotide at this position. Therefore, one of skill in the art can compare this reference sequence to a test sequence and determine if the most commonly found nucleotide (G) is present at position 1469 of the test sequence or if another nucleotide (A) is present at position 1469 of the test sequence. Also provided are nucleotide sequence corresponding to any fragment of SEQ ID NO:94 that includes the G at position 1469 or the corresponding sequence with a A at position 1469.

In one aspect, the reference sequence can comprise a fragment of the $Na_v1.7$ nucleic acid sequence. For example, disclosed herein is a reference sequence comprising the nucleotide sequence TGGTGTCGAAGGGCA (SEQ ID NO:95), corresponding to nucleotides 1548 to 1562 of the $Na_v1.7$ gene sequence. This reference sequence has a "G" at position 1555, which is the most commonly found nucleotide at this position. Therefore, one of skill in the art can compare this reference sequence to a test sequence and determine if the most commonly found nucleotide (G) is present at position 1555 of the test sequence or if another nucleotide (A) is present at position 1555 of the test sequence. Also provided are nucleotide sequence corresponding to any fragment of SEQ ID NO:95 that includes the G at position 1469 or the corresponding sequence with a A at position 1555.

In one aspect, the reference sequence can comprise a fragment of the $Na_v1.7$ nucleic acid sequence. For example, disclosed herein is a reference sequence comprising the nucleotide sequence CAAGCATATTAACAA (SEQ ID NO:96), corresponding to nucleotides 2045 to 2059 of the $Na_v1.7$ gene sequence. This reference sequence has an "A" at position 2052, which is the most commonly found nucleotide at this position. Therefore, one of skill in the art can compare this reference sequence to a test sequence and determine if the most commonly found nucleotide (A) is present at position 2052 of the test sequence or if another nucleotide (G) is present at position 2052 of the test sequence. Also provided are nucleotide sequence corresponding to any fragment of SEQ ID NO:96 that includes the A at position 1469 or the corresponding sequence with a G at position 2052.

In one aspect, the reference sequence can comprise a fragment of the $Na_v1.7$ nucleic acid sequence. For example, disclosed herein is a reference sequence comprising the nucleotide sequence CAAAAATGTCCACCT (SEQ ID NO:97), corresponding to nucleotides 2089 to 2103 of the $Na_v1.7$ gene sequence. This reference sequence has a "G" at position 2096, which is the most commonly found nucleotide at this position. Therefore, one of skill in the art can compare this reference sequence to a test sequence and determine if the most commonly found nucleotide (G) is present at position 2096 of the test sequence or if another nucleotide (A) is present at position 2096 of the test sequence. Also provided are nucleotide sequence corresponding to any fragment of SEQ ID NO:97 that includes the G at position 1469 or the corresponding sequence with a A at position 2096.

In one aspect, the reference sequence can comprise a fragment of the $Na_v1.7$ nucleic acid sequence. For example, disclosed herein is a reference sequence comprising the nucleotide sequence TAACATAGAGTCAGG (SEQ ID NO:98), corresponding to nucleotides 3470 to 3484 of the $Na_v1.7$ gene sequence. This reference sequence has a "G" at position 3478, which is the most commonly found nucleotide at this position. Therefore, one of skill in the art can compare this reference sequence to a test sequence and determine if the most commonly found nucleotide (G) is present at position 3478 of the test sequence or if another nucleotide (C) is present at position 3478 of the test sequence. Also provided are nucleotide sequence corresponding to any fragment of SEQ ID NO:98 that includes the G at position 3478 or the corresponding sequence with a C at position 3478.

In one aspect, the reference sequence can comprise a fragment of the $Na_v1.7$ nucleic acid sequence. For example, disclosed herein is a reference sequence comprising the nucleotide sequence AAACACTCTTGGCTA (SEQ ID NO:99), corresponding to nucleotides 3791 to 3805 of the $Na_v1.7$ gene sequence. This reference sequence has a "C" at position 3799, which is the most commonly found nucleotide at this position. Therefore, one of skill in the art can compare this reference sequence to a test sequence and determine if the most commonly found nucleotide (C) is present at position 3799 of the test sequence or if another nucleotide (G) is present at position 3799 of the test sequence. Also provided are nucleotide sequence corresponding to any fragment of SEQ ID NO:99 that includes the C at position 3799 or the corresponding sequence with a G at position 3799.

4. Probes and Primers

Nucleic acids of interest comprising the mutations provided herein can be utilized as probes or primers. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the disclosed nucleic acids or region of the nucleic acids or they hybridize with the complement of the nucleic acids or complement of a region of the nucleic acids.

The size of the primers or probes for interaction with the nucleic acids in certain embodiments can be any size that supports the desired enzymatic manipulation of the primer, such as DNA amplification or the simple hybridization of the probe or primer. A typical primer or probe would be at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments a primer or probe can be less than or equal to 6, 7, 8, 9, 10, 11, 12 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

The primers can be used to produce an amplified DNA product that contains a region of the target nucleic acid. In general, typically the size of the product will be such that the size can be accurately determined to within 3, or 2 or 1 nucleotides.

In certain embodiments this product is at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments the product is less than or equal to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

The complementary sequences of the $Na_v1.7$ nucleic acid sequences disclosed herein are also provided. For the most part, the nucleic acid fragments will be of at least about 15 nucleotides, usually at least about 20 nucleotides, often at least about 50 nucleotides. Such fragments are useful as primers for PCR, hybridization screening, etc. Larger nucleic acid fragments, for example, greater than about 100 nucleotides are useful for production of promoter fragments, motifs, etc. For use in amplification reactions, such as PCR, a pair of primers will be used. The exact composition of primer sequences is not critical to the invention, but for most applications the primers will hybridize to the subject sequence under stringent conditions, as known in the art.

"Probes," as used herein, are molecules capable of interacting with a target nucleic acid, typically in a sequence specific manner, for example, through hybridization. The hybridization of nucleic acids is well understood in the art and is discussed herein. Typically, a probe can be made from any combination of nucleotides or nucleotide derivatives or analogs available in the art.

The term "hybridization" typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize. Generally, the hybridizing portion of the hybridizing nucleic acid is at least 80%, for example, at least 90%, 95%, or 98%, identical to the sequence of or a portion of the $Na_v1.7$ nucleic acid of the invention, or its complement. Hybridizing nucleic acids of the invention can be used, for example, as a cloning probe, a primer (e.g., for PCR), a diagnostic probe, or an antisense probe. Hybridization of the oligonucleotide probe to a nucleic acid sample typically is performed under stringent conditions. Nucleic acid duplex or hybrid stability is expressed as the melting temperature or $T_m$, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE). Assuming that a 1% mismatch results in a 1° C. decrease in the $T_m$, the temperature of the final wash in the hybridization reaction is reduced accordingly (for example, if sequence having >95% identity with the probe are sought, the final wash temperature is decreased by 5° C.). In practice, the change in $T_m$ can be between 0.5° C. and 1.5° C. per 1% mismatch. Stringent conditions involve hybridizing at 68° C. in 5×SSC/5×Denhardt's solution/1.0% SDS, and washing in 0.2×SSC/0.1% SDS at room temperature. Moderately stringent conditions include washing in 3×SSC at 42° C. The parameters of salt concentration and temperature can be varied to achieve the optimal level of identity between the probe and the target nucleic acid. Additional guidance regarding such conditions is readily available in the art, for example, in Sambrook, et al., Molecular Cloning, A Laboratory Manual, Cold Spring Harbor Press, New York, N.Y. (1989); and Ausubel, et al., eds., Current Protocols in Molecular Biology, John Wiley & Sons, New York, N.Y., at Unit 2.10 (1995). Thus, the terms "hybridizing under stringent conditions" or "hybridizing under highly stringent conditions" generally means that the hybridizing portion of the hybridizing nucleic acid, typically comprising at least 15 (e.g., 20, 25, 30, or 50 nucleotides), hybridizes to all or a portion of the provided nucleotide sequence under stringent conditions.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

Synthetic analogs of nucleic acids may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O— phosphorothioate, 3'-$CH_2$-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The alpha-anomer of deoxyribose may be used, where the base is inverted with respect to the natural beta-anomer. The 2'-OH of the ribose sugar may be altered to form 2'-O-methyl or 2'-O-allyl sugars, which provides resistance to degradation without compromising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

In one aspect, disclosed herein are isolated nucleic acids comprising a sequence that hybridizes under stringent conditions to a nucleic acid comprising a nucleotide sequence encoding an amino acid sequence of a mutated Na$_v$1.7 sodium channel alpha-subunit but not to a nucleic acid sequence that encodes the amino acid sequence of the wild-type Na$_v$1.7 sodium channel alpha-subunit.

For example, in one aspect, disclosed herein are isolated nucleic acids comprising a sequence that hybridizes under stringent conditions to a nucleic acid encoding the amino acid sequence SEQ ID NO:2 or the complement thereof but not to a nucleic acid encoding SEQ ID NO:38 or the complement thereof. Thus, disclosed herein are isolated nucleic acids that hybridize under stringent conditions to a nucleic acid consisting of the sequence set forth in SEQ ID NO:2 or the complement thereof but not to a nucleic acid consisting of the sequence set forth in SEQ ID NO:1 or the complement thereof.

In another aspect, disclosed herein are isolated nucleic acids comprising a sequence that hybridizes under stringent conditions to a nucleic acid encoding the amino acid sequence SEQ ID NO:3 or the complement thereof but not to a nucleic acid encoding SEQ ID NO:38 or the complement thereof. Thus, disclosed herein are isolated nucleic acids that hybridizes under stringent conditions to a nucleic acid consisting of the sequence set forth in SEQ ID NO:3 or the complement thereof but not to a nucleic acid consisting of the sequence set forth in SEQ ID NO:1 or the complement thereof.

In another aspect, disclosed herein are isolated nucleic acids comprising a sequence that hybridizes under stringent conditions to a nucleic acid encoding the amino acid sequence SEQ ID NO:4 or the complement thereof but not to a nucleic acid encoding SEQ ID NO:38 or the complement thereof. Thus, disclosed herein are isolated nucleic acids that hybridize under stringent conditions to a nucleic acid consisting of the sequence set forth in SEQ ID NO:4 or the complement thereof but not to a nucleic acid consisting of the sequence set forth in SEQ ID NO:1 or the complement thereof.

In an further aspect, disclosed herein are isolated nucleic acids comprising a sequence that hybridizes under stringent conditions to a nucleic acid encoding the amino acid sequence SEQ ID NO:5 or the complement thereof but not to a nucleic acid encoding SEQ ID NO:38 or the complement thereof. Thus, disclosed herein are isolated nucleic acids that hybridizes under stringent conditions to a nucleic acid consisting of the sequence set forth in SEQ ID NO:5 or the complement thereof but not to a nucleic acid consisting of the sequence set forth in SEQ ID NO:1 or the complement thereof.

In a still further aspect, disclosed herein are isolated nucleic acids comprising a sequence that hybridizes under stringent conditions to a nucleic acid encoding the amino acid sequence SEQ ID NO:6 or the complement thereof but not to a nucleic acid encoding SEQ ID NO:38 or the complement thereof. Thus, disclosed herein are isolated nucleic acids that hybridizes under stringent conditions to a nucleic acid consisting of the sequence set forth in SEQ ID NO:6 or the complement thereof but not to a nucleic acid consisting of the sequence set forth in SEQ ID NO:1 or the complement thereof.

In one aspect, disclosed herein are isolated nucleic acids comprising a sequence that hybridizes under stringent conditions to a nucleic acid encoding the amino acid sequence SEQ ID NO:7 or the complement thereof but not to a nucleic acid encoding SEQ ID NO:38 or the complement thereof. Thus, disclosed herein are isolated nucleic acids that hybridizes under stringent conditions to a nucleic acid consisting of the sequence set forth in SEQ ID NO:7 or the complement thereof but not to a nucleic acid consisting of the sequence set forth in SEQ ID NO:1 or the complement thereof.

In an further aspect, disclosed herein are isolated nucleic acids comprising a sequence that hybridizes under stringent conditions to a nucleic acid encoding the amino acid sequence SEQ ID NO:86 or the complement thereof but not to a nucleic acid encoding SEQ ID NO:38 or the complement thereof. Thus, disclosed herein are isolated nucleic acids that hybridize under stringent conditions to a nucleic acid consisting of the sequence set forth in SEQ ID NO:86 or the complement thereof but not to a nucleic acid consisting of the sequence set forth in SEQ ID NO:1 or the complement thereof.

In an further aspect, disclosed herein are isolated nucleic acids comprising a sequence that hybridizes under stringent conditions to a nucleic acid encoding the amino acid sequence SEQ ID NO:87 or the complement thereof but not to a nucleic acid encoding SEQ ID NO:38 or the complement thereof. Thus, disclosed herein are isolated nucleic acids that hybridizes under stringent conditions to a nucleic acid consisting of the sequence set forth in SEQ ID NO:87 or the complement thereof but not to a nucleic acid consisting of the sequence set forth in SEQ ID NO:1 or the complement thereof.

In an further aspect, disclosed herein are isolated nucleic acids comprising a sequence that hybridizes under stringent conditions to a nucleic acid encoding the amino acid sequence SEQ ID NO:88 or the complement thereof but not to a nucleic acid encoding SEQ ID NO:38 or the complement thereof. Thus, disclosed herein are isolated nucleic acids that hybridizes under stringent conditions to a nucleic acid consisting of the sequence set forth in SEQ ID NO:88 or the complement thereof but not to a nucleic acid consisting of the sequence set forth in SEQ ID NO:1 or the complement thereof.

In an further aspect, disclosed herein are isolated nucleic acids comprising a sequence that hybridizes under stringent conditions to a nucleic acid encoding the amino acid sequence SEQ ID NO:89 or the complement thereof but not to a nucleic acid encoding SEQ ID NO:38 or the complement thereof. Thus, disclosed herein are isolated nucleic acids that hybridizes under stringent conditions to a nucleic acid consisting of the sequence set forth in SEQ ID NO:89 or the complement thereof but not to a nucleic acid consisting of the sequence set forth in SEQ ID NO:1 or the complement thereof.

In an further aspect, disclosed herein are isolated nucleic acids comprising a sequence that hybridizes under stringent conditions to a nucleic acid encoding the amino acid sequence SEQ ID NO:90 or the complement thereof but not to a nucleic acid encoding SEQ ID NO:38 or the complement thereof. Thus, disclosed herein are isolated nucleic acids that hybridizes under stringent conditions to a nucleic acid consisting of the sequence set forth in SEQ ID NO:90 or the complement thereof but not to a nucleic acid consisting of the sequence set forth in SEQ ID NO:1 or the complement thereof.

In an further aspect, disclosed herein are isolated nucleic acids comprising a sequence that hybridizes under stringent conditions to a nucleic acid encoding the amino acid sequence SEQ ID NO:91 or the complement thereof but not to a nucleic acid encoding SEQ ID NO:38 or the complement thereof. Thus, disclosed herein are isolated nucleic acids that hybridizes under stringent conditions to a nucleic acid consisting of the sequence set forth in SEQ ID NO:91 or the complement thereof but not to a nucleic acid consisting of the sequence set forth in SEQ ID NO:1 or the complement thereof.

In an further aspect, disclosed herein are isolated nucleic acids comprising a sequence that hybridizes under stringent conditions to a nucleic acid encoding the amino acid sequence SEQ ID NO:92 or the complement thereof but not to a nucleic acid encoding SEQ ID NO:38 or the complement thereof. Thus, disclosed herein are isolated nucleic acids that hybridizes under stringent conditions to a nucleic acid consisting of the sequence set forth in SEQ ID NO:92 or the complement thereof but not to a nucleic acid consisting of the sequence set forth in SEQ ID NO:1 or the complement thereof.

In another aspect, disclosed herein are isolated nucleic acids comprising a sequence that hybridizes under stringent conditions to a mutated $Na_v1.7$ nucleic acid sequence or a fragment thereof but not to a wild-type $Na_v1.7$ nucleic acid sequence. For example, in one aspect, disclosed herein are isolated nucleic acids comprising a sequence that hybridizes under stringent conditions to a nucleic acid sequence of SEQ ID NO:8, or a fragment thereof, such as SEQ ID NO:14, but not to the nucleic acid sequence of SEQ ID NO:1. In another aspect, disclosed herein are isolated nucleic acids comprising a sequence that hybridizes under stringent conditions to a nucleic acid of SEQ ID NO:9, or a fragment thereof, such as SEQ ID NO:15, but not to the nucleic acid sequence of SEQ ID NO:1. In yet another aspect, disclosed herein are isolated nucleic acids comprising a sequence that hybridizes under stringent conditions to a nucleic acid sequence of SEQ ID NO:10, or a fragment thereof, such as SEQ ID NO:16, but not to the nucleic acid sequence of SEQ ID NO:1. In an further aspect, disclosed herein are isolated nucleic acids comprising a sequence that hybridizes under stringent conditions to a nucleic acid sequence of SEQ ID NO:11, or a fragment thereof, such as SEQ ID NO:17, but not to the nucleic acid sequence of SEQ ID NO:1. In a still further aspect, disclosed herein are isolated nucleic acids comprising a sequence that hybridizes under stringent conditions to a nucleic acid sequence of SEQ ID NO:12, or a fragment thereof, such as SEQ ID NO:18, but not to the nucleic acid sequence of SEQ ID NO:1. In one aspect, disclosed herein are isolated nucleic acids comprising a sequence that hybridizes under stringent conditions to a nucleic acid sequence of SEQ ID NO:13, or a fragment thereof, such as SEQ ID NO:19, but not to the nucleic acid sequence of SEQ ID NO:1. In one aspect, disclosed herein are isolated nucleic acids comprising a sequence that hybridizes under stringent conditions to a nucleic acid sequence of SEQ ID NO:86, or a fragment thereof, such as SEQ ID NO:93, but not to the nucleic acid sequence of SEQ ID NO:1. In one aspect, disclosed herein are isolated nucleic acids comprising a sequence that hybridizes under stringent conditions to a nucleic acid sequence of SEQ ID NO:87, or a fragment thereof, such as SEQ ID NO:94, but not to the nucleic acid sequence of SEQ ID NO:1. In one aspect, disclosed herein are isolated nucleic acids comprising a sequence that hybridizes under stringent conditions to a nucleic acid sequence of SEQ ID NO:88, or a fragment thereof, such as SEQ ID NO:95, but not to the nucleic acid sequence of SEQ ID NO:1. In one aspect, disclosed herein are isolated nucleic acids comprising a sequence that hybridizes under stringent conditions to a nucleic acid sequence of SEQ ID NO:89, or a fragment thereof, such as SEQ ID NO:96, but not to the nucleic acid sequence of SEQ ID NO:1. In one aspect, disclosed herein are isolated nucleic acids comprising a sequence that hybridizes under stringent conditions to a nucleic acid sequence of SEQ ID NO:90, or a fragment thereof, such as SEQ ID NO:97, but not to the nucleic acid sequence of SEQ ID NO:1. In one aspect, disclosed herein are isolated nucleic acids comprising a sequence that hybridizes under stringent conditions to a nucleic acid sequence of SEQ ID NO:91, or a fragment thereof, such as SEQ ID NO:98, but not to the nucleic acid sequence of SEQ ID NO:1. In one aspect, disclosed herein are isolated nucleic acids comprising a sequence that hybridizes under stringent conditions to a nucleic acid sequence of SEQ ID NO:92, or a fragment thereof, such as SEQ ID NO:99, but not to the nucleic acid sequence of SEQ ID NO:1.

In yet another aspect, disclosed herein are isolated nucleic acids that hybridizes under stringent conditions to a nucleic acid encoding a mutated $Na_v1.7$ but not to a nucleic acid sequence encoding wild-type $Na_v1.7$. For example, in one aspect, disclosed herein are isolated nucleic acids that hybridizes under stringent conditions to a nucleic acid encoding the amino acid sequence of SEQ ID NO:2 but not to a nucleic acid sequence consisting of SEQ ID NO:1. In another aspect, disclosed herein are isolated nucleic acids that hybridizes under stringent conditions to a nucleic acid encoding the amino acid sequence of SEQ ID NO:3 but not to a nucleic acid sequence consisting of SEQ ID NO:1. In yet another aspect, disclosed herein are isolated nucleic acids that hybridizes under stringent conditions to a nucleic acid encoding the amino acid sequence of SEQ ID NO:4 but not to a nucleic acid sequence consisting of SEQ ID NO:1. In an further aspect, disclosed herein are isolated nucleic acids that hybridize under stringent conditions to a nucleic acid encoding the amino acid sequence of SEQ ID NO:5 but not to a nucleic acid sequence consisting of SEQ ID NO:1. In a still further aspect, disclosed herein are isolated nucleic acids that hybridizes under stringent conditions to a nucleic acid encoding the amino acid sequence of SEQ ID NO:6 but not to a nucleic acid sequence consisting of SEQ ID NO:1. In one aspect, disclosed herein are isolated nucleic acids that hybridize under stringent conditions to a nucleic acid encoding the amino acid sequence of SEQ ID NO:7 but not to a nucleic acid sequence consisting of SEQ ID NO:1. In one aspect, disclosed herein are isolated nucleic acids that hybridizes under stringent conditions to a nucleic acid encoding the amino acid sequence of SEQ ID NO:86 but not to a nucleic acid sequence consisting of SEQ ID NO:1. In one aspect, disclosed herein are isolated nucleic acids that hybridize under stringent conditions to a nucleic acid encoding the amino acid sequence of SEQ ID NO:87 but not to a nucleic acid sequence consisting of SEQ ID NO:1. In one aspect, disclosed herein are isolated nucleic acids that hybridizes under stringent conditions to a nucleic acid encoding the amino acid sequence of SEQ ID NO:88 but not to a nucleic acid sequence consisting of SEQ ID NO:1. In one aspect, disclosed herein are isolated nucleic acids that hybridize under stringent conditions to a nucleic acid encoding the amino acid sequence of SEQ ID NO:89 but not to a nucleic acid sequence consisting of SEQ ID NO:1. In one aspect, disclosed herein are isolated nucleic acids that hybridizes under stringent conditions to a nucleic acid encoding the amino acid sequence of SEQ ID NO:90 but not to a nucleic acid sequence consisting of SEQ ID NO:1. In one aspect, disclosed herein are isolated nucleic acids that hybridize under stringent conditions to a nucleic acid encoding the amino acid sequence of SEQ ID NO:91 but not to a nucleic acid sequence consisting of SEQ ID NO:1. In one aspect, disclosed herein are isolated nucleic acids that hybridizes under stringent conditions to a nucleic acid encoding the amino acid sequence of SEQ ID NO:92 but not to a nucleic acid sequence consisting of SEQ ID NO:1.

5. Arrays

Also disclosed herein is an array of oligonucleotides for identification of mutations, where discrete positions on the array are complementary to one or more of the provided mutated sequences, e.g. oligonucleotides of at least 12 nucleotides, frequently 15 nucleotides, 20 nucleotides, or larger, and including the sequence flanking the mutated position. Such an array may comprise a series of oligonucleotides, each of which can specifically hybridize to a different mutation of the disclosed compositions. An array may comprise all or a subset of nucleic acid sequences having SEQ ID NOs:8, 9, 10, 11, 12, 13, 86, 87, 88, 89, 90, 91, and/or 92, or any fragment of at least 2, 3, 4, 5, 6, 7, 8, 9, 10, 11, 12, 13, 14, 15, 16, 17, 18, 19, 20, 25, 30, 35, 40, 45, 50, 60, 70, 80, 90, 100 contiguous nucleotides thereof, for example SEQ ID NOs:14, 15, 16, 17, 18, 19, 93, 94, 95, 96, 97, 98 and/or 99. Usually such an array will include at least 2 different mutated sequences, i.e., mutations located at unique positions within the locus, and may include all of the provided mutations. Therefore, the array can include wild-type sequences comprising the most commonly found alleles. The array can optionally comprise the most commonly found allele at a first, second, third, fourth, fifth, or more positions as well as other nucleotides at each of these positions. Each oligonucleotide sequence on the array can usually be at least about 2, 3, 4, 5, 6, 7, 8, 9, 10, 11, 12, 13, 14, 15, 16, 17, 18, 19, 20, 25, 30, 35, 40, 45, 50, 60, 70, 80, 90, 100 nucleotides in length, such as 10, 11, 12, 13, 14, 15 nucleotides in length, may be the length of the provided mutated sequences, or may extend into the flanking regions to generate fragments of about 100 to about 200 nucleotides in length. For examples of arrays, see Ramsay, (1998) Nat Biotech 16:4044; Hacia, et al. (1996) Nature Genetics 14:441-447; Lockhart, et al. (1996) Nature Biotechnol 14:1675-1680; and De Risi, et al. (1996) Nature Genetics 14:457-460, which are incorporated by reference in their entirety for the methods of making and using arrays.

An array is an orderly arrangement of samples, providing a medium for matching known and unknown DNA samples based on base-pairing rules and automating the process of identifying the unknowns. An array experiment can make use of common assay systems such as microplates or standard blotting membranes, and can be created by hand or make use of robotics to deposit the sample. In general, arrays are described as macroarrays or microarrays, the difference being the size of the sample spots.

Macroarrays contain sample spot sizes of about 300 microns or larger and can be easily imaged by existing gel and blot scanners. The sample spot sizes in microarray can be 300 microns or less, but typically less than 200 microns in diameter and these arrays usually contains thousands of spots. Microarrays require specialized robotics and/or imaging equipment that generally are not commercially available as a complete system. Terminologies that have been used in the literature to describe this technology include, but not limited to: biochip, DNA chip, DNA microarray, GeneChip® (Affymetrix, Inc which refers to its high density, oligonucleotide-based DNA arrays), and gene array.

A DNA microarray is a collection of microscopic DNA spots attached to a solid surface, such as glass, plastic or silicon chip forming an array for the purpose of expression profiling, monitoring expression levels for thousands of genes simultaneously. DNA microarrays, or DNA chips are fabricated by high-speed robotics, generally on glass or nylon substrates, for which probes with known identity are used to determine complementary binding, thus allowing massively parallel gene expression and gene discovery studies. An experiment with a single DNA chip can provide information on thousands of genes simultaneously. It is herein contemplated that the disclosed microarrays can be used to monitor gene expression, disease diagnosis, gene discovery, drug discovery (pharmacogenomics), and toxicological research or toxicogenomics.

The affixed DNA segments are generally known as probes, thousands of which can be placed in known locations on a single DNA microarray. Microarray technology evolved from Southern blotting, whereby fragmented DNA is attached to a substrate and then probed with a known gene or fragment. Measuring gene expression using microarrays is relevant to many areas of biology and medicine, such as studying treatments, disease, and developmental stages. For example, microarrays can be used to identify disease genes by comparing gene expression in diseased and normal cells.

There are two variants of the DNA microarray technology, in terms of the property of arrayed DNA sequence with known identity. Type I microarrays comprise a probe cDNA (500~5,000 bases long) that is immobilized to a solid surface such as glass using robot spotting and exposed to a set of targets either separately or in a mixture. This method is traditionally referred to as DNA microarray. With Type I microarrays, localized multiple copies of one or more polynucleotide sequences, preferably copies of a single polynucleotide sequence are immobilized on a plurality of defined regions of the substrate's surface. A polynucleotide refers to a chain of nucleotides ranging from 5 to 10,000 nucleotides. These immobilized copies of a polynucleotide sequence are suitable for use as probes in hybridization experiments.

Type II microarrays comprise an array of oligonucleotides (20-80-mer oligos) or peptide nucleic acid (PNA) probes that is synthesized either in situ (on-chip) or by conventional synthesis followed by on-chip immobilization. The array is exposed to labeled sample DNA, hybridized, and the identity/abundance of complementary sequences are determined. This method, "historically" called DNA chips, was developed at Affymetrix, Inc., which sells its photolithographically fabricated products under the GeneChip® trademark.

The basic concept behind the use of Type II arrays for gene expression is simple: labeled cDNA or cRNA targets derived from the mRNA of an experimental sample are hybridized to nucleic acid probes attached to the solid support. By monitoring the amount of label associated with each DNA location, it is possible to infer the abundance of each mRNA species represented. Although hybridization has been used for decades to detect and quantify nucleic acids, the combination of the miniaturization of the technology and the large and growing amounts of sequence information, have enormously expanded the scale at which gene expression can be studied.

In spotted microarrays (or two-channel or two-colour microarrays), the probes are oligonucleotides, cDNA or small fragments of PCR products corresponding to mRNAs. This type of array is typically hybridized with cDNA from two samples to be compared (e.g., patient and control) that are labeled with two different fluorophores. The samples can be mixed and hybridized to one single microarray that is then scanned, allowing the visualization of up-regulated and down-regulated genes in one go. The downside of this is that the absolute levels of gene expression cannot be observed, but only one chip is needed per experiment. One example of a provider for such microarrays is Eppendorf with their DualChip® platform.

In oligonucleotide microarrays (or single-channel microarrays), the probes are designed to match parts of the sequence of known or predicted mRNAs. There are commercially available designs that cover complete genomes from companies such as GE Healthcare, Affymetrix, Ocimum Biosolutions, or Agilent. These microarrays give estimations of gene expression and therefore the comparison of two conditions requires the use of two separate microarrays.

Long Oligonucleotide Arrays are composed of 60-mers, or 50-mers and are produced by ink-jet printing on a silica substrate. Short Oligonucleotide Arrays are composed of 25-mer or 30-mer and are produced by photolithographic synthesis (Affymetrix) on a silica substrate or piezoelectric deposition (GE Healthcare) on an acrylamide matrix. More recently, Maskless Array Synthesis from NimbleGen Systems has combined flexibility with large numbers of probes. Arrays can contain up to 390,000 spots, from a custom array design. New array formats are being developed to study specific pathways or disease states for a systems biology approach.

Oligonucleotide microarrays often contain control probes designed to hybridize with RNA spike-ins. The degree of hybridization between the spike-ins and the control probes is used to normalize the hybridization measurements for the target probes.

SNP microarrays are a particular type of DNA microarrays that are used to identify genetic variation in individuals and across populations. Short oligonucleotide arrays can be used to identify the single nucleotide polymorphisms (SNPs) that are thought to be responsible for genetic variation and the source of susceptibility to genetically caused diseases. Generally termed genotyping applications, DNA microarrays may be used in this fashion for forensic applications, rapidly discovering or measuring genetic predisposition to disease, or identifying DNA-based drug candidates.

These SNP microarrays are also being used to profile somatic mutations in cancer, specifically loss of heterozygosity events and amplifications and deletions of regions of DNA. Amplifications and deletions can also be detected using comparative genomic hybridization in conjunction with micro arrays.

Resequencing arrays have also been developed to sequence portions of the genome in individuals. These arrays may be used to evaluate germline mutations in individuals, or somatic mutations in cancers.

Genome tiling arrays include overlapping oligonucleotides designed to blanket an entire genomic region of interest. Many companies have successfully designed tiling arrays that cover whole human chromosomes.

Samples may be any sample containing polynucleotides (polynucleotide targets) of interest and obtained from any bodily fluid (blood, urine, saliva, phlegm, gastric juices, etc.), cultured cells, biopsies, or other tissue preparations. DNA or RNA can be isolated from the sample according to any of a number of methods well known to those of skill in the art. For example, methods of purification of nucleic acids are described in Laboratory Techniques in Biochemistry and Molecular Biology: Hybridization With Nucleic Acid Probes. Part I. Theory and Nucleic Acid Preparation, P. Tijssen, ed. Elsevier (1993). In one embodiment, total RNA is isolated using the TRIzol total RNA isolation reagent (Life Technologies, Inc., Rockville, Md.) and RNA is isolated using oligo d(T) column chromatography or glass beads. After hybridization and processing, the hybridization signals obtained should reflect accurately the amounts of control target polynucleotide added to the sample.

Some of the key elements of selection and design are common to the production of all microarrays, regardless of their intended application. Strategies to optimize probe hybridization, for example, are invariably included in the process of probe selection. Hybridization under particular pH, salt, and temperature conditions can be optimized by taking into account melting temperatures and using empirical rules that correlate with desired hybridization behaviors.

To obtain a complete picture of a gene's activity, some probes are selected from regions shared by multiple splice or polyadenylation variants. In other cases, unique probes that distinguish between variants are favored. Inter-probe distance is also factored into the selection process.

A different set of strategies is used to select probes for genotyping arrays that rely on multiple probes to interrogate individual nucleotides in a sequence. The identity of a target base can be deduced using four identical probes that vary only in the target position, each containing one of the four possible bases.

Alternatively, the presence of a consensus sequence can be tested using one or two probes representing specific alleles. To genotype heterozygous or genetically mixed samples, arrays with many probes can be created to provide redundant information, resulting in unequivocal genotyping. In addition, generic probes can be used in some applications to maximize flexibility. Some probe arrays, for example, allow the separation and analysis of individual reaction products from complex mixtures, such as those used in some protocols to identify single nucleotide polymorphisms (SNPs).

The plurality of defined regions on the substrate can be arranged in a variety of formats. For example, the regions may be arranged perpendicular or in parallel to the length of the casing. Furthermore, the targets do not have to be directly bound to the substrate, but rather can be bound to the substrate through a linker group. The linker groups may typically vary from about 6 to 50 atoms long. Preferred linker groups include ethylene glycol oligomers, diamines, diacids and the like. Reactive groups on the substrate surface react with one of the terminal portions of the linker to bind the linker to the substrate. The other terminal portion of the linker is then functionalized for binding the probes.

Sample polynucleotides may be labeled with one or more labeling moieties to allow for detection of hybridized probe/target polynucleotide complexes. The labeling moieties can include compositions that can be detected by spectroscopic, photochemical, biochemical, bioelectronic, immunochemical, electrical, optical or chemical means. The labeling moieties include radioisotopes, such as $^{32}$P, $^{33}$P or $^{35}$S, chemiluminescent compounds, labeled binding proteins, heavy metal atoms, spectroscopic markers, such as fluorescent markers and dyes, magnetic labels, linked enzymes, mass spectrometry tags, spin labels, electron transfer donors and acceptors, biotin, and the like.

Labeling can be carried out during an amplification reaction, such as polymerase chain reaction and in vitro or in vivo transcription reactions. Alternatively, the labeling moiety can be incorporated after hybridization once a probe-target complex his formed. In one preferred embodiment, biotin is first incorporated during an amplification step as described above. After the hybridization reaction, unbound nucleic acids are rinsed away so that the only biotin remaining bound to the substrate is that attached to target polynucleotides that are hybridized to the polynucleotide probes. Then, an avidin-conjugated fluorophore, such as avidin-phycoerythrin, that binds with high affinity to biotin is added.

Hybridization causes a polynucleotide probe and a complementary target to form a stable duplex through base pairing. Hybridization methods are well known to those skilled in the art Stringent conditions for hybridization can be defined by salt concentration, temperature, and other chemicals and conditions. Varying additional parameters, such as hybridization time, the concentration of detergent (sodium dodecyl sulfate, SDS) or solvent (formamide), and the inclusion or exclusion of carrier DNA, are well known to those skilled in the art. Additional variations on these conditions will be readily apparent to those skilled in the art (Wahl, G. M. and S. L. Berger (1987) Methods Enzymol. 152:399-407; Kimmel, A. R. (1987) Methods Enzymol. 152:507-511; Ausubel, F. M. et al. (1997) Short Protocols in Molecular Biology, John Wiley & Sons, New York, N.Y.; and Sambrook, J. et al. (1989) Molecular Cloning, A Laboratory Manual, Cold Spring Harbor Press, Plainview, N.Y.).

Methods for detecting complex formation are well known to those skilled in the art. In a preferred embodiment, the polynucleotide probes are labeled with a fluorescent label and measurement of levels and patterns of complex formation is accomplished by fluorescence microscopy, preferably confocal fluorescence microscopy. An argon ion laser excites the fluorescent label, emissions are directed to a photomultiplier and the amount of emitted light detected and quantitated. The detected signal should be proportional to the amount of probe/target polynucleotide complex at each position of the microarray. The fluorescence microscope can be associated with a computer-driven scanner device to generate a quantitative two-dimensional image of hybridization intensities. The scanned image is examined to determine the abundance/expression level of each hybridized target polynucleotide.

In a differential hybridization experiment, polynucleotide targets from two or more different biological samples are labeled with two or more different fluorescent labels with different emission wavelengths. Fluorescent signals are detected separately with different photomultipliers set to detect specific wavelengths. The relative abundances/expression levels of the target polynucleotides in two or more samples is obtained. Typically, microarray fluorescence intensities can be normalized to take into account variations in hybridization intensities when more than one microarray is used under similar test conditions. In one embodiment, individual polynucleotide probe/target complex hybridization intensities are normalized using the intensities derived from internal normalization controls contained on each microarray.

Microarray manufacturing can begin with a 5-inch square quartz wafer. Initially the quartz is washed to ensure uniform hydroxylation across its surface. Because quartz is naturally hydroxylated, it provides an excellent substrate for the attachment of chemicals, such as linker molecules, that are later used to position the probes on the arrays.

The wafer is placed in a bath of silane, which reacts with the hydroxyl groups of the quartz, and forms a matrix of covalently linked molecules. The distance between these silane molecules determines the probes' packing density, allowing arrays to hold over 500,000 probe locations, or features, within a mere 1.28 square centimeters. Each of these features harbors millions of identical DNA molecules. The silane film provides a uniform hydroxyl density to initiate probe assembly. Linker molecules, attached to the silane matrix, provide a surface that may be spatially activated by light.

Probe synthesis occurs in parallel, resulting in the addition of an A, C, T, or G nucleotide to multiple growing chains simultaneously. To define which oligonucleotide chains will receive a nucleotide in each step, photolithographic masks, carrying 18 to 20 square micron windows that correspond to the dimensions of individual features, are placed over the coated wafer. The windows are distributed over the mask based on the desired sequence of each probe. When ultraviolet light is shone over the mask in the first step of synthesis, the exposed linkers become deprotected and are available for nucleotide coupling.

Once the desired features have been activated, a solution containing a single type of deoxynucleotide with a removable protection group is flushed over the wafer's surface. The nucleotide attaches to the activated linkers, initiating the synthesis process.

Although each position in the sequence of an oligonucleotide can be occupied by 1 of 4 nucleotides, resulting in an apparent need for 25×4, or 100, different masks per wafer, the synthesis process can be designed to significantly reduce this requirement. Algorithms that help minimize mask usage calculate how to best coordinate probe growth by adjusting synthesis rates of individual probes and identifying situations when the same mask can be used multiple times.

Microarrays can be fabricated using a variety of technologies, including printing with fine-pointed pins onto glass slides, photolithography using pre-made masks, photolithography using dynamic micromirror devices, ink-jet printing (Lausted C, et al. Genome Biol. 2004; 5(8):R58), or electrochemistry on microelectrode arrays.

To create arrays, single-stranded polynucleotide probes can be spotted onto a substrate in a two-dimensional matrix or array. Each single-stranded polynucleotide probe can comprise at least 6, 7, 8, 9, 10, 11, 12, 13, 14, 15, 16, 17, 18, 19, 20, 25, or 30 or more contiguous nucleotides.

The substrate can be any substrate to which polynucleotide probes can be attached, including but not limited to glass, nitrocellulose, silicon, and nylon. Polynucleotide probes can be bound to the substrate by either covalent bonds or by non-specific interactions, such as hydrophobic interactions. Techniques for constructing arrays and methods of using these arrays are described in EP No. 0 799 897; PCT No. WO 97/29212; PCT No. WO 97/27317; EP No. 0 785 280; PCT No. WO 97/02357; U.S. Pat. Nos. 5,593,839; 5,578,832; EP No. 0 728 520; U.S. Pat. No. 5,599,695; EP No. 0 721 016; U.S. Pat. No. 5,556,752; PCT No. WO 95/22058; and U.S. Pat. No. 5,631,734, which are hereby incorporated by reference for the teaching of making and using polynucleotide arrays. Commercially available polynucleotide arrays, such as Affymetrix GeneChip™, can also be used. Use of the GeneChip™ to detect gene expression is described, for example, in Lockhart et al., Nature Biotechnology 14:1675 (1996); Chee et al., Science 274:610 (1996); Hacia et al., Nature Genetics 14:441, 1996; and Kozal et al., Nature Medicine 2:753, 1996.

Typical dispensers include a micropipette delivering solution to the substrate with a robotic system to control the position of the micropipette with respect to the substrate. There can be a multiplicity of dispensers so that reagents can be delivered to the reaction regions simultaneously. For example, a microarray can be formed by using ink-jet technology based on the piezoelectric effect, whereby a narrow tube containing a liquid of interest, such as oligonucleotide synthesis reagents, is encircled by an adapter. An electric charge sent across the adapter causes the adapter to expand at a different rate than the tube and forces a small drop of liquid onto a substrate (Baldeschweiler et al. PCT publication WO95/251116).

6. Delivery of the Na$_v$1.7 Nucleic Acid Sequence

Optionally, the nucleic acids described herein are delivered to various expression systems. There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, et al. (1990) Science 247:1465-1468; and Wolff, (1991) Nature 352:815-818. Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

In one aspect, disclosed herein are expression vectors comprising a nucleic acid comprising a nucleotide sequence encoding an amino acid sequence of mutated Na$_v$1.7 sodium channel alpha-subunit wherein the nucleotide sequence is operably linked to an expression control sequence. For example, in one aspect, disclosed herein are expression vectors comprising a nucleic acid comprising a nucleotide sequence encoding the amino acid sequence of SEQ ID NO:2 operably linked to an expression control sequence. In another aspect, disclosed herein are expression vectors comprising a nucleic acid comprising a nucleotide sequence encoding the amino acid sequence of SEQ ID NO:3 operably linked to an expression control sequence. In yet another aspect, disclosed herein are expression vectors comprising a nucleic acid comprising a nucleotide sequence encoding the amino acid sequence of SEQ ID NO:4 operably linked to an expression control sequence. In a further aspect, disclosed herein are expression vectors comprising a nucleic acid comprising a nucleotide sequence encoding the amino acid sequence of SEQ ID NO:5 operably linked to an expression control sequence. In a still further aspect, disclosed herein are expression vectors comprising a nucleic acid comprising a nucleotide sequence encoding the amino acid sequence of SEQ ID NO:6 operably linked to an expression control sequence. In one aspect, disclosed herein are expression vectors comprising a nucleic acid comprising a nucleotide sequence encoding the amino acid sequence of SEQ ID NO:7 operably linked to an expression control sequence. In one aspect, disclosed herein are expression vectors comprising a nucleic acid comprising a nucleotide sequence encoding the amino acid sequence of SEQ ID NO:79 operably linked to an expression control sequence. In one aspect, disclosed herein are expression vectors comprising a nucleic acid comprising a nucleotide sequence encoding the amino acid sequence of SEQ ID NO:80 operably linked to an expression control sequence. In one aspect, disclosed herein are expression vectors comprising a nucleic acid comprising a nucleotide sequence encoding the amino acid sequence of SEQ ID NO:81 operably linked to an expression control sequence. In one aspect, disclosed herein are expression vectors comprising a nucleic acid comprising a nucleotide sequence encoding the amino acid sequence of SEQ ID NO:82 operably linked to an expression control sequence. In one aspect, disclosed herein are expression vectors comprising a nucleic acid comprising a nucleotide sequence encoding the amino acid sequence of SEQ ID NO:83 operably linked to an expression control sequence. In one aspect, disclosed herein are expression vectors comprising a nucleic acid comprising a nucleotide sequence encoding the amino acid sequence of SEQ ID NO:84 operably linked to an expression control sequence. In one aspect, disclosed herein are expression vectors comprising a nucleic acid comprising a nucleotide sequence encoding the amino acid sequence of SEQ ID NO:85 operably linked to an expression control sequence.

Further provided are expression vectors comprising any fragment of the nucleic acid encoding SEQ ID NOs:2-7, 79-85. Such fragments preferably encode at least 2, 3, 4, 5, 6, 7, 8, 9, 10, 11, 12, 13, 14, 15, 16, 17, 18, 19, 20, 25, 30 contiguous amino acid sequences of SEQ ID NOs:2-7, 79-85. Also provided are expression vectors comprising any fragment of the nucleic acid comprising at least 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120 contiguous nucleic acids set forth in SEQ ID NOs:8, 9, 10, 11, 12, 13, 86, 87, 88, 89, 90, 91, and/or 92.

Expression or transfer vectors can be any nucleotide construction used to deliver genes into cells (e.g., a plasmid), or as part of a general strategy to deliver genes, e.g., as part of recombinant retrovirus or adenovirus (Ram, et al. (1993) Cancer Res 53:83-88).

As used herein, plasmid or viral vectors are agents that transport the disclosed nucleic acids, such as SEQ ID NOs:8, 9, 10, 11, 12, 13, 86, 87, 88, 89, 90, 91, and/or 92 into the cell without degradation and include a promoter yielding expression of the gene in the cells into which it is delivered. Viral vectors are, for example, Adenovirus, Adeno-associated virus, Herpes virus, Vaccinia virus, Polio virus, AIDS virus, neuronal trophic virus, Sindbis and other RNA viruses, including those viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. In some aspects, the viral vector has been engineered so as to suppress the immune response of the host organism, elicited by the viral antigens.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

A retrovirus is an animal virus belonging to the virus family of Retroviridae, including any types, subfamilies, genus, or tropisms. Retroviral vectors, in general, are described by Verma, Retroviral vectors for gene transfer. In Microbiology-1985, American Society for Microbiology, pp. 229-232, Washington, (1985), which is incorporated by reference herein in its entirety for retroviral vectors and methods of making them. Examples of methods for using retroviral vectors for gene therapy are described in U.S. Pat. Nos. 4,868,116 and 4,980,286; PCT applications WO 90/02806 and WO 89/07136; and Mulligan, (Science 260: 926-932 (1993)); the teachings of which are incorporated by reference herein in its entirety for retroviral vectors and methods of using them.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

The construction of replication-defective adenoviruses has been described (Berkner, et al. (1987) J Virology 61:1213-1220; Massie, et al. (1986) Mol Cell Biol 6:2872-2883; Haj-Ahmad, et al. (1986) J Virology 57:267-274; Davidson, et al. (1987) J Virology 61:1226-1239; Zhang, (1993) BioTechniques 15:868-872). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, (1993) J Clin Invest 92:1580-1586; Kirshenbaum, (1993) J Clin Invest 92:381-387; Roessler, (1993) J Clin Invest 92:1085-1092; Moullier, (1993) Nature Genetics 4:154-159; La Salle, (1993) Science 259:988-990; Gomez-Foix, (1992) J Biol Chem 267:25129-25134; Rich, (1993) Human Gene Therapy 4:461-476; Zabner, (1994) Nature Genetics 6:75-83; Guzman, (1993) Circulation Res 73:1201-1207; Bout, (1994) Human Gene Therapy 5:3-10; Zabner, (1993) Cell 75:207-216; Caillaud, (1993) Eur. J. Neuroscience 5:1287-1291; Ragot, (1993) J Gen Virology 74:501-507). Recombinant adenoviruses achieve gene transduction by binding to specific cell surface receptors, after which the virus is internalized by receptor-mediated endocytosis, in the same manner as wild type or replication-defective adenovirus (Chardonnet, et al. (1970) Virology 40:462-477; Brown, et al. (1973) J Virology 12:386-396; Svensson, et al. (1985) J Virology 55:442-449; Seth, et al. (1985) J Virol 51:650-655; Seth, et al. (1984) Mol Cell Biol 4:1528-1533; Varga, et al. (1991) J Virology 65:6061-6070; Wickham, et al. (1993) Cell 73:309-319).

A viral vector can be one based on an adenovirus which has had the E1 gene removed and these virons are generated in a cell line such as the human 293 cell line. In another aspect, both the E1 and E3 genes are removed from the adenovirus genome.

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is incorporated by reference herein in its entirety for material related to the AAV vector.

The disclosed vectors described throughout thus provide nucleic acids which are capable of integration into a mammalian chromosome without substantial toxicity. The vectors can also provide nucleic acids that can be expressed in oocytes (including, e.g., Xenopus oocytes).

The inserted genes in viral and retroviral usually contain promoters, and/or enhancers to help control the expression of the desired gene product. A promoter is generally a sequence or sequences of nucleic acids that function when in a relatively fixed location in regard to the transcription start site. A promoter contains core elements required for basic interaction of RNA polymerase and transcription factors, and may contain upstream elements and response elements.

Molecular genetic experiments with large human herpesviruses have provided a means whereby large heterologous DNA fragments can be cloned, propagated and established in cells permissive for infection with herpesviruses (Sun, et al. (1994) Nature Genetics 8:33-41; Cotter, et al. (1999) Curr Opin Mol Ther 5:633-644). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable. The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

The disclosed compositions can also be delivered to the target cells in a variety of ways other than through nucleic acid based methods. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed mutant $Na_v1.7$ nucleic acid sequences or vectors, for example, lipids such as liposomes, such as cationic liposomes (e.g., DOTMA, DOPE, DC cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham, et al. (1989) Am J Resp Cell Mol Biol 1:95-100; Felgner, et al. (1987) Proc Natl Acad Sci USA 84:7413-7417; U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution or suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al. (1991) Bioconjugate Chem. 2:447-451; Bagshawe, et al. (1998) Br J Cancer 60:275-281; Bagshawe, et al. (1988) Br J Cancer 58:700-703; Senter, et al. (1993) Bioconjugate Chem 4:3-9; Battelli, et al. (1992) Cancer Immunol Immunother 35:421-425; Pietersz, et al. (1992) Immunolog Rev 129:57-80; Roffler, et al. (1991) Biochem Pharmacol 42:2062-2065). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes, et al. (1989) Cancer Res 49:6214-6220; Litzinger, et al. (1992) Biochimica et Biophysica Acta 1104:179-187). In general, receptors are involved in pathways of endocytosis, either constitutive or ligand induced. These receptors cluster in clathrin coated pits, enter the cell via clathrin coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor level regulation. Many receptors follow more than one intracellular pathway, depending on the cell type, receptor concentration, type of ligand, ligand valency, and ligand concentration. Molecular and cellular mechanisms of receptor mediated endocytosis has been reviewed (see Brown, et al. (1991) DNA and Cell Biology 10:399-409).

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

7. Expression

The nucleic acids that are delivered to cells typically contain expression controlling systems. For example, the inserted genes in viral and retroviral systems usually contain expression control sequences, i.e., promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Preferred promoters controlling transcription from vectors in mammalian host cells may be obtained from various sources, for example, the genomes of viruses such as: polyoma, Simian Virus 40 (SV40), adenovirus, retroviruses, hepatitis B virus and most preferably cytomegalovirus, or from heterologous mammalian promoters, e.g., beta-actin promoter. The early and late promoters of the SV40 virus are conveniently obtained as an SV40 restriction fragment which also contains the SV40 viral origin of replication (Fiers, et al. (1978) Nature 273: 113). The immediate early promoter of the human cytomegalovirus is conveniently obtained as a HindIII E restriction fragment (see Greenway, et al. (1982) Gene 18:355-360). Of course, promoters from the host cell or related species also are useful herein.

Enhancer generally refers to a sequence of DNA that functions at no fixed distance from the transcription start site and can be either 5' (Laimins, et al. (1981) Proc Natl Acad Sci USA 78:993) or 3' (Lusky, et al. (1983) Mol Cell Bio 3:1108) to the transcription unit. Furthermore, enhancers can be within an intron (Banerji, et al. (1983) Cell 33:729) as well as within the coding sequence itself (Osborne, et al. (1984) Mol Cell Bio 4:1293). They are usually between 10 and 300 by in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (e.g., globin, elastase, albumin, fetoprotein, and insulin), typically, one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments, the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full-length promoter), and retroviral vector LTF.

It has been shown that all specific regulatory elements can be cloned and used to construct expression vectors that are selectively expressed in specific cell types such as melanoma cells. For example, the glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3'-untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

The viral vectors can include nucleic acid sequence encoding a marker product. This marker product is used to determine if the gene has been delivered to the cell and once delivered is being expressed. Preferred marker genes are the E. Coli lacZ gene, which encodes beta-galactosidase, and green fluorescent protein (GFP).

Marker product, as used herein, is synonymous with "reporter protein." As used herein, a "reporter protein" is any protein that can be specifically detected when expressed. Reporter proteins are useful for detecting or quantifying expression from expression sequences. Many reporter proteins are known to one of skill in the art. These include, but are not limited to, beta-galactosidase, luciferase, and alkaline phosphatase that produce specific detectable products. Fluorescent reporter proteins can also be used, such as green fluorescent protein (GFP), green reef coral fluorescent protein (G-RCFP), cyan fluorescent protein (CFP), red fluorescent protein (RFP) and yellow fluorescent protein (YFP).

In some embodiments the marker or reporter protein may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR cells and mouse LTK cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern, et al. (1982) J Molec Appl Genet. 1:327), mycophenolic acid, (Mulligan, et al. (1980) Science 209:1422) or hygromycin, (Sugden, et al. (1985) Mol Cell Biol 5:410-413). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

8. Cultured Cells

Also disclosed herein is a method of making a mutant Nav1.7 sodium channel alpha subunit comprising culturing the cells comprising vectors comprising mutant $Na_v1.7$ nucleic acids under conditions allowing expression of the polypeptide encoded by the nucleic acid, wherein the polypeptide comprises a mutant $Na_v1.7$ sodium channel. Thus, disclosed herein is a cell comprising any peptide, nucleic acid, or expression vector disclosed herein.

The term "cell" as used herein also refers to individual cells, cell lines, primary culture, or cultures derived from such cells unless specifically indicated. A "culture" refers to a composition comprising isolated cells of the same or a different type. A cell line is a culture of a particular type of cell that can be reproduced indefinitely, thus making the cell line "immortal." A cell culture can be a population of cells grown on a medium such as agar. A primary cell culture is a culture from a cell or taken directly from a living organism, which is not immortalized.

The cell can by any cell type, including but not limited to Keratinizing Epithelial Cells, Epidermal keratinocyte (differentiating epidermal cell), Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell (stem cell), Wet Stratified Barrier Epithelial Cells, Surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, Urinary epithelium cell (lining bladder and urinary ducts), Exocrine Secretory Epithelial Cells, Salivary gland mucous cell (polysaccharide-rich secretion), Salivary gland serous cell (glycoprotein enzyme-rich secretion), Von Ebner's gland cell in tongue (washes taste buds), Mammary gland cell (milk secretion), Lacrimal gland cell (tear secretion), Ceruminous gland cell in ear (wax secretion), Eccrine sweat gland dark cell (glycoprotein secretion), Eccrine sweat gland clear cell (small molecule secretion), Apocrine sweat gland cell (odoriferous secretion, sex-hormone sensitive), Gland of Moll cell in eyelid (specialized sweat gland), Sebaceous gland cell (lipid-rich sebum secretion), Bowman's gland cell in nose (washes olfactory epithelium), Brunner's gland cell in duodenum (enzymes and alkaline mucus), Seminal vesicle cell (secretes seminal fluid components, including fructose for swimming sperm), Prostate gland cell (secretes seminal fluid components), Bulbourethral gland cell (mucus secretion), Bartholin's gland cell (vaginal lubricant secretion), Gland of Littre cell (mucus secretion), Uterus endometrium cell (carbohydrate secretion), Isolated goblet cell of respiratory and digestive tracts (mucus secretion), Stomach lining mucous cell (mucus secretion), Gastric gland zymogenic cell (pepsinogen secretion), Gastric gland oxyntic cell (HCl secretion), Pancreatic acinar cell (bicarbonate and digestive enzyme secretion), Paneth cell of small intestine (lysozyme secretion), Type II pneumocyte of lung (surfactant secretion), Clara cell of lung, Hormone Secreting Cells, Anterior pituitary cell secreting growth hormone, Anterior pituitary cell secreting follicle-stimulating hormone, Anterior pituitary cell secreting luteinizing hormone, Anterior pituitary cell secreting prolactin, Anterior pituitary cell secreting adrenocorticotropic hormone, Anterior pituitary cell secreting thyroid-stimulating hormone, Intermediate pituitary cell secreting melanocyte-stimulating hormone, Posterior pituitary cell secreting oxytocin, Posterior pituitary cell secreting vasopressin, Gut and respiratory tract cell secreting serotonin, Gut and respiratory tract cell secreting endorphin, Gut and respiratory tract cell secreting somatostatin, Gut and respiratory tract cell secreting gastrin, Gut and respiratory tract cell secreting secretin, Gut and respiratory tract cell secreting cholecystokinin, Gut and respiratory tract cell secreting insulin, Gut and respiratory tract cell secreting glucagon, Gut and respiratory tract cell secreting bombesin, Thyroid gland cell secreting thyroid hormone, Thyroid gland cell secreting calcitonin, Parathyroid gland cell secreting parathyroid hormone, Parathyroid gland oxyphil cell, Adrenal gland cell secreting epinephrine, Adrenal gland cell secreting norepinephrine, Adrenal gland cell secreting steroid hormones (mineralcorticoids and gluco corticoids), Leydig cell of testes secreting testosterone, Theca interna cell of ovarian follicle secreting estrogen, Corpus luteum cell of ruptured ovarian follicle secreting progesterone, Kidney juxtaglomerular apparatus cell (renin secretion), Macula densa cell of kidney, Peripolar cell of kidney, Mesangial cell of kidney, Epithelial Absorptive Cells (Gut, Exocrine Glands and Urogenital Tract), Intestinal brush border cell (with microvilli), Exocrine gland striated duct cell, Gall bladder epithelial cell, Kidney proximal tubule brush border cell, Kidney distal tubule cell, Ductulus efferens nonciliated cell, Epididymal principal cell, Epididymal basal cell, Metabolism and Storage Cells, Hepatocyte (liver cell), White fat cell, Brown fat cell, Liver lipocyte, Barrier Function Cells (Lung, Gut, Exocrine Glands and Urogenital Tract), Type I pneumocyte (lining air space of lung), Pancreatic duct cell (centroacinar cell), Nonstriated duct cell (of sweat gland, salivary gland, mammary gland, etc.), Kidney glomerulus parietal cell, Kidney glomerulus podocyte, Loop of Henle thin segment cell (in kidney), Kidney collecting duct cell, Duct cell (of seminal vesicle, prostate gland, etc.), Epithelial Cells Lining Closed Internal Body Cavities, Blood vessel and lymphatic vascular endothelial fenestrated cell, Blood vessel and lymphatic vascular endothelial continuous cell, Blood vessel and lymphatic vascular endothelial splenic cell, Synovial cell (lining joint cavities, hyaluronic acid secretion), Serosal cell (lining peritoneal, pleural, and pericardial cavities), Squamous cell (lining perilymphatic space of ear), Squamous cell (lining endolymphatic space of ear), Columnar cell of endolymphatic sac with microvilli (lining endolymphatic space of ear), Columnar cell of endolymphatic sac without microvilli (lining endolymphatic space of ear), Dark cell (lining endolymphatic space of ear), Vestibular membrane cell (lining endolymphatic space of ear), Stria vascularis basal cell (lining endolymphatic space of ear), Stria vascularis marginal cell (lining endolymphatic space of ear), Cell of Claudius (lining endolymphatic space of ear), Cell of Boettcher (lining endolymphatic space of ear), Choroid plexus cell (cerebrospinal fluid secretion), Pia-arachnoid squamous cell, Pigmented ciliary epithelium cell of eye, Nonpigmented ciliary epithelium cell of eye, Corneal endothelial cell, Ciliated Cells with Propulsive Function, Respiratory tract ciliated cell, Oviduct ciliated cell (in female), Uterine endometrial ciliated cell (in female), Rete testis cilated cell (in male), Ductulus efferens ciliated cell (in male), Ciliated ependymal cell of central nervous system (lining brain cavities), Extracellular Matrix Secretion Cells, Ameloblast epithelial cell (tooth enamel secretion), Planum semilunatum epithelial cell of vestibular apparatus of ear (proteoglycan secretion), Organ of Corti interdental epithelial cell (secreting tectorial membrane covering hair cells), Loose connective tissue fibroblasts, Corneal fibroblasts, Tendon fibroblasts, Bone marrow reticular tissue fibroblasts, Other (nonepithelial) fibroblasts, Blood capillary pericyte, Nucleus pulposus cell of intervertebral disc, Cementoblast/cementocyte (tooth root bonelike cementum secretion), Odontoblast/odontocyte (tooth dentin secretion), Hyaline cartilage chondrocyte, Fibrocartilage chondrocyte, Elastic cartilage chondrocyte, Osteoblast/osteocyte, Osteoprogenitor cell (stem cell of osteoblasts), Hyalocyte of vitreous body of eye, Stellate cell of perilymphatic space of ear, Contractile Cells, Red skeletal muscle cell (slow), White skeletal muscle cell (fast), Intermediate skeletal muscle cell, Muscle spindle—nuclear bag cell, Muscle spindle—nuclear chain cell, Satellite cell (stem cell), Ordinary heart muscle cell, Nodal heart muscle cell, Purkinje fiber cell, Smooth muscle cell (various types), Myoepithelial cell of iris, Myoepithelial cell of exocrine glands, Blood and Immune System Cells, Erythrocyte (red blood cell), Megakaryocyte, Monocyte, Connective tissue macrophage (various types), Epidermal Langerhans cell, Osteoclast (in bone), Dendritic cell (in lymphoid tissues), Microglial cell (in central nervous system), Neutrophil, Eosinophil, Basophil, Mast cell, Helper T lymphocyte cell, Suppressor T lymphocyte cell, Killer T lymphocyte cell, IgM B lymphocyte cell, IgG B lymphocyte cell, IgA B lymphocyte cell, IgE B lymphocyte cell, Killer cell, Stem cells and committed progenitors for the blood and immune system (various types), Sensory Transducer Cells, Photoreceptor rod cell of eye, Photoreceptor blue-sensitive cone cell of eye, Photoreceptor green-sensitive cone cell of eye, Photoreceptor red-sensitive cone cell of eye, Auditory inner hair cell of organ of Corti, Auditory outer hair cell of organ of Corti, Type I hair cell of vestibular apparatus of ear (acceleration and gravity), Type II hair cell of vestibular apparatus of ear (acceleration and gravity), Type I taste bud cell, Olfactory neuron, Basal cell of olfactory epithelium (stem cell for olfactory neurons), Type I carotid body cell (blood pH sensor), Type II carotid body cell (blood pH sensor), Merkel cell of epidermis (touch sensor), Touch-sensitive primary sensory neurons (various types), Cold-sensitive primary sensory neurons, Heat-sensitive primary sensory neurons, Pain-sensitive primary sensory neurons (various types), Proprioceptive primary sensory neurons (various types), Autonomic Neuron Cells, Cholinergic neural cell (various types), Adrenergic neural cell (various types), Peptidergic neural cell (various types), Sense Organ and Peripheral Neuron Supporting Cells, Inner pillar cell of organ of Corti, Outer pillar cell of organ of Corti, Inner phalangeal cell of organ of Corti, Outer phalangeal cell of organ of Corti, Border cell of organ of Corti, Hensen cell of organ of Corti, Vestibular apparatus supporting cell, Type I taste bud supporting cell, Olfactory epithelium supporting cell, Schwann cell, Satellite cell (encapsulating peripheral nerve cell bodies), Enteric glial cell, Central Nervous System Neurons and Glial Cells, Neuron cell (large variety of types, still poorly classified), Astrocyte glial cell (various types), Oligodendrocyte glial cell, Lens Cells, Anterior lens epithelial cell, Crystallin-containing lens fiber cell, Pigment Cells, Melanocyte, Retinal pigmented epithelial cell, Germ Cells, Oogonium/oocyte, Spermatocyte, Spermatogonium cell (stem cell for spermatocyte), Nurse Cells, Ovarian follicle cell, Sertoli cell (in testis), and Thymus epithelial cell.

9. Transgenic Animals

In one aspect, disclosed herein are transgenic non-human animals that express one or more of the mutant $Na_v1.7$ sodium channels described herein. For example, disclosed herein is a transgenic mouse comprising cells that encode a mutant $Na_v1.7$ sodium channel alpha-subunit, wherein the mouse exhibits increased seizure activity as compared to the wild-type animal.

Thus, provided herein are non-human transgenic animals wherein nucleated cells of the animal comprise a nucleic acid encoding a mutant $Na_v1.7$ sodium channel alpha subunit protein operably linked to an expression control sequence, wherein the non-human mammal exhibits one or more symptoms of neurological disease, such as seizure, such as febrile seizure or severe myoclonic epilepsy of infancy. In some aspects, the expression control sequence is not a naturally occurring promoter and is therefore not operably linked to a nucleic acid encoding $Na_v1.7$ in nature. In some aspects, the expression control sequence is a constitutive promoter. In some aspects, the expression control sequence is an inducible promoter.

"Transgenic animal" is used herein to mean an animal comprising a transgene. By a "transgene" is meant a nucleic acid sequence that is inserted by artifice into a cell and becomes a part of the genome of that cell and its progeny. Such a transgene may be (but is not necessarily) partly or entirely heterologous (for example, derived from a different species) to the cell. A transgenic animal can be any non-human animal, such as a mouse, rat, guinea pig, sheep, pig, goat, and the like. Transgenic animals are made by techniques that are well known in the art. For example, a transgenic animal can be prepared by the method used in U.S. Pat. No. 4,736,866

The term "transgene" broadly refers to any nucleic acid that is introduced into an animal's genome, including but not limited to genes or DNA having sequences which are perhaps not normally present in the genome, genes which are present, but not normally transcribed and translated ("expressed") in a given genome, or any other gene or DNA which one desires to introduce into the genome. This may include genes which may normally be present in the non-transgenic genome but which one desires to have altered in expression, or which one desires to introduce in an altered or variant form or in a different chromosomal location. A transgene can include one or more transcriptional regulatory sequences and any other nucleic acid, such as introns, that may be useful or necessary for optimal expression of a selected nucleic acid. A transgene can be as few as a couple of nucleotides long, but is preferably at least about 50, 100, 150, 200, 250, 300, 350, 400, or 500 nucleotides long or even longer and can be, e.g., an entire genome. A transgene can be coding or non-coding sequences, or a combination thereof. A transgene usually comprises a regulatory element that is capable of driving the expression of one or more transgenes under appropriate conditions. By "transgenic animal" is meant an animal comprising a transgene as described above. Transgenic animals are made by techniques that are well known in the art. The disclosed nucleic acids, in whole or in part, in any combination, can be transgenes as disclosed herein.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein.

The disclosed transgenic animals can be any non-human animal, including a non-human mammal (e.g., mouse, rat, rabbit, squirrel, hamster, rabbits, guinea pigs, pigs, micropigs, prairie dogs, baboons, squirrel monkeys and chimpanzees, etc), bird or an amphibian, in which one or more cells contain heterologous nucleic acid introduced by way of human intervention, such as by transgenic techniques well known in the art. For example, the animal can be selected from the group consisting of avian, bovine, canine, caprine, equine, feline, leporine, murine, ovine, porcine, non-human primate. Thus, the animal can be a mouse, a rabbit, or a rat.

Generally, the nucleic acid is introduced into the cell, directly or indirectly, by introduction into a precursor of the cell, such as by microinjection or by infection with a recombinant virus. The disclosed transgenic animals can also include the progeny of animals which had been directly manipulated or which were the original animal to receive one or more of the disclosed nucleic acids. This molecule may be integrated within a chromosome, or it may be extrachromosomally replicating DNA. For techniques related to the production of transgenic animals, see, inter alia, Hogan et al (1986) Manipulating the Mouse Embryo—A Laboratory Manual Cold Spring Harbor Laboratory, Cold Spring Harbor, N.Y., 1986).

Animals suitable for transgenic experiments can be obtained from standard commercial sources such as Charles River (Wilmington, Mass.), Taconic (Germantown, N.Y.), and Harlan Sprague Dawley (Indianapolis, Ind.). For example, if the transgenic animal is a mouse, many mouse strains are suitable, but C57BL/6 female mice can be used for embryo retrieval and transfer. C57BL/6 males can be used for mating and vasectomized C57BL/6 studs can be used to stimulate pseudopregnancy. Vasectomized mice and rats can be obtained from the supplier. Transgenic animals can be made by any known procedure, including microinjection methods, and embryonic stem cells methods. The procedures for manipulation of the rodent embryo and for microinjection of DNA are described in detail in Hogan et al., Manipulating the Mouse Embryo (Cold Spring Harbor Laboratory, Cold Spring Harbor, N.Y., 1986), the teachings of which are generally known and are incorporated herein.

Transgenic animals can be identified by analyzing their DNA. For this purpose, for example, when the transgenic animal is an animal with a tail, such as rodent, tail samples (1 to 2 cm) can be removed from three week old animals. DNA from these or other samples can then be prepared and analyzed, for example, by Southern blot, PCR, or slot blot to detect transgenic founder (F(0)) animals and their progeny (F(1) and F(2)). Thus, also provided are transgenic non-human animals that are progeny of crosses between a transgenic animal of the invention and a second animal Transgenic animals can be bred with other transgenic animals, where the two transgenic animals were generated using different transgenes, to test the effect of one gene product on another gene product or to test the combined effects of two gene products.

10. Antibodies to Mutant $Na_v1.7$ Sodium Channels

Also disclosed herein are purified antibodies that selectively bind to an epitope of a mutant $Na_v1.7$ sodium channel alpha-subunit. In one aspect, the purified antibody selectively binds to an epitope of the I62V mutant $Na_v1.7$ sodium channel alpha-subunit. In another aspect, the purified antibody selectively binds to an epitope of the P149Q mutant $Na_v1.7$ sodium channel alpha-subunit. In yet another aspect, the purified antibody selectively binds to an epitope of the N641Y mutant $Na_v1.7$ sodium channel alpha-subunit. In a further aspect, the purified antibody selectively binds to an epitope of the K655R mutant $Na_v1.7$ sodium channel alpha-subunit. In a still further aspect, the purified antibody selectively binds to an epitope of the I739V mutant $Na_v1.7$ sodium channel alpha-subunit. In one aspect, the purified antibody selectively binds to an epitope of the L1123F mutant $Na_v1.7$ sodium channel alpha-subunit. In one aspect, the purified antibody selectively binds to an epitope of the 1228M mutant $Na_v1.7$ sodium channel alpha-subunit. In one aspect, the purified antibody selectively binds to an epitope of the S490M mutant $Na_v1.7$ sodium channel alpha-subunit. In one aspect, the purified antibody selectively binds to an epitope of the E519K mutant $Na_v1.7$ sodium channel alpha-subunit. In one aspect, the purified antibody selectively binds to an epitope of the I684M mutant $Na_v1.7$ sodium channel alpha-subunit. In one aspect, the purified antibody selectively binds to an epitope of the C699Y mutant $Na_v1.7$ sodium channel alpha-subunit. In one aspect, the purified antibody selectively binds to an epitope of the E1160Q mutant $Na_v1.7$ sodium channel alpha-subunit. In one aspect, the purified antibody selectively binds to an epitope of the L1267V mutant $Na_v1.7$ sodium channel alpha-subunit.

By "selectively binds" or "specifically binds" is meant that the antibody binds to the mutant $Na_v1.7$ sodium channel without appreciably binding to the non-mutant $Na_v1.7$ sodium channel. By "binding" is meant such that the signal that indicates binding is at least about 1.5 times the signal for a non-binding control. Thus, without appreciable binding is meant less than or equal to 1.5 times the background of a non-binding control.

The term "antibodies" is used herein in a broad sense and includes both polyclonal and monoclonal antibodies, as well as humanized, fully human, and non-human antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to selectively bind with epitopes of mutant $Na_v1.7$ sodium channel alpha-subunits. The antibodies can be tested for their desired activity using the in vitro assays described herein, or by analogous methods, after which their in vivo therapeutic and/or prophylactic activities are tested according to known clinical testing methods. Optionally, the antibodies are labeled directly or indirectly and can be used with imaging technologies to detect expression of the mutant $Na_v1.7$.

As used herein, the term "epitope" is meant to include any determinant capable of specific interaction with the anti-mutant $Na_v1.7$ antibodies disclosed. Epitopic determinants usually consist of chemically active surface groupings of molecules such as amino acids or sugar side chains and usually have specific three dimensional structural characteristics, as well as specific charge characteristics.

An "epitope tag" denotes a short peptide sequence unrelated to the function of the antibody or molecule that can be used for purification or crosslinking of the molecule with anti-epitope tag antibodies or other reagents.

As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

As used herein, the term "antibody or fragments thereof" encompasses chimeric antibodies and hybrid antibodies, with dual or multiple antigen or epitope specificities, and fragments, such as F(ab')2, Fab', Fab and the like, including hybrid fragments, which are capable of binding the epitopic determinant. Thus, fragments of the antibodies that retain the ability to bind their specific antigens are provided. For example, fragments of antibodies which maintain mutant $Na_v1.7$ sodium channel alpha-subunit binding activity are included within the meaning of the term "antibody or fragment thereof" Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

An isolated immunogenically specific paratope or fragment of the antibody is also provided. A specific immunogenic epitope of the antibody can be isolated from the whole antibody by chemical or mechanical disruption of the molecule. The purified fragments thus obtained are tested to determine their immunogenicity and specificity by the methods taught herein. Immunoreactive paratopes of the antibody, optionally, are synthesized directly. An immunoreactive fragment is defined as an amino acid sequence of at least about two to five consecutive amino acids derived from the antibody amino acid sequence.

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

Also disclosed are fragments of antibodies which have bioactivity. The polypeptide fragments can be recombinant proteins obtained by cloning nucleic acids encoding the polypeptide in an expression system capable of producing the polypeptide fragments thereof, such as an adenovirus or baculovirus expression system. For example, one can determine the active domain of an antibody from a specific hybridoma that can cause a biological effect associated with the interaction of the antibody with mutant $Na_v1.7$ sodium channel alpha-subunit. For example, amino acids found to not contribute to either the activity or the binding specificity or affinity of the antibody can be deleted without a loss in the respective activity. For example, in various embodiments, amino or carboxy-terminal amino acids are sequentially removed from either the native or the modified non-immunoglobulin molecule or the immunoglobulin molecule and the respective activity assayed in one of many available assays. In another example, a fragment of an antibody comprises a modified antibody wherein at least one amino acid has been substituted for the naturally occurring amino acid at a specific position, and a portion of either amino terminal or carboxy terminal amino acids, or even an internal region of the antibody, has been replaced with a polypeptide fragment or other moiety, such as biotin, which can facilitate in the purification of the modified antibody. For example, a modified antibody can be fused to a maltose binding protein, through either peptide chemistry or cloning the respective nucleic acids encoding the two polypeptide fragments into an expression vector such that the expression of the coding region results in a hybrid polypeptide. The hybrid polypeptide can be affinity purified by passing it over an amylose affinity column, and the modified antibody receptor can then be separated from the maltose binding region by cleaving the hybrid polypeptide with the specific protease factor Xa. (See, for example, New England Biolabs Product Catalog, 1996, pg. 164.). Similar purification procedures are available for isolating hybrid proteins from eukaryotic cells as well.

The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller M J et al. Nucl. Acids Res. 10:6487-500 (1982).

Techniques can also be adapted for the production of single-chain antibodies specific to an antigenic protein of the present disclosure (see e.g., U.S. Pat. No. 4,946,778). In addition, methods can be adapted for the construction of F (ab) expression libraries (see e.g., Huse, et al., 1989 Science 246: 1275-1281) to allow rapid and effective identification of monoclonal F (ab)fragments with the desired specificity for a protein or derivatives, fragments, analogs or homologs thereof. Antibody fragments that contain the idiotypes to a protein antigen may be produced by techniques known in the art including, but not limited to: (i) an F((ab'))(2)fragment produced by pepsin digestion of an antibody molecule; (ii) an Fab fragment generated by reducing the disulfide bridges of an F((ab'))(2)fragment; (iii) an F (ab)fragment generated by the treatment of the antibody molecule with papain and a reducing agent and (iv) F (v), fragments.

Methods for the production of single-chain antibodies are well known to those of skill in the art. The skilled artisan is referred to U.S. Pat. No. 5,359,046, (incorporated herein by reference) for such methods. A single chain antibody is created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding (Bedzyk et al., 1990; Chaudhary et al., 1990). The linker is chosen to permit the heavy chain and light chain to bind together in their proper conformational orientation. See, for example, Huston, J. S., et al., Methods in Enzym. 203:46-121 (1991), which is incorporated herein by reference. These Fvs lack the constant regions (Fc) present in the heavy and light chains of the native antibody.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

In hybrid antibodies, one heavy and light chain pair is homologous to that found in an antibody raised against one antigen recognition feature, e.g., epitope, while the other heavy and light chain pair is homologous to a pair found in an antibody raised against another epitope. This results in the property of multi-functional valency, i.e., ability to bind at least two different epitopes simultaneously. As used herein, the term "hybrid antibody" refers to an antibody wherein each chain is separately homologous with reference to a mammalian antibody chain, but the combination represents a novel assembly so that two different antigens are recognized by the antibody. Such hybrids can be formed by fusion of hybridomas producing the respective component antibodies, or by recombinant techniques. Such hybrids may, of course, also be formed using chimeric chains.

The encoded antibodies can be anti-idiotypic antibodies (antibodies that bind other antibodies) as described, for example, in U.S. Pat. No. 4,699,880. Such anti-idiotypic antibodies could bind endogenous or foreign antibodies in a treated individual, thereby to ameliorate or prevent pathological conditions associated with an immune response, e.g., in the context of an autoimmune disease.

The targeting function of the antibody can be used therapeutically by coupling the antibody or a fragment thereof with a therapeutic agent. Such coupling of the antibody or fragment (e.g., at least a portion of an immunoglobulin constant region (Fc)) with the therapeutic agent can be achieved by making an immunoconjugate or by making a fusion protein, comprising the antibody or antibody fragment and the therapeutic agent.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates disclosed can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, [α]-interferon, [β]-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982). Alternatively, an antibody can be conjugated to a second antibody to form an antibody heteroconjugate as described by Segal in U.S. Pat. No. 4,676,980.

One method of producing proteins comprising the antibodies is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the antibody, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof (Grant GA (1992) Synthetic Peptides: A User Guide. W.H. Freeman and Co., N.Y. (1992); Bodansky M and Trost B., Ed. (1993) Principles of Peptide Synthesis. Springer-Verlag Inc., NY. Alternatively, the peptide or polypeptide is independently synthesized in vivo as described above. Once isolated, these independent peptides or polypeptides may be linked to form an antibody or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison, et al. (1984) Proc Natl Acad Sci USA, 81:6851-6855).

The disclosed monoclonal antibodies can be made using any procedure which produces monoclonal antibodies. For example, disclosed monoclonal antibodies can be prepared using hybridoma methods, such as those described by Kohler, et al. (1975) Nature 256:495). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the mutant $Na_v1.7$ channels described herein.

The monoclonal antibodies may also be made by recombinant DNA methods, such as those described in U.S. Pat. No. 4,816,567. DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. Nos. 5,804,440 and 6,096,441.

If these approaches do not produce neutralizing antibodies, cells expressing cell surface localized versions of these proteins will be used to immunize mice, rats or other species. Traditionally, the generation of monoclonal antibodies has depended on the availability of purified protein or peptides for use as the immunogen. More recently DNA based immunizations have shown promise as a way to elicit strong immune responses and generate monoclonal antibodies. In this approach, DNA-based immunization can be used, wherein DNA encoding extracellular fragments of mutant $Na_v1.7$ sodium channel alpha-subunits expressed as a fusion protein with human IgG1 or an epitope tag is injected into the host animal according to methods known in the art (e.g., Kilpatrick K E, et al. Gene gun delivered DNA-based immunizations mediate rapid production of murine monoclonal antibodies to the Flt-3 receptor. Hybridoma. 1998 December; 17(6):569-76; Kilpatrick K E et al. High-affinity monoclonal antibodies to PED/PEA-15 generated using 5 microg of DNA. Hybridoma. 2000 August; 19(4):297-302, which are incorporated herein by referenced in full for the methods of antibody production) and as described in the examples.

An alternate approach to immunizations with either purified protein or DNA is to use antigen expressed in baculovirus. The advantages to this system include ease of generation, high levels of expression, and post-translational modifications that are highly similar to those seen in mammalian systems. Use of this system involves expressing the mutant $Na_v1.7$ sodium channel alpha-subunits as fusion proteins with a signal sequence fragment. The antigen is produced by inserting a gene fragment in-frame between the signal sequence and the mature protein domain of the mutant $Na_v1.7$ sodium channel alpha-subunits nucleotide sequence. This results in the display of the foreign proteins on the surface of the virion. This method allows immunization with whole virus, eliminating the need for purification of target antigens.

Generally, either peripheral blood lymphocytes ("PBLs") are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, "Monoclonal Antibodies: Principles and Practice" Academic Press, (1986) pp. 59-103) Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, J. Immunol., 133:3001 (1984); Brodeur et al., "Monoclonal Antibody Production Techniques and Applications" Marcel Dekker, Inc., New York, (1987) pp. 51-63). The culture medium in which the hybridoma cells are cultured can then be assayed for the presence of monoclonal antibodies directed against mutant $Na_v1.7$ sodium channel alpha-subunits. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below or in Harlow and Lane "Antibodies, A Laboratory Manual" Cold Spring Harbor Publications, New York, (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal The monoclonal antibodies secreted by the subclones may be isolated or purified from the culture medium or ascites fluid by conventional immunoglobulin purification procedures such as, for example, protein A-Sepharose, protein G, hydroxylapatite chromatography, gel electrophoresis, dialysis, or affinity chromatography.

In vitro methods are also suitable for preparing monovalent antibodies, including, for example, scfv antibodies. Digestion of antibodies to produce fragments thereof, particularly, Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields an Fc fragment and an $F(ab)_2$ fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (See Zoller, (1992) J Curr Opin Biotechnol 3:348-354).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA, 90:2551-255 (1993); Jakobovits et al., Nature, 362:255-258 (1993); Bruggemann et al., Year in Immuno., 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cote et al. and Boerner et al. are also available for the preparation of human monoclonal antibodies (Cole et al., Monoclonal Antibodies and Cancer Therapy, Alan R. Liss, p. 77 (1985); Boerner et al., J. Immunol., 147(1):86-95 (1991)).

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992))

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, a humanized form of a non-human antibody (or a fragment thereof) is a chimeric antibody or fragment (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody (Sims et al., J. Immunol., 151:2296 (1993) and Chothia et al., J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see, WO 94/04679, published 3 Mar. 1994).

The antibody can be bound to a substrate or labeled with a detectable moiety or both bound and labeled. The detectable moieties contemplated with the present compositions include fluorescent, enzymatic and radioactive markers.

Administration of the antibodies can be done as disclosed herein. Nucleic acid approaches for antibody delivery also exist. The broadly neutralizing anti-mutant $Na_v1.7$ antibodies and antibody fragments can also be administered to patients or subjects as a nucleic acid preparation (e.g., DNA or RNA) that encodes the antibody or antibody fragment, such that the patient's or subject's own cells take up the nucleic acid and produce and secrete the encoded antibody or antibody fragment. The delivery of the nucleic acid can be by any means, as disclosed herein, for example.

11. Computer Readable Forms

It will be appreciated by those skilled in the art that the nucleic acids provided herein as well as the nucleic acid and amino acid sequences identified from subjects can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate a list of sequences comprising one or more of the nucleic acids of the invention. Another aspect of the present invention is a computer readable medium having recorded thereon at least 2, 5, 10, 15, 20, 25, 30, 50, 100, 200, 250, 300, 400, 500, 1000, 2000, 3000, 4000 or 5000 nucleic acids of the invention or nucleic acid sequences identified from subjects.

Computer readable media include magnetically readable media, optically readable media, electronically readable media and magnetic/optical media. For example, the computer readable media may be a hard disc, a floppy disc, a magnetic tape, CD-ROM, DVD, RAM, or ROM as well as other types of other media known to those skilled in the art.

Embodiments of the present invention include systems, particularly computer systems which contain the sequence information described herein. As used herein, "a computer system" refers to the hardware components, software components, and data storage components used to store and/or analyze the nucleotide sequences of the present invention or other sequences. The computer system preferably includes the computer readable media described above, and a processor for accessing and manipulating the sequence data.

Preferably, the computer is a general purpose system that comprises a central processing unit (CPU), one or more data storage components for storing data, and one or more data retrieving devices for retrieving the data stored on the data storage components. A skilled artisan can readily appreciate that any one of the currently available computer systems are suitable.

In one particular aspect, the computer system includes a processor connected to a bus which is connected to a main memory, preferably implemented as RAM, and one or more data storage devices, such as a hard drive and/or other computer readable media having data recorded thereon. In some embodiments, the computer system further includes one or more data retrieving devices for reading the data stored on the data storage components. The data retrieving device may represent, for example, a floppy disk drive, a compact disk drive, a magnetic tape drive, a hard disk drive, a CD-ROM drive, a DVD drive, etc. In some embodiments, the data storage component is a removable computer-readable medium such as a floppy disk, a compact disk, a magnetic tape, etc. containing control logic and/or data recorded thereon. The computer system may advantageously include or be programmed by appropriate software for reading the control logic and/or the data from the data storage component once inserted in the data retrieving device. Software for accessing and processing the nucleotide sequences of the nucleic acids of the invention (such as search tools, compare tools, modeling tools, etc.) may reside in main memory during execution.

In some aspects, the computer system may further comprise a sequence comparer for comparing the nucleic acid sequences stored on a computer readable medium to another test sequence stored on a computer readable medium. A "sequence comparer" refers to one or more programs which are implemented on the computer system to compare a nucleotide sequence with other nucleotide sequences.

Accordingly, one aspect of the present invention is a computer system comprising a processor, a data storage device having stored thereon a nucleic acid of the invention, a data storage device having retrievably stored thereon reference nucleotide sequences to be compared with test or sample sequences and a sequence comparer for conducting the comparison. The sequence comparer may indicate a homology level between the sequences compared or identify a difference between the two sequences. For example, a reference sequence comprising SEQ ID NO: 8 or any fragment thereof, such as SEQ ID NO: 14, can be compared with a test sequence from a subject to determine if the test sequence is the same as the reference sequence, e.g., contains an A at position 184 or a different nucleotide (G).

Alternatively, the computer program may be a computer program which compares a test nucleotide sequence(s) from a subject or a plurality of subjects to a reference nucleotide sequence(s) in order to determine whether the test nucleotide sequence(s) differs from or is the same as a reference nucleic acid sequence(s) at one or more positions. Optionally such a program records the length and identity of inserted, deleted or substituted nucleotides with respect to the sequence of either the reference polynucleotide or the test nucleotide sequence. In one embodiment, the computer program may be a program which determines whether the nucleotide sequences of the test nucleotide sequence contains one or more single nucleotide mutations with respect to a reference nucleotide sequence. These single nucleotide mutations may each comprise a single base substitution, insertion, or deletion.

The nucleic acids of the invention (both test nucleic acid sequences and reference nucleic acid sequences) may be stored and manipulated in a variety of data processor programs in a variety of formats. For example, they may be stored as text in a word processing file, such as Microsoft-WORD or WORDPERFECT or as an ASCII file in a variety of database programs familiar to those of skill in the art, such as DB2, SYBASE, or ORACLE. In addition, many computer programs and databases may be used as sequence comparers, identifiers, or sources of reference nucleotide sequences. The following list is intended not to limit the invention but to provide guidance to programs and databases which are useful with the nucleic acid sequences of the invention. The programs and databases which may be used include, but are not limited to: MacPattern (EMBL), Discoveryl)ase (Molecular Applications Group), GeneMine (Molecular Applications Group), Look (Molecular Applications Group), MacLook (Molecular Applications Group), BLAST and BLAST2 (NCBI), BLASTN and BLASTX (Altschul, et al. (1990) J Mol Biol 3:403-410), FASTA (Pearson and Lipman, (1988) Proc Natl Acad Sci USA 85:2444-2448), FASTDB (Brutlag et al., (1990) Compt Appl Biosci 6:237-245), Catalyst (Molecular Simulations Inc.), Catalyst/SHAPE (Molecular Simulations Inc.), Cerius.sup.2.DBAccess (Molecular Simulations Inc.), HypoGen (Molecular Simulations Inc.), Insight II (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the EMBL/Swissprotein database, the MDL Available Chemicals Directory database, the MDL Drug Data Report data base, the Comprehensive Medicinal Chemistry database, Derwents's World Drug Index database, the BioByteMasterFile database, the Genbank database, and the Genseqn database. Many other programs and data bases would be apparent.

12. Kits

The materials described above as well as other materials can be packaged together in any suitable combination as a kit useful for performing, or aiding in the performance of, the disclosed method. It is useful if the kit components in a given kit are designed and adapted for use together in the disclosed method.

C. Methods of Making the Compositions

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

2. Methods of Synthesizing Polypeptides

The peptides, polypeptides, and polypeptide fragments disclosed herein can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the sodium channels disclosed herein, for example, can be synthesized by standard chemical reactions. For example, a peptide or polypeptide fragment can be synthesized and not cleaved from its synthesis resin whereas another peptide or polypeptide fragment can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an sodium channel, or fragment thereof (See Grant GA (1992) Synthetic Peptides: A User Guide. W.H. Freeman and Co., New York, N.Y. (1992); Bodansky M and Trost B., Ed. Principles of Peptide Synthesis. Springer-Verlag Inc., New York, N.Y. (1993)). Alternatively, the peptide or polypeptide is independently synthesized in vivo as described above.

For example, enzymatic ligation of cloned or synthetic peptide segments allow relatively short peptide fragments to be joined to produce larger peptide fragments, polypeptides or whole protein domains (Abrahmsen, et al. (1991) Biochemistry 30:4151). Alternatively, native chemical ligation of synthetic peptides can be utilized to synthetically construct large peptides or polypeptides from shorter peptide fragments. This method consists of a two step chemical reaction (Dawson, et al. (1994) Science 266:776-779). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini, et al. (1992) FEBS Lett. 307:97-101; Clark-Lewis, et al. (1994) J Biol Chem 269:16075; Clark-Lewis, et al. (1991) Biochemistry 30:3128; Rajarathnam, et al. (1994) Biochemistry 33:6623-30).

Alternatively, unprotected peptide segments are chemically linked where the bond formed between the peptide segments as a result of the chemical ligation is an unnatural (non-peptide) bond (Schnolzer, et al. (1992) Science, 256: 221). This technique has been used to synthesize analogs of protein domains as well as large amounts of relatively pure proteins with full biological activity (deLisle Milton, et al. Techniques in Protein Chemistry IV. Academic Press, New York, pp. 257-267 (1992)).

3. Peptide Synthesis

One method of producing the disclosed proteins, such as SEQ ID NO: 2, 3, 4, 5, 6, 7, 79, 80, 81, 82, 83, 84, 85, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof (Grant GA (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product.

Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

4. Transgenic Models

Provided herein is a method of making the herein disclosed non-human animal model of a neurologic disorder, comprising administering to a non-human mammal a nucleic acid encoding a mutant $Na_v1.7$ sodium channel alpha-subunit protein. In some aspects, the neurologic disorder is a seizure disorder. For example, the seizure disorder can be a febrile seizure disorder. In some aspects, the seizure disorder is Dravet syndrome.

Provided herein is a method of making the herein disclosed non-human animal model of a neurologic disorder, comprising administering to a non-human mammal a nucleic acid encoding a mutant $Na_v1.7$ sodium channel alpha-subunit protein. In some aspects, the neurologic disorder is a seizure disorder. For example, the seizure disorder can be a febrile seizure disorder. In some aspects, the seizure disorder is Dravet syndrome.

The mutant $Na_v1.7$ sodium channel alpha-subunit protein can be any mutant $Na_v1.7$ sodium channel alpha-subunit proteins disclosed herein. For example, the mutant $Na_v1.7$ sodium channel alpha-subunit protein can comprise a mutation, such as valine (V), at amino acid residue 62. The mutant $Na_v1.7$ sodium channel alpha-subunit protein can comprise a mutation, such as glutamine (Q), at amino acid residue 149. The mutant $Na_v1.7$ sodium channel alpha-subunit protein can comprise a mutation, such tyrosine (Y), at amino acid residue 641. The mutant $Na_v1.7$ sodium channel alpha-subunit protein can comprise a mutation, such as arginine (R), at amino acid residue 655. The mutant $Na_v1.7$ sodium channel alpha-subunit protein can comprise a mutation, such as valine (V), at amino acid residue 739. The mutant $Na_v1.7$ sodium channel alpha-subunit protein can comprise a mutation, such as phenylalanine (F), at amino acid residue 1123. The mutant $Na_v1.7$ sodium channel alpha-subunit protein can comprise a mutation, such as methionine (M), at amino acid residue 228. The mutant $Na_v1.7$ sodium channel alpha-subunit protein can comprise a mutation, such as asparagine (N), at amino acid residue 490. The mutant $Na_v1.7$ sodium channel alpha-subunit protein can comprise a mutation, such as lysine (K), at amino acid residue 519. The mutant $Na_v1.7$ sodium channel alpha-subunit protein can comprise a mutation, such as methionine (M), at amino acid residue 684. The mutant $Na_v1.7$ sodium channel alpha-subunit protein can comprise a mutation, such as tyrosine (Y), at amino acid residue 699. The mutant $Na_v1.7$ sodium channel alpha-subunit protein can comprise a mutation, such as glutamic acid (E), at amino acid residue 1160. The mutant $Na_v1.7$ sodium channel alpha-subunit protein can comprise a mutation, such as valine (V), at amino acid residue 1267.

i. Methods of Producing Transgenic Animals

The nucleic acids and vectors provided herein can be used to produce transgenic animals. Various methods are known for producing a transgenic animal. In one method, an embryo at the pronuclear stage (a "one cell embryo") is harvested from a female and the transgene is microinjected into the embryo, in which case the transgene will be chromosomally integrated into the germ cells and somatic cells of the resulting mature animal. In another method, embryonic stem cells are isolated and the transgene is incorporated into the stem cells by electroporation, plasmid transfection or microinjection; the stem cells are then reintroduced into the embryo, where they colonize and contribute to the germ line. Methods for microinjection of polynucleotides into mammalian species are described, for example, in U.S. Pat. No. 4,873,191, which is incorporated herein by reference. In yet another method, embryonic cells are infected with a retrovirus containing the transgene, whereby the germ cells of the embryo have the transgene chromosomally integrated therein. When the animals to be made transgenic are avian, microinjection into the pronucleus of the fertilized egg is problematic because avian fertilized ova generally go through cell division for the first twenty hours in the oviduct and, therefore, the pronucleus is inaccessible. Thus, the retrovirus infection method is preferred for making transgenic avian species (see U.S. Pat. No. 5,162,215, which is incorporated herein by reference). If microinjection is to be used with avian species, however, the embryo can be obtained from a sacrificed hen approximately 2.5 hours after the laying of the previous laid egg, the transgene is microinjected into the cytoplasm of the germinal disc and the embryo is cultured in a host shell until maturity (Love et al., Biotechnology 12, 1994). When the animals to be made transgenic are bovine or porcine, microinjection can be hampered by the opacity of the ova, thereby making the nuclei difficult to identify by traditional differential interference-contrast microscopy. To overcome this problem, the ova first can be centrifuged to segregate the pronuclei for better visualization.

The transgene can be introduced into embryonal target cells at various developmental stages, and different methods are selected depending on the stage of development of the embryonal target cell. The zygote is the best target for microinjection. The use of zygotes as a target for gene transfer has a major advantage in that the injected DNA can incorporate into the host gene before the first cleavage (Brinster et al., Proc. Natl. Acad. Sci., USA 82:4438-4442, 1985). As a consequence, all cells of the transgenic non-human animal carry the incorporated transgene, thus contributing to efficient transmission of the transgene to offspring of the founder, since 50% of the germ cells will harbor the transgene.

A transgenic animal can be produced by crossbreeding two chimeric animals, each of which includes exogenous genetic material within cells used in reproduction. Twenty-five percent of the resulting offspring will be transgenic animals that are homozygous for the exogenous genetic material, 50% of the resulting animals will be heterozygous, and the remaining 25% will lack the exogenous genetic material and have a wild type phenotype.

In the microinjection method, the transgene is digested and purified free from any vector DNA, for example, by gel electrophoresis. The transgene can include an operatively associated promoter, which interacts with cellular proteins involved in transcription, and provides for constitutive expression, tissue specific expression, developmental stage specific expression, or the like. Such promoters include those from cytomegalovirus (CMV), Moloney leukemia virus (MLV), and herpes virus, as well as those from the genes encoding metallothionein, skeletal actin, phosphenolpyruvate carboxylase (PEPCK), phosphoglycerate (PGK), dihydrofolate reductase (DHFR), and thymidine kinase (TK). Promoters from viral long terminal repeats (LTRs) such as Rous sarcoma virus LTR also can be employed. When the animals to be made transgenic are avian, preferred promoters include those for the chicken [bgr]-globin gene, chicken lysozyme gene, and avian leukosis virus. Constructs useful in plasmid transfection of embryonic stem cells will employ additional regulatory elements, including, for example, enhancer elements to stimulate transcription, splice acceptors, termination and polyadenylation signals, ribosome binding sites to permit translation, and the like.

In the retroviral infection method, the developing non-human embryo can be cultured in vitro to the blastocyst stage. During this time, the blastomeres can be targets for retroviral infection (Jaenich, Proc. Natl. Acad. Sci. USA 73:1260-1264, 1976). Efficient infection of the blastomeres is obtained by enzymatic treatment to remove the zona pellucida (Hogan et al., Manipulating the Mouse Embryo (Cold Spring Harbor Laboratory Press, 1986). The viral vector system used to introduce the transgene is typically a replication-defective retrovirus carrying the transgene (Jahner et al., Proc. Natl. Acad. Sci., USA 82:6927-6931, 1985; Van der Putten et al., Proc. Natl. Acad. Sci. USA 82:6148-6152, 1985). Transfection is easily and efficiently obtained by culturing the blastomeres on a monolayer of virus producing cells (Van der Putten et al., supra, 1985; Stewart et al., EMBO J. 6:383-388, 1987). Alternatively, infection can be performed at a later stage. Virus or virus-producing cells can be injected into the blastocoele (Jahner et al., Nature 298:623-628, 1982). Most of the founders will be mosaic for the transgene since incorporation occurs only in a subset of the cells which formed the transgenic nonhuman animal Further, the founder can contain various retroviral insertions of the transgene at different positions in the genome, which generally will segregate in the offspring. In addition, it is also possible to introduce transgenes into the germ line, albeit with low efficiency, by intrauterine retroviral infection of the mid-gestation embryo (Jahner et al., supra, 1982).

Embryonal stem cell (ES) also can be targeted for introduction of the transgene. ES cells are obtained from pre-implantation embryos cultured in vitro and fused with embryos (Evans et al. Nature 292:154-156, 1981; Bradley et al., Nature 309:255-258, 1984; Gossler et al., Proc. Natl. Acad. Sci., USA 83:9065-9069, 1986; Robertson et al., Nature 322:445-448, 1986). Transgenes can be efficiently introduced into the ES cells by DNA transfection or by retrovirus mediated transduction. Such transformed ES cells can thereafter be combined with blastocysts from a nonhuman animal. The ES cells thereafter colonize the embryo and contribute to the germ line of the resulting chimeric animal (see Jaenisch, Science 240:1468-1474, 1988).

"Founder" generally refers to a first transgenic animal, which has been obtained from any of a variety of methods, e.g., pronuclei injection. An "inbred animal line" is intended to refer to animals which are genetically identical at all endogenous loci.

5. Processes for Making the Compositions

Disclosed are processes for making the compositions as well as making the intermediates leading to the compositions. For example, disclosed are nucleic acids in SEQ ID NO:8, 9, 10, 11, 12, 13, 86, 87, 88, 89, 90, 91, and 92. There are a variety of methods that can be used for making these compositions, such as synthetic chemical methods and standard molecular biology methods. It is understood that the methods of making these and the other disclosed compositions are specifically disclosed.

Disclosed are nucleic acid molecules produced by the process comprising linking in an operative way a nucleic acid comprising the sequence set forth in SEQ ID NO:8, 9, 10, 11, 12, 13, 86, 87, 88, 89, 90, 91, or 92 and a sequence controlling the expression of the nucleic acid.

Also disclosed are nucleic acid molecules produced by the process comprising linking in an operative way a nucleic acid molecule comprising a sequence having 80% identity to a sequence set forth in SEQ ID NO:8, 9, 10, 11, 12, 13, 86, 87, 88, 89, 90, 91, or 92 and a sequence controlling the expression of the nucleic acid.

Disclosed are nucleic acid molecules produced by the process comprising linking in an operative way a nucleic acid molecule comprising a sequence that hybridizes under stringent hybridization conditions to a sequence set forth SEQ ID NO:8, 9, 10, 11, 12, 13, 86, 87, 88, 89, 90, 91, or 92 and a sequence controlling the expression of the nucleic acid.

Disclosed are nucleic acid molecules produced by the process comprising linking in an operative way a nucleic acid molecule comprising a sequence encoding a peptide set forth in SEQ ID NO:2, 3, 4, 5, 6, 7, 79, 80, 81, 82, 83, 84, or 85 and a sequence controlling an expression of the nucleic acid molecule.

Disclosed are nucleic acid molecules produced by the process comprising linking in an operative way a nucleic acid molecule comprising a sequence encoding a peptide having 80% identity to a peptide set forth in SEQ ID NO:2, 3, 4, 5, 6, 7, 79, 80, 81, 82, 83, 84, or 85 and a sequence controlling an expression of the nucleic acid molecule.

Disclosed are nucleic acids produced by the process comprising linking in an operative way a nucleic acid molecule comprising a sequence encoding a peptide having 80% identity to a peptide set forth in SEQ ID NO:2, 3, 4, 5, 6, 7, 79, 80, 81, 82, 83, 84, or 85, wherein any change from the sequence set forth in SEQ ID NO:38 are conservative changes and a sequence controlling an expression of the nucleic acid molecule.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

Also disclose are animals produced by the process of adding to the animal any of the cells disclosed herein.

D. Uses

The disclosed compositions can be used in a variety of ways as research tools. Other uses are disclosed, apparent from the disclosure, and/or will be understood by those in the art.

E. Definitions

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents.

As used in the specification and the appended claims, the singular forms "a," "an," and "the" include plural referents unless the context clearly dictates otherwise. Thus, for example, reference to "a nucleotide" includes mixtures of two or more such nucleotides, reference to "an amino acid" includes mixtures of two or more such amino acids, reference to "the sodium channel" includes mixtures of two or more such sodium channels, and the like.

"Optional" or "optionally" means that the subsequently described event or circumstance can or cannot occur, and that the description includes instances where the event or circumstance occurs and instances where it does not. For example, the phrase "the array can optionally comprise the most commonly found allele at a second . . . position" means that the most commonly found allele at a second position may or may not be present in the array and that the description includes both arrays without the most commonly found allele at the second position and arrays where there is the most commonly found allele at the second position.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Throughout the description and claims of this specification, the word "comprise" and variations of the word, such as "comprising" and "comprises," means "including but not limited to," and is not intended to exclude, for example, other additives, components, integers or steps.

"Subject," as used herein, means an individual. In one aspect, the subject is a mammal such as a primate, and, in another aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, etc.).

"$Na_v1.7$," as used herein, refers to an isoform of a sodium channel known in the art by names such as NaS, hNE-Na, and PN1. The traditional gene symbol for a $Na_v1.7$ sodium channel is SCN9A, and thus the term $Na_v1.7$, as used herein, is synonymous with the term SCN9A. There are a variety of sequences related to the $Na_v1.7$ gene having the following Genbank Accession Numbers: NM 002977 (human), U35238 (rabbit), X82835 (human), U79568 (rat), and AF000368 (rat), these nucleic acid sequences, the polypeptides encoded by them, and other nucleic acid and polypeptide sequences are herein incorporated by reference in their entireties as well as for individual subsequences contained therein. The sequences for the human analogs of these genes, as well as other anlogs, and alleles of these genes, and splice variants and other types of variants, are available in a variety of protein and gene databases, including Genbank. Those sequences available at the time of filing this application at Genbank are herein incorporated by reference in their entireties as well as for individual subsequences contained therein. Genbank can be accessed at http://www.ncbi.nih.gov/entrez/query.fcgi. Those of skill in the art understand how to resolve sequence discrepancies and differences and to adjust the compositions and methods relating to a particular sequence to other related sequences. Primers and/or probes can be designed for any given sequence given the information disclosed herein and known in the art.

There are a variety of compositions disclosed herein that are amino acid based, including for example $Na_v1.7$ sodium channel alpha-subunits. Thus, as used herein, "amino acid," means the typically encountered twenty amino acids which make up polypeptides. In addition, it further includes less typical constituents which are both naturally occurring, such as, but not limited to formylmethionine and selenocysteine, analogs of typically found amino acids, and mimetics of amino acids or amino acid functionalities. Non-limiting examples of these and other molecules are discussed herein.

As used herein, the terms "peptide" and "polypeptide" refer to a class of compounds composed of amino acids chemically bound together. Non-limiting examples of these and other molecules are discussed herein. In general, the amino acids are chemically bound together via amide linkages (CONH); however, the amino acids may be bound together by other chemical bonds known in the art. For example, the amino acids may be bound by amine linkages. Peptide as used herein includes oligomers of amino acids and small and large peptides, including polypeptides and proteins.

There are a variety of compositions disclosed herein that are nucleic acid based, including for example the nucleic acids that encode, for example, $Na_v1.7$ sodium channel alpha-subunits. Thus, as used herein, "nucleic acid" means a molecule made up of, for example, nucleotides, nucleotide analogs, or nucleotide substitutes. Non-limiting examples of these and other molecules are discussed herein. A nucleic acid can be double stranded or single stranded. It is understood that, for example, when a vector is expressed in a cell the expressed mRNA will typically be made up of A, C, G, and U. Likewise, it is understood that if, for example, an antisense molecule is introduced into a cell or cell environment through, for example, exogenous delivery, it is advantageous that the antisense molecule be made up of nucleotide analogs that reduce the degradation of the antisense molecule in the cellular environment.

As used herein, "nucleotide" is a molecule that contains a base moiety, a sugar moiety and a phosphate moiety. Nucleotides can be linked together through their phosphate moieties and sugar moieties creating an internucleoside linkage. The base moiety of a nucleotide can be adenine-9-yl (A), cytosine-1-yl (C), guanine-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate).

"Nucleotide analog," as used herein, is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

"Nucleotide substitutes," as used herein, are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger, et al. (1989) Proc Natl Acad Sci USA, 86:6553-6556.)

A "Watson-Crick interaction" is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A "Hoogsteen interaction" is the interaction that takes place on the Hoogsteen face of a nucleotide or nucleotide analog, which is exposed in the major groove of duplex DNA. The Hoogsteen face includes the N7 position and reactive groups ($NH_2$ or O) at the C6 position of purine nucleotides.

"Deletion," as used herein, refers to a change in an amino acid or nucleotide sequence in which one or more amino acid or nucleotide residues, respectively, are absent relative to the reference sequence.

"Insertion" or "addition," as used herein, refers to a change in an amino acid or nucleotide sequence resulting in the addition of one or more amino acid or nucleotide residues, respectively, as compared to the reference sequence.

"Substitution," as used herein, refers to the replacement of one or more amino acids or nucleotides by one or more different amino acids or nucleotides, respectively, in a reference sequence.

"Isolated," as used herein refers to material, such as a nucleic acid or a polypeptide, which is: (1) substantially or essentially free from components which normally accompany or interact with it as found in its naturally occurring environment. Although, the isolated material optionally comprises material not found with the material in its natural environment; or (2) if the material is in its natural environment, the material has been synthetically (non-naturally) altered by deliberate human intervention to a composition and/or placed at a locus in the cell (e.g., genome or subcellular organelle) not native to a material found in that environment. The alteration to yield the synthetic material can be performed on the material within or removed from its natural state.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

F. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Disclosed is a study of a large Utah family with significant linkage to chromosome 2q24 (Peiffer, A., et al. 1999) that led to the identification of a new febrile seizure (FS) gene SCN9A that harbors a disease-causing N641Y mutation in the large cytoplasmic loop between domains I and II. Knockin mice with the N641Y mutation exhibit significantly reduced thresholds to electrically induced clonic and tonic-clonic seizures. In a collection of unrelated FS patients, additional $Na_v1.7$ missense mutations were identified in 5% of the patients. After one of these children with FS later developed Dravet syndrome, the SCN1A gene was sequenced and a heterozygous frameshift mutation identified. Subsequent analysis of a large SMEI cohort yielded significantly associated SCN9A missense variants in 8% of the patients, of whom 67% also harbored SCN1A mutations. The discovery of mutations in both SCN1A and SCN9A genes provides new evidence for the currently hypothesized oligogenic etiology of SMEI.

i. Results

Febrile seizures (FS) are the most common seizure disorder of early childhood, and exhibit a prevalence of 2-5% in European and North American children. Large FS families reported in the clinical literature support a genetic etiology for febrile seizures and confirm the previously reported 31% incidence of FS in first-degree relatives (Singh, R., et al. 1999). Individuals who experience FS have a 2-9% chance of developing afebrile seizures later in life (Arzimanoglou A., et al. 2004) and this incidence is four times higher if there is a family history of FS (Racacho, L. J., et al. 2000). These later-onset epileptic phenomena include generalized convulsive, as well as simple and complex partial seizures that can be resistant to currently available anticonvulsant therapy (Arzimanoglou A., et al. 2004). Notably, FS occur in up to 75% of children with the catastrophic early-onset epilepsy disorder of severe myoclonic epilepsy of infancy (SMEI, or Dravet syndrome), indicating that alleles that predispose to FS can be found in SMEI patients (Arzimanoglou A., et al. 2004). This led Claes et al. to find a high frequency of mutations in the SCN1A familial FS gene in patients with SMEI (Claes, L. et al. 2003; Claes, L. et al. 2001). Since then, others have proposed a complex genetic etiology for SMEI based on the observations that 50% of SMEI patients have de novo SCN1A mutations yet many belong to families with a history of FS (Fujiwara, T. et al. 2003; Nabbout, R. et al. 2003; Wallace, R. H. et al. 2003), and identical SCN1A missense mutations are associated with widely different seizure severities such as intractable seizures of SMEI, comparatively benign FS and even asymptomatic family members in some cases (Kanai, K. et al. 2004; Mulley, J. C. et al. 2005). However, definite genetic evidence supporting an oligogenic hypothesis of SMEI was lacking (Scheffer, I. E. 2003).

As disclosed above, there is linkage to a 10 centimorgan (cM) region on chromosome 2q24 in a large Utah kindred (K4425) with FS before the age of six years in 21 individuals, including 10 individuals with subsequent afebrile seizures (Peiffer, A., et al. 1999). This region contains five sodium channel α subunit genes including SCN1A, SCN2A and SCN3A, that share over 85% identity and are highly expressed in brain (Catterall, W. A. 2000). SCN1A is commonly mutated in SMEI and mutations in either SCN2A or SCN1A are associated with the generalized epilepsy febrile seizure plus (GEFS+) syndrome (Claes, L. et al. 2003; Escayg, A. et al. 2000; Harkin, L. A. et al. 2007; Ito, M., et al. 2004). Mutations in SCN2A have also been reported in patients with benign familial neonatal-infantile seizures and a single SCN3A mutation has recently been identified in a pediatric patient with partial epilepsy (Herlenius, E. et al. 2007; Holland, K. D. et al. 2008). Sequence analysis of whole blood DNA from patient II-4 and a monosomal hybrid cell line DNA containing the disease chromosome from patient III-26 in K4425 did not reveal any disease-causing variants within the coding region or exon-intron junctions in either SCN1A, SCN2A, or SCN3A. Deletion/duplication analysis of the SCN1A coding region using the multiplex amplicon quantification method (Suls, A. et al. 2006) in two affected K4425 individuals (III-14 and IV-9) was also negative. Furthermore, copy number variation (CNV) analysis of the distal 84% K4425 linkage region was done using the Agilent array comparative genomic hybridization. No shared CNV was found between two affected K4425 individuals, III-12 and IV-9.

Figure 2:
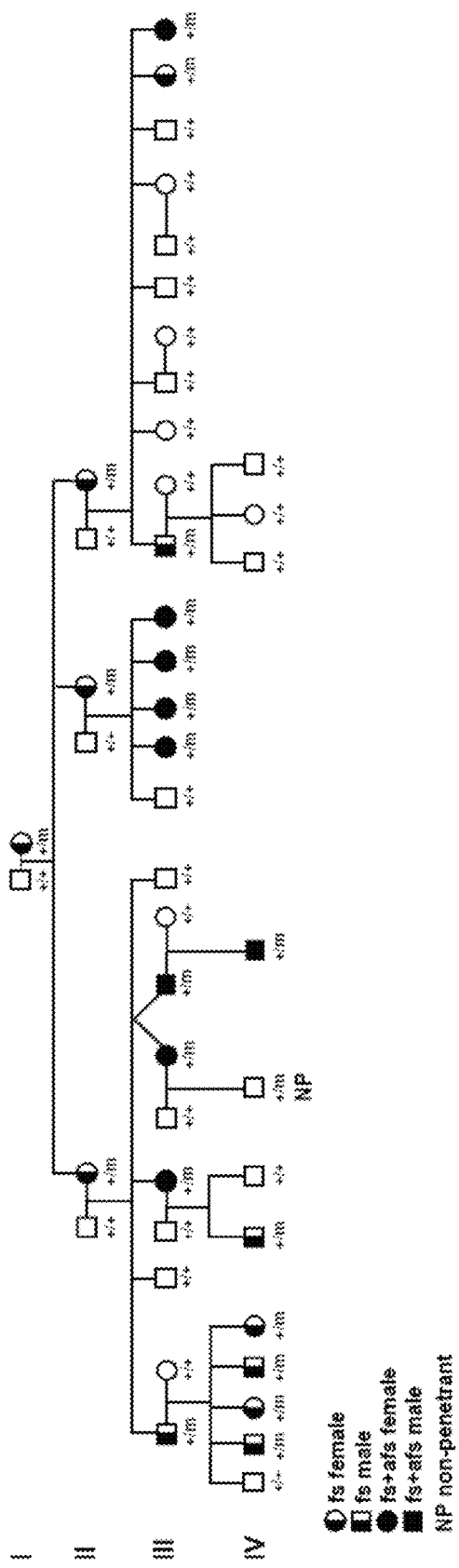
FIG. 2 is a diagram showing the segregation of the $Na_v1.7$ N641Y mutation and phenotypic findings of kindred 4425 (K4425). The following abbreviations are used in the diagram: "fs" means febrile seizures; "afs" means afebrile seizures; "+" means wild type; and "m" means N641Y mutation.

SCN9A, which also resides within the K4425 critical genetic interval (Peiffer, A., et al. 1999), is expressed primarily in neurons of the dorsal root ganglia and has preliminarily been classified as a peripheral nervous system channel (Catterall, W. A. 2000). This expression pattern is consistent with the three phenotypes of primary erythermalgia, paroxysmal extreme pain disorder and the inability to experience pain that are caused by recently described disease-associated SCN9A variants (Cox, J. J. et al. 2006; Fertleman, C. R. et al. 2006). However, select early SCN9A gene cloning papers (Sangameswaran, L. et al. 1997) showed expression of $Na_v1.7$ in brain of rodent and more recent expression analysis experiments have confirmed these observations (Mechaly, I., et al. 2005). SCN9A (NM 002977, NP 002968) was sequenced to demonstrate whether it harbors the disease-causing allele in affected individuals of K4425. Analysis of the large intracellular loop between domains I and II revealed a missense change (N641Y) that cosegregates with all 21 affected K4425 individuals, in addition to a single non-penetrant individual (IV-8) (FIG. 2). This variant was absent from 586 chromosomes from an ethnically matched population of unrelated individuals, providing supporting evidence for this nucleotide change being the disease-causing mutation in this family.

A broad spectrum of seizure manifestations was observed in K4425 family members who harbor the N641Y mutation (Peiffer, A., et al. 1999). Illustrating the milder end of the continuum are 11 individuals from K4425 who experienced only FS before six years of age. The remaining ten of the 21 affected individuals in K4425 experienced FS before six years of age followed by later afebrile seizures. In eight of these ten, the seizures remitted by the age of 16. The clinical course of afebrile seizures that ultimately resolved in these patients indicates an intermediate phenotype within this family. Finally, two individuals, III-14 and IV-9, developed intractable epilepsy. Patient III-14 experienced her first simple FS at age 1.5 years followed before age five by several non-febrile convulsions and at least one prolonged generalized convulsive seizure lasting at least 45 minutes. After age five, she had occasional complex-partial seizures and was diagnosed with left mesial temporal sclerosis at 22 years of age. At about one year of age, patient IV-9 began having frequent simple FS without focal onset and never lasting more than 2 minutes. However, he had as many as 60 such seizures until about 4-5 years of age. Afebrile generalized convulsive seizures began at about 6 years of age followed closely by very frequent typical absence seizures. He has never had prolonged convulsions, hemiclonic or secondarily generalized seizures, drop attacks, myoclonic or astatic seizures or "atypical absence" episodes and there has been no developmental regression. Now 11 years of age, he ultimately has become seizure free with the vagal nerve stimulator (placed at 8 years of age). Electroencephalography demonstrated very frequent frontally predominant generalized 3 to 5 Hz spike and slow wave and polyspike and wave discharges. Additional point mutations were ruled out in other known FS susceptibility genes SCN1A, SCN2A, SCN1B and GABRG2 by sequencing, and either a deletion or duplication of SCN1A by multiplex amplicon quantification in both of these severely affected K4425 patients.

Figure 4D:
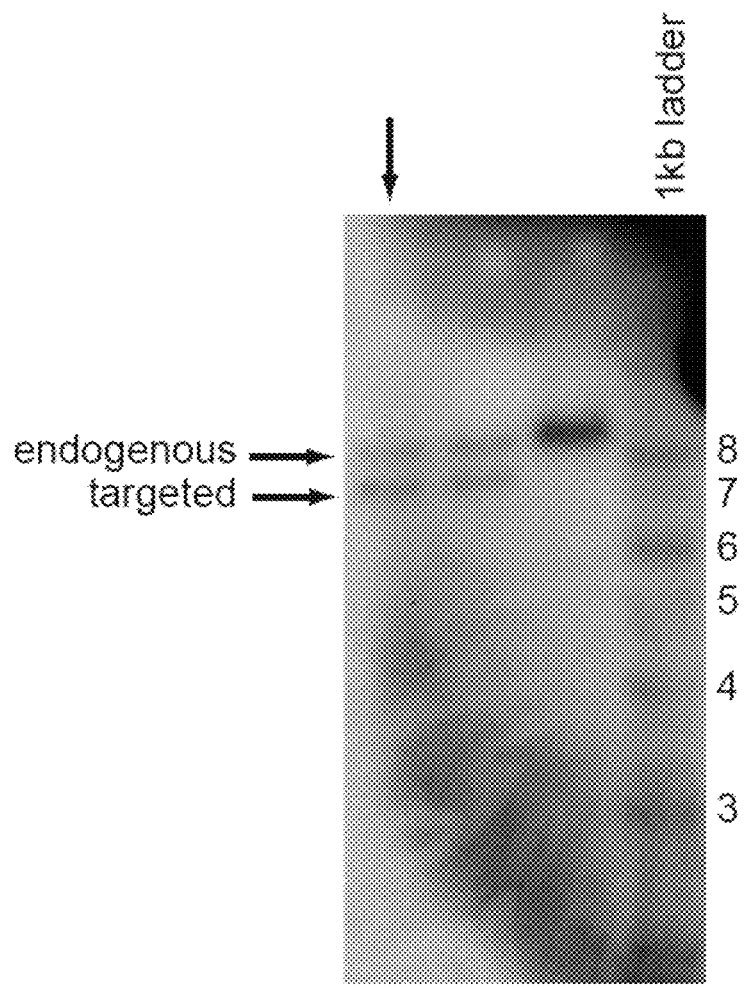
FIG. 4d shows Southern blot of three SspI cut ES cell clones followed by hybridization of probe yields an 8.4 kb endogenous band and a 7.2 kb targeted band (horizontal arrows); vertical arrow denotes clone used to make mouse.
Figure 4E:
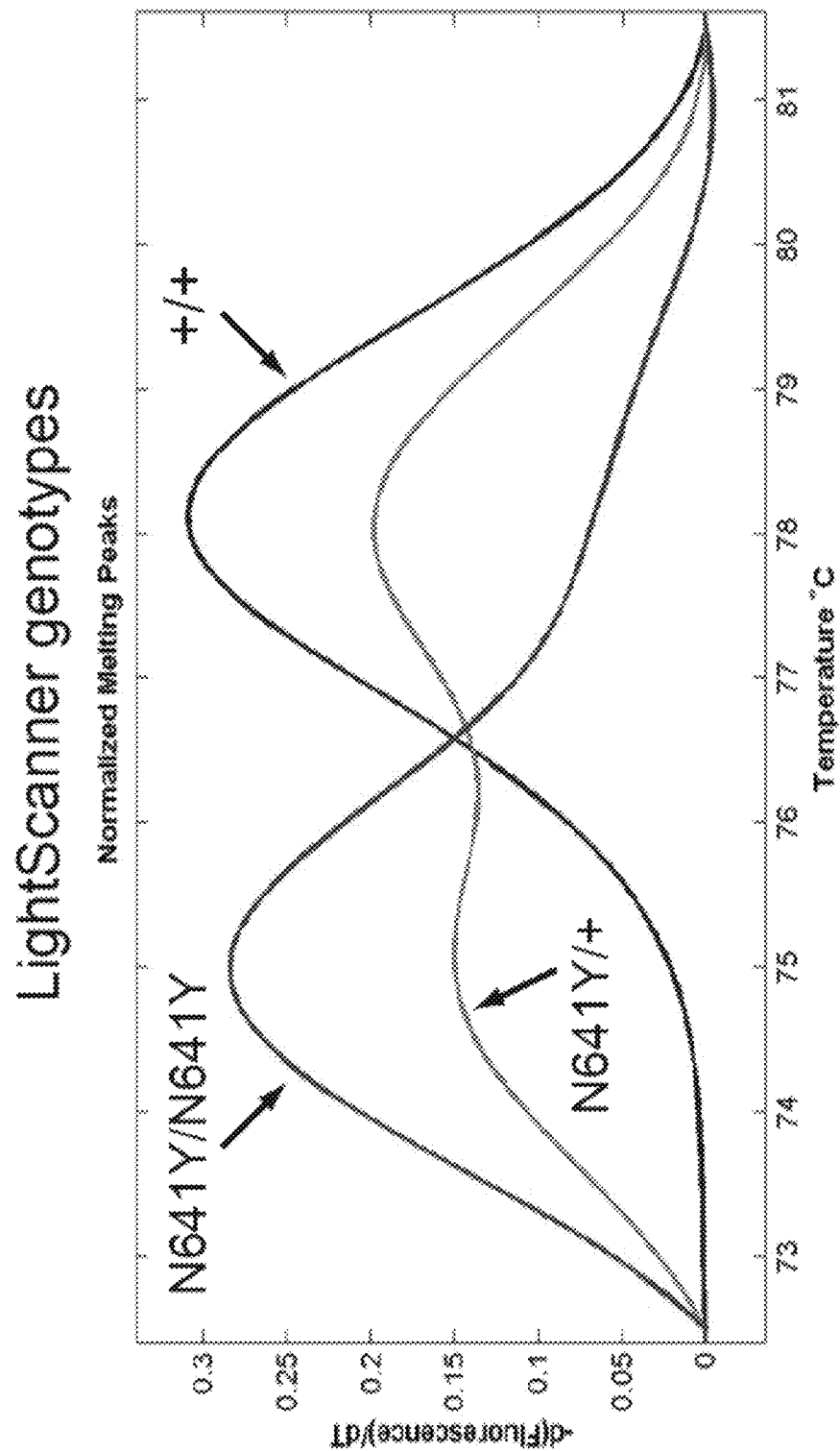
FIG. 4e shows LightScanner normalized melting peaks used to genotype $SCN9A^{+/+}$, $SCN9A^{N641Y/+}$ and $SCN9A^{N641Y/N641Y}$ mice.
Figure 4F:
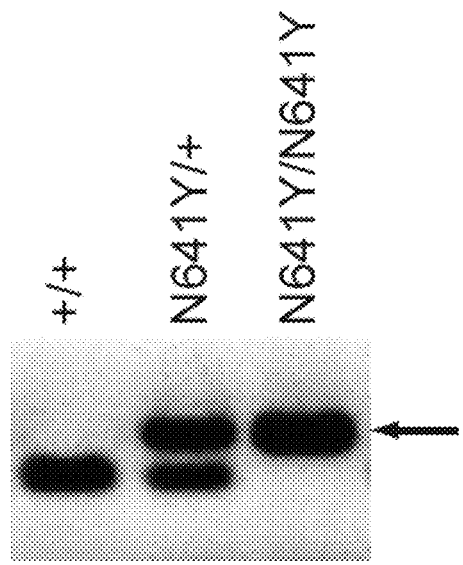
FIG. 4f shows PCR used to verify self-excision of the ACN cassette. Amplicons generated by primers flanking remaining 34 bp loxP site in intron 10 yield distinct $SCN9A^{+/+}$ (left), $SCN9A^{N641Y/+}$ (center) and $SCN9A^{N641Y/N641Y}$ (right, denoted by arrow) bands on 2% agarose.
Figure 5A:
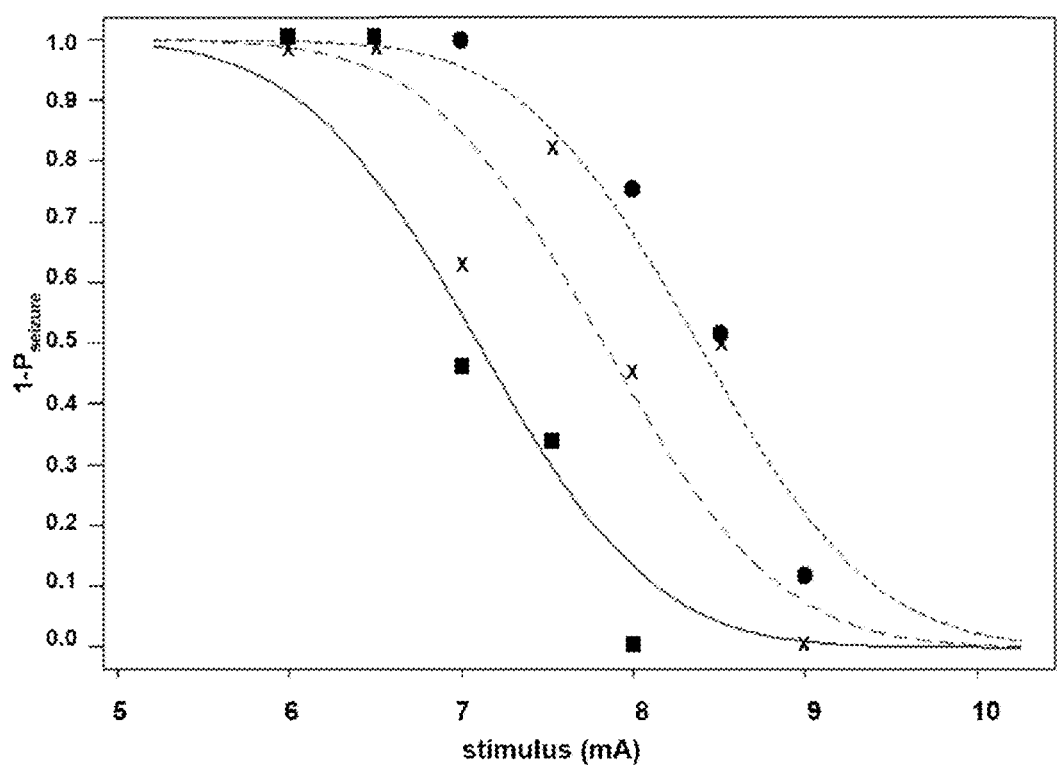
FIG. 5 shows reduced electroconvulsive seizure thresholds of Scn9a knockin mice compared to wild-type littermate controls. Convulsive current curves generated by testing (a) male B6; 129-$Scn9a^{N641Y/N641Y}$ ($CC_{50}$, 7.1 mA), B6; 129-$Scn9a^{N641Y/+}$ ($CC_{50}$, 7.83 mA) and B6; 129-$Scn9a^{+/+}$ ($CC_{50}$, 8.38 mA) mice to minimal clonus electroconvulsive seizures (−/− vs+/−p=0.008; −/− vs+/+p=0.001, n=30-68) and (b) female B6; 129-$Scn9a^{N641Y/N641Y}$ (CC50, 9.44 mA), B6; 1 29-$Scn9a^{N641Y/+}$ ($CC_{50}$, 11.16 mA) and B6; 129-$Scn9a^{+/+}$ ($CC_{50}$, 11.50 mA) mice to minimal tonic hindlimb extension electroconvulsive seizures (−/− vs+/−p<0.001; −/− vs+/+p<0.001, n=26-49). Convulsive current data are expressed in terms of 1-seizure probability (1-$P_{seizure}$) for a given stimulus (mA). Individual data points are shown for homozygote (closed square), heterozygote (x) and wild-type (closed circle) mice are used to construct curves indicated by solid, dashed and dotted lines, respectively.
Figure 5B:
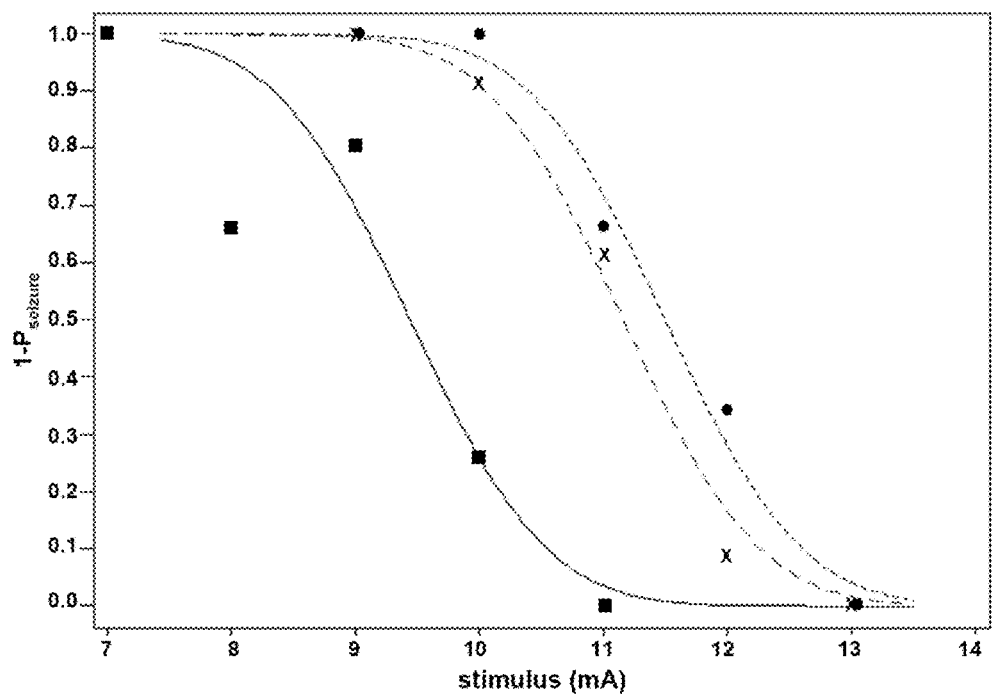

To confirm the role of SCN9A in seizure susceptibility, Scn9a targeted knockin mice were made (FIG. 4a-c) and evaluated for whether the N641Y mutation confers an altered threshold to electrically induced seizures. P25-P47 Scn9a knockin littermate mice were subjected to corneal electrical stimulation to either a clonic seizure endpoint or tonic hindlimb extension seizure endpoint that depolarizes the forebrain and hindbrain regions, respectively (Smith, M., et al. 2007). N1F2 homozygous B6; 129-$Scn9a^{N641Y/N641Y}$ knockin mice exhibited significantly reduced thresholds to minimal clonic (FIG. 5a) and minimal tonic hindlimb extension (FIG. 5b) seizures relative to their wild-type littermates. This increased seizure susceptibility conferred uniquely by the $Na_v1.7$ N641Y family mutation introduced into the mouse implicates $Na_v1.7$ in centrally mediated hyperexcitability and provides additional evidence for this mutation being causative for the seizure phenotype in K4425 affected individuals.

Figure 3:
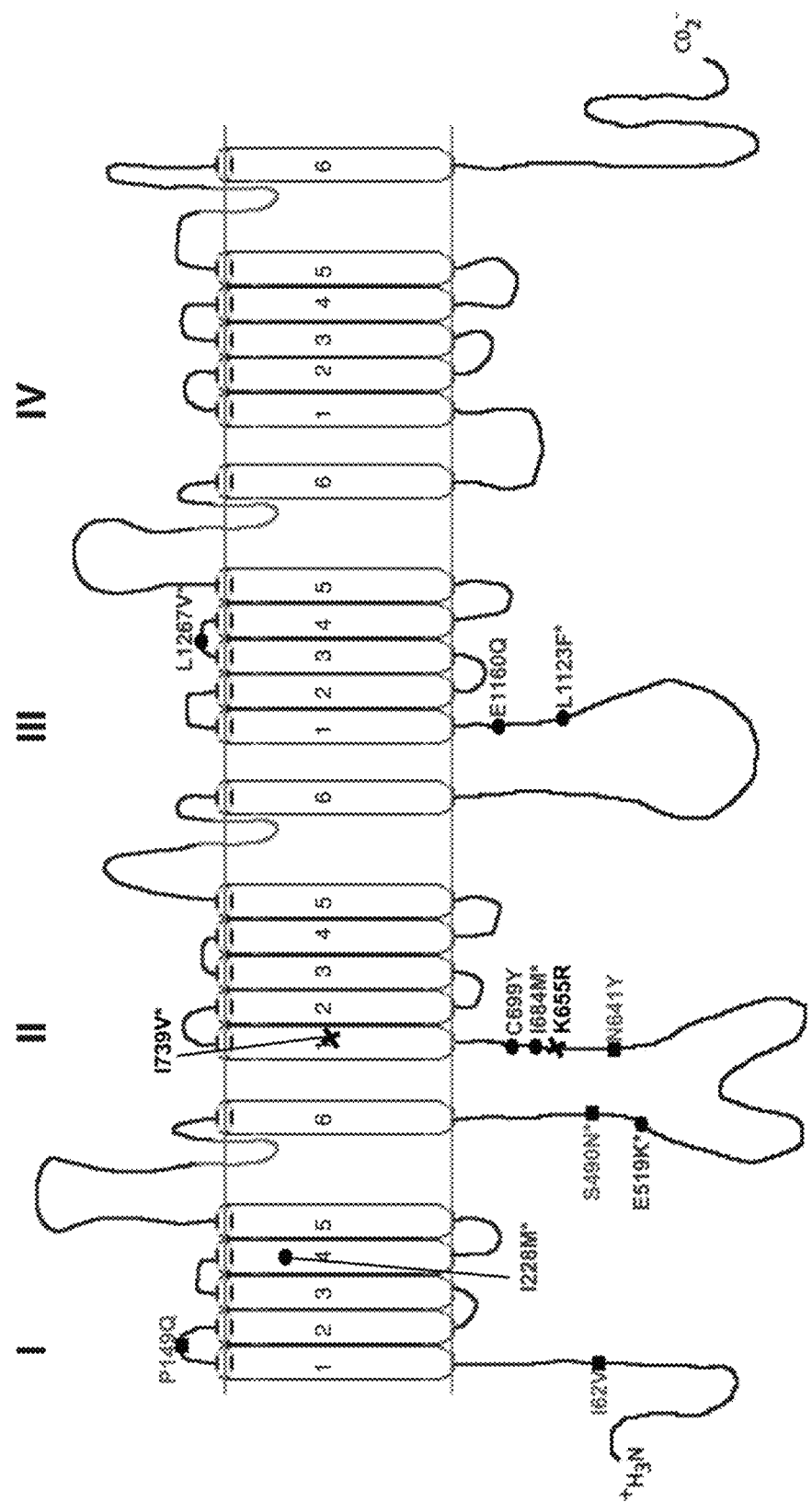
FIG. 3 is a diagram of the secondary structure of a $Na_v1.7$ sodium channel alpha-subunit where the locations of various mutations are identified. Square, mutations in FS patients; circle, mutations in Dravet syndrome patients; X, mutations in both phenotypes; *variants also found in controls.

To further assess the role of Na$_v$1.7 in FS patients, SCN9A was analyzed in a panel of 92 unrelated patients with childhood seizures occurring in the setting of a febrile illness. Four additional missense variants were identified in the Caucasian samples and 1 variant in the Hispanic samples (FIG. 3, Table 2). P149Q and K655R were not found in at least 562 ethnically matched Caucasian population control chromosomes, while S490N and I739V were found only once in at least 562 of the same controls (p=0.03 for 4/180 affected and 2/562 unaffected, Fisher's exact two tailed test). I62V was not found in 276 ethnically matched Hispanic control chromosomes (p=0.01 for 1/4 affected and 0/276 unaffected, Fisher's exact two tailed test). All seizure-associated Na$_v$1.7 variants reported here occur in codons that are highly conserved across species. Table 2 shows SCN9A is mutated in multiple patients with febrile seizures (FS) and afebrile seizures.

Figure 6:
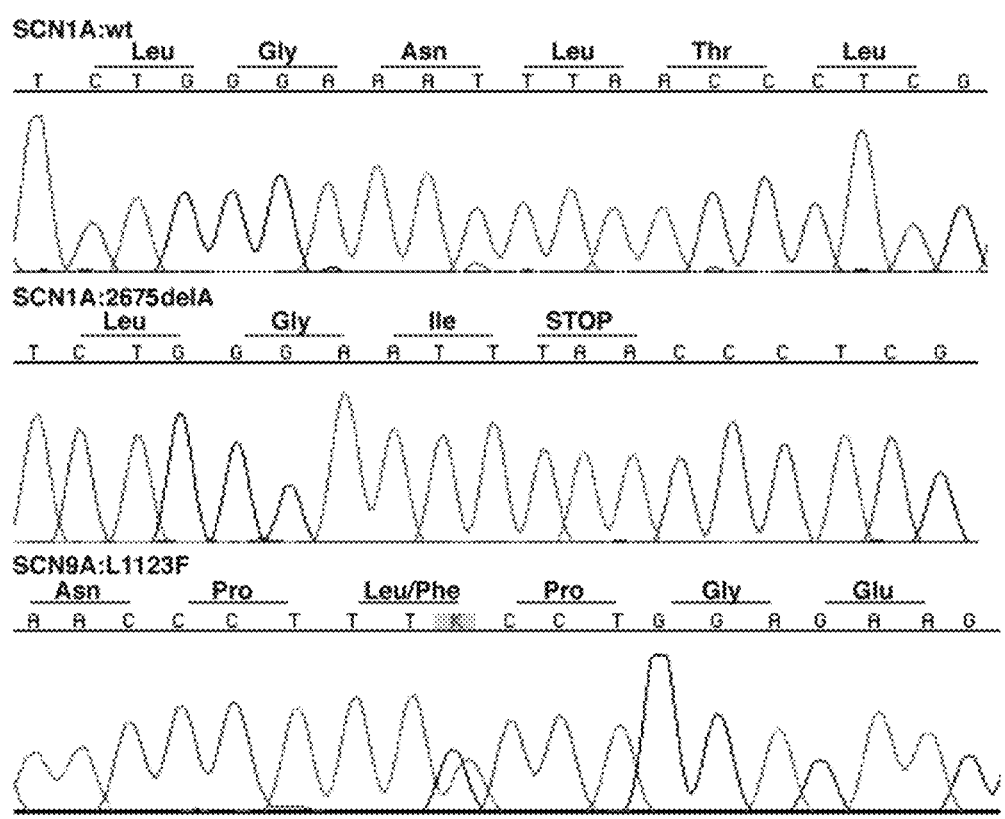
FIG. 6 shows Utah SMEI patient 34302 harbors mutations in both SCN9A and SCN1A. Sequence chromatograms of wild-type (top panel) and mutant (middle panel) clones of SCN1A exon 15 reveals a frameshift mutation (2675de1A, N892fsX2); Sequence chromotogram of genomic DNA shows a heterozygous L1123F in exon 17 of SCN9A (bottom panel).
Figure 7A:
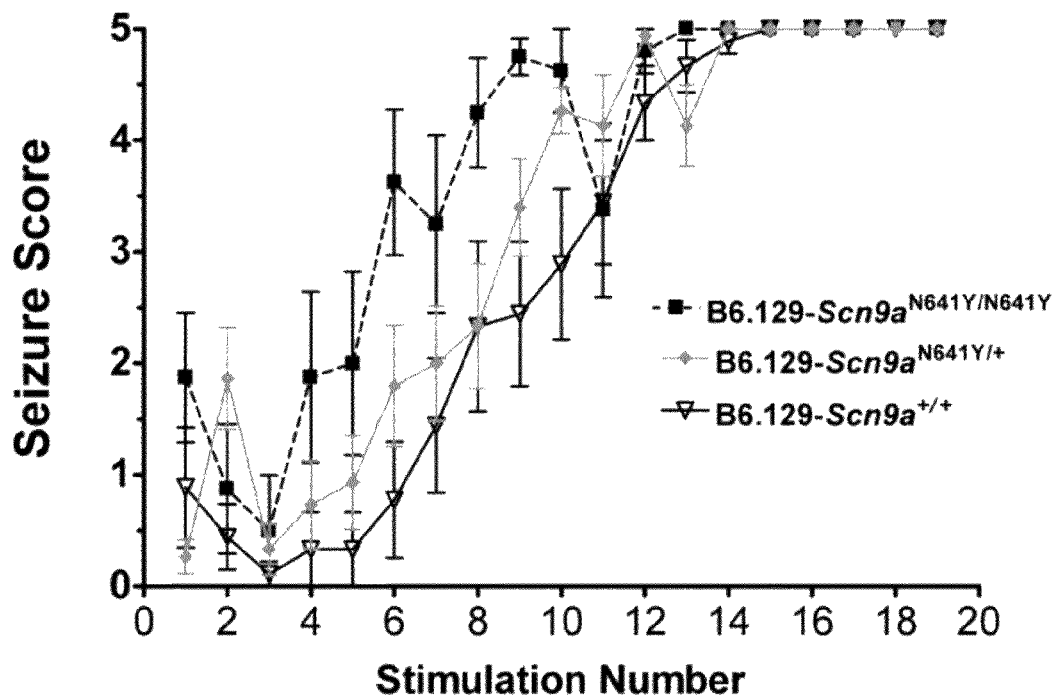
FIG. 7a shows the effect of Scn9a-N641Y on kindling acquisition for B6.129-$Scn9a^{+/+}$, B6.129-$Scn9a^{N641Y/+}$, and B6.129-$Scn9a^{N641Y/N641Y}$ mice; results are expressed as the average seizure score per genotype observed after each stimulation.
Figure 7B:
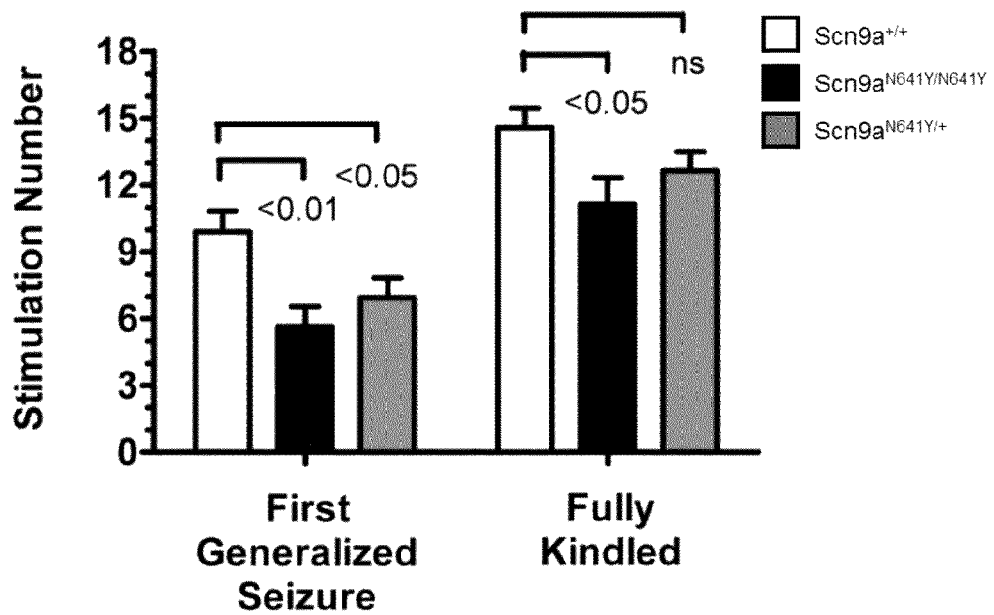
FIG. 7b shows the number of stimulations required to reach the first fully generalized Racine Stage 4-5 seizure, regraphed with p-values from the data in FIG. 7a, is 9.89±0.93 (B6.129-$Scn9a^{+/+}$), 5.63±0.92 (B6.129-$Scn9a^{N641Y/N641Y}$), and 6.93±0.89 (B6.129-$Scn9a^{N641Y/+}$), left panel; the number of stimulations required to reach a fully kindled mouse defined as four consecutive Racine Stage 4-5 seizures, regraphed with p-values from the data in panel A, is 14.56±0.88 (B6.129-$Scn9a^{+/+}$), 11.13±1.2 (B6.129-$Scn9a^{N641Y/N641Y}$), 12.64±0.86 (B6.129-$Scn9a^{N641Y/+}$), right panel.

Sequencing of SCN9A yielded an L1123F missense mutation found only once in 1736 ethnically matched population control chromosomes (Fisher's exact p-value=0.0012; FIG. 6, Table 3). Subsequent sequencing of the SCN1A gene that has a causative role in SMEI uncovered a heterozygous frameshift mutation (2675del1A, N892fsX2) in the intracellular loop between DIIS4 and DIIS5 (FIG. 6, Table 3). The SCN1A frameshift was de novo and misinheritance was ruled out by testing 31 polymorphic microsatellite markers. Segregation analysis showed that the SCN9A L1123F mutation was inherited from the asymptomatic mother with a reported extended family history of seizures.

TABLE 3

SCN9A and SCN1A mutations in SMEI cases

| sample | SCN9A variant | SCN1A variant |
|---|---|---|
| EP272.01 | I228M* | V982L |
| EPD232.1 | E519K* | None |
| EP268.01 | K655R ‡ | M934I |
| EPD72.1 | K655R ‡ | None |
| EP64.03 | I684M* | c.4338 + 1GtoA |

TABLE 2

Patients with SCN9A variants and their corresponding SCN1A mutation

| Sample | Phenotype | SCN9A (inheritance) | SCN1A (inheritance) |
|---|---|---|---|
| K4425 (n = 21) | FS, AFS, TLE | p.N641Y/c.1921A > T (AD) | none |
| 34351 | FS | p.I62V/c.184A > G (n.a.) | none |
| 40095 | FS | p.P149Q/c.446C > A (n.a.) | none |
| EPD279.1 | complex FS | p.S490N*/c.1469G > A (n.a.) | none |
| 34447 | FS, GSW, IGE | p.K655R/c.1964A > G (n.a.) | none |
| 33418 | FS, IGE | p.I739V*/c.2215A > G (P) | none |
| EP272.01 | SMEB-MA | p.I228M*/c.684C > G (M) | p.V982L/c.2944G > C (de novo) |
| EPD232.1 | Dravet | p.E519K*/c.1555G > A (M) | none |
| EP268.01 | Dravet | p.K655R/c.1964A > G (P) | p.M934I/c.2802G > A (de novo) |
| EPD72.1 | Dravet | p.K655R/c.1964A > G (n.a.) | none |
| EP64.03 | Dravet | p.I684M*/c.2052A > G (M) | c.4338+1G > A (de novo) |
| EP260.01 | Dravet | p.C699Y/c.2096G > A (P) | C.1029-1G > A (de novo) |
| EP263.01 | SMEB-MA | p.I739V*/c.2215A > G (P) | p.A1326D/c.3977C > A (de novo) |
| 34302 | Dravet | p.L1123F*/c.3369G > T (M) | p.N892fsX2/c.2675delA (de novo) |
| EPD189.1 | Dravet | p.E1160Q/c.3478G > C (M) | none |
| EPD227.1 | Dravet | p.L1267V*/c.3799C > G (n.a.) | c.3706-2A > G (n.a.) |

*in <0.3% controls; FS, febrile seizures; AFS, afebrile seizures; TLE, temporal lobe epilepsy; GSW, generalized spike wave; IGE, idiopathic generalized epilepsy; SMEB-MA, Dravet syndrome without myoclonic seizures and ataxia.
Reference sequences used are: SCN9A (NP 002968) and SCN1A (Swiss-Prot P35498).
(AD), autosomal dominant;
(P), paternal;
(M), maternal;
(n.a.), parents not available There is conservation across 8 species for 6 FS mutations, including N641Y found in an extended family (bold residues) found in SCN9A (Table 4). DNA sequencing of SCN1A, to rule out its role in FS susceptibility in these 5 FS patients with SCN9A mutations, did not reveal any disease-causing amino acid variations.

During the course of these studies on unrelated FS patients, the diagnosis of one patient 34302 progressed from atypical FS to SMEI. Beginning at five months of age, this patient experienced multiple generalized clonic seizures that were predominantly afebrile, then progressed to frequent episodes of status epilepticus and prolonged complex partial seizures by 16 months. Now 5 years old, this patient continues to have mixed seizures (including myoclonic and astatic seizures) in spite of resolute therapeutic intervention.

TABLE 3-continued

SCN9A and SCN1A mutations in SMEI cases

| sample | SCN9A variant | SCN1A variant |
|---|---|---|
| EP260.01 | C699Y | c.1029 – 1GtoA |
| EP263.01 | 1739V* ‡ | A1326D |
| 34302 | L1123F* | c.2675delA |
| EPD189.1 | E1160Q | None |
| EPD227.1 | L1267V* | c.3706 – 2AtoG |

*in <0.3% controls;
‡ in FS

TABLE 4

Seizure-associated Nav1.7 variants across species

| I62V-FS | | I684M-SMEI | |
|---|---|---|---|
| human ...KQLPFIYGDIP... | SEQ ID NO: 39 | ...MSRASILTNTV... | SEQ ID NO: 61 |
| rhesus ...KQLPFIYGDIP... | SEQ ID NO: 39 | ...MSRASILTNTV... | SEQ ID NO: 61 |
| rat ...KQLPFIYGDIP... | SEQ ID NO: 39 | ...MSRASILTNTV... | SEQ ID NO: 61 |
| mouse ...KQLPFIYGDIP... | SEQ ID NO: 39 | ...MSRASILTNTV... | SEQ ID NO: 61 |
| cow ...KQLPFIYGDIP... | SEQ ID NO: 39 | ...MSRASILTNTV... | SEQ ID NO: 61 |
| dog ...KQLPFIYGDIP... | SEQ ID NO: 39 | ...MSRVSILTNTV... | SEQ ID NO: 62 |
| rabbit ...KQLPFIYGDIP... | SEQ ID NO: 39 | ...MSRASILTNTV... | SEQ ID NO: 61 |
| chicken ...KTLPFIYGDIP... | SEQ ID NO: 39 | ...MSTAGIITNTM... | SEQ ID NO: 63 |

| P149Q-FS | | C699Y-SMEI | |
|---|---|---|---|
| human ...TMNNPPDWTKN... | SEQ ID NO: 40 | ...ESRQKCPPWWY... | SEQ ID NO: 64 |
| rhesus ...TMSNPPDWTKN... | SEQ ID NO: 41 | ...ESRQKCPPWWY... | SEQ ID NO: 64 |
| rat ...TLSNPPEWTKN... | SEQ ID NO: 42 | ...ESRQKCPPWWY... | SEQ ID NO: 64 |
| mouse ...TMSNPPDWTKN... | SEQ ID NO: 41 | ...ESRQKCPPWWY... | SEQ ID NO: 64 |
| cow ...TMSNPPDWTKN... | SEQ ID NO: 41 | ...ESRQKCPPWWY... | SEQ ID NO: 64 |
| dog ...TMSNPPDWTKN... | SEQ ID NO: 41 | ...ESRQKCPPWWY... | SEQ ID NO: 64 |
| rabbit ...TMNNPAEWTKN... | SEQ ID NO: 43 | ...ESRQKCPSWWY... | SEQ ID NO: 64 |
| chicken ...TWSKLPEWTKN... | SEQ ID NO: 44 | ...ESRQKCPPCWY... | SEQ ID NO: 64 |

| I228M-SMEI | | I739V-FS&SMEI | |
|---|---|---|---|
| human ...KTISVIPGLKT... | SEQ ID NO: 45 | ...FVDLAITICIV... | SEQ ID NO: 65 |
| rhesus ...KTISVIPGLKT... | SEQ ID NO: 45 | ...FVDLAITICIV... | SEQ ID NO: 65 |
| rat ...KTISVIPGLKT... | SEQ ID NO: 45 | ...FVDLAITICIV... | SEQ ID NO: 65 |
| mouse ...KTISVIPGLKT... | SEQ ID NO: 45 | ...FVDLAITICIV... | SEQ ID NO: 65 |
| cow ...KTISVIPGLKT... | SEQ ID NO: 45 | ...FVDLAITICIV... | SEQ ID NO: 65 |
| dog ...KTISVIPGLKT... | SEQ ID NO: 45 | ...FVDLAITICIV... | SEQ ID NO: 65 |
| rabbit ...KTISVIPGLKT... | SEQ ID NO: 45 | ...FVDLAITICIV... | SEQ ID NO: 65 |
| chicken ...KTISVIPGLKT... | SEQ ID NO: 45 | ...LVDLAITICII... | SEQ ID NO: 66 |

| S490N-FS | | L1123F-SMEI | |
|---|---|---|---|
| human ...QKKLSSGEEKG... | SEQ ID NO: 46 | ...TVDNPLPGEGE... | SEQ ID NO: 67 |
| rhesus ...QKKLSSGEEKG... | SEQ ID NO: 46 | ...TVDNPLPGEGE... | SEQ ID NO: 67 |
| rat ...QK-MSSGEEKG... | SEQ ID NO: 47 | ...TVDNPLPGE-E... | SEQ ID NO: 68 |
| mouse ...QK-LSSGEEKG... | SEQ ID NO: 48 | ...TVDNPLPGE-E... | SEQ ID NO: 68 |
| cow ...QKKLSSGEEKG... | SEQ ID NO: 46 | ...TVDNPVPGEGE... | SEQ ID NO: 69 |
| dog ...QKKLSSGEEKG... | SEQ ID NO: 46 | ...TVDNPLPGEGE... | SEQ ID NO: 69 |
| rabbit ...QKKLSSGEEKG... | SEQ ID NO: 46 | ...TVDNALPGEGE... | SEQ ID NO: 70 |
| chicken ...QREH-SGEEDN... | SEQ ID NO: 49 | ...TVNLALFGE-E... | SEQ ID NO: 71 |

| E519K-SMEI | | E1160Q-SMEI | |
|---|---|---|---|
| human ...FHLGVEGHRRA... | SEQ ID NO: 50 | ...CQVNIESGKGK... | SEQ ID NO: 72 |
| rhesus ...FHLGVEGHRRA... | SEQ ID NO: 50 | ...CQVNIESGKGK... | SEQ ID NO: 72 |
| rat ...FHLGVEGHHRT... | SEQ ID NO: 51 | ...CQVNVDSGKGK... | SEQ ID NO: 73 |
| mouse ...FHLGVEGHHRA... | SEQ ID NO: 50 | ...CQVNIDSGKGK... | SEQ ID NO: 72 |
| cow ...FHLGVEGHRRA... | SEQ ID NO: 50 | ...CQVNIESGKGK... | SEQ ID NO: 72 |
| dog ...FHLGVEGHRRA... | SEQ ID NO: 50 | ...CQVDIESGKGK... | SEQ ID NO: 74 |
| rabbit ...FHLGVEGHRLA... | SEQ ID NO: 50 | ...CQVSIESGKGK... | SEQ ID NO: 75 |
| chicken ...FRFSFDGNKLA... | SEQ ID NO: 52 | ...CRCSIESKRGI... | SEQ ID NO: 76 |

| N641Y-FS | | L1267V-SMEI | |
|---|---|---|---|
| human ...ALMLPNGQLLP... | SEQ ID NO: 53 | ...LVANTLGYSDL... | SEQ ID NO: 77 |
| rhesus ...almlpngqllp... | SEQ ID NO: 53 | ...LVANTLGYSDL... | SEQ ID NO: 77 |
| rat ...ALMLPNGQLLP... | SEQ ID NO: 53 | ...LVANTLGYSDL... | SEQ ID NO: 77 |
| mouse ...ALMLPNGQLLP... | SEQ ID NO: 53 | ...LVANTLGYSDL... | SEQ ID NO: 77 |
| cow ...ALMLPNGQLLP... | SEQ ID NO: 53 | ...LVANTLGYSDL... | SEQ ID NO: 77 |
| dog ...ALMLPNGQLLP... | SEQ ID NO: 53 | ...LVANTLGYSDL... | SEQ ID NO: 77 |
| rabbit ...ALMLPTGQLLP... | SEQ ID NO: 54 | ...LVANTLGYSDL... | SEQ ID NO: 77 |
| chicken ...CLLSPTGQLLP... | SEQ ID NO: 55 | ...LVATALGESEL... | SEQ ID NO: 78 |

TABLE 4-continued

Seizure-associated Nav1.7 variants across species

K655R FS&SMEI

| | | |
|---|---|---|
| human | ...TNQIHKKRRCS... | SEQ ID NO: 56 |
| rhesus | ...TNQIHKKRRCS... | SEQ ID NO: 56 |
| rat | ...TNQMRKKRLSS... | SEQ ID NO: 57 |
| mouse | ...TNQMRKKRLSS... | SEQ ID NO: 57 |
| cow | ...TNQIHKKRRHS... | SEQ ID NO: 58 |
| dog | ...TNQIHKKRRSS... | SEQ ID NO: 58 |
| rabbit | ...T-QIRKKRRSS... | SEQ ID NO: 59 |
| chicken | ...TEMEIKKRRSS... | SEQ ID NO: 60 |

Upper case, amino acids from the UCSC genome browser (genome.ucsc.edu)
Lower case (rhesus, N641Y), amino acid translation inferred from corresponding bac clones.

The finding of both SCN1A and SCN9A variants in a single patient led to investigation of whether additional disease-associated alleles in SCN9A contribute to SMEI. In an analysis of a cohort of 109 SMEI patients, 8 additional variants within the transmembrane domains and intracellular loops of Na$_v$1.7 were identified in 9 patients. C699Y, K655R and E1160Q were not found in at least 576 control chromosomes and the remaining 5 variants were found in 0.3% of at least 576 control chromosomes (p=0.004 for 9/218 SMEI syndrome cases and 5/576 population controls, Fisher's exact two-tailed test). Of the 9 SMEI patients with SCN9A variants, six harbor either splice site or missense mutations in SCN1A (Table 3,). Two of these mutations (K655R and I739V) are also found in the FS patients. In the three remaining SMEI patients without SCN1A mutations, additional proconvulsive genes that act in concert with SCN9A can be uncovered. This genetic data strongly supports the notion that mutations in at least two separate genes can occur in patients with SMEI.

As demonstrated herein, variation in the SCN9A sodium channel alpha subunit gene is associated with a wide clinical spectrum of seizure phenotypes, from simple FS to later self-limited afebrile seizures, to SMEI. The discovery of compound SCN9A and SCN1A mutations in SMEI patients explains the especially severe manifestation of seizures compared to the reduced seizure expressivity seen in their relatives with presumed monogenic mutations. The SMEI finding now adds epilepsy to the list of "modifier" digenic inheritance disorders that include polycystic kidney disease and deafness, where additive or epistatic alleles are associated with an increasing spectrum of phenotypes (Ming, J. E. & Muenke, M. 2002). Notably, none of the disclosed FS or SMEI mutations overlap with the disease-associated changes found in the extreme pain or congenital indifference to pain disorders (Cox, J. J. et al. 2006; Fertleman, C. R. et al. 2006; Yang, Y. et al. 2004). Furthermore, an increased incidence of seizures is not reported in patients with SCN9A mutations and primary erythermalgia, paroxysmal extreme pain disorder or the congenital inability to experience pain (Cox, J. J. et al. 2006; Fertleman, C. R. et al. 2006; Yang, Y. et al. 2004). After follow-up questioning, none of the affected members of K4425 reported extreme pain phenotypes. The notion that dysfunction in the same ion channel can be associated in distinct paroxysmal phenotypes is supported by the identification of unique SCN1A mutations in epilepsy and familial hemiplegic migraine (Dichgans, M. et al. 2005). Aberrant electrical properties conferred by SCN9A mutations are clearly neuron specific (Waxman, S. G. 2007) and the current study indicates that they are temperature dependent.

ii. Methods

Mutation detection of patient and control DNA samples. Institutional Review Board informed consent was obtained from all participants. DNA isolated from blood (Puregene) was sequenced using primers designed outside the exons of SCN9A followed by standard ABI technology at the University of Utah Sequencing Core Facility. Sequence was analyzed using the Sequencher program (Gene Codes Corporation). Mutation detection of control and disease cohorts was done either by sequencing or by the LightScanner® system using the manufacturer's recommendations (Idaho Technology). Copy number variation analysis comparing two affected individuals and their respective unaffected parent was performed using the Agilent array comparative genomic hybridization platform in accordance with the manufacturer's specifications and deletion duplication analysis was performed using the multiplex amplicon quantification method (Suls, A. et al. 2006). Fisher's exact two-tailed test was performed to assess significance.

Generation of B6.129-Scn9a knockin mice. Wild-type clones of Scn9A were isolated from a mouse BAC clone library (CHORI) and subcloned into pUC18. The N641Y point mutation in exon 11 was introduced using the Quick-Change® II XL system (Stratagene). The ACN cassette was cloned into a PmII site in intron 10 and this construct was cloned into a thymidine kinase (TK) vector (Bunting, M., et al. 1999). Within the ACN cassette the neomycin (neo) gene driven by the mouse RNA polymerase II promoter (polII) confers positive selection and the TK gene confers negative selection of ES cells. The targeting vector was linearized with NotI, introduced by electroporation into R1 ES cells (Nagy et al., 1993) and selected for resistance to G418 and FIAU. DNA from 104 colonies was isolated and screened for homologous recombination by PCR using primers designed outside the construct and within the ACN cassette. Three positives were sequenced to determine the presence of the mutation. Southern blot analysis was done on three SspI cut ES cell clones to verify presence and orientation of endogenous and targeted alleles. Hybridization of $^{32}$P-labelled probe in intron 11 yields an 8.4 kb endogenous band and a 7.2 kb targeted band in mutation positive sample. ES cells from this single targeted clone were aggregated with C57BL/6-derived morulae, and implanted into a pseudo-pregnant C57BL/6 female. During chimeric male spermatogenesis, Cre recombinase (Cre) driven by the murine angiotensin-converting enzyme promoter, tACE, confers loxP-mediated excision of the ACN cassette to yield a single remaining loxP site. Chimeric progeny were identified by coat color and nine males were crossed to C57BL/6J (Jackson labs) females for the generation of F1 offspring. F1 offspring were intercrossed to generate F2 experimental animals.

To detect Cre-mediated self-excision of the ACN cassette and presence of the mutation, genomic DNA obtained from tail biopsies of F1 and F2 animals was analyzed. PCR primers were used to asymmetrically amplify a product containing the mutated base pair. An unlabeled oligonucleotide probe complimentary to the excess strand in the region surrounding the mutated base was included and the reaction melted using a LightScanner® (Idaho Technology) instrument. Melt curves were analyzed using LightScanner® software (Idaho Technology) and distinct melt profiles were recognizable for each genotype. To verify self-excision, primers surrounding the remaining loxP site were used to amplify PCR products that were electrophoresed on a 2% agarose gel. The presence of a single loxP site verifies self-excision. Mouse colonies were maintained and used experimentally at the University of Utah in accordance with Institutional Animal Care and Use Committee approved protocols.

Evaluation of electrical thresholds in $Scn9a^{+/+}$, $Scn9a^{+/N641Y}$ and $Scn9a^{N641Y/N641Y}$ littermate mice. For baseline seizure threshold estimates, seizure incidence was determined at several different stimulus intensities according to the staircase estimation procedure (White, H. S., et al. 2002). Convulsive current (CC) curves were then constructed from these data by Probit analysis, and $CC_{1-99}$ values statistical comparisons were calculated using Minitab 13 (State College, Pa., U.S.A.) and p values are calculated for full CC curve comparisons. CC curves for knockin mice were compared with those of littermate wild-type mice and seizure thresholds were considered significantly different at p<0.05. Two different stimulation protocols were used in an effort to differentiate the effects of genotype on forebrain (minimal clonic) and hindbrain (minimal tonic hindlimb extension) seizure thresholds. Seizures were induced at varying intensities using a 60-Hz, 0.2-ms sinusoidal current pulse with a stimulator previously described (White, H. S., et al. 2002). A drop of tetracaine (0.5%) was administered to each eye just before testing. Minimal clonic seizures are characterized by rhythmic face and forelimb clonus, rearing and falling and ventral neck flexion. Minimal tonic hindlimb extension seizures are characterized by a tonic-clonic flexion-extension sequence that starts with tonic forelimb extension, followed by hindlimb flexion, and terminates in full tonic hindlimb extension (180 degrees to the torso; White, H. S., et al. 2002).

What is claimed is:

1. An expression vector comprising an isolated nucleic acid that encodes an amino acid comprising the sequence set forth in any of SEQ ID NOs: 79, 80, 81, 82, 83, 84, or 85 operably linked to an expression control sequence, wherein the isolated nucleic acid is heterologous to the expression vector.

2. The expression vector of claim 1, wherein the isolated nucleic acid comprises the sequence as set forth in any of SEQ ID NOs: 86, 87, 88, 89, 90, 91, or 92.

3. A cultured cell comprising the vector of claim 1.

4. A method of making a mutant Nav1.7 sodium channel alpha subunit comprising culturing the cell of claim 3 under conditions allowing expression of the polypeptide encoded by the nucleic acid, wherein the polypeptide comprises a mutant Nav1.7 sodium channel.

* * * * *

SEQUENCE LISTING

```
<160> NUMBER OF SEQ ID NOS: 99

<210> SEQ ID NO 1
<211> LENGTH: 5934
<212> TYPE: DNA
<213> ORGANISM: Homo sapiens

<400> SEQUENCE: 1
atggcaatgt tgcctccccc aggacctcag agctttgtcc atttcacaaa acagtctctt      60
gccctcattg aacaacgcat tgctgaaaga aaatcaaagg aacccaaaga agaaaagaaa     120
gatgatgatg aagaagcccc aaagccaagc agtgacttgg aagctggcaa acaactgccc     180
ttcatctatg gggacattcc tcccggcatg gtgtcagagc ccctggagga cttggacccc     240
tactatgcag acaaaaagac tttcatagta ttgaacaaag ggaaaacaat cttccgtttc     300
aatgccacac ctgctttata tatgctttct cctttcagtc ctctaagaag aatatctatt     360
aagattttag tacactcctt attcagcatg ctcatcatgt gcactattct gacaaactgc     420
atatttatga ccatgaataa cccgccggac tggaccaaaa atgtcgagta cactttttact     480 ggaatatata cttttgaatc acttgtaaaa atccttgcaa gaggcttctg tgtaggagaa     540 ttcactttc ttcgtgaccc gtggaactgg ctggattttg tcgtcattgt ttttgcgtat     600
ttaacagaat ttgtaaacct aggcaatgtt tcagctcttc gaactttcag agtattgaga     660
gctttgaaaa ctatttctgt aatcccaggc ctgaagacaa ttgtaggggc tttgatccag     720
tcagtgaaga agctttctga tgtcatgatc ctgactgtgt tctgtctgag tgtgtttgca     780
ctaattggac tacagctgtt catgggaaac ctgaagcata aatgttttcg aaattcactt     840
gaaaataatg aaacattaga aagcataatg aataccctag agagtgaaga agactttaga     900
aaatattttt attacttgga aggatccaaa gatgctctcc tttgtggttt cagcacagat     960
tcaggtcagt gtccagaggg gtacacctgt gtgaaaattg gcagaaaccc tgattatggc    1020
tacacgagct ttgacacttt cagctgggcc ttcttagcct tgtttaggct aatgacccaa    1080
gattactggg aaaaccttta ccaacagacg ctgcgtgctg ctggcaaaac ctacatgatc    1140
ttctttgtcg tagtgatttt cctgggctcc tttatcctaa taaacttgat cctggctgtg    1200
```

```
gttgccatgg catatgaaga acagaaccag gcaaacattg aagaagctaa acagaaagaa      1260
ttagaatttc aacagatgtt agaccgtctt aaaaaagagc aagaagaagc tgaggcaatt      1320
gcagcggcag cggctgaata tacaagtatt aggagaagca gaattatggg cctctcagag      1380
agttcttctg aaacatccaa actgagctct aaaagtgcta agaaagaag aaacagaaga      1440 aagaaaaaga atcaaaagaa gctctccagt ggagaggaaa agggagatgc tgagaaattg      1500
tcgaaatcag aatcagagga cagcatcaga agaaaaagtt ccaccttgg tgtcgaaggg      1560 cataggcgag cacatgaaaa gaggttgtct accccaatc agtcaccact cagcattcgt      1620
ggctccttgt tttctgcaag gcgaagcagc agaacaagtc ttttagttt caaaggcaga      1680 ggaagagata taggatctga gactgaattt gccgatgatg agcacagcat ttttggagac      1740
aatgagagca gaaggggctc actgtttgtg ccccacagac cccaggagcg acgcagcagt      1800
aacatcagcc aagccagtag gtccccacca atgctgccgg tgaacgggaa aatgcacagt      1860
gctgtggact gcaacggtgt ggtctccctg gttgatggac gctcagccct catgctcccc      1920 aatgacagc ttctgccaga gggcacgacc aatcaaatac acaagaaaag gcgttgtagt      1980
tcctatctcc tttcagagga tatgctgaat gatcccaacc tcagacagag agcaatgagt      2040
agagcaagca tattaacaaa cactgtggaa gaacttgaag agtccagaca aaaatgtcca      2100
ccttggtggt acagatttgc acacaaattc ttgatctgga attgctctcc atattggata      2160
aaattcaaaa agtgtatcta ttttattgta atggatcctt ttgtagatct tgcaattacc      2220
atttgcatag ttttaaacac attatttatg gctatggaac accacccaat gactgaggaa      2280
ttcaaaaatg tacttgctat aggaaatttg gtctttactg gaatctttgc agctgaaatg      2340
gtattaaaac tgattgccat ggatccatat gagtatttcc aagtaggctg gaatattttt      2400
gacagcctta ttgtgacttt aagtttagtg gagctctttc tagcagatgt ggaaggattg      2460
tcagttctgc gatcattcag actgctccga gtcttcaagt tggcaaaatc ctggccaaca      2520
ttgaacatgt tgattaagat cattggtaac tcagtagggg ctctaggtaa cctcaccctta      2580 gtgttggcca tcatcgtctt cattttttgct gtggtcggca tgcagctctt tggtaagagc      2640
tacaaagaat gtgtctgcaa gatcaatgat gactgtacgc tcccacggtg gcacatgaac      2700
gacttcttcc actccttcct gattgtgttc cgcgtgctgt gtggagagtg gatagagacc      2760
atgtgggact gtatggaggt cgctggtcaa gctatgtgcc ttattgtta catgatggtc      2820 atggtcattg gaaacctggt ggtcctaaac ctatttctgg ccttattatt gagctcattt      2880
agttcagaca atcttacagc aattgaagaa gaccctgatg caaacaacct ccagattgca      2940
gtgactagaa ttaaaaaggg aataaattat gtgaaacaaa ccttacgtga atttattcta      3000
aaagcatttt ccaaaaagcc aaagatttcc agggagataa gacaagcaga agatctgaat      3060
actaagaagg aaaactatat ttctaaccat acacttgctg aaatgagcaa aggtcacaat      3120
ttcctcaagg aaaaagataa aatcagtggt tttggaagca gcgtggacaa acacttgatg      3180
gaagacagtg atggtcaatc atttattcac aatcccagcc tcacagtgac agtgccaatt      3240
gcacctgggg aatccgattt ggaaaatatg aatgctgagg aacttagcag tgattcggat      3300
agtgaataca gcaaagtgag attaaaccgg tcaagctcct cagagtgcag cacagttgat      3360 aacccttgc ctggagaagg agaagaagca gaggctgaac ctatgaattc cgatgagcca      3420
gaggcctgtt tcacagatgg ttgtgtacgg aggttctcat gctgccaagt taacatagag      3480
tcagggaaag gaaaaatctg gtggaacatc aggaaaacct gctacaagat tgttgaacac      3540
agttggtttg aaagcttcat tgtcctcatg atcctgctca gcagtggtgc cctggctttt      3600
```

```
gaagatattt atattgaaag gaaaaagacc attaagatta tcctggagta tgcagacaag    3660
atcttcactt acatcttcat tctggaaatg cttctaaaat ggatagcata tggttataaa    3720
acatatttca ccaatgcctg gtgttggctg gatttcctaa ttgttgatgt ttctttggtt    3780
actttagtgg caaacactct tggctactca gatcttggcc ccattaaatc ccttcggaca    3840
ctgagagctt taagacctct aagagcctta tctagatttg aaggaatgag ggtcgttgtg    3900
aatgcactca taggagcaat tccttccatc atgaatgtgc tacttgtgtg tcttatattc    3960
tggctgatat tcagcatcat gggagtaaat ttgtttgctg gcaagttcta tgagtgtatt    4020
aacaccacag atgggtcacg gtttcctgca agtcaagttc caaatcgttc cgaatgtttt    4080
gcccttatga atgttagtca aaatgtgcga tggaaaaacc tgaaagtgaa ctttgataat    4140
gtcggacttg gttacctatc tctgcttcaa gttgcaactt ttaagggatg gacgattatt    4200
atgtatgcag cagtggattc tgttaatgta gacaagcagc ccaaatatga atatagcctc    4260
tacatgtata tttattttgt cgtctttatc atctttgggt cattcttcac tttgaacttg    4320
ttcattggtg tcatcataga taatttcaac caacagaaaa agaagcttgg aggtcaagac    4380
atctttatga cagaagaaca gaagaaatac tataatgcaa tgaaaaagct ggggtccaag    4440
aagccacaaa agccaattcc tcgaccaggg aacaaaatcc aaggatgtat atttgaccta    4500
gtgacaaatc aagcctttga tattagtatc atggttctta tctgtctcaa catggtaacc    4560
atgatggtag aaaaggaggg tcaaagtcaa catatgactg aagtttttata ttggataaat    4620 gtggtttta taatcctttt cactggagaa tgtgtgctaa aactgatctc cctcagacac    4680
tactacttca ctgtaggatg gaatattttt gattttgtgg ttgtgattat ctccattgta    4740
ggtatgtttc tagctgattt gattgaaacg tattttgtgt cccctaccct gttccgagtg    4800
atccgtcttg ccaggattgg ccgaatccta cgtctagtca aaggagcaaa ggggatccgc    4860
acgctgctct ttgctttgat gatgtccctt cctgcgttgt taacatcgg cctcctgctc    4920 ttcctggtca tgttcatcta cgccatcttt ggaatgtcca actttgccta tgttaaaaag    4980
gaagatggaa ttaatgacat gttcaatttt gagacctttg caacagtat gatttgcctg    5040 ttccaaatta caacctctgc tggctgggat ggattgctag cacctattct taacagtaag    5100
ccacccgact gtgacccaaa aaaagttcat cctggaagtt cagttgaagg agactgtggt    5160
aacccatctg ttgaatatt ctactttgtt agttatatca tcatatcctt cctggttgtg    5220
gtgaacatgt acattgcagt catactggag aattttagtg ttgccactga agaaagtact    5280
gaacctctga gtgaggatga ctttgagatg ttctatgagg tttgggagaa gtttgatccc    5340
gatgcgaccc agtttataga gttctctaaa ctctctgatt ttgcagctgc cctggatcct    5400
cctcttctca tagcaaaacc caacaaagtc cagctcattg ccatggatct gcccatggtt    5460
agtggtgacc ggatccattg tcttgacatc ttatttgctt ttacaaagcg tgttttgggt    5520
gagagtgggg agatggattc tcttcgttca cagatggaag aaaggttcat gtctgcaaat    5580
ccttccaaag tgtcctatga acccatcaca accacactaa aacggaaaca agaggatgtg    5640
tctgctactg tcattcagcg tgcttataga cgttaccgct taaggcaaaa tgtcaaaaat    5700
atatcaagta tatacataaa agatggagac agagatgatg atttactcaa taaaaaagat    5760
atggcttttg ataatgttaa tgagaactca agtccagaaa aacagatgc cacttcatcc    5820 accacctctc caccttcata tgatagtgta acaaagccag acaaagagaa atatgaacaa    5880
gacagaacag aaaaggaaga caaagggaaa gacagcaagg aaagcaaaaa atag          5934
```

```
<210> SEQ ID NO 2
<211> LENGTH: 1977
<212> TYPE: PRT
<213> ORGANISM: Homo sapiens

<400> SEQUENCE: 2

Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
            20                  25                  30

Lys Glu Pro Lys Glu Glu Lys Lys Asp Asp Asp Glu Glu Ala Pro Lys
        35                  40                  45

Pro Ser Ser Asp Leu Glu Ala Gly Lys Gln Leu Pro Phe Val Tyr Gly
    50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
    210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
        275                 280                 285

Ile Met Asn Thr Leu Glu Ser Glu Glu Asp Phe Arg Lys Tyr Phe Tyr
    290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
        355                 360                 365

Gln Thr Leu Arg Ala Ala Gly Lys Thr Tyr Met Ile Phe Phe Val Val
    370                 375                 380
```

```
Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
            405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Glu Tyr Thr
        435                 440                 445

Ser Ile Arg Arg Ser Arg Ile Met Gly Leu Ser Glu Ser Ser Ser Glu
        450                 455                 460

Thr Ser Lys Leu Ser Ser Lys Ser Ala Lys Glu Arg Arg Asn Arg Arg
465                 470                 475                 480

Lys Lys Lys Asn Gln Lys Lys Leu Ser Ser Gly Glu Glu Lys Gly Asp
            485                 490                 495

Ala Glu Lys Leu Ser Lys Ser Glu Ser Glu Asp Ser Ile Arg Arg Lys
            500                 505                 510

Ser Phe His Leu Gly Val Glu Gly His Arg Arg Ala His Glu Lys Arg
        515                 520                 525

Leu Ser Thr Pro Asn Gln Ser Pro Leu Ser Ile Arg Gly Ser Leu Phe
    530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
            565                 570                 575

Ile Phe Gly Asp Asn Glu Ser Arg Arg Gly Ser Leu Phe Val Pro His
            580                 585                 590

Arg Pro Gln Glu Arg Arg Ser Ser Asn Ile Ser Gln Ala Ser Arg Ser
        595                 600                 605

Pro Pro Met Leu Pro Val Asn Gly Lys Met His Ser Ala Val Asp Cys
        610                 615                 620

Asn Gly Val Val Ser Leu Val Asp Gly Arg Ser Ala Leu Met Leu Pro
625                 630                 635                 640

Asn Gly Gln Leu Leu Pro Glu Gly Thr Thr Asn Gln Ile His Lys Lys
            645                 650                 655

Arg Arg Cys Ser Ser Tyr Leu Leu Ser Glu Asp Met Leu Asn Asp Pro
            660                 665                 670

Asn Leu Arg Gln Arg Ala Met Ser Arg Ala Ser Ile Leu Thr Asn Thr
        675                 680                 685

Val Glu Glu Leu Glu Glu Ser Arg Gln Lys Cys Pro Pro Trp Trp Tyr
    690                 695                 700

Arg Phe Ala His Lys Phe Leu Ile Trp Asn Cys Ser Pro Tyr Trp Ile
705                 710                 715                 720

Lys Phe Lys Lys Cys Ile Tyr Phe Ile Val Met Asp Pro Phe Val Asp
            725                 730                 735

Leu Ala Ile Thr Ile Cys Ile Val Leu Asn Thr Leu Phe Met Ala Met
            740                 745                 750

Glu His His Pro Met Thr Glu Glu Phe Lys Asn Val Leu Ala Ile Gly
        755                 760                 765

Asn Leu Val Phe Thr Gly Ile Phe Ala Ala Glu Met Val Leu Lys Leu
    770                 775                 780

Ile Ala Met Asp Pro Tyr Glu Tyr Phe Gln Val Gly Trp Asn Ile Phe
785                 790                 795                 800
```

-continued

```
Asp Ser Leu Ile Val Thr Leu Ser Leu Val Glu Leu Phe Leu Ala Asp
            805                 810                 815
Val Glu Gly Leu Ser Val Leu Arg Ser Phe Arg Leu Leu Arg Val Phe
        820                 825                 830
Lys Leu Ala Lys Ser Trp Pro Thr Leu Asn Met Leu Ile Lys Ile Ile
    835                 840                 845
Gly Asn Ser Val Gly Ala Leu Gly Asn Leu Thr Leu Val Leu Ala Ile
850                 855                 860
Ile Val Phe Ile Phe Ala Val Val Gly Met Gln Leu Phe Gly Lys Ser
865                 870                 875                 880
Tyr Lys Glu Cys Val Cys Lys Ile Asn Asp Asp Cys Thr Leu Pro Arg
                885                 890                 895
Trp His Met Asn Asp Phe Phe His Ser Phe Leu Ile Val Phe Arg Val
            900                 905                 910
Leu Cys Gly Glu Trp Ile Glu Thr Met Trp Asp Cys Met Glu Val Ala
        915                 920                 925
Gly Gln Ala Met Cys Leu Ile Val Tyr Met Met Val Met Val Ile Gly
    930                 935                 940
Asn Leu Val Val Leu Asn Leu Phe Leu Ala Leu Leu Leu Ser Ser Phe
945                 950                 955                 960
Ser Ser Asp Asn Leu Thr Ala Ile Glu Glu Asp Pro Asp Ala Asn Asn
                965                 970                 975
Leu Gln Ile Ala Val Thr Arg Ile Lys Lys Gly Ile Asn Tyr Val Lys
            980                 985                 990
Gln Thr Leu Arg Glu Phe Ile Leu Lys Ala Phe Ser Lys Lys Pro Lys
        995                 1000                1005
Ile Ser Arg Glu Ile Arg Gln Ala Glu Asp Leu Asn Thr Lys Lys
        1010                1015                1020
Glu Asn Tyr Ile Ser Asn His Thr Leu Ala Glu Met Ser Lys Gly
        1025                1030                1035
His Asn Phe Leu Lys Glu Lys Asp Lys Ile Ser Gly Phe Gly Ser
        1040                1045                1050
Ser Val Asp Lys His Leu Met Glu Asp Ser Asp Gly Gln Ser Phe
        1055                1060                1065
Ile His Asn Pro Ser Leu Thr Val Thr Val Pro Ile Ala Pro Gly
        1070                1075                1080
Glu Ser Asp Leu Glu Asn Met Asn Ala Glu Glu Leu Ser Ser Asp
        1085                1090                1095
Ser Asp Ser Glu Tyr Ser Lys Val Arg Leu Asn Arg Ser Ser Ser
        1100                1105                1110
Ser Glu Cys Ser Thr Val Asp Asn Pro Leu Pro Gly Glu Gly Glu
        1115                1120                1125
Glu Ala Glu Ala Glu Pro Met Asn Ser Asp Glu Pro Glu Ala Cys
        1130                1135                1140
Phe Thr Asp Gly Cys Val Arg Arg Phe Ser Cys Cys Gln Val Asn
        1145                1150                1155
Ile Glu Ser Gly Lys Gly Lys Ile Trp Trp Asn Ile Arg Lys Thr
        1160                1165                1170
Cys Tyr Lys Ile Val Glu His Ser Trp Phe Glu Ser Phe Ile Val
        1175                1180                1185
Leu Met Ile Leu Leu Ser Ser Gly Ala Leu Ala Phe Glu Asp Ile
        1190                1195                1200
Tyr Ile Glu Arg Lys Lys Thr Ile Lys Ile Ile Leu Glu Tyr Ala
```

-continued

```
            1205                1210                1215
Asp Lys Ile Phe Thr Tyr Ile Phe Ile Leu Glu Met Leu Leu Lys
    1220                1225                1230
Trp Ile Ala Tyr Gly Tyr Lys Thr Tyr Phe Thr Asn Ala Trp Cys
    1235                1240                1245
Trp Leu Asp Phe Leu Ile Val Asp Val Ser Leu Val Thr Leu Val
    1250                1255                1260
Ala Asn Thr Leu Gly Tyr Ser Asp Leu Gly Pro Ile Lys Ser Leu
    1265                1270                1275
Arg Thr Leu Arg Ala Leu Arg Pro Leu Arg Ala Leu Ser Arg Phe
    1280                1285                1290
Glu Gly Met Arg Val Val Val Asn Ala Leu Ile Gly Ala Ile Pro
    1295                1300                1305
Ser Ile Met Asn Val Leu Leu Val Cys Leu Ile Phe Trp Leu Ile
    1310                1315                1320
Phe Ser Ile Met Gly Val Asn Leu Phe Ala Gly Lys Phe Tyr Glu
    1325                1330                1335
Cys Ile Asn Thr Thr Asp Gly Ser Arg Phe Pro Ala Ser Gln Val
    1340                1345                1350
Pro Asn Arg Ser Glu Cys Phe Ala Leu Met Asn Val Ser Gln Asn
    1355                1360                1365
Val Arg Trp Lys Asn Leu Lys Val Asn Phe Asp Asn Val Gly Leu
    1370                1375                1380
Gly Tyr Leu Ser Leu Leu Gln Val Ala Thr Phe Lys Gly Trp Thr
    1385                1390                1395
Ile Ile Met Tyr Ala Ala Val Asp Ser Val Asn Val Asp Lys Gln
    1400                1405                1410
Pro Lys Tyr Glu Tyr Ser Leu Tyr Met Tyr Ile Tyr Phe Val Val
    1415                1420                1425
Phe Ile Ile Phe Gly Ser Phe Phe Thr Leu Asn Leu Phe Ile Gly
    1430                1435                1440
Val Ile Ile Asp Asn Phe Asn Gln Gln Lys Lys Lys Leu Gly Gly
    1445                1450                1455
Gln Asp Ile Phe Met Thr Glu Glu Gln Lys Lys Tyr Tyr Asn Ala
    1460                1465                1470
Met Lys Lys Leu Gly Ser Lys Lys Pro Gln Lys Pro Ile Pro Arg
    1475                1480                1485
Pro Gly Asn Lys Ile Gln Gly Cys Ile Phe Asp Leu Val Thr Asn
    1490                1495                1500
Gln Ala Phe Asp Ile Ser Ile Met Val Leu Ile Cys Leu Asn Met
    1505                1510                1515
Val Thr Met Met Val Glu Lys Glu Gly Gln Ser Gln His Met Thr
    1520                1525                1530
Glu Val Leu Tyr Trp Ile Asn Val Val Phe Ile Ile Leu Phe Thr
    1535                1540                1545
Gly Glu Cys Val Leu Lys Leu Ile Ser Leu Arg His Tyr Tyr Phe
    1550                1555                1560
Thr Val Gly Trp Asn Ile Phe Asp Phe Val Val Val Ile Ile Ser
    1565                1570                1575
Ile Val Gly Met Phe Leu Ala Asp Leu Ile Glu Thr Tyr Phe Val
    1580                1585                1590
Ser Pro Thr Leu Phe Arg Val Ile Arg Leu Ala Arg Ile Gly Arg
    1595                1600                1605
```

```
Ile Leu Arg Leu Val Lys Gly Ala Lys Gly Ile Arg Thr Leu Leu
1610                1615                1620

Phe Ala Leu Met Met Ser Leu Pro Ala Leu Phe Asn Ile Gly Leu
1625                1630                1635

Leu Leu Phe Leu Val Met Phe Ile Tyr Ala Ile Phe Gly Met Ser
1640                1645                1650

Asn Phe Ala Tyr Val Lys Lys Glu Asp Gly Ile Asn Asp Met Phe
1655                1660                1665

Asn Phe Glu Thr Phe Gly Asn Ser Met Ile Cys Leu Phe Gln Ile
1670                1675                1680

Thr Thr Ser Ala Gly Trp Asp Gly Leu Leu Ala Pro Ile Leu Asn
1685                1690                1695

Ser Lys Pro Pro Asp Cys Asp Pro Lys Lys Val His Pro Gly Ser
1700                1705                1710

Ser Val Glu Gly Asp Cys Gly Asn Pro Ser Val Gly Ile Phe Tyr
1715                1720                1725

Phe Val Ser Tyr Ile Ile Ile Ser Phe Leu Val Val Val Asn Met
1730                1735                1740

Tyr Ile Ala Val Ile Leu Glu Asn Phe Ser Val Ala Thr Glu Glu
1745                1750                1755

Ser Thr Glu Pro Leu Ser Glu Asp Asp Phe Glu Met Phe Tyr Glu
1760                1765                1770

Val Trp Glu Lys Phe Asp Pro Asp Ala Thr Gln Phe Ile Glu Phe
1775                1780                1785

Ser Lys Leu Ser Asp Phe Ala Ala Ala Leu Asp Pro Pro Leu Leu
1790                1795                1800

Ile Ala Lys Pro Asn Lys Val Gln Leu Ile Ala Met Asp Leu Pro
1805                1810                1815

Met Val Ser Gly Asp Arg Ile His Cys Leu Asp Ile Leu Phe Ala
1820                1825                1830

Phe Thr Lys Arg Val Leu Gly Glu Ser Gly Glu Met Asp Ser Leu
1835                1840                1845

Arg Ser Gln Met Glu Glu Arg Phe Met Ser Ala Asn Pro Ser Lys
1850                1855                1860

Val Ser Tyr Glu Pro Ile Thr Thr Thr Leu Lys Arg Lys Gln Glu
1865                1870                1875

Asp Val Ser Ala Thr Val Ile Gln Arg Ala Tyr Arg Arg Tyr Arg
1880                1885                1890

Leu Arg Gln Asn Val Lys Asn Ile Ser Ser Ile Tyr Ile Lys Asp
1895                1900                1905

Gly Asp Arg Asp Asp Asp Leu Leu Asn Lys Lys Asp Met Ala Phe
1910                1915                1920

Asp Asn Val Asn Glu Asn Ser Ser Pro Glu Lys Thr Asp Ala Thr
1925                1930                1935

Ser Ser Thr Thr Ser Pro Pro Ser Tyr Asp Ser Val Thr Lys Pro
1940                1945                1950

Asp Lys Glu Lys Tyr Glu Gln Asp Arg Thr Glu Lys Glu Asp Lys
1955                1960                1965

Gly Lys Asp Ser Lys Glu Ser Lys Lys
1970                1975

<210> SEQ ID NO 3
<211> LENGTH: 1977
```

<212> TYPE: PRT
<213> ORGANISM: Homo sapiens

<400> SEQUENCE: 3

```
Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
            20                  25                  30

Lys Glu Pro Lys Glu Lys Lys Asp Asp Glu Gly Ala Pro Lys
        35                  40                  45

Pro Ser Ser Asp Leu Glu Ala Gly Lys Gln Leu Pro Phe Ile Tyr Gly
    50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
            115                 120                 125

Ser Met Leu Ile Met Cys Thr Ile Leu Thr Asn Cys Ile Phe Met Thr
130                 135                 140

Met Asn Asn Pro Gln Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
            195                 200                 205

Asn Val Ser Ala Leu Arg Thr Phe Arg Val Leu Arg Ala Leu Lys Thr
210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
            275                 280                 285

Ile Met Asn Thr Leu Glu Ser Glu Glu Asp Phe Arg Lys Tyr Phe Tyr
290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
            355                 360                 365

Gln Thr Leu Arg Ala Ala Gly Lys Thr Tyr Met Ile Phe Phe Val Val
            370                 375                 380

Val Ile Phe Leu Gly Ser Phe Tyr Leu Ile Asn Leu Ile Leu Ala Val
385                 390                 395                 400
```

```
Val Ala Met Ala Tyr Glu Glu Gln Asn Gln Ala Asn Ile Glu Glu Ala
                405                 410                 415
Lys Gln Lys Glu Leu Glu Phe Gln Gln Met Leu Asp Arg Leu Lys Lys
            420                 425                 430
Glu Gln Glu Glu Ala Glu Ala Ile Ala Ala Ala Ala Glu Tyr Thr
        435                 440                 445
Ser Ile Arg Arg Ser Arg Ile Met Gly Leu Ser Glu Ser Ser Ser Glu
    450                 455                 460
Thr Ser Lys Leu Ser Ser Lys Ser Ala Lys Glu Arg Arg Asn Arg Arg
465                 470                 475                 480
Lys Lys Lys Asn Gln Lys Lys Leu Ser Ser Gly Glu Glu Lys Gly Asp
                485                 490                 495
Ala Glu Lys Leu Ser Lys Ser Glu Ser Glu Asp Ser Ile Arg Arg Lys
            500                 505                 510
Ser Phe His Leu Gly Val Glu Gly His Arg Arg Ala His Glu Lys Arg
    515                 520                 525
Leu Ser Thr Pro Asn Gln Ser Pro Leu Ser Ile Arg Gly Ser Leu Phe
    530                 535                 540
Ser Ala Arg Arg Ser Ser Arg Thr Ser Leu Phe Ser Phe Lys Gly Arg
545                 550                 555                 560
Gly Arg Asp Ile Gly Ser Glu Thr Glu Phe Ala Asp Asp Glu His Ser
                565                 570                 575
Ile Phe Gly Asp Asn Glu Ser Arg Arg Gly Ser Leu Phe Val Pro His
            580                 585                 590
Arg Pro Gln Glu Arg Arg Ser Ser Asn Ile Ser Gln Ala Ser Arg Ser
                595                 600                 605
Pro Pro Met Leu Pro Val Asn Gly Lys Met His Ser Ala Val Asp Cys
    610                 615                 620
Asn Gly Val Val Ser Leu Val Asp Gly Arg Ser Ala Leu Met Leu Pro
625                 630                 635                 640
Asn Gly Gln Leu Leu Pro Glu Gly Thr Thr Asn Gln Ile His Lys Lys
                645                 650                 655
Arg Arg Cys Ser Ser Tyr Leu Leu Ser Glu Asp Met Leu Asn Asp Pro
            660                 665                 670
Asn Leu Arg Gln Arg Ala Met Ser Arg Ala Ser Ile Leu Thr Asn Thr
    675                 680                 685
Val Glu Glu Leu Glu Glu Ser Arg Gln Lys Cys Pro Pro Trp Trp Tyr
    690                 695                 700
Arg Phe Ala His Lys Phe Leu Ile Trp Asn Cys Ser Pro Tyr Trp Ile
705                 710                 715                 720
Lys Phe Lys Lys Cys Ile Tyr Phe Ile Val Met Asp Pro Phe Val Asp
                725                 730                 735
Leu Ala Ile Thr Ile Cys Ile Val Leu Asn Thr Leu Phe Met Ala Met
            740                 745                 750
Glu His His Pro Met Thr Glu Glu Phe Lys Asn Val Leu Ala Ile Gly
        755                 760                 765
Asn Leu Val Phe Thr Gly Ile Phe Ala Ala Glu Met Val Leu Lys Leu
    770                 775                 780
Ile Ala Met Asp Pro Tyr Glu Tyr Phe Gln Val Gly Trp Asn Ile Phe
785                 790                 795                 800
Asp Ser Leu Ile Val Thr Leu Ser Leu Val Glu Leu Phe Leu Ala Asp
                805                 810                 815
```

-continued

```
Val Glu Gly Leu Ser Val Leu Arg Ser Phe Arg Leu Leu Arg Val Phe
            820                 825                 830

Lys Leu Ala Lys Ser Trp Pro Thr Leu Asn Met Leu Ile Lys Ile Ile
            835                 840                 845

Gly Asn Ser Val Gly Ala Leu Gly Asn Leu Thr Leu Val Leu Ala Ile
            850                 855                 860

Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
                    885                 890                 895

Trp His Met Asn Asp Phe Phe His Ser Phe Leu Ile Val Phe Arg Val
                    900                 905                 910

Leu Cys Gly Glu Trp Ile Glu Thr Met Trp Asp Cys Met Glu Val Ala
                    915                 920                 925

Gly Gln Ala Met Cys Leu Ile Val Tyr Met Met Val Met Val Ile Gly
            930                 935                 940

Asn Leu Val Val Leu Asn Leu Phe Leu Ala Leu Leu Leu Ser Ser Phe
945                 950                 955                 960

Ser Ser Asp Asn Leu Thr Ala Ile Glu Glu Asp Pro Asp Ala Asn Asn
                    965                 970                 975

Leu Gln Ile Ala Val Thr Arg Ile Lys Lys Gly Ile Asn Tyr Val Lys
                    980                 985                 990

Gln Thr Leu Arg Glu Phe Ile Leu Lys Ala Phe Ser Lys Lys Pro Lys
            995                 1000                1005

Ile Ser Arg Glu Ile Arg Gln Ala Glu Asp Leu Asn Thr Lys Lys
            1010                1015                1020

Glu Asn Tyr Ile Ser Asn His Thr Leu Ala Glu Met Ser Lys Gly
            1025                1030                1035

His Asn Phe Leu Lys Glu Lys Asp Lys Ile Ser Gly Phe Gly Ser
            1040                1045                1050

Ser Val Asp Lys His Leu Met Glu Asp Ser Asp Gly Gln Ser Phe
            1055                1060                1065

Ile His Asn Pro Ser Leu Thr Val Thr Val Pro Ile Ala Pro Gly
            1070                1075                1080

Glu Ser Asp Leu Glu Asn Met Asn Ala Glu Glu Leu Ser Ser Asp
            1085                1090                1095

Ser Asp Ser Glu Tyr Ser Lys Val Arg Leu Asn Arg Ser Ser Ser
            1100                1105                1110

Ser Glu Cys Ser Thr Val Asp Asn Pro Leu Pro Gly Glu Gly Glu
            1115                1120                1125

Glu Ala Glu Ala Glu Pro Met Asn Ser Asp Glu Pro Glu Ala Cys
            1130                1135                1140

Phe Thr Asp Gly Cys Val Arg Arg Phe Ser Cys Cys Gln Val Asn
            1145                1150                1155

Ile Glu Ser Gly Lys Gly Lys Ile Trp Trp Asn Ile Arg Lys Thr
            1160                1165                1170

Cys Tyr Lys Ile Val Glu His Ser Trp Phe Glu Ser Phe Ile Val
            1175                1180                1185

Leu Met Ile Leu Leu Ser Ser Gly Ala Leu Ala Phe Glu Asp Ile
            1190                1195                1200

Tyr Ile Glu Arg Lys Lys Thr Ile Lys Ile Ile Leu Glu Tyr Ala
            1205                1210                1215

Asp Lys Ile Phe Thr Tyr Ile Phe Ile Leu Glu Met Leu Leu Lys
```

-continued

```
               1220                1225                1230
Trp Ile Ala Tyr Gly Tyr Lys Thr Tyr Phe Thr Asn Ala Trp Cys
   1235                1240                1245
Trp Leu Asp Phe Leu Ile Val Asp Val Ser Leu Val Thr Leu Val
   1250                1255                1260
Ala Asn Thr Leu Gly Tyr Ser Asp Leu Gly Pro Ile Lys Ser Leu
   1265                1270                1275
Arg Thr Leu Arg Ala Leu Arg Pro Leu Arg Ala Leu Ser Arg Phe
   1280                1285                1290
Glu Gly Met Arg Val Val Val Asn Ala Leu Ile Gly Ala Ile Pro
   1295                1300                1305
Ser Ile Met Asn Val Leu Leu Val Cys Leu Ile Phe Trp Leu Ile
   1310                1315                1320
Phe Ser Ile Met Gly Val Asn Leu Phe Ala Gly Lys Phe Tyr Glu
   1325                1330                1335
Cys Ile Asn Thr Thr Asp Gly Ser Arg Phe Pro Ala Ser Gln Val
   1340                1345                1350
Pro Asn Arg Ser Glu Cys Phe Ala Leu Met Asn Val Ser Gln Asn
   1355                1360                1365
Val Arg Trp Lys Asn Leu Lys Val Asn Phe Asp Asn Val Gly Leu
   1370                1375                1380
Gly Tyr Leu Ser Leu Leu Gln Val Ala Thr Phe Lys Gly Trp Thr
   1385                1390                1395
Ile Ile Met Tyr Ala Ala Val Asp Ser Val Asn Val Asp Lys Gln
   1400                1405                1410
Pro Lys Tyr Glu Tyr Ser Leu Tyr Met Tyr Ile Tyr Phe Val Val
   1415                1420                1425
Phe Ile Ile Phe Gly Ser Phe Phe Thr Leu Asn Leu Phe Ile Gly
   1430                1435                1440
Val Ile Ile Asp Asn Phe Asn Gln Gln Lys Lys Lys Leu Gly Gly
   1445                1450                1455
Gln Asp Ile Phe Met Thr Glu Glu Gln Lys Lys Tyr Tyr Asn Ala
   1460                1465                1470
Met Lys Lys Leu Gly Ser Lys Lys Pro Gln Lys Pro Ile Pro Arg
   1475                1480                1485
Pro Gly Asn Lys Ile Gln Gly Cys Ile Phe Asp Leu Val Thr Asn
   1490                1495                1500
Gln Ala Phe Asp Ile Ser Ile Met Val Leu Ile Cys Leu Asn Met
   1505                1510                1515
Val Thr Met Met Val Glu Lys Glu Gly Gln Ser Gln His Met Thr
   1520                1525                1530
Glu Val Leu Tyr Trp Ile Asn Val Val Phe Ile Ile Leu Phe Thr
   1535                1540                1545
Gly Glu Cys Val Leu Lys Leu Ile Ser Leu Arg His Tyr Tyr Phe
   1550                1555                1560
Thr Val Gly Trp Asn Ile Phe Asp Phe Val Val Val Ile Ile Ser
   1565                1570                1575
Ile Val Gly Met Phe Leu Ala Asp Leu Ile Glu Thr Tyr Phe Val
   1580                1585                1590
Ser Pro Thr Leu Phe Arg Val Ile Arg Leu Ala Arg Ile Gly Arg
   1595                1600                1605
Ile Leu Arg Leu Val Lys Gly Ala Lys Gly Ile Arg Thr Leu Leu
   1610                1615                1620
```

```
Phe Ala Leu Met Met Ser Leu Pro Ala Leu Phe Asn Ile Gly Leu
    1625                1630                1635

Leu Leu Phe Leu Val Met Phe Ile Tyr Ala Ile Phe Gly Met Ser
    1640                1645                1650

Asn Phe Ala Tyr Val Lys Lys Glu Asp Gly Ile Asn Asp Met Phe
    1655                1660                1665

Asn Phe Glu Thr Phe Gly Asn Ser Met Ile Cys Leu Phe Gln Ile
    1670                1675                1680

Thr Thr Ser Ala Gly Trp Asp Gly Leu Leu Ala Pro Ile Leu Asn
    1685                1690                1695

Ser Lys Pro Pro Asp Cys Asp Pro Lys Lys Val His Pro Gly Ser
    1700                1705                1710

Ser Val Glu Gly Asp Cys Gly Asn Pro Ser Val Gly Ile Phe Tyr
    1715                1720                1725

Phe Val Ser Tyr Ile Ile Ile Ser Phe Leu Val Val Val Asn Met
    1730                1735                1740

Tyr Ile Ala Val Ile Leu Glu Asn Phe Ser Val Ala Thr Glu Glu
    1745                1750                1755

Ser Thr Glu Pro Leu Ser Glu Asp Asp Phe Glu Met Phe Tyr Glu
    1760                1765                1770

Val Trp Glu Lys Phe Asp Pro Asp Ala Thr Gln Phe Ile Glu Phe
    1775                1780                1785

Ser Lys Leu Ser Asp Phe Ala Ala Ala Leu Asp Pro Pro Leu Leu
    1790                1795                1800

Ile Ala Lys Pro Asn Lys Val Gln Leu Ile Ala Met Asp Leu Pro
    1805                1810                1815

Met Val Ser Gly Asp Arg Ile His Cys Leu Asp Ile Leu Phe Ala
    1820                1825                1830

Phe Thr Lys Arg Val Leu Gly Glu Ser Gly Glu Met Asp Ser Leu
    1835                1840                1845

Arg Ser Gln Met Glu Glu Arg Phe Met Ser Ala Asn Pro Ser Lys
    1850                1855                1860

Val Ser Tyr Glu Pro Ile Thr Thr Thr Leu Lys Arg Lys Gln Glu
    1865                1870                1875

Asp Val Ser Ala Thr Val Ile Gln Arg Ala Tyr Arg Arg Tyr Arg
    1880                1885                1890

Leu Arg Gln Asn Val Lys Asn Ile Ser Ser Ile Tyr Ile Lys Asp
    1895                1900                1905

Gly Asp Arg Asp Asp Asp Leu Leu Asn Lys Lys Asp Met Ala Phe
    1910                1915                1920

Asp Asn Val Asn Glu Asn Ser Ser Pro Glu Lys Thr Asp Ala Thr
    1925                1930                1935

Ser Ser Thr Thr Ser Pro Pro Ser Tyr Asp Ser Val Thr Lys Pro
    1940                1945                1950

Asp Lys Glu Lys Tyr Glu Gln Asp Arg Thr Glu Lys Glu Asp Lys
    1955                1960                1965

Gly Lys Asp Ser Lys Glu Ser Lys Lys
    1970                1975

<210> SEQ ID NO 4
<211> LENGTH: 1977
<212> TYPE: PRT
<213> ORGANISM: Homo sapiens
```

```
<400> SEQUENCE: 4

Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
            20                  25                  30

Lys Glu Pro Lys Glu Lys Lys Asp Asp Asp Glu Ala Pro Lys
        35                  40                  45

Pro Ser Ser Asp Leu Glu Ala Gly Lys Gln Leu Pro Phe Ile Tyr Gly
    50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
            115                 120                 125

Ser Met Leu Ile Met Cys Thr Ile Leu Thr Asn Cys Ile Phe Met Thr
130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
            195                 200                 205

Asn Val Ser Ala Leu Arg Thr Phe Arg Val Leu Arg Ala Leu Lys Thr
210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
            275                 280                 285

Ile Met Asn Thr Leu Glu Ser Glu Glu Asp Phe Arg Lys Tyr Phe Tyr
290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
            355                 360                 365

Gln Thr Leu Arg Ala Ala Gly Lys Thr Tyr Met Ile Phe Phe Val Val
            370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415
```

```
Lys Gln Lys Glu Leu Glu Phe Gln Gln Met Leu Asp Arg Leu Lys Lys
                420                 425                 430

Glu Gln Glu Glu Ala Glu Ala Ile Ala Ala Ala Ala Glu Tyr Thr
            435                 440                 445

Ser Ile Arg Arg Ser Arg Ile Met Gly Leu Ser Glu Ser Ser Glu
450                 455                 460

Thr Ser Lys Leu Ser Ser Lys Ser Ala Lys Glu Arg Arg Asn Arg Arg
465                 470                 475                 480

Lys Lys Lys Asn Gln Lys Leu Ser Ser Gly Glu Lys Gly Asp
                485                 490                 495

Ala Glu Lys Leu Ser Lys Ser Glu Ser Glu Asp Ser Ile Arg Arg Lys
            500                 505                 510

Ser Phe His Leu Gly Val Glu Gly His Arg Arg Ala His Glu Lys Arg
            515                 520                 525

Leu Ser Thr Pro Asn Gln Ser Pro Leu Ser Ile Arg Gly Ser Leu Phe
            530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
                565                 570                 575

Ile Phe Gly Asp Asn Glu Ser Arg Arg Gly Ser Leu Phe Val Pro His
            580                 585                 590

Arg Pro Gln Glu Arg Arg Ser Ser Asn Ile Ser Gln Ala Ser Arg Ser
            595                 600                 605

Pro Pro Met Leu Pro Val Asn Gly Lys Met His Ser Ala Val Asp Cys
            610                 615                 620

Asn Gly Val Val Ser Leu Val Asp Gly Arg Ser Ala Leu Met Leu Pro
625                 630                 635                 640

Tyr Gly Gln Leu Leu Pro Glu Gly Thr Thr Asn Gln Ile His Lys Lys
                645                 650                 655

Arg Arg Cys Ser Ser Tyr Leu Leu Ser Glu Asp Met Leu Asn Asp Pro
            660                 665                 670

Asn Leu Arg Gln Arg Ala Met Ser Arg Ala Ser Ile Leu Thr Asn Thr
            675                 680                 685

Val Glu Glu Leu Glu Glu Ser Arg Gln Lys Cys Pro Pro Trp Trp Tyr
            690                 695                 700

Arg Phe Ala His Lys Phe Leu Ile Trp Asn Cys Ser Pro Tyr Trp Ile
705                 710                 715                 720

Lys Phe Lys Lys Cys Ile Tyr Phe Ile Val Met Asp Pro Phe Val Asp
                725                 730                 735

Leu Ala Ile Thr Ile Cys Ile Val Leu Asn Thr Leu Phe Met Ala Met
            740                 745                 750

Glu His His Pro Met Thr Glu Glu Phe Lys Asn Val Leu Ala Ile Gly
            755                 760                 765

Asn Leu Val Phe Thr Gly Ile Phe Ala Ala Glu Met Val Leu Lys Leu
            770                 775                 780

Ile Ala Met Asp Pro Tyr Glu Tyr Phe Gln Val Gly Trp Asn Ile Phe
785                 790                 795                 800

Asp Ser Leu Ile Val Thr Leu Ser Leu Val Glu Leu Phe Leu Ala Asp
                805                 810                 815

Val Glu Gly Leu Ser Val Leu Arg Ser Phe Arg Leu Leu Arg Val Phe
            820                 825                 830
```

```
Lys Leu Ala Lys Ser Trp Pro Thr Leu Asn Met Leu Ile Lys Ile Ile
            835                 840                 845

Gly Asn Ser Val Gly Ala Leu Gly Asn Leu Thr Leu Val Leu Ala Ile
850                 855                 860

Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
                885                 890                 895

Trp His Met Asn Asp Phe Phe His Ser Phe Leu Ile Val Phe Arg Val
            900                 905                 910

Leu Cys Gly Glu Trp Ile Glu Thr Met Trp Asp Cys Met Glu Val Ala
        915                 920                 925

Gly Gln Ala Met Cys Leu Ile Val Tyr Met Met Val Met Val Ile Gly
    930                 935                 940

Asn Leu Val Val Leu Asn Leu Phe Leu Ala Leu Leu Leu Ser Ser Phe
945                 950                 955                 960

Ser Ser Asp Asn Leu Thr Ala Ile Glu Glu Asp Pro Asp Ala Asn Asn
                965                 970                 975

Leu Gln Ile Ala Val Thr Arg Ile Lys Lys Gly Ile Asn Tyr Val Lys
            980                 985                 990

Gln Thr Leu Arg Glu Phe Ile Leu Lys Ala Phe Ser Lys Lys Pro Lys
        995                 1000                1005

Ile Ser Arg Glu Ile Arg Gln Ala Glu Asp Leu Asn Thr Lys Lys
    1010                1015                1020

Glu Asn Tyr Ile Ser Asn His Thr Leu Ala Glu Met Ser Lys Gly
    1025                1030                1035

His Asn Phe Leu Lys Glu Lys Asp Lys Ile Ser Gly Phe Gly Ser
    1040                1045                1050

Ser Val Asp Lys His Leu Met Glu Asp Ser Asp Gly Gln Ser Phe
    1055                1060                1065

Ile His Asn Pro Ser Leu Thr Val Thr Val Pro Ile Ala Pro Gly
    1070                1075                1080

Glu Ser Asp Leu Glu Asn Met Asn Ala Glu Glu Leu Ser Ser Asp
    1085                1090                1095

Ser Asp Ser Glu Tyr Ser Lys Val Arg Leu Asn Arg Ser Ser Ser
    1100                1105                1110

Ser Glu Cys Ser Thr Val Asp Asn Pro Leu Pro Gly Glu Gly Glu
    1115                1120                1125

Glu Ala Glu Ala Glu Pro Met Asn Ser Asp Glu Pro Glu Ala Cys
    1130                1135                1140

Phe Thr Asp Gly Cys Val Arg Arg Phe Ser Cys Cys Gln Val Asn
    1145                1150                1155

Ile Glu Ser Gly Lys Gly Lys Ile Trp Trp Asn Ile Arg Lys Thr
    1160                1165                1170

Cys Tyr Lys Ile Val Glu His Ser Trp Phe Glu Ser Phe Ile Val
    1175                1180                1185

Leu Met Ile Leu Leu Ser Ser Gly Ala Leu Ala Phe Glu Asp Ile
    1190                1195                1200

Tyr Ile Glu Arg Lys Lys Thr Ile Lys Ile Ile Leu Glu Tyr Ala
    1205                1210                1215

Asp Lys Ile Phe Thr Tyr Ile Phe Ile Leu Glu Met Leu Leu Lys
    1220                1225                1230

Trp Ile Ala Tyr Gly Tyr Lys Thr Tyr Phe Thr Asn Ala Trp Cys
```

-continued

```
            1235                1240                1245
Trp Leu Asp Phe Leu Ile Val Asp Val Ser Leu Val Thr Leu Val
            1250                1255                1260
Ala Asn Thr Leu Gly Tyr Ser Asp Leu Gly Pro Ile Lys Ser Leu
            1265                1270                1275
Arg Thr Leu Arg Ala Leu Arg Pro Leu Arg Ala Leu Ser Arg Phe
            1280                1285                1290
Glu Gly Met Arg Val Val Asn Ala Leu Ile Gly Ala Ile Pro
            1295                1300                1305
Ser Ile Met Asn Val Leu Leu Val Cys Leu Ile Phe Trp Leu Ile
            1310                1315                1320
Phe Ser Ile Met Gly Val Asn Leu Phe Ala Gly Lys Phe Tyr Glu
            1325                1330                1335
Cys Ile Asn Thr Thr Asp Gly Ser Arg Phe Pro Ala Ser Gln Val
            1340                1345                1350
Pro Asn Arg Ser Glu Cys Phe Ala Leu Met Asn Val Ser Gln Asn
            1355                1360                1365
Val Arg Trp Lys Asn Leu Lys Val Asn Phe Asp Asn Val Gly Leu
            1370                1375                1380
Gly Tyr Leu Ser Leu Leu Gln Val Ala Thr Phe Lys Gly Trp Thr
            1385                1390                1395
Ile Ile Met Tyr Ala Ala Val Asp Ser Val Asn Val Asp Lys Gln
            1400                1405                1410
Pro Lys Tyr Glu Tyr Ser Leu Tyr Met Tyr Ile Tyr Phe Val Val
            1415                1420                1425
Phe Ile Ile Phe Gly Ser Phe Phe Thr Leu Asn Leu Phe Ile Gly
            1430                1435                1440
Val Ile Ile Asp Asn Phe Asn Gln Gln Lys Lys Lys Leu Gly Gly
            1445                1450                1455
Gln Asp Ile Phe Met Thr Glu Glu Gln Lys Lys Tyr Tyr Asn Ala
            1460                1465                1470
Met Lys Lys Leu Gly Ser Lys Lys Pro Gln Lys Pro Ile Pro Arg
            1475                1480                1485
Pro Gly Asn Lys Ile Gln Gly Cys Ile Phe Asp Leu Val Thr Asn
            1490                1495                1500
Gln Ala Phe Asp Ile Ser Ile Met Val Leu Ile Cys Leu Asn Met
            1505                1510                1515
Val Thr Met Met Val Glu Lys Glu Gly Gln Ser Gln His Met Thr
            1520                1525                1530
Glu Val Leu Tyr Trp Ile Asn Val Val Phe Ile Ile Leu Phe Thr
            1535                1540                1545
Gly Glu Cys Val Leu Lys Leu Ile Ser Leu Arg His Tyr Tyr Phe
            1550                1555                1560
Thr Val Gly Trp Asn Ile Phe Asp Phe Val Val Val Ile Ile Ser
            1565                1570                1575
Ile Val Gly Met Phe Leu Ala Asp Leu Ile Glu Thr Tyr Phe Val
            1580                1585                1590
Ser Pro Thr Leu Phe Arg Val Ile Arg Leu Ala Arg Ile Gly Arg
            1595                1600                1605
Ile Leu Arg Leu Val Lys Gly Ala Lys Gly Ile Arg Thr Leu Leu
            1610                1615                1620
Phe Ala Leu Met Met Ser Leu Pro Ala Leu Phe Asn Ile Gly Leu
            1625                1630                1635
```

```
Leu Leu Phe Leu Val Met Phe Ile Tyr Ala Ile Phe Gly Met Ser
    1640                1645                1650

Asn Phe Ala Tyr Val Lys Lys Glu Asp Gly Ile Asn Asp Met Phe
    1655                1660                1665

Asn Phe Glu Thr Phe Gly Asn Ser Met Ile Cys Leu Phe Gln Ile
    1670                1675                1680

Thr Thr Ser Ala Gly Trp Asp Gly Leu Leu Ala Pro Ile Leu Asn
    1685                1690                1695

Ser Lys Pro Pro Asp Cys Asp Pro Lys Lys Val His Pro Gly Ser
    1700                1705                1710

Ser Val Glu Gly Asp Cys Gly Asn Pro Ser Val Gly Ile Phe Tyr
    1715                1720                1725

Phe Val Ser Tyr Ile Ile Ile Ser Phe Leu Val Val Val Asn Met
    1730                1735                1740

Tyr Ile Ala Val Ile Leu Glu Asn Phe Ser Val Ala Thr Glu Glu
    1745                1750                1755

Ser Thr Glu Pro Leu Ser Glu Asp Asp Phe Glu Met Phe Tyr Glu
    1760                1765                1770

Val Trp Glu Lys Phe Asp Pro Asp Ala Thr Gln Phe Ile Glu Phe
    1775                1780                1785

Ser Lys Leu Ser Asp Phe Ala Ala Ala Leu Asp Pro Pro Leu Leu
    1790                1795                1800

Ile Ala Lys Pro Asn Lys Val Gln Leu Ile Ala Met Asp Leu Pro
    1805                1810                1815

Met Val Ser Gly Asp Arg Ile His Cys Leu Asp Ile Leu Phe Ala
    1820                1825                1830

Phe Thr Lys Arg Val Leu Gly Glu Ser Gly Glu Met Asp Ser Leu
    1835                1840                1845

Arg Ser Gln Met Glu Glu Arg Phe Met Ser Ala Asn Pro Ser Lys
    1850                1855                1860

Val Ser Tyr Glu Pro Ile Thr Thr Thr Leu Lys Arg Lys Gln Glu
    1865                1870                1875

Asp Val Ser Ala Thr Val Ile Gln Arg Ala Tyr Arg Arg Tyr Arg
    1880                1885                1890

Leu Arg Gln Asn Val Lys Asn Ile Ser Ser Ile Tyr Ile Lys Asp
    1895                1900                1905

Gly Asp Arg Asp Asp Asp Leu Leu Asn Lys Lys Asp Met Ala Phe
    1910                1915                1920

Asp Asn Val Asn Glu Asn Ser Ser Pro Glu Lys Thr Asp Ala Thr
    1925                1930                1935

Ser Ser Thr Thr Ser Pro Pro Ser Tyr Asp Ser Val Thr Lys Pro
    1940                1945                1950

Asp Lys Glu Lys Tyr Glu Gln Asp Arg Thr Glu Lys Glu Asp Lys
    1955                1960                1965

Gly Lys Asp Ser Lys Glu Ser Lys Lys
    1970                1975
```

<210> SEQ ID NO 5
<211> LENGTH: 1977
<212> TYPE: PRT
<213> ORGANISM: Homo sapiens

<400> SEQUENCE: 5

Met Ala Met Leu Pro Pro Pro Gly Pro Gln Ser Phe Val His Phe Thr

-continued

```
1               5                   10                  15
Lys Gln Ser Leu Ala Leu Ile Glu Gln Arg Ile Ala Glu Arg Lys Ser
                20                  25                  30
Lys Glu Pro Lys Glu Lys Lys Asp Asp Glu Glu Ala Pro Lys
                35                  40              45
Pro Ser Ser Asp Leu Glu Ala Gly Lys Gln Leu Pro Phe Ile Tyr Gly
        50                  55                  60
Asp Ile Pro Pro Gly Met Val Ser Glu Pro Leu Glu Asp Leu Asp Pro
65                  70                  75                  80
Tyr Tyr Ala Asp Lys Lys Thr Phe Ile Val Leu Asn Lys Gly Lys Thr
                85                  90                  95
Ile Phe Arg Phe Asn Ala Thr Pro Ala Leu Tyr Met Leu Ser Pro Phe
            100                 105                 110
Ser Pro Leu Arg Arg Ile Ser Ile Lys Ile Leu Val His Ser Leu Phe
            115                 120                 125
Ser Met Leu Ile Met Cys Thr Ile Leu Thr Asn Cys Ile Phe Met Thr
            130                 135                 140
Met Asn Asn Pro Pro Asp Trp Thr Lys Asn Val Glu Tyr Thr Phe Thr
145                 150                 155                 160
Gly Ile Tyr Thr Phe Glu Ser Leu Val Lys Ile Leu Ala Arg Gly Phe
                165                 170                 175
Cys Val Gly Glu Phe Thr Phe Leu Arg Asp Pro Trp Asn Trp Leu Asp
            180                 185                 190
Phe Val Val Ile Val Phe Ala Tyr Leu Thr Glu Phe Val Asn Leu Gly
            195                 200                 205
Asn Val Ser Ala Leu Arg Thr Phe Arg Val Leu Arg Ala Leu Lys Thr
    210                 215                 220
Ile Ser Val Ile Pro Gly Leu Lys Thr Ile Val Gly Ala Leu Ile Gln
225                 230                 235                 240
Ser Val Lys Lys Leu Ser Asp Val Met Ile Leu Thr Val Phe Cys Leu
                245                 250                 255
Ser Val Phe Ala Leu Ile Gly Leu Gln Leu Phe Met Gly Asn Leu Lys
            260                 265                 270
His Lys Cys Phe Arg Asn Ser Leu Glu Asn Asn Glu Thr Leu Glu Ser
            275                 280                 285
Ile Met Asn Thr Leu Glu Ser Glu Glu Asp Phe Arg Lys Tyr Phe Tyr
            290                 295                 300
Tyr Leu Glu Gly Ser Lys Asp Ala Leu Leu Cys Gly Phe Ser Thr Asp
305                 310                 315                 320
Ser Gly Gln Cys Pro Glu Gly Tyr Thr Cys Val Lys Ile Gly Arg Asn
                325                 330                 335
Pro Asp Tyr Gly Tyr Thr Ser Phe Asp Thr Phe Ser Trp Ala Phe Leu
            340                 345                 350
Ala Leu Phe Arg Leu Met Thr Gln Asp Tyr Trp Glu Asn Leu Tyr Gln
            355                 360                 365
Gln Thr Leu Arg Ala Ala Gly Lys Thr Tyr Met Ile Phe Phe Val Val
            370                 375             380
Val Ile Phe Leu Gly Ser Phe Tyr Leu Ile Asn Leu Ile Leu Ala Val
385                 390                 395                 400
Val Ala Met Ala Tyr Glu Glu Gln Asn Gln Ala Asn Ile Glu Glu Ala
                405                 410                 415
Lys Gln Lys Glu Leu Glu Phe Gln Gln Met Leu Asp Arg Leu Lys Lys
                420                 425                 430
```

```
Glu Gln Glu Glu Ala Glu Ala Ile Ala Ala Ala Ala Glu Tyr Thr
    435                 440                 445
Ser Ile Arg Arg Ser Arg Ile Met Gly Leu Ser Glu Ser Ser Glu
450                 455                 460
Thr Ser Lys Leu Ser Ser Lys Ser Ala Lys Glu Arg Arg Asn Arg Arg
465                 470                 475                 480
Lys Lys Lys Asn Gln Lys Lys Leu Ser Ser Gly Glu Glu Lys Gly Asp
                485                 490                 495
Ala Glu Lys Leu Ser Lys Ser Glu Ser Glu Asp Ser Ile Arg Arg Lys
                500                 505                 510
Ser Phe His Leu Gly Val Glu Gly His Arg Arg Ala His Glu Lys Arg
        515                 520                 525
Leu Ser Thr Pro Asn Gln Ser Pro Leu Ser Ile Arg Gly Ser Leu Phe
        530                 535                 540
Ser Ala Arg Arg Ser Ser Arg Thr Ser Leu Phe Ser Phe Lys Gly Arg
545                 550                 555                 560
Gly Arg Asp Ile Gly Ser Glu Thr Glu Phe Ala Asp Asp Glu His Ser
                565                 570                 575
Ile Phe Gly Asp Asn Glu Ser Arg Arg Gly Ser Leu Phe Val Pro His
                580                 585                 590
Arg Pro Gln Glu Arg Arg Ser Ser Asn Ile Ser Gln Ala Ser Arg Ser
        595                 600                 605
Pro Pro Met Leu Pro Val Asn Gly Lys Met His Ser Ala Val Asp Cys
        610                 615                 620
Asn Gly Val Val Ser Leu Val Asp Gly Arg Ser Ala Leu Met Leu Pro
625                 630                 635                 640
Asn Gly Gln Leu Leu Pro Glu Gly Thr Thr Asn Gln Ile His Arg Lys
                645                 650                 655
Arg Arg Cys Ser Ser Tyr Leu Leu Ser Glu Asp Met Leu Asn Asp Pro
                660                 665                 670
Asn Leu Arg Gln Arg Ala Met Ser Arg Ala Ser Ile Leu Thr Asn Thr
        675                 680                 685
Val Glu Glu Leu Glu Ser Arg Gln Lys Cys Pro Pro Trp Trp Tyr
        690                 695                 700
Arg Phe Ala His Lys Phe Leu Ile Trp Asn Cys Ser Pro Tyr Trp Ile
705                 710                 715                 720
Lys Phe Lys Lys Cys Ile Tyr Phe Ile Val Met Asp Pro Phe Val Asp
                725                 730                 735
Leu Ala Ile Thr Ile Cys Ile Val Leu Asn Thr Leu Phe Met Ala Met
                740                 745                 750
Glu His His Pro Met Thr Glu Glu Phe Lys Asn Val Leu Ala Ile Gly
        755                 760                 765
Asn Leu Val Phe Thr Gly Ile Phe Ala Ala Glu Met Val Leu Lys Leu
        770                 775                 780
Ile Ala Met Asp Pro Tyr Glu Tyr Phe Gln Val Gly Trp Asn Ile Phe
785                 790                 795                 800
Asp Ser Leu Ile Val Thr Leu Ser Leu Val Glu Leu Phe Leu Ala Asp
                805                 810                 815
Val Glu Gly Leu Ser Val Leu Arg Ser Phe Arg Leu Leu Arg Val Phe
                820                 825                 830
Lys Leu Ala Lys Ser Trp Pro Thr Leu Asn Met Leu Ile Lys Ile Ile
                835                 840                 845
```

```
Gly Asn Ser Val Gly Ala Leu Gly Asn Leu Thr Leu Val Leu Ala Ile
850                 855                 860

Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
            885                 890                 895

Trp His Met Asn Asp Phe Phe His Ser Phe Leu Ile Val Phe Arg Val
                900                 905                 910

Leu Cys Gly Glu Trp Ile Glu Thr Met Trp Asp Cys Met Glu Val Ala
            915                 920                 925

Gly Gln Ala Met Cys Leu Ile Val Tyr Met Met Val Met Val Ile Gly
930                 935                 940

Asn Leu Val Val Leu Asn Leu Phe Leu Ala Leu Leu Leu Ser Ser Phe
945                 950                 955                 960

Ser Ser Asp Asn Leu Thr Ala Ile Glu Glu Asp Pro Asp Ala Asn Asn
            965                 970                 975

Leu Gln Ile Ala Val Thr Arg Ile Lys Lys Gly Ile Asn Tyr Val Lys
            980                 985                 990

Gln Thr Leu Arg Glu Phe Ile Leu Lys Ala Phe Ser Lys Lys Pro Lys
            995                 1000                1005

Ile Ser Arg Glu Ile Arg Gln Ala Glu Asp Leu Asn Thr Lys Lys
    1010                1015                1020

Glu Asn Tyr Ile Ser Asn His Thr Leu Ala Glu Met Ser Lys Gly
    1025                1030                1035

His Asn Phe Leu Lys Glu Lys Asp Lys Ile Ser Gly Phe Gly Ser
    1040                1045                1050

Ser Val Asp Lys His Leu Met Glu Asp Ser Asp Gly Gln Ser Phe
    1055                1060                1065

Ile His Asn Pro Ser Leu Thr Val Thr Val Pro Ile Ala Pro Gly
    1070                1075                1080

Glu Ser Asp Leu Glu Asn Met Asn Ala Glu Glu Leu Ser Ser Asp
    1085                1090                1095

Ser Asp Ser Glu Tyr Ser Lys Val Arg Leu Asn Arg Ser Ser Ser
    1100                1105                1110

Ser Glu Cys Ser Thr Val Asp Asn Pro Leu Pro Gly Glu Gly Glu
    1115                1120                1125

Glu Ala Glu Ala Glu Pro Met Asn Ser Asp Glu Pro Glu Ala Cys
    1130                1135                1140

Phe Thr Asp Gly Cys Val Arg Arg Phe Ser Cys Cys Gln Val Asn
    1145                1150                1155

Ile Glu Ser Gly Lys Gly Lys Ile Trp Trp Asn Ile Arg Lys Thr
    1160                1165                1170

Cys Tyr Lys Ile Val Glu His Ser Trp Phe Glu Ser Phe Ile Val
    1175                1180                1185

Leu Met Ile Leu Leu Ser Ser Gly Ala Leu Ala Phe Glu Asp Ile
    1190                1195                1200

Tyr Ile Glu Arg Lys Lys Thr Ile Lys Ile Ile Leu Glu Tyr Ala
    1205                1210                1215

Asp Lys Ile Phe Thr Tyr Ile Phe Ile Leu Glu Met Leu Leu Lys
    1220                1225                1230

Trp Ile Ala Tyr Gly Tyr Lys Thr Tyr Phe Thr Asn Ala Trp Cys
    1235                1240                1245

Trp Leu Asp Phe Leu Ile Val Asp Val Ser Leu Val Thr Leu Val
```

```
            1250                1255                1260

Ala  Asn  Thr  Leu  Gly  Tyr  Ser  Asp  Leu  Gly  Pro  Ile  Lys  Ser  Leu
            1265                1270                1275

Arg  Thr  Leu  Arg  Ala  Leu  Arg  Pro  Leu  Arg  Ala  Leu  Ser  Arg  Phe
            1280                1285                1290

Glu  Gly  Met  Arg  Val  Val  Val  Asn  Ala  Leu  Ile  Gly  Ala  Ile  Pro
            1295                1300                1305

Ser  Ile  Met  Asn  Val  Leu  Leu  Val  Cys  Leu  Ile  Phe  Trp  Leu  Ile
            1310                1315                1320

Phe  Ser  Ile  Met  Gly  Val  Asn  Leu  Phe  Ala  Gly  Lys  Phe  Tyr  Glu
            1325                1330                1335

Cys  Ile  Asn  Thr  Thr  Asp  Gly  Ser  Arg  Phe  Pro  Ala  Ser  Gln  Val
            1340                1345                1350

Pro  Asn  Arg  Ser  Glu  Cys  Phe  Ala  Leu  Met  Asn  Val  Ser  Gln  Asn
            1355                1360                1365

Val  Arg  Trp  Lys  Asn  Leu  Lys  Val  Asn  Phe  Asp  Asn  Val  Gly  Leu
            1370                1375                1380

Gly  Tyr  Leu  Ser  Leu  Leu  Gln  Val  Ala  Thr  Phe  Lys  Gly  Trp  Thr
            1385                1390                1395

Ile  Ile  Met  Tyr  Ala  Ala  Val  Asp  Ser  Val  Asn  Val  Asp  Lys  Gln
            1400                1405                1410

Pro  Lys  Tyr  Glu  Tyr  Ser  Leu  Tyr  Met  Tyr  Ile  Tyr  Phe  Val  Val
            1415                1420                1425

Phe  Ile  Ile  Phe  Gly  Ser  Phe  Phe  Thr  Leu  Asn  Leu  Phe  Ile  Gly
            1430                1435                1440

Val  Ile  Ile  Asp  Asn  Phe  Asn  Gln  Gln  Lys  Lys  Lys  Leu  Gly  Gly
            1445                1450                1455

Gln  Asp  Ile  Phe  Met  Thr  Glu  Glu  Gln  Lys  Lys  Tyr  Tyr  Asn  Ala
            1460                1465                1470

Met  Lys  Lys  Leu  Gly  Ser  Lys  Lys  Pro  Gln  Lys  Pro  Ile  Pro  Arg
            1475                1480                1485

Pro  Gly  Asn  Lys  Ile  Gln  Gly  Cys  Ile  Phe  Asp  Leu  Val  Thr  Asn
            1490                1495                1500

Gln  Ala  Phe  Asp  Ile  Ser  Ile  Met  Val  Leu  Ile  Cys  Leu  Asn  Met
            1505                1510                1515

Val  Thr  Met  Met  Val  Glu  Lys  Glu  Gly  Gln  Ser  Gln  His  Met  Thr
            1520                1525                1530

Glu  Val  Leu  Tyr  Trp  Ile  Asn  Val  Val  Phe  Ile  Ile  Leu  Phe  Thr
            1535                1540                1545

Gly  Glu  Cys  Val  Leu  Lys  Leu  Ile  Ser  Leu  Arg  His  Tyr  Tyr  Phe
            1550                1555                1560

Thr  Val  Gly  Trp  Asn  Ile  Phe  Asp  Phe  Val  Val  Val  Ile  Ile  Ser
            1565                1570                1575

Ile  Val  Gly  Met  Phe  Leu  Ala  Asp  Leu  Ile  Glu  Thr  Tyr  Phe  Val
            1580                1585                1590

Ser  Pro  Thr  Leu  Phe  Arg  Val  Ile  Arg  Leu  Ala  Arg  Ile  Gly  Arg
            1595                1600                1605

Ile  Leu  Arg  Leu  Val  Lys  Gly  Ala  Lys  Gly  Ile  Arg  Thr  Leu  Leu
            1610                1615                1620

Phe  Ala  Leu  Met  Met  Ser  Leu  Pro  Ala  Leu  Phe  Asn  Ile  Gly  Leu
            1625                1630                1635

Leu  Leu  Phe  Leu  Val  Met  Phe  Ile  Tyr  Ala  Ile  Phe  Gly  Met  Ser
            1640                1645                1650
```

```
Asn Phe Ala Tyr Val Lys Lys Glu Asp Gly Ile Asn Asp Met Phe
    1655                1660                1665

Asn Phe Glu Thr Phe Gly Asn Ser Met Ile Cys Leu Phe Gln Ile
    1670                1675                1680

Thr Thr Ser Ala Gly Trp Asp Gly Leu Leu Ala Pro Ile Leu Asn
    1685                1690                1695

Ser Lys Pro Pro Asp Cys Asp Pro Lys Lys Val His Pro Gly Ser
    1700                1705                1710

Ser Val Glu Gly Asp Cys Gly Asn Pro Ser Val Gly Ile Phe Tyr
    1715                1720                1725

Phe Val Ser Tyr Ile Ile Ile Ser Phe Leu Val Val Val Asn Met
    1730                1735                1740

Tyr Ile Ala Val Ile Leu Glu Asn Phe Ser Val Ala Thr Glu Glu
    1745                1750                1755

Ser Thr Glu Pro Leu Ser Glu Asp Asp Phe Glu Met Phe Tyr Glu
    1760                1765                1770

Val Trp Glu Lys Phe Asp Pro Asp Ala Thr Gln Phe Ile Glu Phe
    1775                1780                1785

Ser Lys Leu Ser Asp Phe Ala Ala Ala Leu Asp Pro Pro Leu Leu
    1790                1795                1800

Ile Ala Lys Pro Asn Lys Val Gln Leu Ile Ala Met Asp Leu Pro
    1805                1810                1815

Met Val Ser Gly Asp Arg Ile His Cys Leu Asp Ile Leu Phe Ala
    1820                1825                1830

Phe Thr Lys Arg Val Leu Gly Glu Ser Gly Glu Met Asp Ser Leu
    1835                1840                1845

Arg Ser Gln Met Glu Glu Arg Phe Met Ser Ala Asn Pro Ser Lys
    1850                1855                1860

Val Ser Tyr Glu Pro Ile Thr Thr Thr Leu Lys Arg Lys Gln Glu
    1865                1870                1875

Asp Val Ser Ala Thr Val Ile Gln Arg Ala Tyr Arg Arg Tyr Arg
    1880                1885                1890

Leu Arg Gln Asn Val Lys Asn Ile Ser Ser Ile Tyr Ile Lys Asp
    1895                1900                1905

Gly Asp Arg Asp Asp Asp Leu Leu Asn Lys Lys Asp Met Ala Phe
    1910                1915                1920

Asp Asn Val Asn Glu Asn Ser Ser Pro Glu Lys Thr Asp Ala Thr
    1925                1930                1935

Ser Ser Thr Thr Ser Pro Pro Ser Tyr Asp Ser Val Thr Lys Pro
    1940                1945                1950

Asp Lys Glu Lys Tyr Glu Gln Asp Arg Thr Glu Lys Glu Asp Lys
    1955                1960                1965

Gly Lys Asp Ser Lys Glu Ser Lys Lys
    1970                1975

<210> SEQ ID NO 6
<211> LENGTH: 1977
<212> TYPE: PRT
<213> ORGANISM: Homo sapiens

<400> SEQUENCE: 6

Met Ala Met Leu Pro Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
```

```
            20                  25                  30
Lys Glu Pro Lys Glu Lys Lys Asp Asp Glu Glu Ala Pro Lys
            35                  40                  45
Pro Ser Ser Asp Leu Glu Ala Gly Lys Gln Leu Pro Phe Ile Tyr Gly
50                  55                  60
Asp Ile Pro Pro Gly Met Val Ser Glu Pro Leu Glu Asp Leu Asp Pro
65                  70                  75                  80
Tyr Tyr Ala Asp Lys Lys Thr Phe Ile Val Leu Asn Lys Gly Lys Thr
                85                  90                  95
Ile Phe Arg Phe Asn Ala Thr Pro Ala Leu Tyr Met Leu Ser Pro Phe
            100                 105                 110
Ser Pro Leu Arg Arg Ile Ser Ile Lys Ile Leu Val His Ser Leu Phe
            115                 120                 125
Ser Met Leu Ile Met Cys Thr Ile Leu Thr Asn Cys Ile Phe Met Thr
            130                 135                 140
Met Asn Asn Pro Pro Asp Trp Thr Lys Asn Val Glu Tyr Thr Phe Thr
145                 150                 155                 160
Gly Ile Tyr Thr Phe Glu Ser Leu Val Lys Ile Leu Ala Arg Gly Phe
                165                 170                 175
Cys Val Gly Glu Phe Thr Phe Leu Arg Asp Pro Trp Asn Trp Leu Asp
                180                 185                 190
Phe Val Val Ile Val Phe Ala Tyr Leu Thr Glu Phe Val Asn Leu Gly
                195                 200                 205
Asn Val Ser Ala Leu Arg Thr Phe Arg Val Leu Arg Ala Leu Lys Thr
            210                 215                 220
Ile Ser Val Ile Pro Gly Leu Lys Thr Ile Val Gly Ala Leu Ile Gln
225                 230                 235                 240
Ser Val Lys Lys Leu Ser Asp Val Met Ile Leu Thr Val Phe Cys Leu
                245                 250                 255
Ser Val Phe Ala Leu Ile Gly Leu Gln Leu Phe Met Gly Asn Leu Lys
                260                 265                 270
His Lys Cys Phe Arg Asn Ser Leu Glu Asn Asn Glu Thr Leu Glu Ser
            275                 280                 285
Ile Met Asn Thr Leu Glu Ser Glu Glu Asp Phe Arg Lys Tyr Phe Tyr
            290                 295                 300
Tyr Leu Glu Gly Ser Lys Asp Ala Leu Leu Cys Gly Phe Ser Thr Asp
305                 310                 315                 320
Ser Gly Gln Cys Pro Glu Gly Tyr Thr Cys Val Lys Ile Gly Arg Asn
                325                 330                 335
Pro Asp Tyr Gly Tyr Thr Ser Phe Asp Thr Phe Ser Trp Ala Phe Leu
            340                 345                 350
Ala Leu Phe Arg Leu Met Thr Gln Asp Tyr Trp Glu Asn Leu Tyr Gln
            355                 360                 365
Gln Thr Leu Arg Ala Ala Gly Lys Thr Tyr Met Ile Phe Phe Val Val
            370                 375                 380
Val Ile Phe Leu Gly Ser Phe Tyr Leu Ile Asn Leu Ile Leu Ala Val
385                 390                 395                 400
Val Ala Met Ala Tyr Glu Glu Gln Asn Gln Ala Asn Ile Glu Glu Ala
                405                 410                 415
Lys Gln Lys Glu Leu Glu Phe Gln Gln Met Leu Asp Arg Leu Lys Lys
            420                 425                 430
Glu Gln Glu Glu Ala Glu Ala Ile Ala Ala Ala Ala Glu Tyr Thr
            435                 440                 445
```

```
Ser Ile Arg Arg Ser Arg Ile Met Gly Leu Ser Glu Ser Ser Glu
    450                 455                 460

Thr Ser Lys Leu Ser Ser Lys Ser Ala Lys Glu Arg Arg Asn Arg Arg
465                 470                 475                 480

Lys Lys Lys Asn Gln Lys Lys Leu Ser Ser Gly Glu Glu Lys Gly Asp
                485                 490                 495

Ala Glu Lys Leu Ser Lys Ser Glu Ser Glu Asp Ser Ile Arg Arg Lys
                500                 505                 510

Ser Phe His Leu Gly Val Glu Gly His Arg Arg Ala His Glu Lys Arg
            515                 520                 525

Leu Ser Thr Pro Asn Gln Ser Pro Leu Ser Ile Arg Gly Ser Leu Phe
    530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
                565                 570                 575

Ile Phe Gly Asp Asn Glu Ser Arg Arg Gly Ser Leu Phe Val Pro His
            580                 585                 590

Arg Pro Gln Glu Arg Arg Ser Ser Asn Ile Ser Gln Ala Ser Arg Ser
    595                 600                 605

Pro Pro Met Leu Pro Val Asn Gly Lys Met His Ser Ala Val Asp Cys
610                 615                 620

Asn Gly Val Val Ser Leu Val Asp Gly Arg Ser Ala Leu Met Leu Pro
625                 630                 635                 640

Asn Gly Gln Leu Leu Pro Glu Gly Thr Thr Asn Gln Ile His Lys Lys
                645                 650                 655

Arg Arg Cys Ser Ser Tyr Leu Leu Ser Glu Asp Met Leu Asn Asp Pro
            660                 665                 670

Asn Leu Arg Gln Arg Ala Met Ser Arg Ala Ser Ile Leu Thr Asn Thr
    675                 680                 685

Val Glu Glu Leu Glu Glu Ser Arg Gln Lys Cys Pro Pro Trp Trp Tyr
690                 695                 700

Arg Phe Ala His Lys Phe Leu Ile Trp Asn Cys Ser Pro Tyr Trp Ile
705                 710                 715                 720

Lys Phe Lys Lys Cys Ile Tyr Phe Ile Val Met Asp Pro Phe Val Asp
                725                 730                 735

Leu Ala Val Thr Ile Cys Ile Val Leu Asn Thr Leu Phe Met Ala Met
                740                 745                 750

Glu His His Pro Met Thr Glu Glu Phe Lys Asn Val Leu Ala Ile Gly
            755                 760                 765

Asn Leu Val Phe Thr Gly Ile Phe Ala Ala Glu Met Val Leu Lys Leu
    770                 775                 780

Ile Ala Met Asp Pro Tyr Glu Tyr Phe Gln Val Gly Trp Asn Ile Phe
785                 790                 795                 800

Asp Ser Leu Ile Val Thr Leu Ser Leu Val Glu Leu Phe Leu Ala Asp
                805                 810                 815

Val Glu Gly Leu Ser Val Leu Arg Ser Phe Arg Leu Leu Arg Val Phe
                820                 825                 830

Lys Leu Ala Lys Ser Trp Pro Thr Leu Asn Met Leu Ile Lys Ile Ile
            835                 840                 845

Gly Asn Ser Val Gly Ala Leu Gly Asn Leu Thr Leu Val Leu Ala Ile
    850                 855                 860
```

-continued

```
Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
                885                 890                 895

Trp His Met Asn Asp Phe Phe His Ser Phe Leu Ile Val Phe Arg Val
            900                 905                 910

Leu Cys Gly Glu Trp Ile Glu Thr Met Trp Asp Cys Met Glu Val Ala
            915                 920                 925

Gly Gln Ala Met Cys Leu Ile Val Tyr Met Met Val Met Val Ile Gly
        930                 935                 940

Asn Leu Val Val Leu Asn Leu Phe Leu Ala Leu Leu Leu Ser Ser Phe
945                 950                 955                 960

Ser Ser Asp Asn Leu Thr Ala Ile Glu Glu Asp Pro Asp Ala Asn Asn
                965                 970                 975

Leu Gln Ile Ala Val Thr Arg Ile Lys Lys Gly Ile Asn Tyr Val Lys
            980                 985                 990

Gln Thr Leu Arg Glu Phe Ile Leu Lys Ala Phe Ser Lys Lys Pro Lys
        995                 1000                1005

Ile Ser Arg Glu Ile Arg Gln Ala Glu Asp Leu Asn  Thr Lys Lys
    1010                1015                1020

Glu Asn Tyr Ile Ser Asn His  Thr Leu Ala Glu Met  Ser Lys Gly
    1025                1030                1035

His Asn Phe Leu Lys Glu Lys Asp Lys Ile Ser Gly  Phe Gly Ser
    1040                1045                1050

Ser Val Asp Lys His Leu Met  Glu Asp Ser Asp Gly  Gln Ser Phe
    1055                1060                1065

Ile His Asn Pro Ser Leu Thr  Val Thr Val Pro Ile  Ala Pro Gly
    1070                1075                1080

Glu Ser Asp Leu Glu Asn Met  Asn Ala Glu Glu Leu  Ser Ser Asp
    1085                1090                1095

Ser Asp Ser Glu Tyr Ser Lys  Val Arg Leu Asn Arg  Ser Ser Ser
    1100                1105                1110

Ser Glu Cys Ser Thr Val Asp  Asn Pro Leu Pro Gly  Glu Gly Glu
    1115                1120                1125

Glu Ala Glu Ala Glu Pro Met  Asn Ser Asp Glu Pro  Glu Ala Cys
    1130                1135                1140

Phe Thr Asp Gly Cys Val Arg  Arg Phe Ser Cys Cys  Gln Val Asn
    1145                1150                1155

Ile Glu Ser Gly Lys Gly Lys  Ile Trp Trp Asn Ile  Arg Lys Thr
    1160                1165                1170

Cys Tyr Lys Ile Val Glu His  Ser Trp Phe Glu Ser  Phe Ile Val
    1175                1180                1185

Leu Met Ile Leu Leu Ser Ser  Gly Ala Leu Ala Phe  Glu Asp Ile
    1190                1195                1200

Tyr Ile Glu Arg Lys Lys Thr  Ile Lys Ile Ile Leu  Glu Tyr Ala
    1205                1210                1215

Asp Lys Ile Phe Thr Tyr Ile  Phe Ile Leu Glu Met  Leu Leu Lys
    1220                1225                1230

Trp Ile Ala Tyr Gly Tyr Lys  Thr Tyr Phe Thr Asn  Ala Trp Cys
    1235                1240                1245

Trp Leu Asp Phe Leu Ile Val  Asp Val Ser Leu Val  Thr Leu Val
    1250                1255                1260

Ala Asn Thr Leu Gly Tyr Ser  Asp Leu Gly Pro Ile  Lys Ser Leu
```

-continued

```
            1265                1270                1275
Arg Thr Leu Arg Ala Leu Arg Pro Leu Arg Ala Leu Ser Arg Phe
            1280                1285                1290

Glu Gly Met Arg Val Val Asn Ala Leu Ile Gly Ala Ile Pro
            1295                1300                1305

Ser Ile Met Asn Val Leu Leu Val Cys Leu Ile Phe Trp Leu Ile
            1310                1315                1320

Phe Ser Ile Met Gly Val Asn Leu Phe Ala Gly Lys Phe Tyr Glu
            1325                1330                1335

Cys Ile Asn Thr Thr Asp Gly Ser Arg Phe Pro Ala Ser Gln Val
            1340                1345                1350

Pro Asn Arg Ser Glu Cys Phe Ala Leu Met Asn Val Ser Gln Asn
            1355                1360                1365

Val Arg Trp Lys Asn Leu Lys Val Asn Phe Asp Asn Val Gly Leu
            1370                1375                1380

Gly Tyr Leu Ser Leu Leu Gln Val Ala Thr Phe Lys Gly Trp Thr
            1385                1390                1395

Ile Ile Met Tyr Ala Ala Val Asp Ser Val Asn Val Asp Lys Gln
            1400                1405                1410

Pro Lys Tyr Glu Tyr Ser Leu Tyr Met Tyr Ile Tyr Phe Val Val
            1415                1420                1425

Phe Ile Ile Phe Gly Ser Phe Phe Thr Leu Asn Leu Phe Ile Gly
            1430                1435                1440

Val Ile Ile Asp Asn Phe Asn Gln Gln Lys Lys Lys Leu Gly Gly
            1445                1450                1455

Gln Asp Ile Phe Met Thr Glu Glu Gln Lys Lys Tyr Tyr Asn Ala
            1460                1465                1470

Met Lys Lys Leu Gly Ser Lys Lys Pro Gln Lys Pro Ile Pro Arg
            1475                1480                1485

Pro Gly Asn Lys Ile Gln Gly Cys Ile Phe Asp Leu Val Thr Asn
            1490                1495                1500

Gln Ala Phe Asp Ile Ser Ile Met Val Leu Ile Cys Leu Asn Met
            1505                1510                1515

Val Thr Met Met Val Glu Lys Glu Gly Gln Ser Gln His Met Thr
            1520                1525                1530

Glu Val Leu Tyr Trp Ile Asn Val Val Phe Ile Ile Leu Phe Thr
            1535                1540                1545

Gly Glu Cys Val Leu Lys Leu Ile Ser Leu Arg His Tyr Tyr Phe
            1550                1555                1560

Thr Val Gly Trp Asn Ile Phe Asp Phe Val Val Val Ile Ile Ser
            1565                1570                1575

Ile Val Gly Met Phe Leu Ala Asp Leu Ile Glu Thr Tyr Phe Val
            1580                1585                1590

Ser Pro Thr Leu Phe Arg Val Ile Arg Leu Ala Arg Ile Gly Arg
            1595                1600                1605

Ile Leu Arg Leu Val Lys Gly Ala Lys Gly Ile Arg Thr Leu Leu
            1610                1615                1620

Phe Ala Leu Met Met Ser Leu Pro Ala Leu Phe Asn Ile Gly Leu
            1625                1630                1635

Leu Leu Phe Leu Val Met Phe Ile Tyr Ala Ile Phe Gly Met Ser
            1640                1645                1650

Asn Phe Ala Tyr Val Lys Lys Glu Asp Gly Ile Asn Asp Met Phe
            1655                1660                1665
```

```
Asn Phe Glu Thr Phe Gly Asn Ser Met Ile Cys Leu Phe Gln Ile
    1670            1675                1680

Thr Thr Ser Ala Gly Trp Asp Gly Leu Leu Ala Pro Ile Leu Asn
    1685            1690                1695

Ser Lys Pro Pro Asp Cys Asp Pro Lys Lys Val His Pro Gly Ser
    1700            1705                1710

Ser Val Glu Gly Asp Cys Gly Asn Pro Ser Val Gly Ile Phe Tyr
    1715            1720                1725

Phe Val Ser Tyr Ile Ile Ile Ser Phe Leu Val Val Val Asn Met
    1730            1735                1740

Tyr Ile Ala Val Ile Leu Glu Asn Phe Ser Val Ala Thr Glu Glu
    1745            1750                1755

Ser Thr Glu Pro Leu Ser Glu Asp Asp Phe Glu Met Phe Tyr Glu
    1760            1765                1770

Val Trp Glu Lys Phe Asp Pro Asp Ala Thr Gln Phe Ile Glu Phe
    1775            1780                1785

Ser Lys Leu Ser Asp Phe Ala Ala Ala Leu Asp Pro Pro Leu Leu
    1790            1795                1800

Ile Ala Lys Pro Asn Lys Val Gln Leu Ile Ala Met Asp Leu Pro
    1805            1810                1815

Met Val Ser Gly Asp Arg Ile His Cys Leu Asp Ile Leu Phe Ala
    1820            1825                1830

Phe Thr Lys Arg Val Leu Gly Glu Ser Gly Glu Met Asp Ser Leu
    1835            1840                1845

Arg Ser Gln Met Glu Glu Arg Phe Met Ser Ala Asn Pro Ser Lys
    1850            1855                1860

Val Ser Tyr Glu Pro Ile Thr Thr Thr Leu Lys Arg Lys Gln Glu
    1865            1870                1875

Asp Val Ser Ala Thr Val Ile Gln Arg Ala Tyr Arg Arg Tyr Arg
    1880            1885                1890

Leu Arg Gln Asn Val Lys Asn Ile Ser Ser Ile Tyr Ile Lys Asp
    1895            1900                1905

Gly Asp Arg Asp Asp Asp Leu Leu Asn Lys Lys Asp Met Ala Phe
    1910            1915                1920

Asp Asn Val Asn Glu Asn Ser Ser Pro Glu Lys Thr Asp Ala Thr
    1925            1930                1935

Ser Ser Thr Thr Ser Pro Pro Ser Tyr Asp Ser Val Thr Lys Pro
    1940            1945                1950

Asp Lys Glu Lys Tyr Glu Gln Asp Arg Thr Glu Lys Glu Asp Lys
    1955            1960                1965

Gly Lys Asp Ser Lys Glu Ser Lys Lys
    1970            1975

<210> SEQ ID NO 7
<211> LENGTH: 1977
<212> TYPE: PRT
<213> ORGANISM: Homo sapiens

<400> SEQUENCE: 7

Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
            20                  25                  30

Lys Glu Pro Lys Glu Glu Lys Lys Asp Asp Asp Glu Glu Ala Pro Lys
```

```
                35                  40                  45
Pro Ser Ser Asp Leu Glu Ala Gly Lys Gln Leu Pro Phe Ile Tyr Gly
 50                  55                  60

Asp Ile Pro Pro Gly Met Val Ser Glu Pro Leu Glu Asp Leu Asp Pro
 65                  70                  75                  80

Tyr Tyr Ala Asp Lys Lys Thr Phe Ile Val Leu Asn Lys Gly Lys Thr
                 85                  90                  95

Ile Phe Arg Phe Asn Ala Thr Pro Ala Leu Tyr Met Leu Ser Pro Phe
                100                 105                 110

Ser Pro Leu Arg Arg Ile Ser Ile Lys Ile Leu Val His Ser Leu Phe
            115                 120                 125

Ser Met Leu Ile Met Cys Thr Ile Leu Thr Asn Cys Ile Phe Met Thr
        130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
        275                 280                 285

Ile Met Asn Thr Leu Glu Ser Glu Glu Asp Phe Arg Lys Tyr Phe Tyr
290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
        355                 360                 365

Gln Thr Leu Arg Ala Ala Gly Lys Thr Tyr Met Ile Phe Phe Val Val
    370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Glu Tyr Thr
        435                 440                 445

Ser Ile Arg Arg Ser Arg Ile Met Gly Leu Ser Glu Ser Ser Glu
450                 455                 460
```

```
Thr Ser Lys Leu Ser Ser Lys Ser Ala Lys Glu Arg Arg Asn Arg Arg
465                 470                 475                 480

Lys Lys Lys Asn Gln Lys Lys Leu Ser Ser Gly Glu Glu Lys Gly Asp
            485                 490                 495

Ala Glu Lys Leu Ser Lys Ser Glu Ser Glu Asp Ser Ile Arg Arg Lys
                500                 505                 510

Ser Phe His Leu Gly Val Glu Gly His Arg Arg Ala His Glu Lys Arg
            515                 520                 525

Leu Ser Thr Pro Asn Gln Ser Pro Leu Ser Ile Arg Gly Ser Leu Phe
530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
                565                 570                 575

Ile Phe Gly Asp Asn Glu Ser Arg Arg Gly Ser Leu Phe Val Pro His
            580                 585                 590

Arg Pro Gln Glu Arg Arg Ser Ser Asn Ile Ser Gln Ala Ser Arg Ser
            595                 600                 605

Pro Pro Met Leu Pro Val Asn Gly Lys Met His Ser Ala Val Asp Cys
610                 615                 620

Asn Gly Val Val Ser Leu Val Asp Gly Arg Ser Ala Leu Met Leu Pro
625                 630                 635                 640

Asn Gly Gln Leu Leu Pro Glu Gly Thr Thr Asn Gln Ile His Lys Lys
                645                 650                 655

Arg Arg Cys Ser Ser Tyr Leu Leu Ser Glu Asp Met Leu Asn Asp Pro
            660                 665                 670

Asn Leu Arg Gln Arg Ala Met Ser Arg Ala Ser Ile Leu Thr Asn Thr
            675                 680                 685

Val Glu Glu Leu Glu Glu Ser Arg Gln Lys Cys Pro Pro Trp Trp Tyr
    690                 695                 700

Arg Phe Ala His Lys Phe Leu Ile Trp Asn Cys Ser Pro Tyr Trp Ile
705                 710                 715                 720

Lys Phe Lys Lys Cys Ile Tyr Phe Ile Val Met Asp Pro Phe Val Asp
                725                 730                 735

Leu Ala Ile Thr Ile Cys Ile Val Leu Asn Thr Leu Phe Met Ala Met
                740                 745                 750

Glu His His Pro Met Thr Glu Glu Phe Lys Asn Val Leu Ala Ile Gly
            755                 760                 765

Asn Leu Val Phe Thr Gly Ile Phe Ala Ala Glu Met Val Leu Lys Leu
    770                 775                 780

Ile Ala Met Asp Pro Tyr Glu Tyr Phe Gln Val Gly Trp Asn Ile Phe
785                 790                 795                 800

Asp Ser Leu Ile Val Thr Leu Ser Leu Val Glu Leu Phe Leu Ala Asp
                805                 810                 815

Val Glu Gly Leu Ser Val Leu Arg Ser Phe Arg Leu Leu Arg Val Phe
                820                 825                 830

Lys Leu Ala Lys Ser Trp Pro Thr Leu Asn Met Leu Ile Lys Ile Ile
                835                 840                 845

Gly Asn Ser Val Gly Ala Leu Gly Asn Leu Thr Leu Val Leu Ala Ile
            850                 855                 860

Ile Val Phe Ile Phe Ala Val Val Gly Met Gln Leu Phe Gly Lys Ser
865                 870                 875                 880
```

-continued

```
Tyr Lys Glu Cys Val Cys Lys Ile Asn Asp Asp Cys Thr Leu Pro Arg
            885                 890                 895

Trp His Met Asn Asp Phe Phe His Ser Phe Leu Ile Val Phe Arg Val
        900                 905                 910

Leu Cys Gly Glu Trp Ile Glu Thr Met Trp Asp Cys Met Glu Val Ala
        915                 920                 925

Gly Gln Ala Met Cys Leu Ile Val Tyr Met Met Val Met Val Ile Gly
        930                 935                 940

Asn Leu Val Val Leu Asn Leu Phe Leu Ala Leu Leu Leu Ser Ser Phe
945                 950                 955                 960

Ser Ser Asp Asn Leu Thr Ala Ile Glu Glu Asp Pro Asp Ala Asn Asn
            965                 970                 975

Leu Gln Ile Ala Val Thr Arg Ile Lys Lys Gly Ile Asn Tyr Val Lys
            980                 985                 990

Gln Thr Leu Arg Glu Phe Ile Leu Lys Ala Phe Ser Lys Lys Pro Lys
            995                 1000                1005

Ile Ser Arg Glu Ile Arg Gln Ala Glu Asp Leu Asn Thr Lys Lys
    1010                1015                1020

Glu Asn Tyr Ile Ser Asn His Thr Leu Ala Glu Met Ser Lys Gly
    1025                1030                1035

His Asn Phe Leu Lys Glu Lys Asp Lys Ile Ser Gly Phe Gly Ser
    1040                1045                1050

Ser Val Asp Lys His Leu Met Glu Asp Ser Asp Gly Gln Ser Phe
    1055                1060                1065

Ile His Asn Pro Ser Leu Thr Val Thr Val Pro Ile Ala Pro Gly
    1070                1075                1080

Glu Ser Asp Leu Glu Asn Met Asn Ala Glu Glu Leu Ser Ser Asp
    1085                1090                1095

Ser Asp Ser Glu Tyr Ser Lys Val Arg Leu Asn Arg Ser Ser Ser
    1100                1105                1110

Ser Glu Cys Ser Thr Val Asp Asn Pro Phe Pro Gly Glu Gly Glu
    1115                1120                1125

Glu Ala Glu Ala Glu Pro Met Asn Ser Asp Glu Pro Glu Ala Cys
    1130                1135                1140

Phe Thr Asp Gly Cys Val Arg Phe Ser Cys Cys Gln Val Asn
    1145                1150                1155

Ile Glu Ser Gly Lys Gly Lys Ile Trp Trp Asn Ile Arg Lys Thr
    1160                1165                1170

Cys Tyr Lys Ile Val Glu His Ser Trp Phe Glu Ser Phe Ile Val
    1175                1180                1185

Leu Met Ile Leu Leu Ser Ser Gly Ala Leu Ala Phe Glu Asp Ile
    1190                1195                1200

Tyr Ile Glu Arg Lys Lys Thr Ile Lys Ile Ile Leu Glu Tyr Ala
    1205                1210                1215

Asp Lys Ile Phe Thr Tyr Ile Phe Ile Leu Glu Met Leu Leu Lys
    1220                1225                1230

Trp Ile Ala Tyr Gly Tyr Lys Thr Tyr Phe Thr Asn Ala Trp Cys
    1235                1240                1245

Trp Leu Asp Phe Leu Ile Val Asp Val Ser Leu Val Thr Leu Val
    1250                1255                1260

Ala Asn Thr Leu Gly Tyr Ser Asp Leu Gly Pro Ile Lys Ser Leu
    1265                1270                1275

Arg Thr Leu Arg Ala Leu Arg Pro Leu Arg Ala Leu Ser Arg Phe
```

-continued

```
            1280                1285                1290
Glu Gly Met Arg Val Val Asn Ala Leu Ile Gly Ala Ile Pro
            1295                1300                1305
Ser Ile Met Asn Val Leu Leu Val Cys Leu Ile Phe Trp Leu Ile
            1310                1315                1320
Phe Ser Ile Met Gly Val Asn Leu Phe Ala Gly Lys Phe Tyr Glu
            1325                1330                1335
Cys Ile Asn Thr Thr Asp Gly Ser Arg Phe Pro Ala Ser Gln Val
            1340                1345                1350
Pro Asn Arg Ser Glu Cys Phe Ala Leu Met Asn Val Ser Gln Asn
            1355                1360                1365
Val Arg Trp Lys Asn Leu Lys Val Asn Phe Asp Asn Val Gly Leu
            1370                1375                1380
Gly Tyr Leu Ser Leu Leu Gln Val Ala Thr Phe Lys Gly Trp Thr
            1385                1390                1395
Ile Ile Met Tyr Ala Ala Val Asp Ser Val Asn Val Asp Lys Gln
            1400                1405                1410
Pro Lys Tyr Glu Tyr Ser Leu Tyr Met Tyr Ile Tyr Phe Val Val
            1415                1420                1425
Phe Ile Ile Phe Gly Ser Phe Phe Thr Leu Asn Leu Phe Ile Gly
            1430                1435                1440
Val Ile Ile Asp Asn Phe Asn Gln Gln Lys Lys Lys Leu Gly Gly
            1445                1450                1455
Gln Asp Ile Phe Met Thr Glu Glu Gln Lys Lys Tyr Tyr Asn Ala
            1460                1465                1470
Met Lys Lys Leu Gly Ser Lys Lys Pro Gln Lys Pro Ile Pro Arg
            1475                1480                1485
Pro Gly Asn Lys Ile Gln Gly Cys Ile Phe Asp Leu Val Thr Asn
            1490                1495                1500
Gln Ala Phe Asp Ile Ser Ile Met Val Leu Ile Cys Leu Asn Met
            1505                1510                1515
Val Thr Met Met Val Glu Lys Glu Gly Gln Ser Gln His Met Thr
            1520                1525                1530
Glu Val Leu Tyr Trp Ile Asn Val Val Phe Ile Ile Leu Phe Thr
            1535                1540                1545
Gly Glu Cys Val Leu Lys Leu Ile Ser Leu Arg His Tyr Tyr Phe
            1550                1555                1560
Thr Val Gly Trp Asn Ile Phe Asp Phe Val Val Val Ile Ile Ser
            1565                1570                1575
Ile Val Gly Met Phe Leu Ala Asp Leu Ile Glu Thr Tyr Phe Val
            1580                1585                1590
Ser Pro Thr Leu Phe Arg Val Ile Arg Leu Ala Arg Ile Gly Arg
            1595                1600                1605
Ile Leu Arg Leu Val Lys Gly Ala Lys Gly Ile Arg Thr Leu Leu
            1610                1615                1620
Phe Ala Leu Met Met Ser Leu Pro Ala Leu Phe Asn Ile Gly Leu
            1625                1630                1635
Leu Leu Phe Leu Val Met Phe Ile Tyr Ala Ile Phe Gly Met Ser
            1640                1645                1650
Asn Phe Ala Tyr Val Lys Lys Glu Asp Gly Ile Asn Asp Met Phe
            1655                1660                1665
Asn Phe Glu Thr Phe Gly Asn Ser Met Ile Cys Leu Phe Gln Ile
            1670                1675                1680
```

| | | | | | | | | | |
|---|---|---|---|---|---|---|---|---|---|
| Thr | Thr | Ser | Ala | Gly | Trp | Asp | Gly | Leu | Leu | Ala | Pro | Ile | Leu | Asn |
| | 1685 | | | | 1690 | | | | 1695 | | | | | |
| Ser | Lys | Pro | Pro | Asp | Cys | Asp | Pro | Lys | Lys | Val | His | Pro | Gly | Ser |
| | 1700 | | | | 1705 | | | | 1710 | | | | | |
| Ser | Val | Glu | Gly | Asp | Cys | Gly | Asn | Pro | Ser | Val | Gly | Ile | Phe | Tyr |
| | 1715 | | | | 1720 | | | | 1725 | | | | | |
| Phe | Val | Ser | Tyr | Ile | Ile | Ile | Ser | Phe | Leu | Val | Val | Asn | Met |
| | 1730 | | | | 1735 | | | | 1740 | | | | | |
| Tyr | Ile | Ala | Val | Ile | Leu | Glu | Asn | Phe | Ser | Val | Ala | Thr | Glu | Glu |
| | 1745 | | | | 1750 | | | | 1755 | | | | | |
| Ser | Thr | Glu | Pro | Leu | Ser | Glu | Asp | Asp | Phe | Glu | Met | Phe | Tyr | Glu |
| | 1760 | | | | 1765 | | | | 1770 | | | | | |
| Val | Trp | Glu | Lys | Phe | Asp | Pro | Asp | Ala | Thr | Gln | Phe | Ile | Glu | Phe |
| | 1775 | | | | 1780 | | | | 1785 | | | | | |
| Ser | Lys | Leu | Ser | Asp | Phe | Ala | Ala | Ala | Leu | Asp | Pro | Pro | Leu | Leu |
| | 1790 | | | | 1795 | | | | 1800 | | | | | |
| Ile | Ala | Lys | Pro | Asn | Lys | Val | Gln | Leu | Ile | Ala | Met | Asp | Leu | Pro |
| | 1805 | | | | 1810 | | | | 1815 | | | | | |
| Met | Val | Ser | Gly | Asp | Arg | Ile | His | Cys | Leu | Asp | Ile | Leu | Phe | Ala |
| | 1820 | | | | 1825 | | | | 1830 | | | | | |
| Phe | Thr | Lys | Arg | Val | Leu | Gly | Glu | Ser | Gly | Glu | Met | Asp | Ser | Leu |
| | 1835 | | | | 1840 | | | | 1845 | | | | | |
| Arg | Ser | Gln | Met | Glu | Glu | Arg | Phe | Met | Ser | Ala | Asn | Pro | Ser | Lys |
| | 1850 | | | | 1855 | | | | 1860 | | | | | |
| Val | Ser | Tyr | Glu | Pro | Ile | Thr | Thr | Thr | Leu | Lys | Arg | Lys | Gln | Glu |
| | 1865 | | | | 1870 | | | | 1875 | | | | | |
| Asp | Val | Ser | Ala | Thr | Val | Ile | Gln | Arg | Ala | Tyr | Arg | Arg | Tyr | Arg |
| | 1880 | | | | 1885 | | | | 1890 | | | | | |
| Leu | Arg | Gln | Asn | Val | Lys | Asn | Ile | Ser | Ser | Ile | Tyr | Ile | Lys | Asp |
| | 1895 | | | | 1900 | | | | 1905 | | | | | |
| Gly | Asp | Arg | Asp | Asp | Asp | Leu | Leu | Asn | Lys | Lys | Asp | Met | Ala | Phe |
| | 1910 | | | | 1915 | | | | 1920 | | | | | |
| Asp | Asn | Val | Asn | Glu | Asn | Ser | Ser | Pro | Glu | Lys | Thr | Asp | Ala | Thr |
| | 1925 | | | | 1930 | | | | 1935 | | | | | |
| Ser | Ser | Thr | Thr | Ser | Pro | Pro | Ser | Tyr | Asp | Ser | Val | Thr | Lys | Pro |
| | 1940 | | | | 1945 | | | | 1950 | | | | | |
| Asp | Lys | Glu | Lys | Tyr | Glu | Gln | Asp | Arg | Thr | Glu | Lys | Glu | Asp | Lys |
| | 1955 | | | | 1960 | | | | 1965 | | | | | |
| Gly | Lys | Asp | Ser | Lys | Glu | Ser | Lys | Lys | | | | | | |
| | 1970 | | | | 1975 | | | | | | | | | |

<210> SEQ ID NO 8
<211> LENGTH: 5934
<212> TYPE: DNA
<213> ORGANISM: Homo sapiens

<400> SEQUENCE: 8

| | | |
|---|---|---|
| atggcaatgt tgcctccccc aggacctcag agctttgtcc atttcacaaa acagtctctt | 60 |
| gccctcattg aacaacgcat tgctgaaaga aatcaaagg aacccaaaga agaaaagaaa | 120 |
| gatgatgatg aagaagcccc aaagccaagc agtgacttgg aagctggcaa acaactgccc | 180 |
| ttcgtctatg gggacattcc tcccggcatg gtgtcagagc ccctggagga cttggacccc | 240 |
| tactatgcag acaaaaagac tttcatagta ttgaacaaag ggaaaacaat cttccgtttc | 300 |

```
aatgccacac ctgctttata tatgctttct cctttcagtc ctctaagaag aatatctatt      360
aagattttag tacactcctt attcagcatg ctcatcatgt gcactattct gacaaactgc      420
atatttatga ccatgaataa cccgccggac tggaccaaaa atgtcgagta cacttttact      480
ggaatatata cttttgaatc acttgtaaaa atccttgcaa gaggcttctg tgtaggagaa      540
ttcactttc ttcgtgaccc gtggaactgg ctggattttg tcgtcattgt ttttgcgtat       600
ttaacagaat ttgtaaacct aggcaatgtt tcagctcttc gaactttcag agtattgaga      660
gctttgaaaa ctatttctgt aatcccaggc ctgaagacaa ttgtaggggc tttgatccag      720
tcagtgaaga agctttctga tgtcatgatc ctgactgtgt tctgtctgag tgtgttttgca     780
ctaattggac tacagctgtt catgggaaac ctgaagcata aatgttttcg aaattcactt      840
gaaaataatg aaacattaga aagcataatg aatacctag agagtgaaga agactttaga       900
aaatattttt attacttgga aggatccaaa gatgctctcc tttgtggttt cagcacagat      960
tcaggtcagt gtccagaggg gtacacctgt gtgaaaattg gcagaaaccc tgattatggc     1020
tacacgagct ttgacacttt cagctgggcc ttcttagcct tgtttaggct aatgacccaa     1080
gattactggg aaaaccttta ccaacagacg ctgcgtgctg ctggcaaaac ctacatgatc     1140
ttctttgtcg tagtgatttt cctggctcc ttttatctaa taaacttgat cctggctgtg      1200
gttgccatgg catatgaaga acagaaccag gcaaacattg aagaagctaa acagaaagaa     1260
ttagaattc aacagatgtt agaccgtctt aaaaaagagc aagaagaagc tgaggcaatt      1320
gcagcggcag cggctgaata tacaagtatt aggagaagca gaattatggg cctctcagag     1380
agttcttctg aaacatccaa actgagctct aaaagtgcta agaaagaag aaacagaaga     1440
aagaaaaaga atcaaaagaa gctctccagt ggagaggaaa agggagatgc tgagaaattg     1500
tcgaaatcag aatcagagga cagcatcaga agaaaaagtt ccaccttgg tgtcgaaggg     1560
cataggcgag cacatgaaaa gaggttgtct acccccaatc agtcaccact cagcattcgt     1620
ggctccttgt tttctgcaag gcgaagcagc agaacaagtc tttttagttt caaaggcaga    1680
ggaagagata taggatctga gactgaattt gccgatgatg agcacagcat ttttggagac    1740
aatgagagca gaagggggctc actgtttgtg ccccacagac cccaggagcg acgcagcagt    1800
aacatcagcc aagccagtag gtccccacca atgctgccgg tgaacgggaa aatgcacagt    1860
gctgtggact gcaacggtgt ggtctccctg gttgatggac gctcagccct catgctcccc    1920
aatggacagc ttctgccaga gggcacgacc aatcaaatac acaagaaaag gcgttgtagt    1980
tcctatctcc tttcagagga tatgctgaat gatcccaacc tcagacagag agcaatgagt    2040
agagcaagca tattaacaaa cactgtggaa gaacttgaag agtccagaca aaaatgtcca    2100
ccttggtggt acagatttgc acacaaattc ttgatctgga attgctctcc atattggata    2160
aaattcaaaa agtgtatcta ttttattgta atggatcctt ttgtagatct tgcaattacc    2220
atttgcatag tttaaacac attatttatg gctatggaac accacccaat gactgaggaa    2280
ttcaaaaatg tacttgctat aggaaatttg gtctttactg gaatctttgc agctgaaatg    2340
gtattaaaac tgattgccat ggatccatat gagtatttcc aagtaggctg gaatattttt    2400
gacagcctta ttgtgacttt aagtttagtg gagctctttc tagcagatgt ggaaggattg    2460
tcagttctgc gatcattcag actgctccga gtcttcaagt tggcaaaatc ctggccaaca    2520
ttgaacatgc tgattaagat cattggtaac tcagtagggg ctctaggtaa cctcaccttta   2580
gtgttggcca tcatcgtctt catttttgct gtggtcggca tgcagctctt tggtaagagc    2640
tacaaagaat gtgtctgcaa gatcaatgat gactgtacgc tcccacggtg gcacatgaac    2700
```

```
gacttcttcc actccttcct gattgtgttc cgcgtgctgt gtggagagtg gatagagacc    2760
atgtgggact gtatggaggt cgctggtcaa gctatgtgcc ttattgttta catgatggtc    2820
atggtcattg gaaacctggt ggtcctaaac ctatttctgg ccttattatt gagctcattt    2880
agttcagaca atcttacagc aattgaagaa gaccctgatg caaacaacct ccagattgca    2940
gtgactagaa ttaaaagggg aataaattat gtgaaacaaa ccttacgtga atttattcta    3000
aaagcatttt ccaaaaagcc aaagatttcc agggagataa gacaagcaga agatctgaat    3060
actaagaagg aaaactatat ttctaaccat acacttgctg aaatgagcaa aggtcacaat    3120
ttcctcaagg aaaaagataa aatcagtggt tttggaagca gcgtggacaa acacttgatg    3180
gaagacagtg atggtcaatc atttattcac aatcccagcc tcacagtgac agtgccaatt    3240
gcacctgggg aatccgattt ggaaaatatg aatgctgagg aacttagcag tgattcggat    3300
agtgaataca gcaaagtgag attaaaccgg tcaagctcct cagagtgcag cacagttgat    3360 aacccttgc ctggagaagg agaagaagca gaggctgaac ctatgaattc cgatgagcca    3420
gaggcctgtt tcacagatgg ttgtgtacgg aggttctcat gctgccaagt taacatagag    3480
tcagggaaag gaaaaatctg gtggaacatc aggaaaacct gctacaagat tgttgaacac    3540
agttggtttg aaagcttcat tgtcctcatg atcctgctca gcagtggtgc cctggctttt    3600
gaagatattt atattgaaag gaaaaagacc attaagatta tcctggagta tgcagacaag    3660
atcttcactt acatcttcat tctggaaatg cttctaaaat ggatagcata tggttataaa    3720
acatatttca ccaatgcctg tgttggctg gatttcctaa ttgttgatgt ttctttggtt    3780
actttagtgg caaacactct tggctactca gatcttggcc ccattaaatc ccttcggaca    3840
ctgagagctt taagacctct aagagcctta tctagatttg aaggaatgag ggtcgttgtg    3900
aatgcactca taggagcaat tccttccatc atgaatgtgc tacttgtgtg tcttatattc    3960
tggctgatat tcagcatcat gggagtaaat ttgtttgctg gcaagttcta tgagtgtatt    4020
aacaccacag atgggtcacg gtttcctgca agtcaagttc caaatcgttc cgaatgtttt    4080
gcccttatga atgttagtca aaatgtgcga tggaaaaacc tgaaagtgaa ctttgataat    4140
gtcggacttg gttacctatc tctgcttcaa gttgcaactt ttaagggatg gacgattatt    4200
atgtatgcag cagtggattc tgttaatgta gacaagcagc ccaaatatga atatagcctc    4260
tacatgtata tttattttgt cgtctttatc atctttgggt cattcttcac tttgaacttg    4320
ttcattggtg tcatcataga taatttcaac caacagaaaa agaagcttgg aggtcaagac    4380
atctttatga cagaagaaca gaagaaatac tataatgcaa tgaaaagct ggggtccaag    4440 aagccacaaa agccaattcc tcgaccaggg aacaaaatcc aaggatgtat atttgaccta    4500
gtgacaaatc aagcctttga tattagtatc atggttctta tctgtctcaa catggtaacc    4560
atgatggtag aaaaggaggg tcaaagtcaa catatgactg aagttttata ttggataaat    4620 gtggtttta taatccttt cactggagaa tgtgtgctaa aactgatctc cctcagacac    4680
tactacttca ctgtaggatg gaatatttt gattttgtgg ttgtgattat ctccattgta    4740
ggtatgtttc tagctgattt gattgaaacg tattttgtgt cccctaccct gttccgagtg    4800
atccgtcttg ccaggattgg ccgaatccta cgtctagtca aaggagcaaa ggggatccgc    4860
acgctgctct tgctttgat gatgtccctt cctgcgttgt taacatcgg cctcctgctc    4920 ttcctggtca tgttcatcta cgccatcttt ggaatgtcca actttgccta tgttaaaaag    4980
gaagatggaa ttaatgacat gttcaatttt gagacctttg caacagtat gatttgcctg    5040
```

```
ttccaaatta caacctctgc tggctgggat ggattgctag cacctattct taacagtaag    5100
ccacccgact gtgacccaaa aaaagttcat cctggaagtt cagttgaagg agactgtggt    5160
aacccatctg ttggaatatt ctactttgtt agttatatca tcatatcctt cctggttgtg    5220
gtgaacatgt acattgcagt catactggag aattttagtg ttgccactga agaaagtact    5280
gaacctctga gtgaggatga ctttgagatg ttctatgagg tttgggagaa gtttgatccc    5340
gatgcgaccc agtttataga gttctctaaa ctctctgatt ttgcagctgc cctggatcct    5400
cctcttctca tagcaaaacc caacaaagtc cagctcattg ccatggatct gcccatggtt    5460
agtggtgacc ggatccattg tcttgacatc ttatttgctt ttacaaagcg tgttttgggt    5520
gagagtgggg agatggattc tcttcgttca cagatggaag aaaggttcat gtctgcaaat    5580
ccttccaaag tgtcctatga acccatcaca accacactaa aacggaaaca agaggatgtg    5640
tctgctactg tcattcagcg tgcttataga cgttaccgct taaggcaaaa tgtcaaaaat    5700
atatcaagta tatacataaa agatggagac agagatgatg atttactcaa taaaaaagat    5760
atggcttttg ataatgttaa tgagaactca agtccagaaa aacagatgc cacttcatcc     5820 accacctctc caccttcata tgatagtgta acaaagccag acaaagagaa atatgaacaa    5880
gacagaacag aaaaggaaga caaagggaaa gacagcaagg aaagcaaaaa atag           5934

<210> SEQ ID NO 9
<211> LENGTH: 5934
<212> TYPE: DNA
<213> ORGANISM: Homo sapiens

<400> SEQUENCE: 9
atggcaatgt tgcctccccc aggacctcag agctttgtcc atttcacaaa acagtctctt      60
gccctcattg aacaacgcat tgctgaaaga aaatcaaagg aacccaaaga agaaaagaaa    120
gatgatgatg aagaagcccc aaagccaagc agtgacttgg aagctggcaa caactgccc    180 ttcgtctatg gggacattcc tcccggcatg tgtcagagc cctggagga cttgaccccc    240 tactatgcag acaaaaagac tttcatagta ttgaacaaag ggaaaacaat cttccgtttc    300
aatgccacac ctgctttata tatgcttttct cctttcagtc ctctaagaag aatatctatt    360
aagattttag tacactcctt attcagcatg ctcatcatgt gcactattct gacaaactgc    420
atatttatga ccatgaataa cccgccggac tggaccaaaa atgtcgagta cacttttact    480
ggaatatata cttttgaatc acttgtaaaa atccttgcaa gaggcttctg tgtaggagaa    540
ttcacttttc ttcgtgaccc gtggaactgg ctggattttg tcgtcattgt ttttgcgtat    600
ttaacagaat ttgtaaacct aggcaatgtt tcagctcttc gaactttcag agtattgaga    660
gctttgaaaa ctatttctgt aatcccaggc ctgaagacaa ttgtaggggc tttgatccag    720
tcagtgaaga agctttctga tgtcatgatc ctgactgtgt tctgtctgag tgtgtttgca    780
ctaattggac tacagctgtt catgggaaac ctgaagcata atgttttcg aaattcactt    840 gaaaataatg aaacattaga agcataatg aatacctag agagtgaaga agactttaga    900
aaatattttt attacttgga aggatccaaa gatgctctcc tttgtggttt cagcacagat    960
tcaggtcagt gtccagaggg gtacacctgt gtgaaaattg cagaaacccc tgattatggc    1020
tacacgagct ttgacacttt cagctgggcc ttcttagcct tgtttaggct aatgacccaa    1080
gattactggg aaaaccttta ccaacagacg ctgcgtgctg ctggcaaaac ctacatgatc    1140
ttctttgtcg tagtgatttt cctgggctcc tttatctaa taaacttgat cctggctgtg    1200
gttgccatgg catatgaaga acagaaccag gcaaacattg aagaagctaa acagaaagaa    1260
```

```
ttagaatttc aacagatgtt agaccgtctt aaaaaagagc aagaagaagc tgaggcaatt    1320
gcagcggcag cggctgaata tacaagtatt aggagaagca gaattatggg cctctcagag    1380
agttcttctg aaacatccaa actgagctct aaaagtgcta agaaagaag aaacagaaga     1440 aagaaaaga atcaaaagaa gctctccagt ggagaggaaa agggagatgc tgagaaattg     1500
tcgaaatcag aatcagagga cagcatcaga agaaaaagtt tccaccttgg tgtcgaaggg    1560
cataggcgag cacatgaaaa gaggttgtct accccccaatc agtcaccact cagcattcgt   1620
ggctccttgt tttctgcaag gcgaagcagc agaacaagtc ttttagttt caaaggcaga     1680 ggaagagata taggatctga gactgaattt gccgatgatg agcacagcat ttttggagac    1740
aatgagagca gaaggggctc actgtttgtg ccccacagac cccaggagcg acgcagcagt    1800
aacatcagcc aagccagtag gtccccacca atgctgccgg tgaacgggaa aatgcacagt    1860
gctgtggact gcaacggtgt ggtctccctg gttgatggac gctcagccct catgctcccc    1920
aatggacagc ttctgccaga gggcacgacc aatcaaatac acaagaaaag gcgttgtagt    1980
tcctatctcc tttcagagga tatgctgaat gatcccaacc tcagacagag agcaatgagt    2040
agagcaagca tattaacaaa cactgtggaa gaacttgaag agtccagaca aaaatgtcca    2100
ccttggtggt acagatttgc acacaaattc ttgatctgga attgctctcc atattggata    2160
aaattcaaaa agtgtatcta ttttattgta atggatcctt ttgtagatct tgcaattacc    2220
atttgcatag ttttaaacac attatttatg gctatggaac accacccaat gactgaggaa    2280
ttcaaaaatg tacttgctat aggaaatttg gtctttactg gaatctttgc agctgaaatg    2340
gtattaaaac tgattgccat ggatccatat gagtatttcc aagtaggctg gaatatttt    2400 gacagcctta ttgtgacttt aagtttagtg gagctctttc tagcagatgt ggaaggattg    2460
tcagttctgc gatcattcag actgctccga gtcttcaagt tggcaaaatc ctggccaaca    2520
ttgaacatgc tgattaagat cattggtaac tcagtagggg ctctaggtaa cctcaccta    2580 gtgttggcca tcatcgtctt catttttgct gtggtcggca tgcagctctt tggtaagagc    2640
tacaaagaat gtgtctgcaa gatcaatgat gactgtacgc tcccacggtg gcacatgaac    2700
gacttcttcc actccttcct gattgtgttc cgcgtgctgt gtggagagtg gatagagacc    2760
atgtgggact gtatggaggt cgctggtcaa gctatgtgcc ttattgttta catgatggtc    2820
atggtcattg gaaacctggt ggtcctaaac ctatttctgg ccttattatt gagctcattt    2880
agttcagaca atcttacagc aattgaagaa gaccctgatg caaacaacct ccagattgca    2940
gtgactagaa ttaaaaaggg aataaattat gtgaaacaaa ccttacgtga atttattcta    3000
aaagcatttt ccaaaaagcc aaagatttcc agggagataa gacaagcaga agatctgaat    3060
actaagaagg aaaactatat ttctaaccat acacttgctg aaatgagcaa aggtcacaat    3120
ttcctcaagg aaaagataa aatcagtggt tttggaagca gcgtggacaa acacttgatg    3180
gaagacagtg atggtcaatc atttattcac aatcccagcc tcacagtgac agtgccaatt    3240
gcacctgggg aatccgattt ggaaaatatg aatgctgagg aacttagcag tgattcggat    3300
agtgaataca gcaaagtgag attaaaccgg tcaagctcct cagagtgcag cacagttgat    3360 aacccttgc ctgagaagg agaagaagca gaggctgaac ctatgaattc cgatgagcca    3420
gaggcctgtt tcacagatgg ttgtgtacgg aggttctcat gctgccaagt taacatagag    3480
tcagggaaag gaaaaatctg gtggaacatc aggaaaacct gctacaagat tgttgaacac    3540
agttggtttg aaagcttcat tgtcctcatg atcctgctca gcagtggtgc cctggctttt    3600
```

```
gaagatattt atattgaaag gaaaaagacc attaagatta tcctggagta tgcagacaag    3660
atcttcactt acatcttcat tctggaaatg cttctaaaat ggatagcata tggttataaa    3720
acatatttca ccaatgcctg tgttggctg gatttcctaa ttgttgatgt ttctttggtt    3780
actttagtgg caaacactct tggctactca gatcttggcc ccattaaatc ccttcggaca    3840
ctgagagctt taagacctct aagagcctta tctagatttg aaggaatgag ggtcgttgtg    3900
aatgcactca taggagcaat tccttccatc atgaatgtgc tacttgtgtg tcttatattc    3960
tggctgatat tcagcatcat gggagtaaat ttgtttgctg gcaagttcta tgagtgtatt    4020
aacaccacag atgggtcacg gtttcctgca agtcaagttc caaatcgttc cgaatgtttt    4080
gcccttatga atgttagtca aaatgtgcga tggaaaaacc tgaaagtgaa ctttgataat    4140
gtcggacttg gttacctatc tctgcttcaa gttgcaactt ttaagggatg gacgattatt    4200
atgtatgcag cagtggattc tgttaatgta gacaagcagc ccaaatatga atatagcctc    4260
tacatgtata tttatttgt cgtctttatc atctttgggt cattcttcac tttgaacttg    4320
ttcattggtg tcatcataga taatttcaac caacagaaaa agaagcttgg aggtcaagac    4380
atctttatga cagaagaaca gaagaaatac tataatgcaa tgaaaaagct ggggtccaag    4440
aagccacaaa agccaattcc tcgaccaggg aacaaaatcc aaggatgtat atttgaccta    4500
gtgacaaatc aagcctttga tattagtatc atggttctta tctgtctcaa catggtaacc    4560
atgatggtag aaaaggaggg tcaaagtcaa catatgactg aagttttata ttggataaat    4620
gtggttttta taatcctttt cactggagaa tgtgtgctaa aactgatctc cctcagacac    4680
tactacttca ctgtaggatg gaatattttt gattttgtgg ttgtgattat ctccattgta    4740
ggtatgtttc tagctgattt gattgaaacg tattttgtgt ccctacccct gttccgagtg    4800
atccgtcttg ccaggattgg ccgaatccta cgtctagtca aaggagcaaa ggggatccgc    4860
acgctgctct ttgctttgat gatgtccctt cctgcgttgt ttaacatcgg cctcctgctc    4920
ttcctggtca tgttcatcta cgccatcttt ggaatgtcca actttgccta tgttaaaaag    4980
gaagatggaa ttaatgacat gttcaatttt gagacctttg gcaacagtat gatttgcctg    5040
ttccaaatta caacctctgc tggctgggat ggattgctag cacctattct taacagtaag    5100
ccacccgact gtgacccaaa aaaagttcat cctggaagtt cagttgaagg agactgtggt    5160
aacccatctg ttggaatatt ctactttgtt agttatatca tcatatcctt cctggttgtg    5220
gtgaacatgt acattgcagt catactggag aattttagtg ttgccactga agaaagtact    5280
gaacctctga gtgaggatga ctttgagatg ttctatgagg tttgggagaa gtttgatccc    5340
gatgcgaccc agtttataga gttctctaaa ctctctgatt ttgcagctgc cctggatcct    5400
cctcttctca tagcaaaacc caacaaagtc cagctcattg ccatggatct gcccatggtt    5460
agtggtgacc ggatccattg tcttgacatc ttatttgctt ttacaaagcg tgttttgggt    5520
gagagtgggg agatggattc tcttcgttca cagatggaag aaaggttcat gtctgcaaat    5580
ccttccaaag tgtcctatga acccatcaca accacactaa aacggaaaca agaggatgtg    5640
tctgctactg tcattcagcg tgcttataga cgttaccgct taaggcaaaa tgtcaaaaat    5700
atatcaagta tatacataaa agatggagac agagatgatg atttactcaa taaaaaagat    5760
atggcttttg ataatgttaa tgagaactca agtccagaaa aaacagatgc cacttcatcc    5820
accacctctc caccttcata tgatagtgta acaaagccag acaaagagaa atatgaacaa    5880
gacagaacag aaaaggaaga caaagggaaa gacagcaagg aaagcaaaaa atag          5934
```

<210> SEQ ID NO 10
<211> LENGTH: 5934
<212> TYPE: DNA
<213> ORGANISM: Homo sapiens

<400> SEQUENCE: 10

| | | | | | |
|---|---|---|---|---|---|
| atggcaatgt | tgcctccccc | aggacctcag | agctttgtcc | atttcacaaa | acagtctctt | 60 |
| gccctcattg | aacaacgcat | tgctgaaaga | aaatcaaagg | aacccaaaga | agaaaagaaa | 120 |
| gatgatgatg | aagaagcccc | aaagccaagc | agtgacttgg | aagctggcaa | acaactgccc | 180 |
| ttcatctatg | gggacattcc | tcccggcatg | gtgtcagagc | cctggagga | cttggacccc | 240 |
| tactatgcag | acaaaaagac | tttcatagta | ttgaacaaag | ggaaaacaat | cttccgtttc | 300 |
| aatgccacac | ctgctttata | tatgctttct | cctttcagtc | ctctaagaag | aatatctatt | 360 |
| aagattttag | tacactcctt | attcagcatg | ctcatcatgt | gcactattct | gacaaactgc | 420 |
| atatttatga | ccatgaataa | cccgccggac | tggaccaaaa | atgtcgagta | cacttttact | 480 |
| ggaatatata | cttttgaatc | acttgtaaaa | atccttgcaa | gaggcttctg | tgtaggagaa | 540 |
| ttcactttc | ttcgtgaccc | gtggaactgg | ctggattttg | tcgtcattgt | ttttgcgtat | 600 |
| ttaacagaat | ttgtaaacct | aggcaatgtt | tcagctcttc | gaactttcag | agtattgaga | 660 |
| gctttgaaaa | ctatttctgt | aatcccaggc | ctgaagacaa | ttgtaggggc | tttgatccag | 720 |
| tcagtgaaga | agctttctga | tgtcatgatc | ctgactgtgt | tctgtctgag | tgtgtttgca | 780 |
| ctaattggac | tacagctgtt | catgggaaac | ctgaagcata | aatgttttcg | aaattcactt | 840 |
| gaaaataatg | aaacattaga | aagcataatg | aatacccctag | agagtgaaga | agactttaga | 900 |
| aaatattttt | attacttgga | aggatccaaa | gatgctctcc | tttgtggttt | cagcacagat | 960 |
| tcaggtcagt | gtccagaggg | gtacacctgt | gtgaaaattg | gcagaaaccc | tgattatggc | 1020 |
| tacacgagct | ttgacacttt | cagctgggcc | ttcttagcct | tgtttaggct | aatgacccaa | 1080 |
| gattactggg | aaaacccttta | ccaacagacg | ctgcgtgctg | ctggcaaaac | ctacatgatc | 1140 |
| ttctttgtcg | tagtgatttt | cctgggctcc | ttttatctaa | taaacttgat | cctggctgtg | 1200 |
| gttgccatgg | catatgaaga | acagaaccag | gcaaacattg | aagaagctaa | acagaaagaa | 1260 |
| ttagaatttc | aacagatgtt | agaccgtctt | aaaaaagagc | aagaagaagc | tgaggcaatt | 1320 |
| gcagcggcag | cggctgaata | tacaagtatt | aggagaagca | gaattatggg | cctctcagag | 1380 |
| agttcttctg | aaacatccaa | actgagctct | aaaagtgcta | agaaagaag | aaacagaaga | 1440 |
| aagaaaaaga | atcaaaagaa | gctctccagt | ggagaggaaa | agggagatgc | tgagaaattg | 1500 |
| tcgaaatcag | aatcagagga | cagcatcaga | agaaaaagtt | tccaccttgg | tgtcgaaggg | 1560 |
| cataggcgag | cacatgaaaa | gaggttgtct | accccaatc | agtcaccact | cagcattcgt | 1620 |
| ggctccttgt | tttctgcaag | gcgaagcagc | agaacaagtc | ttttttagttt | caaaggcaga | 1680 |
| ggaagagata | taggatctga | gactgaattt | gccgatgatg | agcacagcat | ttttggagac | 1740 |
| aatgagagca | gaaggggctc | actgtttgtg | ccccacagac | cccaggagcg | acgcagcagt | 1800 |
| aacatcagcc | aagccagtag | gtccccacca | atgctgccgg | tgaacgggaa | aatgcacagt | 1860 |
| gctgtggact | gcaacggtgt | ggtctccctg | gttgatggac | gctcagccct | catgctcccc | 1920 |
| tatgacagc | ttctgccaga | gggcacgacc | aatcaaatac | acaagaaaag | gcgttgtagt | 1980 |
| tcctatctcc | tttcagagga | tatgctgaat | gatcccaacc | tcagacagag | agcaatgagt | 2040 |
| agagcaagca | tattaacaaa | cactgtggaa | gaacttgaag | agtccagaca | aaaatgtcca | 2100 |
| ccttggtggt | acagatttgc | acacaaattc | ttgatctgga | attgctctcc | atattggata | 2160 |

```
aaattcaaaa agtgtatcta ttttattgta atggatcctt ttgtagatct tgcaattacc   2220
atttgcatag ttttaaacac attatttatg gctatggaac accacccaat gactgaggaa   2280
ttcaaaaatg tacttgctat aggaaatttg gtctttactg gaatctttgc agctgaaatg   2340
gtattaaaac tgattgccat ggatccatat gagtatttcc aagtaggctg gaatatttt    2400
gacagcctta ttgtgacttt aagtttagtg gagctctttc tagcagatgt ggaaggattg   2460
tcagttctgc gatcattcag actgctccga gtcttcaagt tggcaaaatc ctggccaaca   2520
ttgaacatgc tgattaagat cattggtaac tcagtagggg ctctaggtaa cctcacctta   2580
gtgttggcca tcatcgtctt catttttgct gtggtcggca tgcagctctt tggtaagagc   2640
tacaaagaat gtgtctgcaa gatcaatgat gactgtacgc tcccacggtg gcacatgaac   2700
gacttcttcc actccttcct gattgtgttc cgcgtgctgt gtggagagtg gatagagacc   2760
atgtgggact gtatggaggt cgctggtcaa gctatgtgcc ttattgttta catgatggtc   2820
atggtcattg gaaacctggt ggtcctaaac ctatttctgg ccttattatt gagctcattt   2880
agttcagaca atcttacagc aattgaagaa gaccctgatg caaacaacct ccagattgca   2940
gtgactagaa ttaaaagggg aataaattat gtgaaacaaa ccttacgtga atttattcta   3000
aaagcatttt ccaaaaagcc aaagatttcc agggagataa gacaagcaga agatctgaat   3060
actaagaagg aaaactatat ttctaaccat acacttgctg aaatgagcaa aggtcacaat   3120
ttcctcaagg aaaaagataa aatcagtggt tttggaagca gcgtggacaa acacttgatg   3180
gaagacagtg atggtcaatc atttattcac aatcccagcc tcacagtgac agtgccaatt   3240
gcacctgggg aatccgattt ggaaaatatg aatgctgagg aacttagcag tgattcggat   3300
agtgaataca gcaaagtgag attaaaccgg tcaagctcct cagagtgcag cacagttgat   3360
aacccttgc ctggagaagg agaagaagca gaggctgaac ctatgaattc cgatgagcca   3420
gaggcctgtt tcacagatgg ttgtgtacgg aggttctcat gctgccaagt taacatagag   3480
tcagggaaag gaaaaatctg gtggaacatc aggaaaacct gctacaagat tgttgaacac   3540
agttggttg aaagcttcat tgtcctcatg atcctgctca gcagtggtgc cctggctttt   3600
gaagatattt atattgaaag gaaaagacc attaagatta tcctggagta tgcagacaag   3660
atcttcactt acatcttcat tctggaaatg cttctaaaat ggatagcata tggttataaa   3720
acatatttca ccaatgcctg tgttggctg gatttcctaa ttgttgatgt ttctttggtt   3780
actttagtgg caaacactct tggctactca gatcttggcc ccattaaatc ccttcggaca   3840
ctgagagctt taagacctct aagagcctta tctagatttg aaggaatgag ggtcgttgtg   3900
aatgcactca taggagcaat tccttccatc atgaatgtgc tacttgtgtg tcttatattc   3960
tggctgatat tcagcatcat gggagtaaat ttgtttgctg gcaagttcta tgagtgtatt   4020
aacaccacag atgggtcacg gtttcctgca agtcaagttc aaatcgttc cgaatgttt    4080
gcccttatga atgttagtca aatgtgcga tggaaaaacc tgaaagtgaa ctttgataat   4140
gtcggacttg gttacctatc tctgcttcaa gttgcaactt taagggatg gacgattatt   4200
atgtatgcag cagtggattc tgttaatgta gacaagcagc ccaaatatga atatagcctc   4260
tacatgtata tttattttgt cgtctttatc atctttgggt cattcttcac tttgaacttg   4320
ttcattggtg tcatcataga taatttcaac caacagaaaa agaagcttgg aggtcaagac   4380
atctttatga cagaagaaca gaagaaatac tataatgcaa tgaaaagct ggggtccaag   4440
aagccacaaa agccaattcc tcgaccaggg aacaaaatcc aaggatgtat atttgaccta   4500
gtgacaaatc aagcctttga tattagtatc atggttctta tctgtctcaa catggtaacc   4560
```

```
atgatggtag aaaaggaggg tcaaagtcaa catatgactg aagtttata ttggataaat    4620
gtggttttta taatccttt cactggagaa tgtgtgctaa aactgatctc cctcagacac    4680
tactacttca ctgtaggatg gaatatttt gattttgtgg ttgtgattat ctccattgta    4740
ggtatgtttc tagctgattt gattgaaacg tattttgtgt ccctaccct gttccgagtg    4800
atccgtcttg ccaggattgg ccgaatccta cgtctagtca aaggagcaaa ggggatccgc    4860
acgctgctct ttgctttgat gatgtccctt cctgcgttgt taacatcgg cctcctgctc    4920
ttcctggtca tgttcatcta cgccatcttt ggaatgtcca actttgccta tgttaaaaag    4980
gaagatggaa ttaatgacat gttcaatttt gagaccttg gcaacagtat gatttgcctg    5040
ttccaaatta caacctctgc tggctgggat ggattgctag cacctattct taacagtaag    5100
ccacccgact gtgaccccaaa aaagttcat cctggaagtt cagttgaagg agactgtggt    5160
aacccatctg ttgaatatat ctactttgtt agttatatca tcatatcctt cctggttgtg    5220
gtgaacatgt acattgcagt catactggag aattttagtg ttgccactga agaaagtact    5280
gaacctctga gtgaggatga ctttgagatg ttctatgagg tttgggagaa gtttgatccc    5340
gatgcgaccc agtttataga gttctctaaa ctctctgatt ttgcagctgc cctggatcct    5400
cctcttctca tagcaaaacc caacaaagtc cagctcattg ccatggatct gcccatggtt    5460
agtggtgacc ggatccattg tcttgacatc ttatttgctt ttacaaagcg tgttttgggt    5520
gagagtgggg agatggattc tcttcgttca cagatggaag aaaggttcat gtctgcaaat    5580
ccttccaaag tgtcctatga acccatcaca accacactaa acggaaaaca agaggatgtg    5640
tctgctactg tcattcagcg tgcttataga cgttaccgct taaggcaaaa tgtcaaaaat    5700
atatcaagta tatacataaa agatggagac agagatgatg atttactcaa taaaaaagat    5760
atggcttttg ataatgttaa tgagaactca agtccagaaa aaacagatgc cacttcatcc    5820
accacctctc caccttcata tgatagtgta acaaagccag acaaagaaa atatgaacaa    5880
gacagaacag aaaaggaaga caagggaaa gacagcaagg aaagcaaaaa atag          5934
```

<210> SEQ ID NO 11
<211> LENGTH: 5934
<212> TYPE: DNA
<213> ORGANISM: Homo sapiens

<400> SEQUENCE: 11

```
atggcaatgt tgcctccccc aggacctcag agctttgtcc atttcacaaa acagtctctt     60
gccctcattg aacaacgcat tgctgaaaga aatcaaagg aacccaaaga agaaaagaaa    120
gatgatgatg aagaagcccc aaagccaagc agtgacttgg aagctggcaa caactgccc    180
ttcatctatg gggacattcc tcccggcatg gtgtcagagc cctggagga cttggaccc    240
tactatgcag acaaaaagac tttcatagta ttgaacaaag ggaaaacaat cttccgtttc    300
aatgccacac tgctttata tatgctttct cctttcagtc ctctaagaag aatatctatt    360
aagattttag tacactcctt attcagcatg ctcatcatgt gcactattct gacaaactgc    420
atatttatga ccatgaataa cccgccggac tggaccaaaa atgtcgagta cactttact    480
ggaatatata cttttgaatc acttgtaaaa atccttgcaa gaggcttctg tgtaggagaa    540
ttcacttttc ttcgtgaccc gtggaactgg ctggattttg tcgtcattgt ttttgcgtat    600
ttaacagaat ttgtaaacct aggcaatgtt tcagctcttc gaactttcag agtattgaga    660
gctttgaaaa ctatttctgt aatcccaggc ctgaagacaa ttgtaggggc tttgatccag    720
```

```
tcagtgaaga agctttctga tgtcatgatc ctgactgtgt tctgtctgag tgtgtttgca        780
ctaattggac tacagctgtt catgggaaac ctgaagcata aatgttttcg aaattcactt        840
gaaaataatg aaacattaga aagcataatg aataccctag agagtgaaga agactttaga        900
aaatattttt attacttgga aggatccaaa gatgctctcc tttgtggttt cagcacagat        960
tcaggtcagt gtccagaggg gtacacctgt gtgaaaattg gcagaaaccc tgattatggc       1020
tacacgagct ttgacacttt cagctgggcc ttcttagcct tgtttaggct aatgacccaa       1080
gattactggg aaaaccttta ccaacagacg ctgcgtgctg ctggcaaaac ctacatgatc       1140
ttctttgtcg tagtgatttt cctgggctcc ttttatctaa taaacttgat cctggctgtg       1200
gttgccatgg catatgaaga acagaaccag gcaaacattg aagaagctaa acagaaagaa       1260
ttagaatttc aacagatgtt agaccgtctt aaaaaagagc aagaagagc tgaggcaatt       1320 gcagcggcag cggctgaata tacaagtatt aggagaagca gaattatggg cctctcagag       1380
agttcttctg aaacatccaa actgagctct aaaagtgcta agaaagaag aaacagaaga       1440 aagaaaaga atcaaaagaa gctctccagt ggagaggaaa agggagatgc tgagaaattg       1500
tcgaaatcag aatcagagga cagcatcaga agaaaaagtt ccaccttgg tgtcgaaggg       1560 cataggcgag cacatgaaaa gaggttgtct acccccaatc agtcaccact cagcattcgt       1620
ggctccttgt tttctgcaag gcgaagcagc agaacaagtc tttttagttt caaaggcaga       1680
ggaagagata taggatctga gactgaattt gccgatgatg agcacagcat ttttggagac       1740
aatgagagca gaagggctc actgtttgtg ccccacagac cccaggagcg acgcagcagt       1800
aacatcagcc aagccagtag gtccccacca atgctgccgg tgaacgggaa aatgcacagt       1860
gctgtggact gcaacggtgt ggtctccctg gttgatggac gctcagccct catgctcccc       1920 aatgacagc ttctgccaga gggcacgacc aatcaaatac acaggaaaag gcgttgtagt       1980
tcctatctcc tttcagagga tatgctgaat gatcccaacc tcagacagag agcaatgagt       2040
agagcaagca tattaacaaa cactgtggaa gaacttgaag agtccagaca aaaatgtcca       2100
ccttggtggt acagatttgc acacaaattc ttgatctgga attgctctcc atattggata       2160
aaattcaaaa agtgtatcta ttttattgta atggatcctt tgtagatct tgcaattacc       2220 atttgcatag ttttaaacac attatttatg gctatggaac accacccaat gactgaggaa       2280
ttcaaaaatg tacttgctat aggaaatttg gtctttactg gaatctttgc agctgaaatg       2340
gtattaaaac tgattgccat ggatccatat gagtatttcc aagtaggctg gaatattttt       2400
gacagcctta ttgtgacttt aagtttagtg gagctctttc tagcagatgt ggaaggattg       2460
tcagttctgc gatcattcag actgctccga gtcttcaagt tggcaaaatc ctggccaaca       2520
ttgaacatgc tgattaagat cattggtaac tcagtagggg ctctaggtaa cctcacctta       2580
gtgttggcca tcatcgtctt catttttgct gtggtcggca tgcagctctt tggtaagagc       2640
tacaaagaat gtgtctgcaa gatcaatgat gactgtacgc tcccacggtg gcacatgaac       2700
gacttcttcc actccttcct gattgtgttc cgcgtgctgt gtggagagtg gatagagacc       2760
atgtgggact gtatggaggt cgctggtcaa gctatgtgcc ttattgttta catgatggtc       2820
atggtcattg gaaacctggt ggtcctaaac ctatttctgg ccttattatt gagctcattt       2880
agttcagaca atcttacagc aattgaagaa gaccctgatg caaacaacct ccagattgca       2940
gtgactagaa ttaaaaaggg aataaattat gtgaaacaaa ccttacgtga atttattcta       3000
aaagcatttt ccaaaagcc aaagattcc agggagataa gacaagcaga agatctgaat       3060
actaagaagg aaaactatat ttctaaccat acacttgctg aaatgagcaa aggtcacaat       3120
```

```
ttcctcaagg aaaaagataa aatcagtggt tttggaagca gcgtggacaa acacttgatg    3180
gaagacagtg atggtcaatc atttattcac aatcccagcc tcacagtgac agtgccaatt    3240
gcacctgggg aatccgattt ggaaaatatg aatgctgagg aacttagcag tgattcggat    3300
agtgaataca gcaaagtgag attaaaccgg tcaagctcct cagagtgcag cacagttgat    3360
aacccttttgc ctggagaagg agaagaagca gaggctgaac ctatgaattc cgatgagcca    3420
gaggcctgtt tcacagatgg ttgtgtacgg aggttctcat gctgccaagt taacatagag    3480
tcagggaaag gaaaaatctg gtggaacatc aggaaaacct gctacaagat tgttgaacac    3540
agttggtttg aaagcttcat tgtcctcatg atcctgctca gcagtggtgc cctggctttt    3600
gaagatattt atattgaaag gaaaaagacc attaagatta tcctggagta tgcagacaag    3660
atcttcactt acatcttcat tctggaaatg cttctaaaat ggatagcata tggttataaa    3720
acatatttca ccaatgcctg tgtgttggctg gatttcctaa ttgttgatgt ttctttggtt    3780
actttagtgg caaacactct tggctactca gatcttggcc ccattaaatc ccttcggaca    3840
ctgagagctt taagacctct aagagcctta tctagatttg aaggaatgag ggtcgttgtg    3900
aatgcactca taggagcaat tccttccatc atgaatgtgc tacttgtgtg tcttatattc    3960
tggctgatat tcagcatcat gggagtaaat ttgtttgctg gcaagttcta tgagtgtatt    4020
aacaccacag atgggtcacg gtttcctgca agtcaagttc caaatcgttc cgaatgtttt    4080
gcccttatga atgttagtca aaatgtgcga tggaaaaacc tgaaagtgaa ctttgataat    4140
gtcggacttg gttacctatc tctgcttcaa gttgcaactt ttaagggatg gacgattatt    4200
atgtatgcag cagtggattc tgttaatgta gacaagcagc ccaaatatga atatagcctc    4260
tacatgtata tttattttgt cgtctttatc atctttgggt cattcttcac tttgaacttg    4320
ttcattggtg tcatcataga taatttcaac caacagaaaa agaagcttgg aggtcaagac    4380
atctttatga cagaagaaca gaagaaatac tataatgcaa tgaaaaagct ggggtccaag    4440
aagccacaaa agccaattcc tcgaccaggg aacaaaatcc aaggatgtat atttgaccta    4500
gtgacaaatc aagcctttga tattagtatc atggttctta tctgtctcaa catggtaacc    4560
atgatggtag aaaaggaggg tcaaagtcaa catatgactaa agtttttata ttggataaat    4620
gtggttttta taatcctttt cactggagaa tgtgtgctaa aactgatctc cctcagacac    4680
tactacttca ctgtaggatg gaatattttt gattttgtgg ttgtgattat ctccattgta    4740
ggtatgtttc tagctgattt gattgaaacg tattttgtgt cccctaccct gttccgagtg    4800
atccgtcttg ccaggattgg ccgaatccta cgtctagtca aaggagcaaa ggggatccgc    4860
acgctgctct ttgctttgat gatgtcccctt cctgcgttgt ttaacatcgg cctcctgctc    4920
ttcctggtca tgttcatcta cgccatcttt ggaatgtcca actttgccta tgttaaaaag    4980
gaagatggaa ttaatgacat gttcaatttt gagacctttg caacagtat gatttgcctg    5040
ttccaaatta caacctctgc tggctgggat ggattgctag cacctattct taacagtaag    5100
ccacccgact gtgacccaaa aaaagttcat cctggaagtt cagttgaagg agactgtggt    5160
aacccatctg ttggaatatt ctactttgtt agttatatca tcatatcctt cctggttgtg    5220
gtgaacatgt acattgcagt catactggag aattttagtt tgccactga agaaagtact    5280
gaacctctga gtgaggatga ctttgagatg ttctatgagg tttgggagaa gtttgatccc    5340
gatgcgaccc agtttataga gttctctaaa ctctctgatt ttgcagctgc cctggatcct    5400
cctcttctca tagcaaaacc caacaaagtc cagctcattg ccatggatct gcccatggtt    5460
```

| | |
|---|---|
| agtggtgacc ggatccattg tcttgacatc ttatttgctt ttacaaagcg tgttttgggt | 5520 |
| gagagtgggg agatggattc tcttcgttca cagatggaag aaaggttcat gtctgcaaat | 5580 |
| ccttccaaag tgtcctatga acccatcaca accacactaa aacgaaaaca agaggatgtg | 5640 |
| tctgctactg tcattcagcg tgcttataga cgttaccgct taaggcaaaa tgtcaaaaat | 5700 |
| atatcaagta tatacataaa agatgggagac agagatgatg atttactcaa taaaaaagat | 5760 |
| atggcttttg ataatgttaa tgagaactca agtccagaaa aaacagatgc cacttcatcc | 5820 |
| accacctctc caccttcata tgatagtgta acaaagccag acaaagagaa atatgaacaa | 5880 |
| gacagaacag aaaaggaaga caaagggaaa gacagcaagg aaagcaaaaa atag | 5934 |

<210> SEQ ID NO 12
<211> LENGTH: 5934
<212> TYPE: DNA
<213> ORGANISM: Homo sapiens

<400> SEQUENCE: 12

| | |
|---|---|
| atggcaatgt tgcctccccc aggacctcag agctttgtcc atttcacaaa acagtctctt | 60 |
| gccctcattg aacaacgcat tgctgaaaga aaatcaaagg aacccaaaga agaaaagaaa | 120 |
| gatgatgatg aagaagcccc aaagccaagc agtgacttgg aagctggcaa acaactgccc | 180 |
| ttcatctatg gggacattcc tcccggcatg gtgtcagagc ccctggagga cttggacccc | 240 |
| tactatgcag acaaaaagac tttcatagta ttgaacaaag ggaaaacaat cttccgtttc | 300 |
| aatgccacac ctgctttata tatgctttct cctttcagtc ctctaagaag aatatctatt | 360 |
| aagatttttag tacactcctt attcagcatg ctcatcatgt gcactattct gacaaactgc | 420 |
| atatttatga ccatgaataa cccgccggac tggaccaaaa atgtcgagta cacttttact | 480 |
| ggaatatata cttttgaatc acttgtaaaa atccttgcaa gaggcttctg tgtaggagaa | 540 |
| ttcactttc ttcgtgaccc gtggaactgg ctggattttg tcgtcattgt ttttgcgtat | 600 |
| ttaacagaat ttgtaaaacct aggcaatgtt tcagctcttc gaacttttcag agtattgaga | 660 |
| gctttgaaaa ctatttctgt aatcccaggc ctgaagacaa ttgtaggggc tttgatccag | 720 |
| tcagtgaaga agctttctga tgtcatgatc ctgactgtgt tctgtctgag tgtgtttgca | 780 |
| ctaattggac tacagctgtt catgggaaac ctgaagcata aatgttttcg aaattcactt | 840 |
| gaaaataatg aaacattaga aagcataatg aatacccctag agagtgaaga agactttaga | 900 |
| aaatattttt attacttgga aggatccaaa gatgctctcc tttgtggttt cagcacagat | 960 |
| tcaggtcagt gtccagaggg gtacacctgt gtgaaaattg gcagaaaccc tgattatggc | 1020 |
| tacacgagct ttgacacttt cagctgggcc ttcttagcct tgtttaggct aatgaccaa | 1080 |
| gattactggg aaaaccttta ccaacagacg ctgcgtgctg ctggcaaaac ctacatgatc | 1140 |
| ttctttgtcg tagtgatttt cctgggctcc ttttatctaa taaacttgat cctggctgtg | 1200 |
| gttgccatgg catatgaaga acagaaccag gcaaacattg aagaagctaa acagaaagaa | 1260 |
| ttagaatttc aacagatgtt agaccgtctt aaaaaagagc aagaagaagc tgaggcaatt | 1320 |
| gcagcggcag cggctgaata tacaagtatt aggagaagca gaattatggg cctctcagag | 1380 |
| agttcttctg aaacatccaa actgagctct aaaagtgcta agaaagaag aaacagaaga | 1440 |
| aagaaaaaga atcaaaagaa gctctccagt ggagaggaaa agggagatgc tgagaaattg | 1500 |
| tcgaaatcag aatcagagga cagcatcaga agaaaaagtt ccacccttgg tgtcgaaggg | 1560 |
| cataggcgag cacatgaaaa gaggttgtct acccccaatc agtcaccact cagcattcgt | 1620 |
| ggctccttgt tttctgcaag gcgaagcagc agaacaagtc ttttttagttt caaaggcaga | 1680 |

```
ggaagagata taggatctga gactgaattt gccgatgatg agcacagcat ttttggagac    1740
aatgagagca gaaggggctc actgtttgtg ccccacagac cccaggagcg acgcagcagt    1800
aacatcagcc aagccagtag gtccccacca atgctgccgg tgaacgggaa aatgcacagt    1860
gctgtggact gcaacggtgt ggtctccctg gttgatggac gctcagccct catgctcccc    1920
aatggacagc ttctgccaga gggcacgacc aatcaaatac aagaaaag gcgttgtagt    1980 tcctatctcc tttcagagga tatgctgaat gatcccaacc tcagacagag agcaatgagt    2040
agagcaagca tattaacaaa cactgtggaa gaacttgaag agtccagaca aaaatgtcca    2100
ccttggtggt acagatttgc acacaaattc ttgatctgga attgctctcc atattggata    2160
aaattcaaaa agtgtatcta ttttattgta atggatcctt ttgtagatct tgcagttacc    2220
atttgcatag ttttaaacac attatttatg gctatggaac accacccaat gactgaggaa    2280
ttcaaaaatg tacttgctat aggaaatttg gtctttactg aatctttgc agctgaaatg    2340 gtattaaaac tgattgccat ggatccatat gagtatttcc aagtaggctg aatatttt    2400 gacagcctta ttgtgacttt aagtttagtg gagctctttc tagcagatgt ggaaggattg    2460
tcagttctgc gatcattcag actgctccga gtcttcaagt tggcaaaatc ctggccaaca    2520
ttgaacatgc tgattaagat cattggtaac tcagtagggg ctctaggtaa cctcaccta    2580 gtgttggcca tcatcgtctt cattttttgct gtggtcggca tgcagctctt tggtaagagc    2640
tacaaagaat gtgtctgcaa gatcaatgat gactgtacgc tcccacggtg gcacatgaac    2700
gacttcttcc actccttcct gattgtgttc cgcgtgctgt gtggagagtg gatagagacc    2760
atgtgggact gtatggaggt cgctggtcaa gctatgtgcc ttattgttta catgatggtc    2820
atggtcattg gaaacctggt ggtcctaaac ctatttctgg ccttattatt gagctcattt    2880
agttcagaca atcttacagc aattgaagaa gaccctgatg caaacaacct ccagattgca    2940
gtgactagaa ttaaaaaggg aataaattat gtgaaacaaa ccttacgtga atttattcta    3000
aaagcatttt ccaaaaagcc aaagatttcc agggagataa gacaagcaga agatctgaat    3060
actaagaagg aaaactatat ttctaaccat acacttgctg aaatgagcaa aggtcacaat    3120
ttcctcaagg aaaaagataa aatcagtggt tttggaagca gcgtggacaa acacttgatg    3180
gaagacagtg atggtcaatc atttattcac aatcccagcc tcacagtgac agtgccaatt    3240
gcacctgggg aatccgattt ggaaaatatg aatgctgagg aacttagcag tgattcggat    3300
agtgaataca gcaaagtgag attaaaccgg tcaagctcct cagagtgcag cacagttgat    3360
aaccctttgc ctgagaagg agaagaagca gaggctgaac ctatgaattc cgatgagcca    3420
gaggcctgtt tcacagatgg ttgtgtacgg aggttctcat gctgccaagt taacatagag    3480
tcagggaaag gaaaaatctg gtggaacatc aggaaaacct gctacaagat tgttgaacac    3540
agttggtttg aaagcttcat tgtcctcatg atcctgctca gcagtggtgc cctggctttt    3600
gaagatattt atattgaaag gaaaaagacc attaagatta tcctggagta tgcagacaag    3660
atcttcactt acatcttcat tctggaaatg cttctaaaat ggatagcata tggttatataaa    3720 acatatttca ccaatgcctg tgttggctg gatttcctaa ttgttgatgt ttctttggtt    3780
actttagtgg caaacactct tggctactca gatcttggcc ccattaaatc ccttcggaca    3840
ctgagagctt taagacctct aagagcctta tctagatttg aaggaatgag ggtcgttgtg    3900
aatgcactca taggagcaat tccttccatc atgaatgtgc tacttgtgtg tcttatattc    3960
tggctgatat tcagcatcat gggagtaaat ttgtttgctg gcaagttcta tgagtgtatt    4020
```

| | |
|---|---:|
| aacaccacag atgggtcacg gtttcctgca agtcaagttc caaatcgttc cgaatgtttt | 4080 |
| gcccttatga atgttagtca aaatgtgcga tggaaaaacc tgaaagtgaa ctttgataat | 4140 |
| gtcggacttg gttacctatc tctgcttcaa gttgcaactt ttaagggatg gacgattatt | 4200 |
| atgtatgcag cagtggattc tgttaatgta gacaagcagc ccaaatatga atatagcctc | 4260 |
| tacatgtata tttattttgt cgtctttatc atctttgggt cattcttcac tttgaacttg | 4320 |
| ttcattggtg tcatcataga taatttcaac caacagaaaa agaagcttgg aggtcaagac | 4380 |
| atctttatga cagaagaaca gaagaaatac tataatgcaa tgaaaaagct ggggtccaag | 4440 |
| aagccacaaa agccaattcc tcgaccaggg aacaaaatcc aaggatgtat atttgaccta | 4500 |
| gtgacaaatc aagcctttga tattagtatc atggttctta tctgtctcaa catggtaacc | 4560 |
| atgatggtag aaaaggaggg tcaaagtcaa catatgactg aagttttata ttggataaat | 4620 |
| gtggttttta taatccttttt cactggagaa tgtgtgctaa aactgatctc cctcagacac | 4680 |
| tactacttca ctgtaggatg gaatattttt gattttgtgg ttgtgattat ctccattgta | 4740 |
| ggtatgtttc tagctgattt gattgaaacg tattttgtgt cccctaccct gttccgagtg | 4800 |
| atccgtcttg ccaggattgg ccgaatccta cgtctagtca aaggagcaaa ggggatccgc | 4860 |
| acgctgctct ttgctttgat gatgtccctt cctgcgttgt ttaacatcgg cctcctgctc | 4920 |
| ttcctggtca tgttcatcta cgccatcttt ggaatgtcca actttgccta tgttaaaaag | 4980 |
| gaagatggaa ttaatgacat gttcaatttt gagacctttg caacagtat gatttgcctg | 5040 |
| ttccaaatta caacctctgc tggctgggat ggattgctag cacctattct taacagtaag | 5100 |
| ccacccgact gtgacccaaa aaagttcat cctggaagtt cagttgaagg agactgtggt | 5160 |
| aacccatctg ttggaatatt ctactttgtt agttatatca tcatatcctt cctggttgtg | 5220 |
| gtgaacatgt acattgcagt catactggag aattttagtg ttgccactga agaaagtact | 5280 |
| gaacctctga gtgaggatga ctttgagatg ttctatgagg tttgggagaa gtttgatccc | 5340 |
| gatgcgaccc agtttataga gttctctaaa ctctctgatt ttgcagctgc cctggatcct | 5400 |
| cctcttctca tagcaaaacc caacaaagtc cagctcattg ccatggatct gcccatggtt | 5460 |
| agtggtgacc ggatccattg tcttgacatc ttatttgctt ttacaaagcg tgttttgggt | 5520 |
| gagagtgggg agatggattc tcttcgttca cagatggaag aaaggttcat gtctgcaaat | 5580 |
| ccttccaaag tgtcctatga acccatcaca accacactaa aacggaaaca agaggatgtg | 5640 |
| tctgctactg tcattcagcg tgcttataga cgttaccgct taaggcaaaa tgtcaaaaat | 5700 |
| atatcaagta tatacataaa agatggagac agagatgatg atttactcaa taaaaaagat | 5760 |
| atggcttttg ataatgttaa tgagaactca agtccagaaa aacagatgc cacttcatcc | 5820 |
| accacctctc caccttcata tgatagtgta acaaagccag acaaagagaa atatgaacaa | 5880 |
| gacagaacag aaaaggaaga caagggaaa gacagcaagg aaagcaaaaa atag | 5934 |

<210> SEQ ID NO 13
<211> LENGTH: 5934
<212> TYPE: DNA
<213> ORGANISM: Homo sapiens

<400> SEQUENCE: 13

| | |
|---|---:|
| atggcaatgt tgcctccccc aggacctcag agctttgtcc atttcacaaa acagtctctt | 60 |
| gccctcattg aacaacgcat tgctgaaaga aaatcaaagg aacccaaaga agaaaagaaa | 120 |
| gatgatgatg aagaagcccc aaagccaagc agtgacttgg aagctggcaa acaactgccc | 180 |
| ttcatctatg gggacattcc tccggcatg gtgtcagagc ccctggagga cttggacccc | 240 |

```
tactatgcag acaaaaagac tttcatagta ttgaacaaag ggaaaacaat cttccgtttc    300
aatgccacac ctgctttata tatgctttct cctttcagtc ctctaagaag aatatctatt    360
aagattttag tacactcctt attcagcatg ctcatcatgt gcactattct gacaaactgc    420
atatttatga ccatgaataa cccgccggac tggaccaaaa atgtcgagta cacttttact    480
ggaatatata cttttgaatc acttgtaaaa atccttgcaa gaggcttctg tgtaggagaa    540
ttcactttc ttcgtgaccc gtggaactgg ctggattttg tcgtcattgt ttttgcgtat     600
ttaacagaat ttgtaaacct aggcaatgtt tcagctcttc gaactttcag agtattgaga    660
gctttgaaaa ctatttctgt aatcccaggc ctgaagacaa ttgtaggggc tttgatccag    720
tcagtgaaga agctttctga tgtcatgatc ctgactgtgt tctgtctgag tgtgtttgca    780
ctaattggac tacagctgtt catgggaaac ctgaagcata aatgttttcg aaattcactt    840
gaaaataatg aaacattaga aagcataatg aatacctag agagtgaaga agactttaga    900
aaatattttt attacttgga aggatccaaa gatgctctcc tttgtggttt cagcacagat    960
tcaggtcagt gtccagaggg gtacacctgt gtgaaaattg gcagaaaccc tgattatggc   1020
tacacgagct ttgacacttt cagctgggcc ttcttagcct tgtttaggct aatgacccaa   1080
gattactggg aaaacctttt ccaacagacg ctgcgtgctg ctggcaaaac ctacatgatc   1140
ttctttgtcg tagtgatttt cctgggctcc ttttatctaa taaacttgat cctggctgtg   1200
gttgccatgg catatgaaga acagaaccag gcaaacattg aagaagctaa acagaaagaa   1260
ttagaatttc aacagatgtt agaccgtctt aaaaagagc aagaagaagc tgaggcaatt   1320
gcagcggcag cggctgaata tacaagtatt aggagaagca gaattatggg cctctcagag   1380
agttcttctg aaacatccaa actgagctct aaaagtgcta agaaagaag aaacagaaga   1440
aagaaaaaga atcaaaagaa gctctccagt ggagaggaaa agggagatgc tgagaaattg   1500
tcgaaatcag aatcagagga cagcatcaga agaaaaagtt ccaccttgg tgtcgaaggg   1560
cataggcgag cacatgaaaa gaggttgtct accccccaatc agtcaccact cagcattcgt   1620
ggctccttgt tttctgcaag gcgaagcagc agaacaagtc ttttttagttt caaaggcaga   1680
ggaagagata taggatctga gactgaattt gccgatgatg agcacagcat ttttggagac   1740
aatgagagca gaaggggctc actgtttgtg ccccacagac cccaggagcg acgcagcagt   1800
aacatcagcc aagccagtag gtccccacca atgctgccgg tgaacgggaa aatgcacagt   1860
gctgtggact gcaacggtgt ggtctccctg gttgatggac gctcagccct catgctcccc   1920
aatgacagc ttctgccaga gggcacgacc aatcaaatac acaagaaaag gcgttgtagt    1980
tcctatctcc tttcagagga tatgctgaat gatcccaacc tcagacagag agcaatgagt   2040
agagcaagca tattaacaaa cactgtggaa gaacttgaag agtccagaca aaaatgtcca   2100
ccttggtggt acagatttgc acacaaattc ttgatctgga attgctctcc atattggata   2160
aaattcaaaa agtgtatcta ttttattgta atggatcctt ttgtagatct tgcaattacc   2220
atttgcatag ttttaaacac attatttatg gctatggaac accacccaat gactgaggaa   2280
ttcaaaaatg tacttgctat aggaaatttg gtctttactg gaatcttgc agctgaaatg   2340
gtattaaaac tgattgccat ggatccatat gagtatttcc aagtaggctg gaatattttt   2400
gacagcctta ttgtgacttt aagtttagtg gagctctttc tagcagatgt ggaaggattg   2460
tcagttctgc gatcattcag actgctccga gtcttcaagt tggcaaaatc ctggccaaca   2520
ttgaacatgc tgattaagat cattggtaac tcagtagggg ctctaggtaa cctcaccta    2580
```

```
gtgttggcca tcatcgtctt cattttttgct gtggtcggca tgcagctctt tggtaagagc    2640
tacaaagaat gtgtctgcaa gatcaatgat gactgtacgc tcccacggtg gcacatgaac    2700
gacttcttcc actccttcct gattgtgttc cgcgtgctgt gtggagagtg gatagagacc    2760
atgtgggact gtatggaggt cgctggtcaa gctatgtgcc ttattgttta catgatggtc    2820
atggtcattg gaaacctggt ggtcctaaac ctatttctgg ccttattatt gagctcattt    2880
agttcagaca tcttacagc aattgaagaa gaccctgatg caaacaacct ccagattgca    2940
gtgactagaa ttaaaaaggg aataaattat gtgaaacaaa ccttacgtga atttattcta    3000
aaagcatttt ccaaaaagcc aaagatttcc agggagataa gacaagcaga agatctgaat    3060
actaagaagg aaaactatat ttctaaccat acacttgctg aaatgagcaa aggtcacaat    3120
ttcctcaagg aaaaagataa aatcagtggt tttggaagca gcgtggacaa acacttgatg    3180
gaagacagtg atggtcaatc atttattcac aatcccagcc tcacagtgac agtgccaatt    3240
gcacctgggg aatccgattt ggaaaatatg aatgctgagg aacttagcag tgattcggat    3300
agtgaataca gcaaagtgag attaaaccgg tcaagctcct cagagtgcag cacagttgat    3360 aaccctttc ctggagaagg agaagaagca gaggctgaac ctatgaattc cgatgagcca    3420
gaggcctgtt tcacagatgg ttgtgtacgg aggttctcat gctgccaagt taacatagag    3480
tcagggaaag gaaaaatctg gtggaacatc aggaaaaacct gctacaagat tgttgaacac    3540
agttggtttg aaagcttcat tgtcctcatg atcctgctca gcagtggtgc cctggctttt    3600
gaagatattt atattgaaag gaaaaagacc attaagatta tcctggagta tgcagacaag    3660
atcttcactt acatcttcat tctgaaatg cttctaaaat ggatagcata tggttataaa    3720
acatatttca ccaatgcctg gtgttggctg gatttcctaa ttgttgatgt ttctttggtt    3780
actttagtgg caaacactct tggctactca gatcttggcc ccattaaatc ccttcggaca    3840
ctgagagctt taagacctct aagagcctta tctagatttg aaggaatgag ggtcgttgtg    3900
aatgcactca taggagcaat tccttccatc atgaatgtgc tacttgtgtg tcttatattc    3960
tggctgatat tcagcatcat gggagtaaat ttgtttgctg gcaagttcta tgagtgtatt    4020
aacaccacag atgggtcacg gtttcctgca agtcaagttc caaatcgttc cgaatgtttt    4080
gcccttatga atgttagtca aaatgtgcga tggaaaaacc tgaaagtgaa cttttgataat    4140 gtcggacttg gttacctatc tctgcttcaa gttgcaactt ttaagggatg gacgattatt    4200
atgtatgcag cagtggattc tgttaatgta gacaagcagc ccaaatatga atatagcctc    4260
tacatgtata tttattttgt cgtctttatc atctttgggt cattcttcac tttgaacttg    4320
ttcattggtg tcatcataga taatttcaac caacagaaaa agaagcttgg aggtcaagac    4380
atctttatga cagaagaaca gaagaaatac tataatgcaa tgaaaaagct ggggtccaag    4440
aagccacaaa agccaattcc tcgaccaggg aacaaaatcc aaggatgtat atttgaccta    4500
gtgacaaatc aagcctttga tattagtatc atggttctta tctgtctcaa catggtaacc    4560
atgatggtag aaaaggaggg tcaaagtcaa catatgactg aagttttata ttggataaat    4620
gtggttttta taatcctttt cactggagaa tgtgtgctaa aactgatctc cctcagacac    4680
tactacttca ctgtaggatg gaatattttt gattttgtgg ttgtgattat ctccattgta    4740
ggtatgtttc tagctgattt gattgaaacg tatttttgtgt cccctaccct gttccgagtg    4800
atccgtcttg ccaggattgg ccgaatccta cgtctagtca aaggagcaaa ggggatccgc    4860
acgctgctct ttgctttgat gatgtccctt cctgcgttgt ttaacatcgg cctcctgctc    4920
ttcctggtca tgttcatcta cgccatcttt ggaatgtcca actttgccta tgttaaaaag    4980
```

-continued

```
gaagatggaa ttaatgacat gttcaattttt gagacctttg gcaacagtat gatttgcctg   5040
ttccaaatta caacctctgc tggctgggat ggattgctag cacctattct taacagtaag    5100
ccacccgact gtgacccaaa aaaagttcat cctggaagtt cagttgaagg agactgtggt    5160
aacccatctg ttggaatatt ctactttgtt agttatatca tcatatcctt cctggttgtg    5220
gtgaacatgt acattgcagt catactggag aattttagtg ttgccactga agaaagtact    5280
gaacctctga gtgaggatga ctttgagatg ttctatgagg tttgggagaa gtttgatccc    5340
gatgcgaccc agtttataga gttctctaaa ctctctgatt ttgcagctgc cctggatcct    5400
cctcttctca tagcaaaacc caacaaagtc cagctcattg ccatggatct gcccatggtt    5460
agtggtgacc ggatccattg tcttgacatc ttatttgctt ttacaaagcg tgttttgggt    5520
gagagtgggg agatggattc tcttcgttca cagatggaag aaaggttcat gtctgcaaat    5580
ccttccaaag tgtcctatga acccatcaca accacactaa aacggaaaca agaggatgtg    5640
tctgctactg tcattcagcg tgcttataga cgttaccgct taaggcaaaa tgtcaaaaat    5700
atatcaagta tatacataaa agatggagac agagatgatg atttactcaa taaaaaagat    5760
atggcttttg ataatgttaa tgagaactca agtccagaaa aaacagatgc cacttcatcc    5820
accacctctc caccttcata tgatagtgta acaaagccag acaaagagaa atatgaacaa    5880
gacagaacag aaaaggaaga caaagggaaa gacagcaagg aaagcaaaaa atag          5934
```

```
<210> SEQ ID NO 14
<211> LENGTH: 15
<212> TYPE: DNA
<213> ORGANISM: Homo sapiens

<400> SEQUENCE: 14
gcccttcatc tatgg                                                      15

<210> SEQ ID NO 15
<211> LENGTH: 15
<212> TYPE: DNA
<213> ORGANISM: Homo sapiens

<400> SEQUENCE: 15
aacccgccgg actgg                                                      15

<210> SEQ ID NO 16
<211> LENGTH: 15
<212> TYPE: DNA
<213> ORGANISM: Homo sapiens

<400> SEQUENCE: 16
gctccccaat ggaca                                                      15

<210> SEQ ID NO 17
<211> LENGTH: 15
<212> TYPE: DNA
<213> ORGANISM: Homo sapiens

<400> SEQUENCE: 17
atacacaaga aaagg                                                      15

<210> SEQ ID NO 18
<211> LENGTH: 15
<212> TYPE: DNA
<213> ORGANISM: Homo sapiens
```

```
<400> SEQUENCE: 18
tcttgcaatt accat                                               15

<210> SEQ ID NO 19
<211> LENGTH: 15
<212> TYPE: DNA
<213> ORGANISM: Homo sapiens

<400> SEQUENCE: 19
accctttgcc tggag                                               15

<210> SEQ ID NO 20
<211> LENGTH: 21
<212> TYPE: DNA
<213> ORGANISM: Homo sapiens

<400> SEQUENCE: 20
gtcccgccca ttgcctgaca c                                        21

<210> SEQ ID NO 21
<211> LENGTH: 25
<212> TYPE: DNA
<213> ORGANISM: Homo sapiens

<400> SEQUENCE: 21
ttctggtcat gatatggtta ttcac                                    25

<210> SEQ ID NO 22
<211> LENGTH: 24
<212> TYPE: DNA
<213> ORGANISM: Homo sapiens

<400> SEQUENCE: 22
tgatagatgc gttgatgaca ttgg                                     24

<210> SEQ ID NO 23
<211> LENGTH: 24
<212> TYPE: DNA
<213> ORGANISM: Homo sapiens

<400> SEQUENCE: 23
ttcataaatg cagtaacttc ctgg                                     24

<210> SEQ ID NO 24
<211> LENGTH: 24
<212> TYPE: DNA
<213> ORGANISM: Homo sapiens

<400> SEQUENCE: 24
tgtttctttt aagtcagtac agag                                     24

<210> SEQ ID NO 25
<211> LENGTH: 22
<212> TYPE: DNA
<213> ORGANISM: Homo sapiens

<400> SEQUENCE: 25
agagccattc acaagaccag ag                                       22

<210> SEQ ID NO 26
<211> LENGTH: 21
<212> TYPE: DNA
<213> ORGANISM: Homo sapiens
```

-continued

```
<400> SEQUENCE: 26
actcagaaag gcagagaggt g                                              21

<210> SEQ ID NO 27
<211> LENGTH: 23
<212> TYPE: DNA
<213> ORGANISM: Homo sapiens

<400> SEQUENCE: 27
ttgccatgtt atcaatgtct gtg                                            23

<210> SEQ ID NO 28
<211> LENGTH: 24
<212> TYPE: DNA
<213> ORGANISM: Homo sapiens

<400> SEQUENCE: 28
gactgatttg tatctggtta ggag                                           24

<210> SEQ ID NO 29
<211> LENGTH: 24
<212> TYPE: DNA
<213> ORGANISM: Homo sapiens

<400> SEQUENCE: 29
gcaatgtaat taggaaggtg tgag                                           24

<210> SEQ ID NO 30
<211> LENGTH: 26
<212> TYPE: DNA
<213> ORGANISM: Homo sapiens

<400> SEQUENCE: 30
tttgaatgaa ctctaaatga actacc                                         26

<210> SEQ ID NO 31
<211> LENGTH: 25
<212> TYPE: DNA
<213> ORGANISM: Homo sapiens

<400> SEQUENCE: 31
taagtattag gcgttaagac aaacc                                          25

<210> SEQ ID NO 32
<211> LENGTH: 5
<212> TYPE: PRT
<213> ORGANISM: Homo sapiens

<400> SEQUENCE: 32

Pro Phe Val Tyr Gly
1               5

<210> SEQ ID NO 33
<211> LENGTH: 5
<212> TYPE: PRT
<213> ORGANISM: Homo sapiens

<400> SEQUENCE: 33

Asn Pro Gln Asp Trp
1               5

<210> SEQ ID NO 34
```

```
<211> LENGTH: 5
<212> TYPE: PRT
<213> ORGANISM: Homo sapiens

<400> SEQUENCE: 34

Leu Pro Tyr Gly Gln
1               5

<210> SEQ ID NO 35
<211> LENGTH: 5
<212> TYPE: PRT
<213> ORGANISM: Homo sapiens

<400> SEQUENCE: 35

Ile His Arg Lys Arg
1               5

<210> SEQ ID NO 36
<211> LENGTH: 5
<212> TYPE: PRT
<213> ORGANISM: Homo sapiens

<400> SEQUENCE: 36

Leu Ala Val Thr Ile
1               5

<210> SEQ ID NO 37
<211> LENGTH: 5
<212> TYPE: PRT
<213> ORGANISM: Homo sapiens

<400> SEQUENCE: 37

Asn Pro Phe Pro Gly
1               5

<210> SEQ ID NO 38
<211> LENGTH: 1977
<212> TYPE: PRT
<213> ORGANISM: Homo sapiens

<400> SEQUENCE: 38

Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
                20                  25                  30

Lys Glu Pro Lys Glu Glu Lys Lys Asp Asp Asp Glu Glu Ala Pro Lys
            35                  40                  45

Pro Ser Ser Asp Leu Glu Ala Gly Lys Gln Leu Pro Phe Ile Tyr Gly
        50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160
```

-continued

```
Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
    210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
        275                 280                 285

Ile Met Asn Thr Leu Glu Ser Glu Glu Asp Phe Arg Lys Tyr Phe Tyr
    290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
        355                 360                 365

Gln Thr Leu Arg Ala Ala Gly Lys Thr Tyr Met Ile Phe Phe Val Val
    370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Ala Glu Tyr Thr
        435                 440                 445

Ser Ile Arg Arg Ser Arg Ile Met Gly Leu Ser Glu Ser Ser Ser Glu
    450                 455                 460

Thr Ser Lys Leu Ser Ser Lys Ser Ala Lys Glu Arg Arg Asn Arg Arg
465                 470                 475                 480

Lys Lys Lys Asn Gln Lys Lys Leu Ser Ser Gly Glu Glu Lys Gly Asp
                485                 490                 495

Ala Glu Lys Leu Ser Lys Ser Glu Ser Glu Asp Ser Ile Arg Arg Lys
            500                 505                 510

Ser Phe His Leu Gly Val Glu Gly His Arg Arg Ala His Glu Lys Arg
        515                 520                 525

Leu Ser Thr Pro Asn Gln Ser Pro Leu Ser Ile Arg Gly Ser Leu Phe
    530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
                565                 570                 575
```

-continued

```
Ile Phe Gly Asp Asn Glu Ser Arg Arg Gly Ser Leu Phe Val Pro His
            580                 585                 590
Arg Pro Gln Glu Arg Arg Ser Ser Asn Ile Ser Gln Ala Ser Arg Ser
        595                 600                 605
Pro Pro Met Leu Pro Val Asn Gly Lys Met His Ser Ala Val Asp Cys
    610                 615                 620
Asn Gly Val Val Ser Leu Val Asp Gly Arg Ser Ala Leu Met Leu Pro
625                 630                 635                 640
Asn Gly Gln Leu Leu Pro Glu Gly Thr Thr Asn Gln Ile His Lys Lys
            645                 650                 655
Arg Arg Cys Ser Ser Tyr Leu Leu Ser Glu Asp Met Leu Asn Asp Pro
        660                 665                 670
Asn Leu Arg Gln Arg Ala Met Ser Arg Ala Ser Ile Leu Thr Asn Thr
    675                 680                 685
Val Glu Glu Leu Glu Glu Ser Arg Gln Lys Cys Pro Pro Trp Trp Tyr
690                 695                 700
Arg Phe Ala His Lys Phe Leu Ile Trp Asn Cys Ser Pro Tyr Trp Ile
705                 710                 715                 720
Lys Phe Lys Lys Cys Ile Tyr Phe Ile Val Met Asp Pro Phe Val Asp
                725                 730                 735
Leu Ala Ile Thr Ile Cys Ile Val Leu Asn Thr Leu Phe Met Ala Met
            740                 745                 750
Glu His His Pro Met Thr Glu Phe Lys Asn Val Leu Ala Ile Gly
        755                 760                 765
Asn Leu Val Phe Thr Gly Ile Phe Ala Ala Glu Met Val Leu Lys Leu
770                 775                 780
Ile Ala Met Asp Pro Tyr Glu Tyr Phe Gln Val Gly Trp Asn Ile Phe
785                 790                 795                 800
Asp Ser Leu Ile Val Thr Leu Ser Leu Val Glu Leu Phe Leu Ala Asp
                805                 810                 815
Val Glu Gly Leu Ser Val Leu Arg Ser Phe Arg Leu Leu Arg Val Phe
            820                 825                 830
Lys Leu Ala Lys Ser Trp Pro Thr Leu Asn Met Leu Ile Lys Ile Ile
        835                 840                 845
Gly Asn Ser Val Gly Ala Leu Gly Asn Leu Thr Leu Val Leu Ala Ile
    850                 855                 860
Ile Val Phe Ile Phe Ala Val Val Gly Met Gln Leu Phe Gly Lys Ser
865                 870                 875                 880
Tyr Lys Glu Cys Val Cys Lys Ile Asn Asp Asp Cys Thr Leu Pro Arg
                885                 890                 895
Trp His Met Asn Asp Phe Phe His Ser Phe Leu Ile Val Phe Arg Val
            900                 905                 910
Leu Cys Gly Glu Trp Ile Glu Thr Met Trp Asp Cys Met Glu Val Ala
        915                 920                 925
Gly Gln Ala Met Cys Leu Ile Val Tyr Met Met Val Met Val Ile Gly
    930                 935                 940
Asn Leu Val Val Leu Asn Leu Phe Leu Ala Leu Leu Leu Ser Ser Phe
945                 950                 955                 960
Ser Ser Asp Asn Leu Thr Ala Ile Glu Glu Asp Pro Asp Ala Asn Asn
                965                 970                 975
Leu Gln Ile Ala Val Thr Arg Ile Lys Lys Gly Ile Asn Tyr Val Lys
            980                 985                 990
Gln Thr Leu Arg Glu Phe Ile Leu  Lys Ala Phe Ser Lys  Lys Pro Lys
```

```
                995              1000              1005
Ile Ser Arg Glu Ile Arg Gln Ala Glu Asp Leu Asn Thr Lys Lys
            1010              1015              1020

Glu Asn Tyr Ile Ser Asn His Thr Leu Ala Glu Met Ser Lys Gly
            1025              1030              1035

His Asn Phe Leu Lys Glu Lys Asp Lys Ile Ser Gly Phe Gly Ser
            1040              1045              1050

Ser Val Asp Lys His Leu Met Glu Asp Ser Asp Gly Gln Ser Phe
            1055              1060              1065

Ile His Asn Pro Ser Leu Thr Val Thr Val Pro Ile Ala Pro Gly
            1070              1075              1080

Glu Ser Asp Leu Glu Asn Met Asn Ala Glu Glu Leu Ser Ser Asp
            1085              1090              1095

Ser Asp Ser Glu Tyr Ser Lys Val Arg Leu Asn Arg Ser Ser Ser
            1100              1105              1110

Ser Glu Cys Ser Thr Val Asp Asn Pro Leu Pro Gly Glu Gly Glu
            1115              1120              1125

Glu Ala Glu Ala Glu Pro Met Asn Ser Asp Glu Pro Glu Ala Cys
            1130              1135              1140

Phe Thr Asp Gly Cys Val Arg Arg Phe Ser Cys Cys Gln Val Asn
            1145              1150              1155

Ile Glu Ser Gly Lys Gly Lys Ile Trp Trp Asn Ile Arg Lys Thr
            1160              1165              1170

Cys Tyr Lys Ile Val Glu His Ser Trp Phe Glu Ser Phe Ile Val
            1175              1180              1185

Leu Met Ile Leu Leu Ser Ser Gly Ala Leu Ala Phe Glu Asp Ile
            1190              1195              1200

Tyr Ile Glu Arg Lys Lys Thr Ile Lys Ile Ile Leu Glu Tyr Ala
            1205              1210              1215

Asp Lys Ile Phe Thr Tyr Ile Phe Ile Leu Glu Met Leu Leu Lys
            1220              1225              1230

Trp Ile Ala Tyr Gly Tyr Lys Thr Tyr Phe Thr Asn Ala Trp Cys
            1235              1240              1245

Trp Leu Asp Phe Leu Ile Val Asp Val Ser Leu Val Thr Leu Val
            1250              1255              1260

Ala Asn Thr Leu Gly Tyr Ser Asp Leu Gly Pro Ile Lys Ser Leu
            1265              1270              1275

Arg Thr Leu Arg Ala Leu Arg Pro Leu Arg Ala Leu Ser Arg Phe
            1280              1285              1290

Glu Gly Met Arg Val Val Val Asn Ala Leu Ile Gly Ala Ile Pro
            1295              1300              1305

Ser Ile Met Asn Val Leu Leu Val Cys Leu Ile Phe Trp Leu Ile
            1310              1315              1320

Phe Ser Ile Met Gly Val Asn Leu Phe Ala Gly Lys Phe Tyr Glu
            1325              1330              1335

Cys Ile Asn Thr Thr Asp Gly Ser Arg Phe Pro Ala Ser Gln Val
            1340              1345              1350

Pro Asn Arg Ser Glu Cys Phe Ala Leu Met Asn Val Ser Gln Asn
            1355              1360              1365

Val Arg Trp Lys Asn Leu Lys Val Asn Phe Asp Asn Val Gly Leu
            1370              1375              1380

Gly Tyr Leu Ser Leu Leu Gln Val Ala Thr Phe Lys Gly Trp Thr
            1385              1390              1395
```

```
Ile Ile Met Tyr Ala Ala Val Asp Ser Val Asn Val Asp Lys Gln
        1400                1405                1410

Pro Lys Tyr Glu Tyr Ser Leu Tyr Met Tyr Ile Tyr Phe Val Val
        1415                1420                1425

Phe Ile Ile Phe Gly Ser Phe Phe Thr Leu Asn Leu Phe Ile Gly
        1430                1435                1440

Val Ile Ile Asp Asn Phe Asn Gln Gln Lys Lys Lys Leu Gly Gly
        1445                1450                1455

Gln Asp Ile Phe Met Thr Glu Glu Gln Lys Lys Tyr Tyr Asn Ala
        1460                1465                1470

Met Lys Lys Leu Gly Ser Lys Lys Pro Gln Lys Pro Ile Pro Arg
        1475                1480                1485

Pro Gly Asn Lys Ile Gln Gly Cys Ile Phe Asp Leu Val Thr Asn
        1490                1495                1500

Gln Ala Phe Asp Ile Ser Ile Met Val Leu Ile Cys Leu Asn Met
        1505                1510                1515

Val Thr Met Met Val Glu Lys Glu Gly Gln Ser Gln His Met Thr
        1520                1525                1530

Glu Val Leu Tyr Trp Ile Asn Val Val Phe Ile Ile Leu Phe Thr
        1535                1540                1545

Gly Glu Cys Val Leu Lys Leu Ile Ser Leu Arg His Tyr Tyr Phe
        1550                1555                1560

Thr Val Gly Trp Asn Ile Phe Asp Phe Val Val Val Ile Ile Ser
        1565                1570                1575

Ile Val Gly Met Phe Leu Ala Asp Leu Ile Glu Thr Tyr Phe Val
        1580                1585                1590

Ser Pro Thr Leu Phe Arg Val Ile Arg Leu Ala Arg Ile Gly Arg
        1595                1600                1605

Ile Leu Arg Leu Val Lys Gly Ala Lys Gly Ile Arg Thr Leu Leu
        1610                1615                1620

Phe Ala Leu Met Met Ser Leu Pro Ala Leu Phe Asn Ile Gly Leu
        1625                1630                1635

Leu Leu Phe Leu Val Met Phe Ile Tyr Ala Ile Phe Gly Met Ser
        1640                1645                1650

Asn Phe Ala Tyr Val Lys Lys Glu Asp Gly Ile Asn Asp Met Phe
        1655                1660                1665

Asn Phe Glu Thr Phe Gly Asn Ser Met Ile Cys Leu Phe Gln Ile
        1670                1675                1680

Thr Thr Ser Ala Gly Trp Asp Gly Leu Leu Ala Pro Ile Leu Asn
        1685                1690                1695

Ser Lys Pro Pro Asp Cys Asp Pro Lys Lys Val His Pro Gly Ser
        1700                1705                1710

Ser Val Glu Gly Asp Cys Gly Asn Pro Ser Val Gly Ile Phe Tyr
        1715                1720                1725

Phe Val Ser Tyr Ile Ile Ile Ser Phe Leu Val Val Val Asn Met
        1730                1735                1740

Tyr Ile Ala Val Ile Leu Glu Asn Phe Ser Val Ala Thr Glu Glu
        1745                1750                1755

Ser Thr Glu Pro Leu Ser Glu Asp Asp Phe Glu Met Phe Tyr Glu
        1760                1765                1770

Val Trp Glu Lys Phe Asp Pro Asp Ala Thr Gln Phe Ile Glu Phe
        1775                1780                1785
```

```
Ser Lys Leu Ser Asp Phe Ala Ala Leu Asp Pro Pro Leu Leu
    1790            1795                1800

Ile Ala Lys Pro Asn Lys Val Gln Leu Ile Ala Met Asp Leu Pro
    1805            1810                1815

Met Val Ser Gly Asp Arg Ile His Cys Leu Asp Ile Leu Phe Ala
    1820            1825                1830

Phe Thr Lys Arg Val Leu Gly Glu Ser Gly Glu Met Asp Ser Leu
    1835            1840                1845

Arg Ser Gln Met Glu Glu Arg Phe Met Ser Ala Asn Pro Ser Lys
    1850            1855                1860

Val Ser Tyr Glu Pro Ile Thr Thr Thr Leu Lys Arg Lys Gln Glu
    1865            1870                1875

Asp Val Ser Ala Thr Val Ile Gln Arg Ala Tyr Arg Arg Tyr Arg
    1880            1885                1890

Leu Arg Gln Asn Val Lys Asn Ile Ser Ser Ile Tyr Ile Lys Asp
    1895            1900                1905

Gly Asp Arg Asp Asp Leu Leu Asn Lys Lys Asp Met Ala Phe
    1910            1915                1920

Asp Asn Val Asn Glu Asn Ser Ser Pro Glu Lys Thr Asp Ala Thr
    1925            1930                1935

Ser Ser Thr Thr Ser Pro Pro Ser Tyr Asp Ser Val Thr Lys Pro
    1940            1945                1950

Asp Lys Glu Lys Tyr Glu Gln Asp Arg Thr Glu Lys Glu Asp Lys
    1955            1960                1965

Gly Lys Asp Ser Lys Glu Ser Lys Lys
    1970            1975

<210> SEQ ID NO 39
<211> LENGTH: 11
<212> TYPE: PRT
<213> ORGANISM: Artificial Sequence
<220> FEATURE:
<223> OTHER INFORMATION: conserved across multiple species

<400> SEQUENCE: 39

Lys Gln Leu Pro Phe Ile Tyr Gly Asp Ile Pro
1               5                   10

<210> SEQ ID NO 40
<211> LENGTH: 11
<212> TYPE: PRT
<213> ORGANISM: Homo sapiens

<400> SEQUENCE: 40

Thr Met Asn Asn Pro Pro Asp Trp Thr Lys Asn
1               5                   10

<210> SEQ ID NO 41
<211> LENGTH: 11
<212> TYPE: PRT
<213> ORGANISM: Artificial Sequence
<220> FEATURE:
<223> OTHER INFORMATION: conserved across multiple species

<400> SEQUENCE: 41

Thr Met Ser Asn Pro Pro Asp Trp Thr Lys Asn
1               5                   10

<210> SEQ ID NO 42
<211> LENGTH: 11
```

```
<212> TYPE: PRT
<213> ORGANISM: Rattus norvegicus

<400> SEQUENCE: 42

Thr Leu Ser Asn Pro Pro Glu Trp Thr Lys Asn
1               5                   10

<210> SEQ ID NO 43
<211> LENGTH: 11
<212> TYPE: PRT
<213> ORGANISM: Oryctolagus cuniculus

<400> SEQUENCE: 43

Thr Met Asn Asn Pro Ala Glu Trp Thr Lys Asn
1               5                   10

<210> SEQ ID NO 44
<211> LENGTH: 11
<212> TYPE: PRT
<213> ORGANISM: Gallus gallus

<400> SEQUENCE: 44

Thr Trp Ser Lys Leu Pro Glu Trp Thr Lys Asn
1               5                   10

<210> SEQ ID NO 45
<211> LENGTH: 11
<212> TYPE: PRT
<213> ORGANISM: Artificial Sequence
<220> FEATURE:
<223> OTHER INFORMATION: conserved across multiple species

<400> SEQUENCE: 45

Lys Thr Ile Ser Val Ile Pro Gly Leu Lys Thr
1               5                   10

<210> SEQ ID NO 46
<211> LENGTH: 11
<212> TYPE: PRT
<213> ORGANISM: Artificial Sequence
<220> FEATURE:
<223> OTHER INFORMATION: conserved across multiple species

<400> SEQUENCE: 46

Gln Lys Lys Leu Ser Ser Gly Glu Glu Lys Gly
1               5                   10

<210> SEQ ID NO 47
<211> LENGTH: 10
<212> TYPE: PRT
<213> ORGANISM: Rattus norvegicus

<400> SEQUENCE: 47

Gln Lys Met Ser Ser Gly Glu Glu Lys Gly
1               5                   10

<210> SEQ ID NO 48
<211> LENGTH: 10
<212> TYPE: PRT
<213> ORGANISM: Mus musculus

<400> SEQUENCE: 48

Gln Lys Leu Ser Ser Gly Glu Glu Lys Gly
1               5                   10
```

```
<210> SEQ ID NO 49
<211> LENGTH: 10
<212> TYPE: PRT
<213> ORGANISM: Gallus gallus

<400> SEQUENCE: 49

Gln Arg Glu His Ser Gly Glu Glu Asp Asn
1               5                   10

<210> SEQ ID NO 50
<211> LENGTH: 11
<212> TYPE: PRT
<213> ORGANISM: Artificial Sequence
<220> FEATURE:
<223> OTHER INFORMATION: conserved across multiple species

<400> SEQUENCE: 50

Phe His Leu Gly Val Glu Gly His Arg Arg Ala
1               5                   10

<210> SEQ ID NO 51
<211> LENGTH: 11
<212> TYPE: PRT
<213> ORGANISM: Rattus norvegicus

<400> SEQUENCE: 51

Phe His Leu Gly Val Glu Gly His His Arg Thr
1               5                   10

<210> SEQ ID NO 52
<211> LENGTH: 11
<212> TYPE: PRT
<213> ORGANISM: Gallus gallus

<400> SEQUENCE: 52

Phe Arg Phe Ser Phe Asp Gly Asn Lys Leu Ala
1               5                   10

<210> SEQ ID NO 53
<211> LENGTH: 11
<212> TYPE: PRT
<213> ORGANISM: Artificial Sequence
<220> FEATURE:
<223> OTHER INFORMATION: conserved across multiple species

<400> SEQUENCE: 53

Ala Leu Met Leu Pro Asn Gly Gln Leu Leu Pro
1               5                   10

<210> SEQ ID NO 54
<211> LENGTH: 11
<212> TYPE: PRT
<213> ORGANISM: Oryctolagus cuniculus

<400> SEQUENCE: 54

Ala Leu Met Leu Pro Thr Gly Gln Leu Leu Pro
1               5                   10

<210> SEQ ID NO 55
<211> LENGTH: 11
<212> TYPE: PRT
<213> ORGANISM: Gallus gallus

<400> SEQUENCE: 55

Cys Leu Leu Ser Pro Thr Gly Gln Leu Leu Pro
1               5                   10
```

```
<210> SEQ ID NO 56
<211> LENGTH: 11
<212> TYPE: PRT
<213> ORGANISM: Artificial Sequence
<220> FEATURE:
<223> OTHER INFORMATION: conserved across multiple species

<400> SEQUENCE: 56

Thr Asn Gln Ile His Lys Lys Arg Arg Cys Ser
1               5                   10

<210> SEQ ID NO 57
<211> LENGTH: 11
<212> TYPE: PRT
<213> ORGANISM: Artificial Sequence
<220> FEATURE:
<223> OTHER INFORMATION: conserved across multiple species

<400> SEQUENCE: 57

Thr Asn Gln Met Arg Lys Lys Arg Leu Ser Ser
1               5                   10

<210> SEQ ID NO 58
<211> LENGTH: 11
<212> TYPE: PRT
<213> ORGANISM: Artificial Sequence
<220> FEATURE:
<223> OTHER INFORMATION: conserved across multiple species

<400> SEQUENCE: 58

Thr Asn Gln Ile His Lys Lys Arg Arg His Ser
1               5                   10

<210> SEQ ID NO 59
<211> LENGTH: 10
<212> TYPE: PRT
<213> ORGANISM: Oryctolagus cuniculus

<400> SEQUENCE: 59

Thr Gln Ile Arg Lys Lys Arg Arg Ser Ser
1               5                   10

<210> SEQ ID NO 60
<211> LENGTH: 11
<212> TYPE: PRT
<213> ORGANISM: Gallus gallus

<400> SEQUENCE: 60

Thr Glu Met Glu Ile Lys Lys Arg Arg Ser Ser
1               5                   10

<210> SEQ ID NO 61
<211> LENGTH: 11
<212> TYPE: PRT
<213> ORGANISM: Artificial Sequence
<220> FEATURE:
<223> OTHER INFORMATION: conserved across multiple species

<400> SEQUENCE: 61

Met Ser Arg Ala Ser Ile Leu Thr Asn Thr Val
1               5                   10

<210> SEQ ID NO 62
<211> LENGTH: 11
<212> TYPE: PRT
```

```
<213> ORGANISM: Canis familiaris

<400> SEQUENCE: 62

Met Ser Arg Val Ser Ile Leu Thr Asn Thr Val
1               5                   10

<210> SEQ ID NO 63
<211> LENGTH: 11
<212> TYPE: PRT
<213> ORGANISM: Gallus gallus

<400> SEQUENCE: 63

Met Ser Ile Ala Gly Ile Ile Thr Asn Thr Met
1               5                   10

<210> SEQ ID NO 64
<211> LENGTH: 11
<212> TYPE: PRT
<213> ORGANISM: Artificial Sequence
<220> FEATURE:
<223> OTHER INFORMATION: conserved across multiple species

<400> SEQUENCE: 64

Glu Ser Arg Gln Lys Cys Pro Pro Trp Trp Tyr
1               5                   10

<210> SEQ ID NO 65
<211> LENGTH: 11
<212> TYPE: PRT
<213> ORGANISM: Artificial Sequence
<220> FEATURE:
<223> OTHER INFORMATION: conserved across multiple species

<400> SEQUENCE: 65

Phe Val Asp Leu Ala Ile Thr Ile Cys Ile Val
1               5                   10

<210> SEQ ID NO 66
<211> LENGTH: 11
<212> TYPE: PRT
<213> ORGANISM: Gallus gallus

<400> SEQUENCE: 66

Leu Val Asp Leu Ala Ile Thr Ile Cys Ile Ile
1               5                   10

<210> SEQ ID NO 67
<211> LENGTH: 11
<212> TYPE: PRT
<213> ORGANISM: Artificial Sequence
<220> FEATURE:
<223> OTHER INFORMATION: conserved across multiple species

<400> SEQUENCE: 67

Thr Val Asp Asn Pro Leu Pro Gly Glu Gly Glu
1               5                   10

<210> SEQ ID NO 68
<211> LENGTH: 10
<212> TYPE: PRT
<213> ORGANISM: Artificial Sequence
<220> FEATURE:
<223> OTHER INFORMATION: conserved across multiple species

<400> SEQUENCE: 68

Thr Val Asp Asn Pro Leu Pro Gly Glu Glu
```

```
<210> SEQ ID NO 69
<211> LENGTH: 11
<212> TYPE: PRT
<213> ORGANISM: Artificial Sequence
<220> FEATURE:
<223> OTHER INFORMATION: conserved across multiple species

<400> SEQUENCE: 69

Thr Val Asp Asn Pro Val Pro Gly Glu Gly Glu
1               5                   10

<210> SEQ ID NO 70
<211> LENGTH: 11
<212> TYPE: PRT
<213> ORGANISM: Oryctolagus cuniculus

<400> SEQUENCE: 70

Thr Val Asp Asn Ala Leu Pro Gly Glu Gly Glu
1               5                   10

<210> SEQ ID NO 71
<211> LENGTH: 10
<212> TYPE: PRT
<213> ORGANISM: Gallus gallus

<400> SEQUENCE: 71

Thr Val Asn Leu Ala Leu Phe Gly Glu Glu
1               5                   10

<210> SEQ ID NO 72
<211> LENGTH: 11
<212> TYPE: PRT
<213> ORGANISM: Artificial Sequence
<220> FEATURE:
<223> OTHER INFORMATION: conserved across multiple species

<400> SEQUENCE: 72

Cys Gln Val Asn Ile Glu Ser Gly Lys Gly Lys
1               5                   10

<210> SEQ ID NO 73
<211> LENGTH: 11
<212> TYPE: PRT
<213> ORGANISM: Rattus norvegicus

<400> SEQUENCE: 73

Cys Gln Val Asn Val Asp Ser Gly Lys Gly Lys
1               5                   10

<210> SEQ ID NO 74
<211> LENGTH: 11
<212> TYPE: PRT
<213> ORGANISM: Canis familiaris

<400> SEQUENCE: 74

Cys Gln Val Asp Ile Glu Ser Gly Lys Gly Lys
1               5                   10

<210> SEQ ID NO 75
<211> LENGTH: 11
<212> TYPE: PRT
<213> ORGANISM: Oryctolagus cuniculus

<400> SEQUENCE: 75
```

```
Cys Gln Val Ser Ile Glu Ser Gly Lys Gly Lys
1               5                   10
```

<210> SEQ ID NO 76
<211> LENGTH: 11
<212> TYPE: PRT
<213> ORGANISM: Gallus gallus

<400> SEQUENCE: 76

```
Cys Arg Cys Ser Ile Glu Ser Arg Arg Gly Ile
1               5                   10
```

<210> SEQ ID NO 77
<211> LENGTH: 11
<212> TYPE: PRT
<213> ORGANISM: Artificial Sequence
<220> FEATURE:
<223> OTHER INFORMATION: conserved across multiple species

<400> SEQUENCE: 77

```
Leu Val Ala Asn Thr Leu Gly Tyr Ser Asp Leu
1               5                   10
```

<210> SEQ ID NO 78
<211> LENGTH: 11
<212> TYPE: PRT
<213> ORGANISM: Gallus gallus

<400> SEQUENCE: 78

```
Leu Val Ala Thr Ala Leu Gly Phe Ser Glu Leu
1               5                   10
```

<210> SEQ ID NO 79
<211> LENGTH: 1977
<212> TYPE: PRT
<213> ORGANISM: Homo sapiens

<400> SEQUENCE: 79

```
Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
                20                  25                  30

Lys Glu Pro Lys Glu Lys Lys Asp Asp Asp Glu Glu Ala Pro Lys
            35                  40                  45

Pro Ser Ser Asp Leu Glu Ala Gly Lys Gln Leu Pro Phe Ile Tyr Gly
        50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175
```

```
Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
            195                 200                 205

Asn Val Ser Ala Leu Arg Thr Phe Arg Val Leu Arg Ala Leu Lys Thr
210                 215                 220

Ile Ser Val Met Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
            275                 280                 285

Ile Met Asn Thr Leu Glu Ser Glu Glu Asp Phe Arg Lys Tyr Phe Tyr
            290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
            355                 360                 365

Gln Thr Leu Arg Ala Ala Gly Lys Thr Tyr Met Ile Phe Phe Val Val
        370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Ala Glu Tyr Thr
            435                 440                 445

Ser Ile Arg Arg Ser Arg Ile Met Gly Leu Ser Glu Ser Ser Ser Glu
450                 455                 460

Thr Ser Lys Leu Ser Ser Lys Ser Ala Lys Glu Arg Arg Asn Arg Arg
465                 470                 475                 480

Lys Lys Lys Asn Gln Lys Lys Leu Ser Ser Gly Glu Glu Lys Gly Asp
                485                 490                 495

Ala Glu Lys Leu Ser Lys Ser Glu Ser Glu Asp Ser Ile Arg Arg Lys
            500                 505                 510

Ser Phe His Leu Gly Val Glu Gly His Arg Arg Ala His Glu Lys Arg
            515                 520                 525

Leu Ser Thr Pro Asn Gln Ser Pro Leu Ser Ile Arg Gly Ser Leu Phe
            530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
                565                 570                 575

Ile Phe Gly Asp Asn Glu Ser Arg Arg Gly Ser Leu Phe Val Pro His
            580                 585                 590
```

-continued

Arg Pro Gln Glu Arg Arg Ser Ser Asn Ile Ser Gln Ala Ser Arg Ser
            595                 600                 605

Pro Pro Met Leu Pro Val Asn Gly Lys Met His Ser Ala Val Asp Cys
610                 615                 620

Asn Gly Val Val Ser Leu Val Asp Gly Arg Ser Ala Leu Met Leu Pro
625                 630                 635                 640

Asn Gly Gln Leu Leu Pro Gly Thr Thr Asn Gln Ile His Lys Lys
            645                 650                 655

Arg Arg Cys Ser Ser Tyr Leu Leu Ser Glu Asp Met Leu Asn Asp Pro
            660                 665                 670

Asn Leu Arg Gln Arg Ala Met Ser Arg Ala Ser Ile Leu Thr Asn Thr
            675                 680                 685

Val Glu Glu Leu Glu Glu Ser Arg Gln Lys Cys Pro Pro Trp Trp Tyr
            690                 695                 700

Arg Phe Ala His Lys Phe Leu Ile Trp Asn Cys Ser Pro Tyr Trp Ile
705                 710                 715                 720

Lys Phe Lys Lys Cys Ile Tyr Phe Ile Val Met Asp Pro Phe Val Asp
            725                 730                 735

Leu Ala Ile Thr Ile Cys Ile Val Leu Asn Thr Leu Phe Met Ala Met
            740                 745                 750

Glu His His Pro Met Thr Glu Glu Phe Lys Asn Val Leu Ala Ile Gly
            755                 760                 765

Asn Leu Val Phe Thr Gly Ile Phe Ala Ala Glu Met Val Leu Lys Leu
            770                 775                 780

Ile Ala Met Asp Pro Tyr Glu Tyr Phe Gln Val Gly Trp Asn Ile Phe
785                 790                 795                 800

Asp Ser Leu Ile Val Thr Leu Ser Leu Val Glu Leu Phe Leu Ala Asp
                805                 810                 815

Val Glu Gly Leu Ser Val Leu Arg Ser Phe Arg Leu Leu Arg Val Phe
            820                 825                 830

Lys Leu Ala Lys Ser Trp Pro Thr Leu Asn Met Leu Ile Lys Ile Ile
            835                 840                 845

Gly Asn Ser Val Gly Ala Leu Gly Asn Leu Thr Leu Val Leu Ala Ile
850                 855                 860

Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
                885                 890                 895

Trp His Met Asn Asp Phe Phe His Ser Phe Leu Ile Val Phe Arg Val
                900                 905                 910

Leu Cys Gly Glu Trp Ile Glu Thr Met Trp Asp Cys Met Glu Val Ala
            915                 920                 925

Gly Gln Ala Met Cys Leu Ile Val Tyr Met Met Val Met Val Ile Gly
            930                 935                 940

Asn Leu Val Val Leu Asn Leu Phe Leu Ala Leu Leu Leu Ser Ser Phe
945                 950                 955                 960

Ser Ser Asp Asn Leu Thr Ala Ile Glu Glu Asp Pro Asp Ala Asn Asn
                965                 970                 975

Leu Gln Ile Ala Val Thr Arg Ile Lys Lys Gly Ile Asn Tyr Val Lys
            980                 985                 990

Gln Thr Leu Arg Glu Phe Ile Leu Lys Ala Phe Ser Lys Lys Pro Lys
            995                 1000                1005

Ile Ser Arg Glu Ile Arg Gln Ala Glu Asp Leu Asn Thr Lys Lys

```
                1010                1015                1020
Glu Asn Tyr Ile Ser Asn His Thr Leu Ala Glu Met Ser Lys Gly
        1025                1030                1035
His Asn Phe Leu Lys Glu Lys Asp Lys Ile Ser Gly Phe Gly Ser
        1040                1045                1050
Ser Val Asp Lys His Leu Met Glu Asp Ser Asp Gly Gln Ser Phe
        1055                1060                1065
Ile His Asn Pro Ser Leu Thr Val Thr Val Pro Ile Ala Pro Gly
        1070                1075                1080
Glu Ser Asp Leu Glu Asn Met Asn Ala Glu Glu Leu Ser Ser Asp
        1085                1090                1095
Ser Asp Ser Glu Tyr Ser Lys Val Arg Leu Asn Arg Ser Ser Ser
        1100                1105                1110
Ser Glu Cys Ser Thr Val Asp Asn Pro Leu Pro Gly Glu Gly Glu
        1115                1120                1125
Glu Ala Glu Ala Glu Pro Met Asn Ser Asp Glu Pro Glu Ala Cys
        1130                1135                1140
Phe Thr Asp Gly Cys Val Arg Arg Phe Ser Cys Cys Gln Val Asn
        1145                1150                1155
Ile Glu Ser Gly Lys Gly Lys Ile Trp Trp Asn Ile Arg Lys Thr
        1160                1165                1170
Cys Tyr Lys Ile Val Glu His Ser Trp Phe Glu Ser Phe Ile Val
        1175                1180                1185
Leu Met Ile Leu Leu Ser Ser Gly Ala Leu Ala Phe Glu Asp Ile
        1190                1195                1200
Tyr Ile Glu Arg Lys Lys Thr Ile Lys Ile Ile Leu Glu Tyr Ala
        1205                1210                1215
Asp Lys Ile Phe Thr Tyr Ile Phe Ile Leu Glu Met Leu Leu Lys
        1220                1225                1230
Trp Ile Ala Tyr Gly Tyr Lys Thr Tyr Phe Thr Asn Ala Trp Cys
        1235                1240                1245
Trp Leu Asp Phe Leu Ile Val Asp Val Ser Leu Val Thr Leu Val
        1250                1255                1260
Ala Asn Thr Leu Gly Tyr Ser Asp Leu Gly Pro Ile Lys Ser Leu
        1265                1270                1275
Arg Thr Leu Arg Ala Leu Arg Pro Leu Arg Ala Leu Ser Arg Phe
        1280                1285                1290
Glu Gly Met Arg Val Val Asn Ala Leu Ile Gly Ala Ile Pro
        1295                1300                1305
Ser Ile Met Asn Val Leu Leu Val Cys Leu Ile Phe Trp Leu Ile
        1310                1315                1320
Phe Ser Ile Met Gly Val Asn Leu Phe Ala Gly Lys Phe Tyr Glu
        1325                1330                1335
Cys Ile Asn Thr Thr Asp Gly Ser Arg Phe Pro Ala Ser Gln Val
        1340                1345                1350
Pro Asn Arg Ser Glu Cys Phe Ala Leu Met Asn Val Ser Gln Asn
        1355                1360                1365
Val Arg Trp Lys Asn Leu Lys Val Asn Phe Asp Asn Val Gly Leu
        1370                1375                1380
Gly Tyr Leu Ser Leu Leu Gln Val Ala Thr Phe Lys Gly Trp Thr
        1385                1390                1395
Ile Ile Met Tyr Ala Ala Val Asp Ser Val Asn Val Asp Lys Gln
        1400                1405                1410
```

```
Pro Lys Tyr Glu Tyr Ser Leu Tyr Met Tyr Ile Tyr Phe Val Val
    1415            1420                1425

Phe Ile Ile Phe Gly Ser Phe Phe Thr Leu Asn Leu Phe Ile Gly
    1430            1435                1440

Val Ile Ile Asp Asn Phe Asn Gln Gln Lys Lys Lys Leu Gly Gly
    1445            1450                1455

Gln Asp Ile Phe Met Thr Glu Glu Gln Lys Lys Tyr Tyr Asn Ala
    1460            1465                1470

Met Lys Lys Leu Gly Ser Lys Lys Pro Gln Lys Pro Ile Pro Arg
    1475            1480                1485

Pro Gly Asn Lys Ile Gln Gly Cys Ile Phe Asp Leu Val Thr Asn
    1490            1495                1500

Gln Ala Phe Asp Ile Ser Ile Met Val Leu Ile Cys Leu Asn Met
    1505            1510                1515

Val Thr Met Met Val Glu Lys Glu Gly Gln Ser Gln His Met Thr
    1520            1525                1530

Glu Val Leu Tyr Trp Ile Asn Val Val Phe Ile Ile Leu Phe Thr
    1535            1540                1545

Gly Glu Cys Val Leu Lys Leu Ile Ser Leu Arg His Tyr Tyr Phe
    1550            1555                1560

Thr Val Gly Trp Asn Ile Phe Asp Phe Val Val Val Ile Ile Ser
    1565            1570                1575

Ile Val Gly Met Phe Leu Ala Asp Leu Ile Glu Thr Tyr Phe Val
    1580            1585                1590

Ser Pro Thr Leu Phe Arg Val Ile Arg Leu Ala Arg Ile Gly Arg
    1595            1600                1605

Ile Leu Arg Leu Val Lys Gly Ala Lys Gly Ile Arg Thr Leu Leu
    1610            1615                1620

Phe Ala Leu Met Met Ser Leu Pro Ala Leu Phe Asn Ile Gly Leu
    1625            1630                1635

Leu Leu Phe Leu Val Met Phe Ile Tyr Ala Ile Phe Gly Met Ser
    1640            1645                1650

Asn Phe Ala Tyr Val Lys Lys Glu Asp Gly Ile Asn Asp Met Phe
    1655            1660                1665

Asn Phe Glu Thr Phe Gly Asn Ser Met Ile Cys Leu Phe Gln Ile
    1670            1675                1680

Thr Thr Ser Ala Gly Trp Asp Gly Leu Leu Ala Pro Ile Leu Asn
    1685            1690                1695

Ser Lys Pro Pro Asp Cys Asp Pro Lys Lys Val His Pro Gly Ser
    1700            1705                1710

Ser Val Glu Gly Asp Cys Gly Asn Pro Ser Val Gly Ile Phe Tyr
    1715            1720                1725

Phe Val Ser Tyr Ile Ile Ile Ser Phe Leu Val Val Val Asn Met
    1730            1735                1740

Tyr Ile Ala Val Ile Leu Glu Asn Phe Ser Val Ala Thr Glu Glu
    1745            1750                1755

Ser Thr Glu Pro Leu Ser Glu Asp Asp Phe Glu Met Phe Tyr Glu
    1760            1765                1770

Val Trp Glu Lys Phe Asp Pro Asp Ala Thr Gln Phe Ile Glu Phe
    1775            1780                1785

Ser Lys Leu Ser Asp Phe Ala Ala Ala Leu Asp Pro Pro Leu Leu
    1790            1795                1800
```

Ile Ala Lys Pro Asn Lys Val Gln Leu Ile Ala Met Asp Leu Pro
    1805            1810                1815

Met Val Ser Gly Asp Arg Ile His Cys Leu Asp Ile Leu Phe Ala
    1820            1825                1830

Phe Thr Lys Arg Val Leu Gly Glu Ser Gly Met Asp Ser Leu
    1835            1840                1845

Arg Ser Gln Met Glu Glu Arg Phe Met Ser Ala Asn Pro Ser Lys
    1850            1855                1860

Val Ser Tyr Glu Pro Ile Thr Thr Thr Leu Lys Arg Lys Gln Glu
    1865            1870                1875

Asp Val Ser Ala Thr Val Ile Gln Arg Ala Tyr Arg Arg Tyr Arg
    1880            1885                1890

Leu Arg Gln Asn Val Lys Asn Ile Ser Ser Ile Tyr Ile Lys Asp
    1895            1900                1905

Gly Asp Arg Asp Asp Asp Leu Leu Asn Lys Lys Asp Met Ala Phe
    1910            1915                1920

Asp Asn Val Asn Glu Asn Ser Ser Pro Glu Lys Thr Asp Ala Thr
    1925            1930                1935

Ser Ser Thr Thr Ser Pro Pro Ser Tyr Asp Ser Val Thr Lys Pro
    1940            1945                1950

Asp Lys Glu Lys Tyr Glu Gln Asp Arg Thr Glu Lys Glu Asp Lys
    1955            1960                1965

Gly Lys Asp Ser Lys Glu Ser Lys Lys
    1970            1975

<210> SEQ ID NO 80
<211> LENGTH: 1977
<212> TYPE: PRT
<213> ORGANISM: Homo sapiens

<400> SEQUENCE: 80

Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
                20                  25                  30

Lys Glu Pro Lys Glu Glu Lys Lys Asp Asp Asp Glu Glu Ala Pro Lys
                35                  40                  45

Pro Ser Ser Asp Leu Glu Ala Gly Lys Gln Leu Pro Phe Ile Tyr Gly
    50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
                100                 105                 110

Ser Pro Leu Arg Arg Ile Ser Ile Lys Ile Leu Val His Ser Leu Phe
                115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
                180                 185                 190

```
Phe Val Val Ile Val Phe Ala Tyr Leu Thr Glu Phe Val Asn Leu Gly
            195                 200                 205

Asn Val Ser Ala Leu Arg Thr Phe Arg Val Leu Arg Ala Leu Lys Thr
210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
            245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
            275                 280                 285

Ile Met Asn Thr Leu Glu Ser Glu Glu Asp Phe Arg Lys Tyr Phe Tyr
            290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
            325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
            355                 360                 365

Gln Thr Leu Arg Ala Ala Gly Lys Thr Tyr Met Ile Phe Phe Val Val
            370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Glu Tyr Thr
            435                 440                 445

Ser Ile Arg Arg Ser Arg Ile Met Gly Leu Ser Glu Ser Ser Ser Glu
            450                 455                 460

Thr Ser Lys Leu Ser Ser Lys Ser Ala Lys Glu Arg Arg Asn Arg Arg
465                 470                 475                 480

Lys Lys Lys Asn Gln Lys Lys Leu Ser Asn Gly Glu Glu Lys Gly Asp
            485                 490                 495

Ala Glu Lys Leu Ser Lys Ser Glu Ser Glu Asp Ser Ile Arg Arg Lys
            500                 505                 510

Ser Phe His Leu Gly Val Glu Gly His Arg Arg Ala His Glu Lys Arg
            515                 520                 525

Leu Ser Thr Pro Asn Gln Ser Pro Leu Ser Ile Arg Gly Ser Leu Phe
            530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
            565                 570                 575

Ile Phe Gly Asp Asn Glu Ser Arg Arg Gly Ser Leu Phe Val Pro His
            580                 585                 590

Arg Pro Gln Glu Arg Arg Ser Ser Asn Ile Ser Gln Ala Ser Arg Ser
            595                 600                 605
```

```
Pro Pro Met Leu Pro Val Asn Gly Lys Met His Ser Ala Val Asp Cys
610                 615                 620

Asn Gly Val Val Ser Leu Val Asp Gly Arg Ser Ala Leu Met Leu Pro
625                 630                 635                 640

Asn Gly Gln Leu Leu Pro Glu Gly Thr Thr Asn Gln Ile His Lys Lys
                645                 650                 655

Arg Arg Cys Ser Ser Tyr Leu Leu Ser Glu Asp Met Leu Asn Asp Pro
                660                 665                 670

Asn Leu Arg Gln Arg Ala Met Ser Arg Ala Ser Ile Leu Thr Asn Thr
            675                 680                 685

Val Glu Glu Leu Glu Glu Ser Arg Gln Lys Cys Pro Pro Trp Trp Tyr
690                 695                 700

Arg Phe Ala His Lys Phe Leu Ile Trp Asn Cys Ser Pro Tyr Trp Ile
705                 710                 715                 720

Lys Phe Lys Lys Cys Ile Tyr Phe Ile Val Met Asp Pro Phe Val Asp
                725                 730                 735

Leu Ala Ile Thr Ile Cys Ile Val Leu Asn Thr Leu Phe Met Ala Met
            740                 745                 750

Glu His His Pro Met Thr Glu Glu Phe Lys Asn Val Leu Ala Ile Gly
            755                 760                 765

Asn Leu Val Phe Thr Gly Ile Phe Ala Ala Glu Met Val Leu Lys Leu
770                 775                 780

Ile Ala Met Asp Pro Tyr Glu Tyr Phe Gln Val Gly Trp Asn Ile Phe
785                 790                 795                 800

Asp Ser Leu Ile Val Thr Leu Ser Leu Val Glu Leu Phe Leu Ala Asp
                805                 810                 815

Val Glu Gly Leu Ser Val Leu Arg Ser Phe Arg Leu Leu Arg Val Phe
            820                 825                 830

Lys Leu Ala Lys Ser Trp Pro Thr Leu Asn Met Leu Ile Lys Ile Ile
            835                 840                 845

Gly Asn Ser Val Gly Ala Leu Gly Asn Leu Thr Leu Val Leu Ala Ile
850                 855                 860

Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
                885                 890                 895

Trp His Met Asn Asp Phe Phe His Ser Phe Leu Ile Val Phe Arg Val
            900                 905                 910

Leu Cys Gly Glu Trp Ile Glu Thr Met Trp Asp Cys Met Glu Val Ala
            915                 920                 925

Gly Gln Ala Met Cys Leu Ile Val Tyr Met Met Val Met Val Ile Gly
930                 935                 940

Asn Leu Val Val Leu Asn Leu Phe Leu Ala Leu Leu Leu Ser Ser Phe
945                 950                 955                 960

Ser Ser Asp Asn Leu Thr Ala Ile Glu Glu Asp Pro Asp Ala Asn Asn
                965                 970                 975

Leu Gln Ile Ala Val Thr Arg Ile Lys Lys Gly Ile Asn Tyr Val Lys
            980                 985                 990

Gln Thr Leu Arg Glu Phe Ile Leu  Lys Ala Phe Ser Lys  Lys Pro Lys
            995                 1000                1005

Ile Ser Arg Glu Ile Arg Gln Ala Glu Asp Leu Asn  Thr Lys Lys
            1010                1015                1020

Glu Asn Tyr Ile Ser Asn His  Thr Leu Ala Glu Met  Ser Lys Gly
```

1025                1030                1035

His Asn Phe Leu Lys Glu Lys Asp Lys Ile Ser Gly Phe Gly Ser
    1040                1045                1050

Ser Val Asp Lys His Leu Met Glu Asp Ser Asp Gly Gln Ser Phe
    1055                1060                1065

Ile His Asn Pro Ser Leu Thr Val Thr Val Pro Ile Ala Pro Gly
    1070                1075                1080

Glu Ser Asp Leu Glu Asn Met Asn Ala Glu Glu Leu Ser Ser Asp
    1085                1090                1095

Ser Asp Ser Glu Tyr Ser Lys Val Arg Leu Asn Arg Ser Ser Ser
    1100                1105                1110

Ser Glu Cys Ser Thr Val Asp Asn Pro Leu Pro Gly Glu Gly Glu
    1115                1120                1125

Glu Ala Glu Ala Glu Pro Met Asn Ser Asp Glu Pro Glu Ala Cys
    1130                1135                1140

Phe Thr Asp Gly Cys Val Arg Arg Phe Ser Cys Cys Gln Val Asn
    1145                1150                1155

Ile Glu Ser Gly Lys Gly Lys Ile Trp Trp Asn Ile Arg Lys Thr
    1160                1165                1170

Cys Tyr Lys Ile Val Glu His Ser Trp Phe Glu Ser Phe Ile Val
    1175                1180                1185

Leu Met Ile Leu Leu Ser Ser Gly Ala Leu Ala Phe Glu Asp Ile
    1190                1195                1200

Tyr Ile Glu Arg Lys Lys Thr Ile Lys Ile Ile Leu Glu Tyr Ala
    1205                1210                1215

Asp Lys Ile Phe Thr Tyr Ile Phe Ile Leu Glu Met Leu Leu Lys
    1220                1225                1230

Trp Ile Ala Tyr Gly Tyr Lys Thr Tyr Phe Thr Asn Ala Trp Cys
    1235                1240                1245

Trp Leu Asp Phe Leu Ile Val Asp Val Ser Leu Val Thr Leu Val
    1250                1255                1260

Ala Asn Thr Leu Gly Tyr Ser Asp Leu Gly Pro Ile Lys Ser Leu
    1265                1270                1275

Arg Thr Leu Arg Ala Leu Arg Pro Leu Arg Ala Leu Ser Arg Phe
    1280                1285                1290

Glu Gly Met Arg Val Val Asn Ala Leu Ile Gly Ala Ile Pro
    1295                1300                1305

Ser Ile Met Asn Val Leu Leu Val Cys Leu Ile Phe Trp Leu Ile
    1310                1315                1320

Phe Ser Ile Met Gly Val Asn Leu Phe Ala Gly Lys Phe Tyr Glu
    1325                1330                1335

Cys Ile Asn Thr Thr Asp Gly Ser Arg Phe Pro Ala Ser Gln Val
    1340                1345                1350

Pro Asn Arg Ser Glu Cys Phe Ala Leu Met Asn Val Ser Gln Asn
    1355                1360                1365

Val Arg Trp Lys Asn Leu Lys Val Asn Phe Asp Asn Val Gly Leu
    1370                1375                1380

Gly Tyr Leu Ser Leu Leu Gln Val Ala Thr Phe Lys Gly Trp Thr
    1385                1390                1395

Ile Ile Met Tyr Ala Ala Val Asp Ser Val Asn Val Asp Lys Gln
    1400                1405                1410

Pro Lys Tyr Glu Tyr Ser Leu Tyr Met Tyr Ile Tyr Phe Val Val
    1415                1420                1425

-continued

```
Phe Ile Ile Phe Gly Ser Phe Phe Thr Leu Asn Leu Phe Ile Gly
    1430            1435            1440

Val Ile Ile Asp Asn Phe Asn Gln Gln Lys Lys Lys Leu Gly Gly
    1445            1450            1455

Gln Asp Ile Phe Met Thr Glu Glu Gln Lys Lys Tyr Tyr Asn Ala
    1460            1465            1470

Met Lys Lys Leu Gly Ser Lys Lys Pro Gln Lys Pro Ile Pro Arg
    1475            1480            1485

Pro Gly Asn Lys Ile Gln Gly Cys Ile Phe Asp Leu Val Thr Asn
    1490            1495            1500

Gln Ala Phe Asp Ile Ser Ile Met Val Leu Ile Cys Leu Asn Met
    1505            1510            1515

Val Thr Met Met Val Glu Lys Glu Gly Gln Ser Gln His Met Thr
    1520            1525            1530

Glu Val Leu Tyr Trp Ile Asn Val Val Phe Ile Ile Leu Phe Thr
    1535            1540            1545

Gly Glu Cys Val Leu Lys Leu Ile Ser Leu Arg His Tyr Tyr Phe
    1550            1555            1560

Thr Val Gly Trp Asn Ile Phe Asp Phe Val Val Val Ile Ile Ser
    1565            1570            1575

Ile Val Gly Met Phe Leu Ala Asp Leu Ile Glu Thr Tyr Phe Val
    1580            1585            1590

Ser Pro Thr Leu Phe Arg Val Ile Arg Leu Ala Arg Ile Gly Arg
    1595            1600            1605

Ile Leu Arg Leu Val Lys Gly Ala Lys Gly Ile Arg Thr Leu Leu
    1610            1615            1620

Phe Ala Leu Met Met Ser Leu Pro Ala Leu Phe Asn Ile Gly Leu
    1625            1630            1635

Leu Leu Phe Leu Val Met Phe Ile Tyr Ala Ile Phe Gly Met Ser
    1640            1645            1650

Asn Phe Ala Tyr Val Lys Lys Glu Asp Gly Ile Asn Asp Met Phe
    1655            1660            1665

Asn Phe Glu Thr Phe Gly Asn Ser Met Ile Cys Leu Phe Gln Ile
    1670            1675            1680

Thr Thr Ser Ala Gly Trp Asp Gly Leu Leu Ala Pro Ile Leu Asn
    1685            1690            1695

Ser Lys Pro Pro Asp Cys Asp Pro Lys Lys Val His Pro Gly Ser
    1700            1705            1710

Ser Val Glu Gly Asp Cys Gly Asn Pro Ser Val Gly Ile Phe Tyr
    1715            1720            1725

Phe Val Ser Tyr Ile Ile Ile Ser Phe Leu Val Val Val Asn Met
    1730            1735            1740

Tyr Ile Ala Val Ile Leu Glu Asn Phe Ser Val Ala Thr Glu Glu
    1745            1750            1755

Ser Thr Glu Pro Leu Ser Glu Asp Asp Phe Glu Met Phe Tyr Glu
    1760            1765            1770

Val Trp Glu Lys Phe Asp Pro Asp Ala Thr Gln Phe Ile Glu Phe
    1775            1780            1785

Ser Lys Leu Ser Asp Phe Ala Ala Ala Leu Asp Pro Pro Leu Leu
    1790            1795            1800

Ile Ala Lys Pro Asn Lys Val Gln Leu Ile Ala Met Asp Leu Pro
    1805            1810            1815
```

Met Val Ser Gly Asp Arg Ile His Cys Leu Asp Ile Leu Phe Ala
1820                1825                1830

Phe Thr Lys Arg Val Leu Gly Glu Ser Gly Glu Met Asp Ser Leu
    1835                1840                1845

Arg Ser Gln Met Glu Glu Arg Phe Met Ser Ala Asn Pro Ser Lys
    1850                1855                1860

Val Ser Tyr Glu Pro Ile Thr Thr Thr Leu Lys Arg Lys Gln Glu
    1865                1870                1875

Asp Val Ser Ala Thr Val Ile Gln Arg Ala Tyr Arg Arg Tyr Arg
    1880                1885                1890

Leu Arg Gln Asn Val Lys Asn Ile Ser Ser Ile Tyr Ile Lys Asp
    1895                1900                1905

Gly Asp Arg Asp Asp Asp Leu Leu Asn Lys Lys Asp Met Ala Phe
    1910                1915                1920

Asp Asn Val Asn Glu Asn Ser Ser Pro Glu Lys Thr Asp Ala Thr
    1925                1930                1935

Ser Ser Thr Thr Ser Pro Pro Ser Tyr Asp Ser Val Thr Lys Pro
    1940                1945                1950

Asp Lys Glu Lys Tyr Glu Gln Asp Arg Thr Glu Lys Glu Asp Lys
    1955                1960                1965

Gly Lys Asp Ser Lys Glu Ser Lys Lys
    1970                1975

<210> SEQ ID NO 81
<211> LENGTH: 1977
<212> TYPE: PRT
<213> ORGANISM: Homo sapiens

<400> SEQUENCE: 81

Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
                20                  25                  30

Lys Glu Pro Lys Glu Glu Lys Lys Asp Asp Asp Glu Glu Ala Pro Lys
            35                  40                  45

Pro Ser Ser Asp Leu Glu Ala Gly Lys Gln Leu Pro Phe Ile Tyr Gly
        50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

```
Asn Val Ser Ala Leu Arg Thr Phe Arg Val Leu Arg Ala Leu Lys Thr
    210                 215                 220
Ile Ser Val Ile Pro Gly Leu Lys Thr Ile Val Gly Ala Leu Ile Gln
225                 230                 235                 240
Ser Val Lys Lys Leu Ser Asp Val Met Ile Leu Thr Val Phe Cys Leu
                245                 250                 255
Ser Val Phe Ala Leu Ile Gly Leu Gln Leu Phe Met Gly Asn Leu Lys
            260                 265                 270
His Lys Cys Phe Arg Asn Ser Leu Glu Asn Asn Glu Thr Leu Glu Ser
        275                 280                 285
Ile Met Asn Thr Leu Glu Ser Glu Glu Asp Phe Arg Lys Tyr Phe Tyr
    290                 295                 300
Tyr Leu Glu Gly Ser Lys Asp Ala Leu Leu Cys Gly Phe Ser Thr Asp
305                 310                 315                 320
Ser Gly Gln Cys Pro Glu Gly Tyr Thr Cys Val Lys Ile Gly Arg Asn
                325                 330                 335
Pro Asp Tyr Gly Tyr Thr Ser Phe Asp Thr Phe Ser Trp Ala Phe Leu
            340                 345                 350
Ala Leu Phe Arg Leu Met Thr Gln Asp Tyr Trp Glu Asn Leu Tyr Gln
        355                 360                 365
Gln Thr Leu Arg Ala Ala Gly Lys Thr Tyr Met Ile Phe Phe Val Val
    370                 375                 380
Val Ile Phe Leu Gly Ser Phe Tyr Leu Ile Asn Leu Ile Leu Ala Val
385                 390                 395                 400
Val Ala Met Ala Tyr Glu Glu Gln Asn Gln Ala Asn Ile Glu Glu Ala
                405                 410                 415
Lys Gln Lys Glu Leu Glu Phe Gln Gln Met Leu Asp Arg Leu Lys Lys
            420                 425                 430
Glu Gln Glu Glu Ala Glu Ala Ile Ala Ala Ala Ala Glu Tyr Thr
        435                 440                 445
Ser Ile Arg Arg Ser Arg Ile Met Gly Leu Ser Glu Ser Ser Ser Glu
    450                 455                 460
Thr Ser Lys Leu Ser Ser Lys Ser Ala Lys Glu Arg Arg Asn Arg Arg
465                 470                 475                 480
Lys Lys Lys Asn Gln Lys Lys Leu Ser Ser Gly Glu Glu Lys Gly Asp
                485                 490                 495
Ala Glu Lys Leu Ser Lys Ser Glu Ser Glu Asp Ser Ile Arg Arg Lys
            500                 505                 510
Ser Phe His Leu Gly Val Lys Gly His Arg Arg Ala His Glu Lys Arg
        515                 520                 525
Leu Ser Thr Pro Asn Gln Ser Pro Leu Ser Ile Arg Gly Ser Leu Phe
    530                 535                 540
Ser Ala Arg Arg Ser Ser Arg Thr Ser Leu Phe Ser Phe Lys Gly Arg
545                 550                 555                 560
Gly Arg Asp Ile Gly Ser Glu Thr Glu Phe Ala Asp Asp Glu His Ser
                565                 570                 575
Ile Phe Gly Asp Asn Glu Ser Arg Arg Gly Ser Leu Phe Val Pro His
            580                 585                 590
Arg Pro Gln Glu Arg Arg Ser Ser Asn Ile Ser Gln Ala Ser Arg Ser
        595                 600                 605
Pro Pro Met Leu Pro Val Asn Gly Lys Met His Ser Ala Val Asp Cys
    610                 615                 620
```

```
Asn Gly Val Val Ser Leu Val Asp Gly Arg Ser Ala Leu Met Leu Pro
625                 630                 635                 640

Asn Gly Gln Leu Leu Pro Glu Gly Thr Thr Asn Gln Ile His Lys Lys
            645                 650                 655

Arg Arg Cys Ser Ser Tyr Leu Leu Ser Glu Asp Met Leu Asn Asp Pro
                660                 665                 670

Asn Leu Arg Gln Arg Ala Met Ser Arg Ala Ser Ile Leu Thr Asn Thr
            675                 680                 685

Val Glu Glu Leu Glu Glu Ser Arg Gln Lys Cys Pro Pro Trp Trp Tyr
690                 695                 700

Arg Phe Ala His Lys Phe Leu Ile Trp Asn Cys Ser Pro Tyr Trp Ile
705                 710                 715                 720

Lys Phe Lys Lys Cys Ile Tyr Phe Ile Val Met Asp Pro Phe Val Asp
                725                 730                 735

Leu Ala Ile Thr Ile Cys Ile Val Leu Asn Thr Leu Phe Met Ala Met
            740                 745                 750

Glu His His Pro Met Thr Glu Glu Phe Lys Asn Val Leu Ala Ile Gly
            755                 760                 765

Asn Leu Val Phe Thr Gly Ile Phe Ala Ala Glu Met Val Leu Lys Leu
770                 775                 780

Ile Ala Met Asp Pro Tyr Glu Tyr Phe Gln Val Gly Trp Asn Ile Phe
785                 790                 795                 800

Asp Ser Leu Ile Val Thr Leu Ser Leu Val Glu Leu Phe Leu Ala Asp
                805                 810                 815

Val Glu Gly Leu Ser Val Leu Arg Ser Phe Arg Leu Leu Arg Val Phe
            820                 825                 830

Lys Leu Ala Lys Ser Trp Pro Thr Leu Asn Met Leu Ile Lys Ile Ile
            835                 840                 845

Gly Asn Ser Val Gly Ala Leu Gly Asn Leu Thr Leu Val Leu Ala Ile
            850                 855                 860

Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
                885                 890                 895

Trp His Met Asn Asp Phe Phe His Ser Phe Leu Ile Val Phe Arg Val
            900                 905                 910

Leu Cys Gly Glu Trp Ile Glu Thr Met Trp Asp Cys Met Glu Val Ala
            915                 920                 925

Gly Gln Ala Met Cys Leu Ile Val Tyr Met Met Val Met Val Ile Gly
930                 935                 940

Asn Leu Val Val Leu Asn Leu Phe Leu Ala Leu Leu Leu Ser Ser Phe
945                 950                 955                 960

Ser Ser Asp Asn Leu Thr Ala Ile Glu Glu Asp Pro Asp Ala Asn Asn
                965                 970                 975

Leu Gln Ile Ala Val Thr Arg Ile Lys Lys Gly Ile Asn Tyr Val Lys
            980                 985                 990

Gln Thr Leu Arg Glu Phe Ile Leu  Lys Ala Phe Ser Lys  Lys Pro Lys
            995                 1000                1005

Ile Ser  Arg Glu Ile Arg Gln  Ala Glu Asp Leu Asn  Thr Lys Lys
            1010                1015                1020

Glu Asn  Tyr Ile Ser Asn His  Thr Leu Ala Glu Met  Ser Lys Gly
            1025                1030                1035

His Asn  Phe Leu Lys Glu Lys  Asp Lys Ile Ser Gly  Phe Gly Ser
```

-continued

```
            1040                1045                1050
Ser Val Asp Lys His Leu Met Glu Asp Ser Asp Gly Gln Ser Phe
        1055                1060                1065
Ile His Asn Pro Ser Leu Thr Val Thr Val Pro Ile Ala Pro Gly
        1070                1075                1080
Glu Ser Asp Leu Glu Asn Met Asn Ala Glu Glu Leu Ser Ser Asp
        1085                1090                1095
Ser Asp Ser Glu Tyr Ser Lys Val Arg Leu Asn Arg Ser Ser Ser
        1100                1105                1110
Ser Glu Cys Ser Thr Val Asp Asn Pro Leu Pro Gly Glu Gly Glu
        1115                1120                1125
Glu Ala Glu Ala Glu Pro Met Asn Ser Asp Glu Pro Glu Ala Cys
        1130                1135                1140
Phe Thr Asp Gly Cys Val Arg Arg Phe Ser Cys Cys Gln Val Asn
        1145                1150                1155
Ile Glu Ser Gly Lys Gly Lys Ile Trp Trp Asn Ile Arg Lys Thr
        1160                1165                1170
Cys Tyr Lys Ile Val Glu His Ser Trp Phe Glu Ser Phe Ile Val
        1175                1180                1185
Leu Met Ile Leu Leu Ser Ser Gly Ala Leu Ala Phe Glu Asp Ile
        1190                1195                1200
Tyr Ile Glu Arg Lys Lys Thr Ile Lys Ile Ile Leu Glu Tyr Ala
        1205                1210                1215
Asp Lys Ile Phe Thr Tyr Ile Phe Ile Leu Glu Met Leu Leu Lys
        1220                1225                1230
Trp Ile Ala Tyr Gly Tyr Lys Thr Tyr Phe Thr Asn Ala Trp Cys
        1235                1240                1245
Trp Leu Asp Phe Leu Ile Val Asp Val Ser Leu Val Thr Leu Val
        1250                1255                1260
Ala Asn Thr Leu Gly Tyr Ser Asp Leu Gly Pro Ile Lys Ser Leu
        1265                1270                1275
Arg Thr Leu Arg Ala Leu Arg Pro Leu Arg Ala Leu Ser Arg Phe
        1280                1285                1290
Glu Gly Met Arg Val Val Val Asn Ala Leu Ile Gly Ala Ile Pro
        1295                1300                1305
Ser Ile Met Asn Val Leu Leu Val Cys Leu Ile Phe Trp Leu Ile
        1310                1315                1320
Phe Ser Ile Met Gly Val Asn Leu Phe Ala Gly Lys Phe Tyr Glu
        1325                1330                1335
Cys Ile Asn Thr Thr Asp Gly Ser Arg Phe Pro Ala Ser Gln Val
        1340                1345                1350
Pro Asn Arg Ser Glu Cys Phe Ala Leu Met Asn Val Ser Gln Asn
        1355                1360                1365
Val Arg Trp Lys Asn Leu Lys Val Asn Phe Asp Asn Val Gly Leu
        1370                1375                1380
Gly Tyr Leu Ser Leu Leu Gln Val Ala Thr Phe Lys Gly Trp Thr
        1385                1390                1395
Ile Ile Met Tyr Ala Ala Val Asp Ser Val Asn Val Asp Lys Gln
        1400                1405                1410
Pro Lys Tyr Glu Tyr Ser Leu Tyr Met Tyr Ile Tyr Phe Val Val
        1415                1420                1425
Phe Ile Ile Phe Gly Ser Phe Phe Thr Leu Asn Leu Phe Ile Gly
        1430                1435                1440
```

```
Val Ile Ile Asp Asn Phe Asn Gln Gln Lys Lys Lys Leu Gly Gly
    1445            1450                1455

Gln Asp Ile Phe Met Thr Glu Glu Gln Lys Lys Tyr Tyr Asn Ala
1460            1465                1470

Met Lys Lys Leu Gly Ser Lys Lys Pro Gln Lys Pro Ile Pro Arg
    1475            1480                1485

Pro Gly Asn Lys Ile Gln Gly Cys Ile Phe Asp Leu Val Thr Asn
    1490            1495                1500

Gln Ala Phe Asp Ile Ser Ile Met Val Leu Ile Cys Leu Asn Met
    1505            1510                1515

Val Thr Met Met Val Glu Lys Glu Gly Gln Ser Gln His Met Thr
    1520            1525                1530

Glu Val Leu Tyr Trp Ile Asn Val Val Phe Ile Ile Leu Phe Thr
    1535            1540                1545

Gly Glu Cys Val Leu Lys Leu Ile Ser Leu Arg His Tyr Tyr Phe
    1550            1555                1560

Thr Val Gly Trp Asn Ile Phe Asp Phe Val Val Val Ile Ile Ser
    1565            1570                1575

Ile Val Gly Met Phe Leu Ala Asp Leu Ile Glu Thr Tyr Phe Val
    1580            1585                1590

Ser Pro Thr Leu Phe Arg Val Ile Arg Leu Ala Arg Ile Gly Arg
    1595            1600                1605

Ile Leu Arg Leu Val Lys Gly Ala Lys Gly Ile Arg Thr Leu Leu
    1610            1615                1620

Phe Ala Leu Met Met Ser Leu Pro Ala Leu Phe Asn Ile Gly Leu
    1625            1630                1635

Leu Leu Phe Leu Val Met Phe Ile Tyr Ala Ile Phe Gly Met Ser
    1640            1645                1650

Asn Phe Ala Tyr Val Lys Lys Glu Asp Gly Ile Asn Asp Met Phe
    1655            1660                1665

Asn Phe Glu Thr Phe Gly Asn Ser Met Ile Cys Leu Phe Gln Ile
    1670            1675                1680

Thr Thr Ser Ala Gly Trp Asp Gly Leu Leu Ala Pro Ile Leu Asn
    1685            1690                1695

Ser Lys Pro Pro Asp Cys Asp Pro Lys Lys Val His Pro Gly Ser
    1700            1705                1710

Ser Val Glu Gly Asp Cys Gly Asn Pro Ser Val Gly Ile Phe Tyr
    1715            1720                1725

Phe Val Ser Tyr Ile Ile Ile Ser Phe Leu Val Val Val Asn Met
    1730            1735                1740

Tyr Ile Ala Val Ile Leu Glu Asn Phe Ser Val Ala Thr Glu Glu
    1745            1750                1755

Ser Thr Glu Pro Leu Ser Glu Asp Asp Phe Glu Met Phe Tyr Glu
    1760            1765                1770

Val Trp Glu Lys Phe Asp Pro Asp Ala Thr Gln Phe Ile Glu Phe
    1775            1780                1785

Ser Lys Leu Ser Asp Phe Ala Ala Ala Leu Asp Pro Pro Leu Leu
    1790            1795                1800

Ile Ala Lys Pro Asn Lys Val Gln Leu Ile Ala Met Asp Leu Pro
    1805            1810                1815

Met Val Ser Gly Asp Arg Ile His Cys Leu Asp Ile Leu Phe Ala
    1820            1825                1830
```

```
Phe Thr Lys Arg Val Leu Gly Glu Ser Gly Glu Met Asp Ser Leu
    1835                1840                1845

Arg Ser Gln Met Glu Glu Arg Phe Met Ser Ala Asn Pro Ser Lys
    1850                1855                1860

Val Ser Tyr Glu Pro Ile Thr Thr Thr Leu Lys Arg Lys Gln Glu
    1865                1870                1875

Asp Val Ser Ala Thr Val Ile Gln Arg Ala Tyr Arg Arg Tyr Arg
    1880                1885                1890

Leu Arg Gln Asn Val Lys Asn Ile Ser Ser Ile Tyr Ile Lys Asp
    1895                1900                1905

Gly Asp Arg Asp Asp Asp Leu Leu Asn Lys Lys Asp Met Ala Phe
    1910                1915                1920

Asp Asn Val Asn Glu Asn Ser Ser Pro Glu Lys Thr Asp Ala Thr
    1925                1930                1935

Ser Ser Thr Thr Ser Pro Pro Ser Tyr Asp Ser Val Thr Lys Pro
    1940                1945                1950

Asp Lys Glu Lys Tyr Glu Gln Asp Arg Thr Glu Lys Glu Asp Lys
    1955                1960                1965

Gly Lys Asp Ser Lys Glu Ser Lys Lys
    1970                1975

<210> SEQ ID NO 82
<211> LENGTH: 1977
<212> TYPE: PRT
<213> ORGANISM: Homo sapiens

<400> SEQUENCE: 82

Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
                20                  25                  30

Lys Glu Pro Lys Glu Glu Lys Lys Asp Asp Asp Glu Glu Ala Pro Lys
        35                  40                  45

Pro Ser Ser Asp Leu Glu Ala Gly Lys Gln Leu Pro Phe Ile Tyr Gly
    50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
    210                 215                 220
```

```
Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
            245                 250                 255

Ser Val Phe Ala Leu Ile Gly Leu Gln Leu Phe Met Gly Asn Leu Lys
        260                 265                 270

His Lys Cys Phe Arg Asn Ser Leu Glu Asn Asn Glu Thr Leu Glu Ser
    275                 280                 285

Ile Met Asn Thr Leu Glu Ser Glu Glu Asp Phe Arg Lys Tyr Phe Tyr
290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
        355                 360                 365

Gln Thr Leu Arg Ala Ala Gly Lys Thr Tyr Met Ile Phe Phe Val Val
370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Ala Glu Tyr Thr
        435                 440                 445

Ser Ile Arg Arg Ser Arg Ile Met Gly Leu Ser Glu Ser Ser Ser Glu
450                 455                 460

Thr Ser Lys Leu Ser Ser Lys Ser Ala Lys Glu Arg Arg Asn Arg Arg
465                 470                 475                 480

Lys Lys Lys Asn Gln Lys Lys Leu Ser Ser Gly Glu Glu Lys Gly Asp
                485                 490                 495

Ala Glu Lys Leu Ser Lys Ser Glu Ser Glu Asp Ser Ile Arg Arg Lys
            500                 505                 510

Ser Phe His Leu Gly Val Glu Gly His Arg Arg Ala His Glu Lys Arg
        515                 520                 525

Leu Ser Thr Pro Asn Gln Ser Pro Leu Ser Ile Arg Gly Ser Leu Phe
530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
                565                 570                 575

Ile Phe Gly Asp Asn Glu Ser Arg Arg Gly Ser Leu Phe Val Pro His
            580                 585                 590

Arg Pro Gln Glu Arg Arg Ser Ser Asn Ile Ser Gln Ala Ser Arg Ser
        595                 600                 605

Pro Pro Met Leu Pro Val Asn Gly Lys Met His Ser Ala Val Asp Cys
610                 615                 620

Asn Gly Val Val Ser Leu Val Asp Gly Arg Ser Ala Leu Met Leu Pro
625                 630                 635                 640
```

-continued

```
Asn Gly Gln Leu Leu Pro Glu Gly Thr Thr Asn Gln Ile His Lys Lys
            645                 650                 655
Arg Arg Cys Ser Ser Tyr Leu Leu Ser Glu Asp Met Leu Asn Asp Pro
            660                 665                 670
Asn Leu Arg Gln Arg Ala Met Ser Arg Ala Ser Met Leu Thr Asn Thr
            675                 680                 685
Val Glu Glu Leu Glu Glu Ser Arg Gln Lys Cys Pro Pro Trp Trp Tyr
            690                 695                 700
Arg Phe Ala His Lys Phe Leu Ile Trp Asn Cys Ser Pro Tyr Trp Ile
705                 710                 715                 720
Lys Phe Lys Lys Cys Ile Tyr Phe Ile Val Met Asp Pro Phe Val Asp
            725                 730                 735
Leu Ala Ile Thr Ile Cys Ile Val Leu Asn Thr Leu Phe Met Ala Met
            740                 745                 750
Glu His His Pro Met Thr Glu Glu Phe Lys Asn Val Leu Ala Ile Gly
            755                 760                 765
Asn Leu Val Phe Thr Gly Ile Phe Ala Ala Glu Met Val Leu Lys Leu
            770                 775                 780
Ile Ala Met Asp Pro Tyr Glu Tyr Phe Gln Val Gly Trp Asn Ile Phe
785                 790                 795                 800
Asp Ser Leu Ile Val Thr Leu Ser Leu Val Glu Leu Phe Leu Ala Asp
            805                 810                 815
Val Glu Gly Leu Ser Val Leu Arg Ser Phe Arg Leu Leu Arg Val Phe
            820                 825                 830
Lys Leu Ala Lys Ser Trp Pro Thr Leu Asn Met Leu Ile Lys Ile Ile
            835                 840                 845
Gly Asn Ser Val Gly Ala Leu Gly Asn Leu Thr Leu Val Leu Ala Ile
            850                 855                 860
Ile Val Phe Ile Phe Ala Val Val Gly Met Gln Leu Phe Gly Lys Ser
865                 870                 875                 880
Tyr Lys Glu Cys Val Cys Lys Ile Asn Asp Asp Cys Thr Leu Pro Arg
            885                 890                 895
Trp His Met Asn Asp Phe Phe His Ser Phe Leu Ile Val Phe Arg Val
            900                 905                 910
Leu Cys Gly Glu Trp Ile Glu Thr Met Trp Asp Cys Met Glu Val Ala
            915                 920                 925
Gly Gln Ala Met Cys Leu Ile Val Tyr Met Met Val Met Val Ile Gly
            930                 935                 940
Asn Leu Val Val Leu Asn Leu Phe Leu Ala Leu Leu Leu Ser Ser Phe
945                 950                 955                 960
Ser Ser Asp Asn Leu Thr Ala Ile Glu Glu Asp Pro Asp Ala Asn Asn
            965                 970                 975
Leu Gln Ile Ala Val Thr Arg Ile Lys Lys Gly Ile Asn Tyr Val Lys
            980                 985                 990
Gln Thr Leu Arg Glu Phe Ile Leu Lys Ala Phe Ser Lys Lys Pro Lys
            995                 1000                1005
Ile Ser Arg Glu Ile Arg Gln Ala Glu Asp Leu Asn Thr Lys Lys
            1010                1015                1020
Glu Asn Tyr Ile Ser Asn His Thr Leu Ala Glu Met Ser Lys Gly
            1025                1030                1035
His Asn Phe Leu Lys Glu Lys Asp Lys Ile Ser Gly Phe Gly Ser
            1040                1045                1050
Ser Val Asp Lys His Leu Met Glu Asp Ser Asp Gly Gln Ser Phe
```

```
            1055                1060                1065

Ile His Asn Pro Ser Leu Thr Val Thr Val Pro Ile Ala Pro Gly
        1070                1075                1080

Glu Ser Asp Leu Glu Asn Met Asn Ala Glu Leu Ser Ser Asp
        1085                1090                1095

Ser Asp Ser Glu Tyr Ser Lys Val Arg Leu Asn Arg Ser Ser Ser
        1100                1105                1110

Ser Glu Cys Ser Thr Val Asp Asn Pro Leu Pro Gly Glu Gly Glu
        1115                1120                1125

Glu Ala Glu Ala Glu Pro Met Asn Ser Asp Glu Pro Glu Ala Cys
        1130                1135                1140

Phe Thr Asp Gly Cys Val Arg Arg Phe Ser Cys Cys Gln Val Asn
        1145                1150                1155

Ile Glu Ser Gly Lys Gly Lys Ile Trp Trp Asn Ile Arg Lys Thr
        1160                1165                1170

Cys Tyr Lys Ile Val Glu His Ser Trp Phe Glu Ser Phe Ile Val
        1175                1180                1185

Leu Met Ile Leu Leu Ser Ser Gly Ala Leu Ala Phe Glu Asp Ile
        1190                1195                1200

Tyr Ile Glu Arg Lys Lys Thr Ile Lys Ile Ile Leu Glu Tyr Ala
        1205                1210                1215

Asp Lys Ile Phe Thr Tyr Ile Phe Ile Leu Glu Met Leu Leu Lys
        1220                1225                1230

Trp Ile Ala Tyr Gly Tyr Lys Thr Tyr Phe Thr Asn Ala Trp Cys
        1235                1240                1245

Trp Leu Asp Phe Leu Ile Val Asp Val Ser Leu Val Thr Leu Val
        1250                1255                1260

Ala Asn Thr Leu Gly Tyr Ser Asp Leu Gly Pro Ile Lys Ser Leu
        1265                1270                1275

Arg Thr Leu Arg Ala Leu Arg Pro Leu Arg Ala Leu Ser Arg Phe
        1280                1285                1290

Glu Gly Met Arg Val Val Val Asn Ala Leu Ile Gly Ala Ile Pro
        1295                1300                1305

Ser Ile Met Asn Val Leu Leu Val Cys Leu Ile Phe Trp Leu Ile
        1310                1315                1320

Phe Ser Ile Met Gly Val Asn Leu Phe Ala Gly Lys Phe Tyr Glu
        1325                1330                1335

Cys Ile Asn Thr Thr Asp Gly Ser Arg Phe Pro Ala Ser Gln Val
        1340                1345                1350

Pro Asn Arg Ser Glu Cys Phe Ala Leu Met Asn Val Ser Gln Asn
        1355                1360                1365

Val Arg Trp Lys Asn Leu Lys Val Asn Phe Asp Asn Val Gly Leu
        1370                1375                1380

Gly Tyr Leu Ser Leu Leu Gln Val Ala Thr Phe Lys Gly Trp Thr
        1385                1390                1395

Ile Ile Met Tyr Ala Ala Val Asp Ser Val Asn Val Asp Lys Gln
        1400                1405                1410

Pro Lys Tyr Glu Tyr Ser Leu Tyr Met Tyr Ile Tyr Phe Val Val
        1415                1420                1425

Phe Ile Ile Phe Gly Ser Phe Phe Thr Leu Asn Leu Phe Ile Gly
        1430                1435                1440

Val Ile Ile Asp Asn Phe Asn Gln Gln Lys Lys Lys Leu Gly Gly
        1445                1450                1455
```

-continued

```
Gln Asp Ile Phe Met Thr Glu Glu Gln Lys Lys Tyr Tyr Asn Ala
    1460            1465                1470

Met Lys Lys Leu Gly Ser Lys Lys Pro Gln Lys Pro Ile Pro Arg
    1475            1480                1485

Pro Gly Asn Lys Ile Gln Gly Cys Ile Phe Asp Leu Val Thr Asn
    1490            1495                1500

Gln Ala Phe Asp Ile Ser Ile Met Val Leu Ile Cys Leu Asn Met
    1505            1510                1515

Val Thr Met Met Val Glu Lys Glu Gly Gln Ser Gln His Met Thr
    1520            1525                1530

Glu Val Leu Tyr Trp Ile Asn Val Val Phe Ile Ile Leu Phe Thr
    1535            1540                1545

Gly Glu Cys Val Leu Lys Leu Ile Ser Leu Arg His Tyr Tyr Phe
    1550            1555                1560

Thr Val Gly Trp Asn Ile Phe Asp Phe Val Val Val Ile Ile Ser
    1565            1570                1575

Ile Val Gly Met Phe Leu Ala Asp Leu Ile Glu Thr Tyr Phe Val
    1580            1585                1590

Ser Pro Thr Leu Phe Arg Val Ile Arg Leu Ala Arg Ile Gly Arg
    1595            1600                1605

Ile Leu Arg Leu Val Lys Gly Ala Lys Gly Ile Arg Thr Leu Leu
    1610            1615                1620

Phe Ala Leu Met Met Ser Leu Pro Ala Leu Phe Asn Ile Gly Leu
    1625            1630                1635

Leu Leu Phe Leu Val Met Phe Ile Tyr Ala Ile Phe Gly Met Ser
    1640            1645                1650

Asn Phe Ala Tyr Val Lys Lys Glu Asp Gly Ile Asn Asp Met Phe
    1655            1660                1665

Asn Phe Glu Thr Phe Gly Asn Ser Met Ile Cys Leu Phe Gln Ile
    1670            1675                1680

Thr Thr Ser Ala Gly Trp Asp Gly Leu Leu Ala Pro Ile Leu Asn
    1685            1690                1695

Ser Lys Pro Pro Asp Cys Asp Pro Lys Lys Val His Pro Gly Ser
    1700            1705                1710

Ser Val Glu Gly Asp Cys Gly Asn Pro Ser Val Gly Ile Phe Tyr
    1715            1720                1725

Phe Val Ser Tyr Ile Ile Ile Ser Phe Leu Val Val Val Asn Met
    1730            1735                1740

Tyr Ile Ala Val Ile Leu Glu Asn Phe Ser Val Ala Thr Glu Glu
    1745            1750                1755

Ser Thr Glu Pro Leu Ser Glu Asp Asp Phe Glu Met Phe Tyr Glu
    1760            1765                1770

Val Trp Glu Lys Phe Asp Pro Asp Ala Thr Gln Phe Ile Glu Phe
    1775            1780                1785

Ser Lys Leu Ser Asp Phe Ala Ala Ala Leu Asp Pro Pro Leu Leu
    1790            1795                1800

Ile Ala Lys Pro Asn Lys Val Gln Leu Ile Ala Met Asp Leu Pro
    1805            1810                1815

Met Val Ser Gly Asp Arg Ile His Cys Leu Asp Ile Leu Phe Ala
    1820            1825                1830

Phe Thr Lys Arg Val Leu Gly Glu Ser Gly Glu Met Asp Ser Leu
    1835            1840                1845
```

```
Arg Ser Gln Met Glu Glu Arg Phe Met Ser Ala Asn Pro Ser Lys
    1850                1855                1860

Val Ser Tyr Glu Pro Ile Thr Thr Thr Leu Lys Arg Lys Gln Glu
    1865                1870                1875

Asp Val Ser Ala Thr Val Ile Gln Arg Ala Tyr Arg Arg Tyr Arg
    1880                1885                1890

Leu Arg Gln Asn Val Lys Asn Ile Ser Ser Ile Tyr Ile Lys Asp
    1895                1900                1905

Gly Asp Arg Asp Asp Asp Leu Leu Asn Lys Lys Asp Met Ala Phe
    1910                1915                1920

Asp Asn Val Asn Glu Asn Ser Ser Pro Glu Lys Thr Asp Ala Thr
    1925                1930                1935

Ser Ser Thr Thr Ser Pro Pro Ser Tyr Asp Ser Val Thr Lys Pro
    1940                1945                1950

Asp Lys Glu Lys Tyr Glu Gln Asp Arg Thr Glu Lys Glu Asp Lys
    1955                1960                1965

Gly Lys Asp Ser Lys Glu Ser Lys Lys
    1970                1975

<210> SEQ ID NO 83
<211> LENGTH: 1977
<212> TYPE: PRT
<213> ORGANISM: Homo sapiens

<400> SEQUENCE: 83

Met Ala Met Leu Pro Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
                20                  25                  30

Lys Glu Pro Lys Glu Glu Lys Lys Asp Asp Asp Glu Gly Ala Pro Lys
            35                  40                  45

Pro Ser Ser Asp Leu Glu Ala Gly Lys Gln Leu Pro Phe Ile Tyr Gly
        50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
    210                 215                 220

Ile Ser Val Ile Pro Gly Leu Lys Thr Ile Val Gly Ala Leu Ile Gln
225                 230                 235                 240
```

```
Ser Val Lys Lys Leu Ser Asp Val Met Ile Leu Thr Val Phe Cys Leu
            245                 250                 255
Ser Val Phe Ala Leu Ile Gly Leu Gln Leu Phe Met Gly Asn Leu Lys
                260                 265                 270
His Lys Cys Phe Arg Asn Ser Leu Glu Asn Asn Glu Thr Leu Glu Ser
            275                 280                 285
Ile Met Asn Thr Leu Glu Ser Glu Glu Asp Phe Arg Lys Tyr Phe Tyr
    290                 295                 300
Tyr Leu Glu Gly Ser Lys Asp Ala Leu Leu Cys Gly Phe Ser Thr Asp
305                 310                 315                 320
Ser Gly Gln Cys Pro Glu Gly Tyr Thr Cys Val Lys Ile Gly Arg Asn
                325                 330                 335
Pro Asp Tyr Gly Tyr Thr Ser Phe Asp Thr Phe Ser Trp Ala Phe Leu
            340                 345                 350
Ala Leu Phe Arg Leu Met Thr Gln Asp Tyr Trp Glu Asn Leu Tyr Gln
            355                 360                 365
Gln Thr Leu Arg Ala Ala Gly Lys Thr Tyr Met Ile Phe Phe Val Val
    370                 375                 380
Val Ile Phe Leu Gly Ser Phe Tyr Leu Ile Asn Leu Ile Leu Ala Val
385                 390                 395                 400
Val Ala Met Ala Tyr Glu Glu Gln Asn Gln Ala Asn Ile Glu Glu Ala
                405                 410                 415
Lys Gln Lys Glu Leu Glu Phe Gln Gln Met Leu Asp Arg Leu Lys Lys
            420                 425                 430
Glu Gln Glu Glu Ala Glu Ala Ile Ala Ala Ala Ala Ala Glu Tyr Thr
            435                 440                 445
Ser Ile Arg Arg Ser Arg Ile Met Gly Leu Ser Glu Ser Ser Ser Glu
    450                 455                 460
Thr Ser Lys Leu Ser Ser Lys Ser Ala Lys Glu Arg Arg Asn Arg Arg
465                 470                 475                 480
Lys Lys Lys Asn Gln Lys Lys Leu Ser Ser Gly Glu Glu Lys Gly Asp
                485                 490                 495
Ala Glu Lys Leu Ser Lys Ser Glu Ser Glu Asp Ser Ile Arg Arg Lys
            500                 505                 510
Ser Phe His Leu Gly Val Glu Gly His Arg Arg Ala His Glu Lys Arg
            515                 520                 525
Leu Ser Thr Pro Asn Gln Ser Pro Leu Ser Ile Arg Gly Ser Leu Phe
    530                 535                 540
Ser Ala Arg Arg Ser Ser Arg Thr Ser Leu Phe Ser Phe Lys Gly Arg
545                 550                 555                 560
Gly Arg Asp Ile Gly Ser Glu Thr Glu Phe Ala Asp Asp Glu His Ser
                565                 570                 575
Ile Phe Gly Asp Asn Glu Ser Arg Arg Gly Ser Leu Phe Val Pro His
            580                 585                 590
Arg Pro Gln Glu Arg Arg Ser Ser Asn Ile Ser Gln Ala Ser Arg Ser
            595                 600                 605
Pro Pro Met Leu Pro Val Asn Gly Lys Met His Ser Ala Val Asp Cys
    610                 615                 620
Asn Gly Val Val Ser Leu Val Asp Gly Arg Ser Ala Leu Met Leu Pro
625                 630                 635                 640
Asn Gly Gln Leu Leu Pro Glu Gly Thr Thr Asn Gln Ile His Lys Lys
                645                 650                 655
```

```
Arg Arg Cys Ser Ser Tyr Leu Leu Ser Glu Asp Met Leu Asn Asp Pro
            660                 665                 670

Asn Leu Arg Gln Arg Ala Met Ser Arg Ala Ser Ile Leu Thr Asn Thr
        675                 680                 685

Val Glu Glu Leu Glu Ser Arg Gln Lys Tyr Pro Pro Trp Trp Tyr
690                 695                 700

Arg Phe Ala His Lys Phe Leu Ile Trp Asn Cys Ser Pro Tyr Trp Ile
705             710                 715                 720

Lys Phe Lys Lys Cys Ile Tyr Phe Ile Val Met Asp Pro Phe Val Asp
                725                 730                 735

Leu Ala Ile Thr Ile Cys Ile Val Leu Asn Thr Leu Phe Met Ala Met
            740                 745                 750

Glu His His Pro Met Thr Glu Glu Phe Lys Asn Val Leu Ala Ile Gly
            755                 760                 765

Asn Leu Val Phe Thr Gly Ile Phe Ala Ala Glu Met Val Leu Lys Leu
            770                 775                 780

Ile Ala Met Asp Pro Tyr Glu Tyr Phe Gln Val Gly Trp Asn Ile Phe
785                 790                 795                 800

Asp Ser Leu Ile Val Thr Leu Ser Leu Val Glu Leu Phe Leu Ala Asp
                805                 810                 815

Val Glu Gly Leu Ser Val Leu Arg Ser Phe Arg Leu Leu Arg Val Phe
            820                 825                 830

Lys Leu Ala Lys Ser Trp Pro Thr Leu Asn Met Leu Ile Lys Ile Ile
            835                 840                 845

Gly Asn Ser Val Gly Ala Leu Gly Asn Leu Thr Leu Val Leu Ala Ile
850                 855                 860

Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
                885                 890                 895

Trp His Met Asn Asp Phe Phe His Ser Phe Leu Ile Val Phe Arg Val
            900                 905                 910

Leu Cys Gly Glu Trp Ile Glu Thr Met Trp Asp Cys Met Glu Val Ala
            915                 920                 925

Gly Gln Ala Met Cys Leu Ile Val Tyr Met Met Val Met Val Ile Gly
930                 935                 940

Asn Leu Val Val Leu Asn Leu Phe Leu Ala Leu Leu Leu Ser Ser Phe
945                 950                 955                 960

Ser Ser Asp Asn Leu Thr Ala Ile Glu Glu Asp Pro Asp Ala Asn Asn
                965                 970                 975

Leu Gln Ile Ala Val Thr Arg Ile Lys Lys Gly Ile Asn Tyr Val Lys
            980                 985                 990

Gln Thr Leu Arg Glu Phe Ile Leu Lys Ala Phe Ser Lys Lys Pro Lys
        995                 1000                1005

Ile Ser Arg Glu Ile Arg Gln Ala Glu Asp Leu Asn Thr Lys Lys
    1010                1015                1020

Glu Asn Tyr Ile Ser Asn His Thr Leu Ala Glu Met Ser Lys Gly
    1025                1030                1035

His Asn Phe Leu Lys Glu Lys Asp Lys Ile Ser Gly Phe Gly Ser
    1040                1045                1050

Ser Val Asp Lys His Leu Met Glu Asp Ser Asp Gly Gln Ser Phe
    1055                1060                1065

Ile His Asn Pro Ser Leu Thr Val Thr Val Pro Ile Ala Pro Gly
```

|          |          |          |          |          |          |          |          |          |          |
|----------|----------|----------|----------|----------|----------|----------|----------|----------|----------|
|          | 1070     |          |          |          | 1075     |          |          |          | 1080     |

Glu Ser Asp Leu Glu Asn Met Asn Ala Glu Glu Leu Ser Ser Asp
         1085                1090                1095

Ser Asp Ser Glu Tyr Ser Lys Val Arg Leu Asn Arg Ser Ser Ser
    1100                1105                1110

Ser Glu Cys Ser Thr Val Asp Asn Pro Leu Pro Gly Glu Gly Glu
    1115                1120                1125

Glu Ala Glu Ala Glu Pro Met Asn Ser Asp Glu Pro Glu Ala Cys
    1130                1135                1140

Phe Thr Asp Gly Cys Val Arg Arg Phe Ser Cys Cys Gln Val Asn
    1145                1150                1155

Ile Glu Ser Gly Lys Gly Lys Ile Trp Trp Asn Ile Arg Lys Thr
    1160                1165                1170

Cys Tyr Lys Ile Val Glu His Ser Trp Phe Glu Ser Phe Ile Val
    1175                1180                1185

Leu Met Ile Leu Leu Ser Ser Gly Ala Leu Ala Phe Glu Asp Ile
    1190                1195                1200

Tyr Ile Glu Arg Lys Lys Thr Ile Lys Ile Ile Leu Glu Tyr Ala
    1205                1210                1215

Asp Lys Ile Phe Thr Tyr Ile Phe Ile Leu Glu Met Leu Leu Lys
    1220                1225                1230

Trp Ile Ala Tyr Gly Tyr Lys Thr Tyr Phe Thr Asn Ala Trp Cys
    1235                1240                1245

Trp Leu Asp Phe Leu Ile Val Asp Val Ser Leu Val Thr Leu Val
    1250                1255                1260

Ala Asn Thr Leu Gly Tyr Ser Asp Leu Gly Pro Ile Lys Ser Leu
    1265                1270                1275

Arg Thr Leu Arg Ala Leu Arg Pro Leu Arg Ala Leu Ser Arg Phe
    1280                1285                1290

Glu Gly Met Arg Val Val Asn Ala Leu Ile Gly Ala Ile Pro
    1295                1300                1305

Ser Ile Met Asn Val Leu Leu Val Cys Leu Ile Phe Trp Leu Ile
    1310                1315                1320

Phe Ser Ile Met Gly Val Asn Leu Phe Ala Gly Lys Phe Tyr Glu
    1325                1330                1335

Cys Ile Asn Thr Thr Asp Gly Ser Arg Phe Pro Ala Ser Gln Val
    1340                1345                1350

Pro Asn Arg Ser Glu Cys Phe Ala Leu Met Asn Val Ser Gln Asn
    1355                1360                1365

Val Arg Trp Lys Asn Leu Lys Val Asn Phe Asp Asn Val Gly Leu
    1370                1375                1380

Gly Tyr Leu Ser Leu Leu Gln Val Ala Thr Phe Lys Gly Trp Thr
    1385                1390                1395

Ile Ile Met Tyr Ala Ala Val Asp Ser Val Asn Val Asp Lys Gln
    1400                1405                1410

Pro Lys Tyr Glu Tyr Ser Leu Tyr Met Tyr Ile Tyr Phe Val Val
    1415                1420                1425

Phe Ile Ile Phe Gly Ser Phe Phe Thr Leu Asn Leu Phe Ile Gly
    1430                1435                1440

Val Ile Ile Asp Asn Phe Asn Gln Gln Lys Lys Lys Leu Gly Gly
    1445                1450                1455

Gln Asp Ile Phe Met Thr Glu Glu Gln Lys Lys Tyr Tyr Asn Ala
    1460                1465                1470

-continued

Met Lys Lys Leu Gly Ser Lys Lys Pro Gln Lys Pro Ile Pro Arg
1475                1480                1485

Pro Gly Asn Lys Ile Gln Gly Cys Ile Phe Asp Leu Val Thr Asn
1490                1495                1500

Gln Ala Phe Asp Ile Ser Ile Met Val Leu Ile Cys Leu Asn Met
1505                1510                1515

Val Thr Met Met Val Glu Lys Glu Gly Gln Ser Gln His Met Thr
1520                1525                1530

Glu Val Leu Tyr Trp Ile Asn Val Val Phe Ile Ile Leu Phe Thr
1535                1540                1545

Gly Glu Cys Val Leu Lys Leu Ile Ser Leu Arg His Tyr Tyr Phe
1550                1555                1560

Thr Val Gly Trp Asn Ile Phe Asp Phe Val Val Val Ile Ile Ser
1565                1570                1575

Ile Val Gly Met Phe Leu Ala Asp Leu Ile Glu Thr Tyr Phe Val
1580                1585                1590

Ser Pro Thr Leu Phe Arg Val Ile Arg Leu Ala Arg Ile Gly Arg
1595                1600                1605

Ile Leu Arg Leu Val Lys Gly Ala Lys Gly Ile Arg Thr Leu Leu
1610                1615                1620

Phe Ala Leu Met Met Ser Leu Pro Ala Leu Phe Asn Ile Gly Leu
1625                1630                1635

Leu Leu Phe Leu Val Met Phe Ile Tyr Ala Ile Phe Gly Met Ser
1640                1645                1650

Asn Phe Ala Tyr Val Lys Lys Glu Asp Gly Ile Asn Asp Met Phe
1655                1660                1665

Asn Phe Glu Thr Phe Gly Asn Ser Met Ile Cys Leu Phe Gln Ile
1670                1675                1680

Thr Thr Ser Ala Gly Trp Asp Gly Leu Leu Ala Pro Ile Leu Asn
1685                1690                1695

Ser Lys Pro Pro Asp Cys Asp Pro Lys Lys Val His Pro Gly Ser
1700                1705                1710

Ser Val Glu Gly Asp Cys Gly Asn Pro Ser Val Gly Ile Phe Tyr
1715                1720                1725

Phe Val Ser Tyr Ile Ile Ile Ser Phe Leu Val Val Val Asn Met
1730                1735                1740

Tyr Ile Ala Val Ile Leu Glu Asn Phe Ser Val Ala Thr Glu Glu
1745                1750                1755

Ser Thr Glu Pro Leu Ser Glu Asp Asp Phe Glu Met Phe Tyr Glu
1760                1765                1770

Val Trp Glu Lys Phe Asp Pro Asp Ala Thr Gln Phe Ile Glu Phe
1775                1780                1785

Ser Lys Leu Ser Asp Phe Ala Ala Ala Leu Asp Pro Pro Leu Leu
1790                1795                1800

Ile Ala Lys Pro Asn Lys Val Gln Leu Ile Ala Met Asp Leu Pro
1805                1810                1815

Met Val Ser Gly Asp Arg Ile His Cys Leu Asp Ile Leu Phe Ala
1820                1825                1830

Phe Thr Lys Arg Val Leu Gly Glu Ser Gly Glu Met Asp Ser Leu
1835                1840                1845

Arg Ser Gln Met Glu Glu Arg Phe Met Ser Ala Asn Pro Ser Lys
1850                1855                1860

```
Val Ser Tyr Glu Pro Ile Thr Thr Leu Lys Arg Lys Gln Glu
    1865                1870                1875

Asp Val Ser Ala Thr Val Ile Gln Arg Ala Tyr Arg Arg Tyr Arg
    1880                1885                1890

Leu Arg Gln Asn Val Lys Asn Ile Ser Ser Ile Tyr Ile Lys Asp
    1895                1900                1905

Gly Asp Arg Asp Asp Asp Leu Leu Asn Lys Lys Asp Met Ala Phe
    1910                1915                1920

Asp Asn Val Asn Glu Asn Ser Ser Pro Glu Lys Thr Asp Ala Thr
    1925                1930                1935

Ser Ser Thr Thr Ser Pro Pro Ser Tyr Asp Ser Val Thr Lys Pro
    1940                1945                1950

Asp Lys Glu Lys Tyr Glu Gln Asp Arg Thr Glu Lys Glu Asp Lys
    1955                1960                1965

Gly Lys Asp Ser Lys Glu Ser Lys Lys
    1970                1975

<210> SEQ ID NO 84
<211> LENGTH: 1977
<212> TYPE: PRT
<213> ORGANISM: Homo sapiens

<400> SEQUENCE: 84

Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
            20                  25                  30

Lys Glu Pro Lys Glu Glu Lys Lys Asp Asp Asp Glu Glu Ala Pro Lys
        35                  40                  45

Pro Ser Ser Asp Leu Glu Ala Gly Lys Gln Leu Pro Phe Ile Tyr Gly
    50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
    210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255
```

```
Ser Val Phe Ala Leu Ile Gly Leu Gln Leu Phe Met Gly Asn Leu Lys
        260                 265                 270

His Lys Cys Phe Arg Asn Ser Leu Glu Asn Asn Glu Thr Leu Glu Ser
        275                 280                 285

Ile Met Asn Thr Leu Glu Ser Glu Glu Asp Phe Arg Lys Tyr Phe Tyr
290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
        355                 360                 365

Gln Thr Leu Arg Ala Ala Gly Lys Thr Tyr Met Ile Phe Phe Val Val
    370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Ala Glu Tyr Thr
                435                 440                 445

Ser Ile Arg Arg Ser Arg Ile Met Gly Leu Ser Glu Ser Ser Ser Glu
        450                 455                 460

Thr Ser Lys Leu Ser Ser Lys Ser Ala Lys Glu Arg Arg Asn Arg Arg
465                 470                 475                 480

Lys Lys Lys Asn Gln Lys Lys Leu Ser Ser Gly Glu Glu Lys Gly Asp
                485                 490                 495

Ala Glu Lys Leu Ser Lys Ser Glu Ser Glu Asp Ser Ile Arg Arg Lys
            500                 505                 510

Ser Phe His Leu Gly Val Glu Gly His Arg Arg Ala His Glu Lys Arg
        515                 520                 525

Leu Ser Thr Pro Asn Gln Ser Pro Leu Ser Ile Arg Gly Ser Leu Phe
    530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
                565                 570                 575

Ile Phe Gly Asp Asn Glu Ser Arg Arg Gly Ser Leu Phe Val Pro His
            580                 585                 590

Arg Pro Gln Glu Arg Arg Ser Ser Asn Ile Ser Gln Ala Ser Arg Ser
        595                 600                 605

Pro Pro Met Leu Pro Val Asn Gly Lys Met His Ser Ala Val Asp Cys
    610                 615                 620

Asn Gly Val Val Ser Leu Val Asp Gly Arg Ser Ala Leu Met Leu Pro
625                 630                 635                 640

Asn Gly Gln Leu Leu Pro Glu Gly Thr Thr Asn Gln Ile His Lys Lys
                645                 650                 655

Arg Arg Cys Ser Ser Tyr Leu Leu Ser Glu Asp Met Leu Asn Asp Pro
            660                 665                 670
```

```
Asn Leu Arg Gln Arg Ala Met Ser Arg Ala Ser Ile Leu Thr Asn Thr
            675                 680                 685

Val Glu Glu Leu Glu Glu Ser Arg Gln Lys Cys Pro Pro Trp Trp Tyr
690                 695                 700

Arg Phe Ala His Lys Phe Leu Ile Trp Asn Cys Ser Pro Tyr Trp Ile
705                 710                 715                 720

Lys Phe Lys Lys Cys Ile Tyr Phe Ile Val Met Asp Pro Phe Val Asp
                725                 730                 735

Leu Ala Ile Thr Ile Cys Ile Val Leu Asn Thr Leu Phe Met Ala Met
            740                 745                 750

Glu His His Pro Met Thr Glu Glu Phe Lys Asn Val Leu Ala Ile Gly
        755                 760                 765

Asn Leu Val Phe Thr Gly Ile Phe Ala Ala Glu Met Val Leu Lys Leu
770                 775                 780

Ile Ala Met Asp Pro Tyr Glu Tyr Phe Gln Val Gly Trp Asn Ile Phe
785                 790                 795                 800

Asp Ser Leu Ile Val Thr Leu Ser Leu Val Glu Leu Phe Leu Ala Asp
                805                 810                 815

Val Glu Gly Leu Ser Val Leu Arg Ser Phe Arg Leu Leu Arg Val Phe
            820                 825                 830

Lys Leu Ala Lys Ser Trp Pro Thr Leu Asn Met Leu Ile Lys Ile Ile
835                 840                 845

Gly Asn Ser Val Gly Ala Leu Gly Asn Leu Thr Leu Val Leu Ala Ile
        850                 855                 860

Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
                885                 890                 895

Trp His Met Asn Asp Phe Phe His Ser Phe Leu Ile Val Phe Arg Val
            900                 905                 910

Leu Cys Gly Glu Trp Ile Glu Thr Met Trp Asp Cys Met Glu Val Ala
        915                 920                 925

Gly Gln Ala Met Cys Leu Ile Val Tyr Met Met Val Met Val Ile Gly
930                 935                 940

Asn Leu Val Val Leu Asn Leu Phe Leu Ala Leu Leu Leu Ser Ser Phe
945                 950                 955                 960

Ser Ser Asp Asn Leu Thr Ala Ile Glu Glu Asp Pro Asp Ala Asn Asn
                965                 970                 975

Leu Gln Ile Ala Val Thr Arg Ile Lys Lys Gly Ile Asn Tyr Val Lys
            980                 985                 990

Gln Thr Leu Arg Glu Phe Ile Leu Lys Ala Phe Ser Lys Lys Pro Lys
        995                 1000                1005

Ile Ser Arg Glu Ile Arg Gln Ala Glu Asp Leu Asn Thr Lys Lys
    1010                1015                1020

Glu Asn Tyr Ile Ser Asn His Thr Leu Ala Glu Met Ser Lys Gly
    1025                1030                1035

His Asn Phe Leu Lys Glu Lys Asp Lys Ile Ser Gly Phe Gly Ser
    1040                1045                1050

Ser Val Asp Lys His Leu Met Glu Asp Ser Asp Gly Gln Ser Phe
    1055                1060                1065

Ile His Asn Pro Ser Leu Thr Val Thr Val Pro Ile Ala Pro Gly
    1070                1075                1080

Glu Ser Asp Leu Glu Asn Met Asn Ala Glu Glu Leu Ser Ser Asp
```

-continued

```
            1085                1090                1095
Ser Asp Ser Glu Tyr Ser Lys Val Arg Leu Asn Arg Ser Ser Ser
            1100                1105                1110

Ser Glu Cys Ser Thr Val Asp Asn Pro Leu Pro Gly Glu Gly Glu
            1115                1120                1125

Glu Ala Glu Ala Glu Pro Met Asn Ser Asp Glu Pro Glu Ala Cys
            1130                1135                1140

Phe Thr Asp Gly Cys Val Arg Arg Phe Ser Cys Cys Gln Val Asn
            1145                1150                1155

Ile Gln Ser Gly Lys Gly Lys Ile Trp Trp Asn Ile Arg Lys Thr
            1160                1165                1170

Cys Tyr Lys Ile Val Glu His Ser Trp Phe Glu Ser Phe Ile Val
            1175                1180                1185

Leu Met Ile Leu Leu Ser Ser Gly Ala Leu Ala Phe Glu Asp Ile
            1190                1195                1200

Tyr Ile Glu Arg Lys Lys Thr Ile Lys Ile Ile Leu Glu Tyr Ala
            1205                1210                1215

Asp Lys Ile Phe Thr Tyr Ile Phe Ile Leu Glu Met Leu Leu Lys
            1220                1225                1230

Trp Ile Ala Tyr Gly Tyr Lys Thr Tyr Phe Thr Asn Ala Trp Cys
            1235                1240                1245

Trp Leu Asp Phe Leu Ile Val Asp Val Ser Leu Val Thr Leu Val
            1250                1255                1260

Ala Asn Thr Leu Gly Tyr Ser Asp Leu Gly Pro Ile Lys Ser Leu
            1265                1270                1275

Arg Thr Leu Arg Ala Leu Arg Pro Leu Arg Ala Leu Ser Arg Phe
            1280                1285                1290

Glu Gly Met Arg Val Val Val Asn Ala Leu Ile Gly Ala Ile Pro
            1295                1300                1305

Ser Ile Met Asn Val Leu Leu Val Cys Leu Ile Phe Trp Leu Ile
            1310                1315                1320

Phe Ser Ile Met Gly Val Asn Leu Phe Ala Gly Lys Phe Tyr Glu
            1325                1330                1335

Cys Ile Asn Thr Thr Asp Gly Ser Arg Phe Pro Ala Ser Gln Val
            1340                1345                1350

Pro Asn Arg Ser Glu Cys Phe Ala Leu Met Asn Val Ser Gln Asn
            1355                1360                1365

Val Arg Trp Lys Asn Leu Lys Val Asn Phe Asp Asn Val Gly Leu
            1370                1375                1380

Gly Tyr Leu Ser Leu Leu Gln Val Ala Thr Phe Lys Gly Trp Thr
            1385                1390                1395

Ile Ile Met Tyr Ala Ala Val Asp Ser Val Asn Val Asp Lys Gln
            1400                1405                1410

Pro Lys Tyr Glu Tyr Ser Leu Tyr Met Tyr Ile Tyr Phe Val Val
            1415                1420                1425

Phe Ile Ile Phe Gly Ser Phe Thr Leu Asn Leu Phe Ile Gly
            1430                1435                1440

Val Ile Ile Asp Asn Phe Asn Gln Gln Lys Lys Lys Leu Gly Gly
            1445                1450                1455

Gln Asp Ile Phe Met Thr Glu Glu Gln Lys Lys Tyr Tyr Asn Ala
            1460                1465                1470

Met Lys Lys Leu Gly Ser Lys Lys Pro Gln Lys Pro Ile Pro Arg
            1475                1480                1485
```

-continued

```
Pro Gly Asn Lys Ile Gln Gly Cys Ile Phe Asp Leu Val Thr Asn
    1490            1495                1500

Gln Ala Phe Asp Ile Ser Ile Met Val Leu Ile Cys Leu Asn Met
    1505            1510                1515

Val Thr Met Met Val Glu Lys Glu Gly Gln Ser Gln His Met Thr
    1520            1525                1530

Glu Val Leu Tyr Trp Ile Asn Val Val Phe Ile Ile Leu Phe Thr
    1535            1540                1545

Gly Glu Cys Val Leu Lys Leu Ile Ser Leu Arg His Tyr Tyr Phe
    1550            1555                1560

Thr Val Gly Trp Asn Ile Phe Asp Phe Val Val Ile Ile Ser
    1565            1570                1575

Ile Val Gly Met Phe Leu Ala Asp Leu Ile Glu Thr Tyr Phe Val
    1580            1585                1590

Ser Pro Thr Leu Phe Arg Val Ile Arg Leu Ala Arg Ile Gly Arg
    1595            1600                1605

Ile Leu Arg Leu Val Lys Gly Ala Lys Gly Ile Arg Thr Leu Leu
    1610            1615                1620

Phe Ala Leu Met Met Ser Leu Pro Ala Leu Phe Asn Ile Gly Leu
    1625            1630                1635

Leu Leu Phe Leu Val Met Phe Ile Tyr Ala Ile Phe Gly Met Ser
    1640            1645                1650

Asn Phe Ala Tyr Val Lys Lys Glu Asp Gly Ile Asn Asp Met Phe
    1655            1660                1665

Asn Phe Glu Thr Phe Gly Asn Ser Met Ile Cys Leu Phe Gln Ile
    1670            1675                1680

Thr Thr Ser Ala Gly Trp Asp Gly Leu Leu Ala Pro Ile Leu Asn
    1685            1690                1695

Ser Lys Pro Pro Asp Cys Asp Pro Lys Lys Val His Pro Gly Ser
    1700            1705                1710

Ser Val Glu Gly Asp Cys Gly Asn Pro Ser Val Gly Ile Phe Tyr
    1715            1720                1725

Phe Val Ser Tyr Ile Ile Ile Ser Phe Leu Val Val Val Asn Met
    1730            1735                1740

Tyr Ile Ala Val Ile Leu Glu Asn Phe Ser Val Ala Thr Glu Glu
    1745            1750                1755

Ser Thr Glu Pro Leu Ser Glu Asp Asp Phe Glu Met Phe Tyr Glu
    1760            1765                1770

Val Trp Glu Lys Phe Asp Pro Asp Ala Thr Gln Phe Ile Glu Phe
    1775            1780                1785

Ser Lys Leu Ser Asp Phe Ala Ala Ala Leu Asp Pro Pro Leu Leu
    1790            1795                1800

Ile Ala Lys Pro Asn Lys Val Gln Leu Ile Ala Met Asp Leu Pro
    1805            1810                1815

Met Val Ser Gly Asp Arg Ile His Cys Leu Asp Ile Leu Phe Ala
    1820            1825                1830

Phe Thr Lys Arg Val Leu Gly Glu Ser Gly Glu Met Asp Ser Leu
    1835            1840                1845

Arg Ser Gln Met Glu Glu Arg Phe Met Ser Ala Asn Pro Ser Lys
    1850            1855                1860

Val Ser Tyr Glu Pro Ile Thr Thr Thr Leu Lys Arg Lys Gln Glu
    1865            1870                1875
```

Asp Val Ser Ala Thr Val Ile Gln Arg Ala Tyr Arg Arg Tyr Arg
    1880            1885                1890

Leu Arg Gln Asn Val Lys Asn Ile Ser Ser Ile Tyr Ile Lys Asp
    1895            1900                1905

Gly Asp Arg Asp Asp Asp Leu Leu Asn Lys Lys Asp Met Ala Phe
    1910            1915                1920

Asp Asn Val Asn Glu Asn Ser Ser Pro Glu Lys Thr Asp Ala Thr
    1925            1930                1935

Ser Ser Thr Thr Ser Pro Pro Ser Tyr Asp Ser Val Thr Lys Pro
    1940            1945                1950

Asp Lys Glu Lys Tyr Glu Gln Asp Arg Thr Glu Lys Glu Asp Lys
    1955            1960                1965

Gly Lys Asp Ser Lys Glu Ser Lys Lys
    1970            1975

<210> SEQ ID NO 85
<211> LENGTH: 1977
<212> TYPE: PRT
<213> ORGANISM: Homo sapiens

<400> SEQUENCE: 85

Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
        20                  25                  30

Lys Glu Pro Lys Glu Glu Lys Lys Asp Asp Asp Glu Glu Ala Pro Lys
        35                  40                  45

Pro Ser Ser Asp Leu Glu Ala Gly Lys Gln Leu Pro Phe Ile Tyr Gly
    50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
    210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

```
His Lys Cys Phe Arg Asn Ser Leu Glu Asn Asn Glu Thr Leu Glu Ser
            275                 280                 285

Ile Met Asn Thr Leu Glu Ser Glu Glu Asp Phe Arg Lys Tyr Phe Tyr
    290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
            355                 360                 365

Gln Thr Leu Arg Ala Ala Gly Lys Thr Tyr Met Ile Phe Phe Val Val
    370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Glu Tyr Thr
    435                 440                 445

Ser Ile Arg Arg Ser Arg Ile Met Gly Leu Ser Glu Ser Ser Ser Glu
    450                 455                 460

Thr Ser Lys Leu Ser Ser Lys Ser Ala Lys Glu Arg Arg Asn Arg Arg
465                 470                 475                 480

Lys Lys Lys Asn Gln Lys Lys Leu Ser Ser Gly Glu Glu Lys Gly Asp
                485                 490                 495

Ala Glu Lys Leu Ser Lys Ser Glu Ser Glu Asp Ser Ile Arg Arg Lys
            500                 505                 510

Ser Phe His Leu Gly Val Glu Gly His Arg Arg Ala His Glu Lys Arg
    515                 520                 525

Leu Ser Thr Pro Asn Gln Ser Pro Leu Ser Ile Arg Gly Ser Leu Phe
    530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
                565                 570                 575

Ile Phe Gly Asp Asn Glu Ser Arg Arg Gly Ser Leu Phe Val Pro His
            580                 585                 590

Arg Pro Gln Glu Arg Arg Ser Ser Asn Ile Ser Gln Ala Ser Arg Ser
            595                 600                 605

Pro Pro Met Leu Pro Val Asn Gly Lys Met His Ser Ala Val Asp Cys
610                 615                 620

Asn Gly Val Val Ser Leu Val Asp Gly Arg Ser Ala Leu Met Leu Pro
625                 630                 635                 640

Asn Gly Gln Leu Leu Pro Glu Gly Thr Thr Asn Gln Ile His Lys Lys
                645                 650                 655

Arg Arg Cys Ser Ser Tyr Leu Leu Ser Glu Asp Met Leu Asn Asp Pro
            660                 665                 670

Asn Leu Arg Gln Arg Ala Met Ser Arg Ala Ser Ile Leu Thr Asn Thr
            675                 680                 685
```

```
Val Glu Glu Leu Glu Glu Ser Arg Gln Lys Cys Pro Pro Trp Trp Tyr
    690                 695                 700

Arg Phe Ala His Lys Phe Leu Ile Trp Asn Cys Ser Pro Tyr Trp Ile
705                 710                 715                 720

Lys Phe Lys Lys Cys Ile Tyr Phe Ile Val Met Asp Pro Phe Val Asp
                725                 730                 735

Leu Ala Ile Thr Ile Cys Ile Val Leu Asn Thr Leu Phe Met Ala Met
                740                 745                 750

Glu His His Pro Met Thr Glu Phe Lys Asn Val Leu Ala Ile Gly
            755                 760                 765

Asn Leu Val Phe Thr Gly Ile Phe Ala Ala Glu Met Val Leu Lys Leu
    770                 775                 780

Ile Ala Met Asp Pro Tyr Glu Tyr Phe Gln Val Gly Trp Asn Ile Phe
785                 790                 795                 800

Asp Ser Leu Ile Val Thr Leu Ser Leu Val Glu Leu Phe Leu Ala Asp
                805                 810                 815

Val Glu Gly Leu Ser Val Leu Arg Ser Phe Arg Leu Leu Arg Val Phe
            820                 825                 830

Lys Leu Ala Lys Ser Trp Pro Thr Leu Asn Met Leu Ile Lys Ile Ile
            835                 840                 845

Gly Asn Ser Val Gly Ala Leu Gly Asn Leu Thr Leu Val Leu Ala Ile
    850                 855                 860

Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
                885                 890                 895

Trp His Met Asn Asp Phe Phe His Ser Phe Leu Ile Val Phe Arg Val
            900                 905                 910

Leu Cys Gly Glu Trp Ile Glu Thr Met Trp Asp Cys Met Glu Val Ala
            915                 920                 925

Gly Gln Ala Met Cys Leu Ile Val Tyr Met Met Val Met Val Ile Gly
    930                 935                 940

Asn Leu Val Val Leu Asn Leu Phe Leu Ala Leu Leu Leu Ser Ser Phe
945                 950                 955                 960

Ser Ser Asp Asn Leu Thr Ala Ile Glu Glu Asp Pro Asp Ala Asn Asn
                965                 970                 975

Leu Gln Ile Ala Val Thr Arg Ile Lys Lys Gly Ile Asn Tyr Val Lys
            980                 985                 990

Gln Thr Leu Arg Glu Phe Ile Leu Lys Ala Phe Ser Lys Lys Pro Lys
        995                 1000                1005

Ile Ser Arg Glu Ile Arg Gln Ala Glu Asp Leu Asn Thr Lys Lys
    1010                1015                1020

Glu Asn Tyr Ile Ser Asn His Thr Leu Ala Glu Met Ser Lys Gly
    1025                1030                1035

His Asn Phe Leu Lys Glu Lys Asp Lys Ile Ser Gly Phe Gly Ser
    1040                1045                1050

Ser Val Asp Lys His Leu Met Glu Asp Ser Asp Gly Gln Ser Phe
    1055                1060                1065

Ile His Asn Pro Ser Leu Thr Val Thr Val Pro Ile Ala Pro Gly
    1070                1075                1080

Glu Ser Asp Leu Glu Asn Met Asn Ala Glu Glu Leu Ser Ser Asp
    1085                1090                1095

Ser Asp Ser Glu Tyr Ser Lys Val Arg Leu Asn Arg Ser Ser Ser
```

```
                    1100                1105                1110
Ser Glu Cys Ser Thr Val Asp Asn Pro Leu Pro Gly Glu Gly Glu
    1115                1120                1125

Glu Ala Glu Ala Glu Pro Met Asn Ser Asp Glu Pro Glu Ala Cys
    1130                1135                1140

Phe Thr Asp Gly Cys Val Arg Arg Phe Ser Cys Cys Gln Val Asn
    1145                1150                1155

Ile Glu Ser Gly Lys Gly Lys Ile Trp Trp Asn Ile Arg Lys Thr
    1160                1165                1170

Cys Tyr Lys Ile Val Glu His Ser Trp Phe Glu Ser Phe Ile Val
    1175                1180                1185

Leu Met Ile Leu Leu Ser Ser Gly Ala Leu Ala Phe Glu Asp Ile
    1190                1195                1200

Tyr Ile Glu Arg Lys Lys Thr Ile Lys Ile Ile Leu Glu Tyr Ala
    1205                1210                1215

Asp Lys Ile Phe Thr Tyr Ile Phe Ile Leu Glu Met Leu Leu Lys
    1220                1225                1230

Trp Ile Ala Tyr Gly Tyr Lys Thr Tyr Phe Thr Asn Ala Trp Cys
    1235                1240                1245

Trp Leu Asp Phe Leu Ile Val Asp Val Ser Leu Val Thr Leu Val
    1250                1255                1260

Ala Asn Thr Val Gly Tyr Ser Asp Leu Gly Pro Ile Lys Ser Leu
    1265                1270                1275

Arg Thr Leu Arg Ala Leu Arg Pro Leu Arg Ala Leu Ser Arg Phe
    1280                1285                1290

Glu Gly Met Arg Val Val Val Asn Ala Leu Ile Gly Ala Ile Pro
    1295                1300                1305

Ser Ile Met Asn Val Leu Leu Val Cys Leu Ile Phe Trp Leu Ile
    1310                1315                1320

Phe Ser Ile Met Gly Val Asn Leu Phe Ala Gly Lys Phe Tyr Glu
    1325                1330                1335

Cys Ile Asn Thr Thr Asp Gly Ser Arg Phe Pro Ala Ser Gln Val
    1340                1345                1350

Pro Asn Arg Ser Glu Cys Phe Ala Leu Met Asn Val Ser Gln Asn
    1355                1360                1365

Val Arg Trp Lys Asn Leu Lys Val Asn Phe Asp Asn Val Gly Leu
    1370                1375                1380

Gly Tyr Leu Ser Leu Leu Gln Val Ala Thr Phe Lys Gly Trp Thr
    1385                1390                1395

Ile Ile Met Tyr Ala Ala Val Asp Ser Val Asn Val Asp Lys Gln
    1400                1405                1410

Pro Lys Tyr Glu Tyr Ser Leu Tyr Met Tyr Ile Tyr Phe Val Val
    1415                1420                1425

Phe Ile Ile Phe Gly Ser Phe Thr Leu Asn Leu Phe Ile Gly
    1430                1435                1440

Val Ile Ile Asp Asn Phe Asn Gln Gln Lys Lys Lys Leu Gly Gly
    1445                1450                1455

Gln Asp Ile Phe Met Thr Glu Glu Gln Lys Lys Tyr Tyr Asn Ala
    1460                1465                1470

Met Lys Lys Leu Gly Ser Lys Lys Pro Gln Lys Pro Ile Pro Arg
    1475                1480                1485

Pro Gly Asn Lys Ile Gln Gly Cys Ile Phe Asp Leu Val Thr Asn
    1490                1495                1500
```

```
Gln Ala Phe Asp Ile Ser Ile Met Val Leu Ile Cys Leu Asn Met
1505                1510                1515

Val Thr Met Met Val Glu Lys Glu Gly Gln Ser Gln His Met Thr
1520                1525                1530

Glu Val Leu Tyr Trp Ile Asn Val Val Phe Ile Ile Leu Phe Thr
1535                1540                1545

Gly Glu Cys Val Leu Lys Leu Ile Ser Leu Arg His Tyr Tyr Phe
1550                1555                1560

Thr Val Gly Trp Asn Ile Phe Asp Phe Val Val Ile Ile Ser
1565                1570                1575

Ile Val Gly Met Phe Leu Ala Asp Leu Ile Glu Thr Tyr Phe Val
1580                1585                1590

Ser Pro Thr Leu Phe Arg Val Ile Arg Leu Ala Arg Ile Gly Arg
1595                1600                1605

Ile Leu Arg Leu Val Lys Gly Ala Lys Gly Ile Arg Thr Leu Leu
1610                1615                1620

Phe Ala Leu Met Met Ser Leu Pro Ala Leu Phe Asn Ile Gly Leu
1625                1630                1635

Leu Leu Phe Leu Val Met Phe Ile Tyr Ala Ile Phe Gly Met Ser
1640                1645                1650

Asn Phe Ala Tyr Val Lys Lys Glu Asp Gly Ile Asn Asp Met Phe
1655                1660                1665

Asn Phe Glu Thr Phe Gly Asn Ser Met Ile Cys Leu Phe Gln Ile
1670                1675                1680

Thr Thr Ser Ala Gly Trp Asp Gly Leu Leu Ala Pro Ile Leu Asn
1685                1690                1695

Ser Lys Pro Pro Asp Cys Asp Pro Lys Lys Val His Pro Gly Ser
1700                1705                1710

Ser Val Glu Gly Asp Cys Gly Asn Pro Ser Val Gly Ile Phe Tyr
1715                1720                1725

Phe Val Ser Tyr Ile Ile Ile Ser Phe Leu Val Val Val Asn Met
1730                1735                1740

Tyr Ile Ala Val Ile Leu Glu Asn Phe Ser Val Ala Thr Glu Glu
1745                1750                1755

Ser Thr Glu Pro Leu Ser Glu Asp Asp Phe Glu Met Phe Tyr Glu
1760                1765                1770

Val Trp Glu Lys Phe Asp Pro Asp Ala Thr Gln Phe Ile Glu Phe
1775                1780                1785

Ser Lys Leu Ser Asp Phe Ala Ala Ala Leu Asp Pro Pro Leu Leu
1790                1795                1800

Ile Ala Lys Pro Asn Lys Val Gln Leu Ile Ala Met Asp Leu Pro
1805                1810                1815

Met Val Ser Gly Asp Arg Ile His Cys Leu Asp Ile Leu Phe Ala
1820                1825                1830

Phe Thr Lys Arg Val Leu Gly Glu Ser Gly Glu Met Asp Ser Leu
1835                1840                1845

Arg Ser Gln Met Glu Glu Arg Phe Met Ser Ala Asn Pro Ser Lys
1850                1855                1860

Val Ser Tyr Glu Pro Ile Thr Thr Thr Leu Lys Arg Lys Gln Glu
1865                1870                1875

Asp Val Ser Ala Thr Val Ile Gln Arg Ala Tyr Arg Arg Tyr Arg
1880                1885                1890
```

| | | | | | | | | | | |
|---|---|---|---|---|---|---|---|---|---|---|
| Leu | Arg | Gln | Asn | Val | Lys | Asn | Ile | Ser | Ser | Ile | Tyr | Ile | Lys | Asp |
| | 1895 | | | | 1900 | | | | 1905 | |
| Gly | Asp | Arg | Asp | Asp | Asp | Leu | Leu | Asn | Lys | Lys | Asp | Met | Ala | Phe |
| 1910 | | | | | 1915 | | | | | 1920 | |
| Asp | Asn | Val | Asn | Glu | Asn | Ser | Ser | Pro | Glu | Lys | Thr | Asp | Ala | Thr |
| | 1925 | | | | 1930 | | | | 1935 | |
| Ser | Ser | Thr | Thr | Ser | Pro | Pro | Ser | Tyr | Asp | Ser | Val | Thr | Lys | Pro |
| | 1940 | | | | 1945 | | | | 1950 | |
| Asp | Lys | Glu | Lys | Tyr | Glu | Gln | Asp | Arg | Thr | Glu | Lys | Glu | Asp | Lys |
| | 1955 | | | | 1960 | | | | 1965 | |
| Gly | Lys | Asp | Ser | Lys | Glu | Ser | Lys | Lys |
| | 1970 | | | | | 1975 |

<210> SEQ ID NO 86
<211> LENGTH: 5934
<212> TYPE: DNA
<213> ORGANISM: Homo sapiens

<400> SEQUENCE: 86

```
atggcaatgt tgcctccccc aggacctcag agctttgtcc atttcacaaa acagtctctt      60
gccctcattg aacaacgcat tgctgaaaga aaatcaaagg aacccaaaga agaaaagaaa     120
gatgatgatg aagaagcccc aaagccaagc agtgacttgg aagctggcaa caactgccc     180
ttcatctatg gggacattcc tcccggcatg gtgtcagagc cctggagga cttggacccc     240
tactatgcag acaaaaagac tttcatagta ttgaacaaag ggaaaacaat cttccgtttc     300
aatgccacac ctgctttata tatgctttct cctttcagtc ctctaagaag aatatctatt     360
aagattttag tacactcctt attcagcatg ctcatcatgt gcactattct gacaaactgc     420
atatttatga ccatgaataa cccgccggac tggaccaaaa atgtcgagta cactttttact     480
ggaatatata cttttgaatc acttgtaaaa atccttgcaa gaggcttctg tgtaggagaa     540
ttcactttc ttcgtgaccc gtggaactgg ctggattttg tcgtcattgt ttttgcgtat     600
ttaacagaat ttgtaaacct aggcaatgtt tcagctcttc gaactttcag agtattgaga     660
gctttgaaaa ctatttctgt aatgccaggc ctgaagacaa ttgtaggggc tttgatccag     720
tcagtgaaga agctttctga tgtcatgatc ctgactgtgt tctgtctgag tgtgtttgca     780
ctaattggac tacagctgtt catgggaaac ctgaagcata atgttttcg aaattcactt     840
gaaaataatg aaacattaga aagcataatg aatccctag agagtgaaga agactttaga     900
aaatattttt attacttgga aggatccaaa gatgctctcc tttgtggttt cagcacagat     960
tcaggtcagt gtccagaggg gtacacctgt gtgaaaattg gcagaaaccc tgattatggc    1020
tacacgagct ttgacacttt cagctgggcc ttcttagcct tgtttaggct aatgaccca    1080
gattactggg aaaaccttta ccaacagacg ctgcgtgctg ctggcaaaac ctacatgatc    1140
ttctttgtcg tagtgatttt cctgggctcc ttttatctaa taaacttgat cctggctgtg    1200
gttgccatgg catatgaaga acagaaccag gcaaacattg aagaagctaa acagaaagaa    1260
ttagaatttc aacagatgtt agaccgtctt aaaaagagc aagaagaagc tgaggcaatt    1320
gcagcggcag cggctgaata tacaagtatt aggagaagca gaattatggg cctctcagag    1380
agttcttctg aaacatccaa actgagctct aaaagtgcta agaaagaag aaacagaaga    1440
aagaaaaaga atcaaagaa gctctccagt ggagaggaaa agggagatgc tgagaaattg    1500
tcgaaatcag aatcagagga cagcatcaga agaaaaagtt tccacttgg tgtcgaaggg    1560
cataggcgag cacatgaaaa gaggttgtct acccccaatc agtcaccact cagcattcgt    1620
```

```
ggctccttgt tttctgcaag gcgaagcagc agaacaagtc ttttagttt caaaggcaga    1680
ggaagagata taggatctga gactgaattt gccgatgatg agcacagcat ttttggagac    1740
aatgagagca gaaggggctc actgtttgtg ccccacagac cccaggagcg acgcagcagt    1800
aacatcagcc aagccagtag gtccccacca atgctgccgg tgaacgggaa aatgcacagt    1860
gctgtggact gcaacggtgt ggtctccctg gttgatggac gctcagccct catgctcccc    1920
aatgacagc ttctgccaga gggcacgacc aatcaaatac acaagaaaag gcgttgtagt     1980
tcctatctcc tttcagagga tatgctgaat gatcccaacc tcagacagag agcaatgagt    2040
agagcaagca tattaacaaa cactgtggaa gaacttgaag agtccagaca aaaatgtcca    2100
ccttggtggt acagatttgc acacaaattc ttgatctgga attgctctcc atattggata    2160
aaattcaaaa agtgtatcta ttttattgta atggatcctt ttgtagatct tgcaattacc    2220
atttgcatag ttttaaacac attatttatg gctatggaac accacccaat gactgaggaa    2280
ttcaaaaatg tacttgctat aggaaatttg gtctttactg gaatctttgc agctgaaatg    2340
gtattaaaac tgattgccat ggatccatat gagtatttcc aagtaggctg gaatattttt    2400
gacagcctta ttgtgacttt aagtttagtg gagctctttc tagcagatgt ggaaggattg    2460
tcagttctgc gatcattcag actgctccga gtcttcaagt tggcaaaatc ctggccaaca    2520
ttgaacatgc tgattaagat cattggtaac tcagtagggg ctctaggtaa cctcaccttta   2580
gtgttggcca tcatcgtctt cattttttgct gtggtcggca tgcagctctt tggtaagagc    2640
tacaaagaat gtgtctgcaa gatcaatgat gactgtacgc tcccacggtg gcacatgaac    2700
gacttcttcc actccttcct gattgtgttc cgcgtgctgt gtggagagtg gatagagacc    2760
atgtgggact gtatggaggt cgctggtcaa gctatgtgcc ttattgttta catgatggtc    2820
atggtcattg gaaacctggt ggtcctaaac ctatttctgg ccttattatt gagctcattt    2880
agttcagaca atcttacagc aattgaagaa gaccctgatg caaacaacct ccagattgca    2940
gtgactagaa ttaaaaaggg aataaattat gtgaaacaaa ccttacgtga atttattcta    3000
aaagcatttt ccaaaaagcc aaagatttcc agggagataa gacaagcaga agatctgaat    3060
actaagaagg aaaactatat ttctaaccat acacttgctg aaatgagcaa aggtcacaat    3120
ttcctcaagg aaaaagataa aatcagtggt tttggaagca gcgtggacaa acacttgatg    3180
gaagacagtg atggtcaatc atttattcac aatcccagcc tcacagtgac agtgccaatt    3240
gcacctgggg aatccgattt ggaaaatatg aatgctgagg aacttagcag tgattcggat    3300
agtgaataca gcaaagtgag attaaaccgg tcaagctcct cagagtgcag cacagttgat    3360
aaccctttgc ctggagaagg agaagaagca gaggctgaac ctatgaattc cgatgagcca    3420
gaggcctgtt tcacagatgg ttgtgtacgg aggttctcat gctgccaagt taacatagag    3480
tcagggaaag gaaaaatctg gtggaacatc aggaaaacct gctacaagat tgttgaacac    3540
agttggttg aaagcttcat tgtcctcatg atcctgctca gcagtggtgc cctggctttt    3600
gaagatattt atattgaaag gaaaaagacc attaagatta tcctggagta tgcagacaag    3660
atcttcactt acatcttcat tctggaaatg cttctaaaat ggatagcata tggttataaa    3720
acatatttca ccaatgcctg gtgttggctg gatttcctaa ttgttgatgt ttctttggtt    3780
actttagtgg caaacactct tggctactca gatcttggcc ccattaaatc ccttcggaca    3840
ctgagagctt aagacctct aagagcctta tctagatttg aaggaatgag ggtcgttgtg     3900
aatgcactca taggagcaat tccttccatc atgaatgtgc tacttgtgtg tcttatattc    3960
```

```
tggctgatat tcagcatcat gggagtaaat ttgtttgctg gcaagttcta tgagtgtatt      4020
aacaccacag atgggtcacg gtttcctgca agtcaagttc caaatcgttc cgaatgtttt      4080
gcccttatga atgttagtca aaatgtgcga tggaaaaacc tgaaagtgaa ctttgataat      4140
gtcggacttg gttacctatc tctgcttcaa gttgcaactt ttaagggatg gacgattatt      4200
atgtatgcag cagtggattc tgttaatgta gacaagcagc ccaaatatga atatagcctc      4260
tacatgtata tttattttgt cgtctttatc atctttgggt cattcttcac tttgaacttg      4320
ttcattggtg tcatcataga taatttcaac caacagaaaa agaagcttgg aggtcaagac      4380
atctttatga cagaagaaca gaagaaatac tataatgcaa tgaaaaagct ggggtccaag      4440
aagccacaaa agccaattcc tcgaccaggg aacaaaatcc aaggatgtat atttgaccta      4500
gtgacaaatc aagcctttga tattagtatc atggttctta tctgtctcaa catggtaacc      4560
atgatggtag aaaaggaggg tcaaagtcaa catatgactg aagttttata ttggataaat      4620
gtggttttta taatcctttt cactggagaa tgtgtgctaa aactgatctc cctcagacac      4680
tactacttca ctgtaggatg gaatattttt gattttgtgg ttgtgattat ctccattgta      4740
ggtatgtttc tagctgattt gattgaaacg tattttgtgt cccctaccct gttccgagtg      4800
atccgtcttg ccaggattgg ccgaatccta cgtctagtca aggagcaaaa ggggatccgc      4860
acgctgctct ttgctttgat gatgtcccct cctgcgttgt ttaacatcgg cctcctgctc      4920
ttcctggtca tgttcatcta cgccatcttt ggaatgtcca actttgccta tgttaaaaag      4980
gaagatggaa ttaatgacat gttcaatttt gagacctttg caacagtat gatttgcctg      5040 ttccaaatta caacctctgc tggctgggat ggattgctag cacctattct taacagtaag      5100
ccacccgact gtgacccaaa aaagttcat cctggaagtt cagttgaagg agactgtggt      5160
aacccatctg ttggaatatt ctactttgtt agttatatca tcatatcctt cctggttgtg      5220
gtgaacatgt acattgcagt catactggag aattttagtg ttgccactga agaaagtact      5280
gaacctctga gtgaggatga ctttgagatg ttctatgagg tttgggagaa gtttgatccc      5340
gatgcgaccc agtttataga gttctctaaa ctctctgatt ttgcagctgc cctggatcct      5400
cctcttctca tagcaaaacc caacaaagtc cagctcattg ccatggatct gcccatggtt      5460
agtggtgacc ggatccattg tcttgacatc ttatttgctt ttacaaagcg tgttttgggt      5520
gagagtgggg agatggattc tcttcgttca cagatggaag aaaggttcat gtctgcaaat      5580
ccttccaaag tgtcctatga acccatcaca accacactaa aacggaaaca agaggatgtg      5640
tctgctactg tcattcagcg tgcttataga cgttaccgct taaggcaaaa tgtcaaaaat      5700
atatcaagta tatacataaa agatggagac agagatgatg atttactcaa taaaaaagat      5760
atggcttttg ataatgttaa tgagaactca agtccagaaa aaacagatgc cacttcatcc      5820
accacctctc caccttcata tgatagtgta acaaagccag acaaagagaa atatgaacaa      5880
gacagaacag aaaaggaaga caaagggaaa gacagcaagg aaagcaaaaa atag            5934
```

<210> SEQ ID NO 87
<211> LENGTH: 5934
<212> TYPE: DNA
<213> ORGANISM: Homo sapiens

<400> SEQUENCE: 87

```
atggcaatgt tgcctccccc aggacctcag agctttgtcc atttcacaaa acagtctctt       60
gccctcattg aacaacgcat tgctgaaaga aaatcaaagg aacccaaaga agaaaagaaa      120
gatgatgatg aagaagcccc aaagccaagc agtgacttgg aagctggcaa acaactgccc      180
```

-continued

| | |
|---|---|
| ttcatctatg gggacattcc tcccggcatg gtgtcagagc ccctggagga cttggacccc | 240 |
| tactatgcag acaaaaagac tttcatagta ttgaacaaag ggaaaacaat cttccgtttc | 300 |
| aatgccacac ctgctttata tatgctttct cctttcagtc ctctaagaag aatatctatt | 360 |
| aagatttttag tacactcctt attcagcatg ctcatcatgt gcactattct gacaaactgc | 420 |
| atatttatga ccatgaataa cccgccggac tggaccaaaa atgtcgagta cacttttact | 480 |
| ggaatatata cttttgaatc acttgtaaaa atccttgcaa gaggcttctg tgtaggagaa | 540 |
| ttcactttc ttcgtgaccc gtggaactgg ctggattttg tcgtcattgt ttttgcgtat | 600 |
| ttaacagaat ttgtaaacct aggcaatgtt tcagctcttc gaactttcag agtattgaga | 660 |
| gctttgaaaa ctatttctgt aatcccaggc ctgaagacaa ttgtaggggc tttgatccag | 720 |
| tcagtgaaga agctttctga tgtcatgatc ctgactgtgt tctgtctgag tgtgtttgca | 780 |
| ctaattggac tacagctgtt catgggaaac ctgaagcata aatgttttcg aaattcactt | 840 |
| gaaaataatg aaacattaga aagcataatg aatacccctag agagtgaaga agactttaga | 900 |
| aaatatttt attacttgga aggatccaaa gatgctctcc tttgtggttt cagcacagat | 960 |
| tcaggtcagt gtccagaggg gtacacctgt gtgaaaattg gcagaaaccc tgattatggc | 1020 |
| tacacgagct ttgacacttt cagctgggcc ttcttagcct tgtttaggct aatgacccaa | 1080 |
| gattactggg aaaacctta ccaacagacg ctgcgtgctg ctggcaaaac ctacatgatc | 1140 |
| ttcctttgtcg tagtgatttt cctgggctcc ttttatctaa taaacttgat cctggctgtg | 1200 |
| gttgccatgg catatgaaga acagaaccag gcaaacattg aagaagctaa acagaaagaa | 1260 |
| ttagaatttc aacagatgtt agaccgtctt aaaaaagagc aagaagaagc tgaggcaatt | 1320 |
| gcagcggcag cggctgaata tacaagtatt aggagaagca gaattatggg cctctcagag | 1380 |
| agttcttctg aaacatccaa actgagctct aaaagtgcta agaaagaag aaacagaaga | 1440 |
| aagaaaaaga atcaaagaa gctctccaat ggagaggaaa agggagatgc tgagaaattg | 1500 |
| tcgaaatcag aatcagagga cagcatcaga agaaaaagtt tccaccttgg tgtcgaaggg | 1560 |
| cataggcgag cacatgaaaa gaggttgtct accccccaatc agtcaccact cagcattcgt | 1620 |
| ggctccttgt tttctgcaag gcgaagcagc agaacaagtc ttttagtttt caaaggcaga | 1680 |
| ggaagagata taggatctga gactgaattt gccgatgatg agcacagcat ttttggagac | 1740 |
| aatgagagca gaagggggctc actgtttgtg ccccacagac cccaggagcg acgcagcagt | 1800 |
| aacatcagcc aagccagtag gtccccacca atgctgccgg tgaacgggaa aatgcacagt | 1860 |
| gctgtggact gcaacggtgt ggtctccctg gttgatggac gctcagccct catgctcccc | 1920 |
| aatggacagc ttctgccaga gggcacgacc aatcaaatac acaagaaaag gcgttgtagt | 1980 |
| tcctatctcc tttcagagga tatgctgaat gatcccaacc tcagacagag agcaatgagt | 2040 |
| agagcaagca tattaacaaa cactgtggaa gaacttgaag agtccagaca aaaatgtcca | 2100 |
| ccttggtggt acagatttgc acacaaattc ttgatctgga attgctctcc atattggata | 2160 |
| aaattcaaaa agtgtatcta ttttattgta atggatcctt ttgtagatct tgcaattacc | 2220 |
| atttgcatag ttttaaacac attatttatg gctatggaac accacccaat gactgaggaa | 2280 |
| ttcaaaaatg tacttgctat aggaaatttg gtctttactg gaatctttgc agctgaaatg | 2340 |
| gtattaaaac tgattgccat ggatccatat gagtatttcc aagtaggctg gaatattttt | 2400 |
| gacagcctta ttgtgacttt aagtttagtg gagctctttc tagcagatgt ggaaggattg | 2460 |
| tcagttctgc gatcattcag actgctccga gtcttcaagt tggcaaaatc ctggccaaca | 2520 |

```
ttgaacatgc tgattaagat cattggtaac tcagtagggg ctctaggtaa cctcaccttta    2580
gtgttggcca tcatcgtctt catttttgct gtggtcggca tgcagctctt tggtaagagc    2640
tacaaagaat gtgtctgcaa gatcaatgat gactgtacgc tcccacggtg gcacatgaac    2700
gacttcttcc actccttcct gattgtgttc cgcgtgctgt gtggagagtg gatagagacc    2760
atgtgggact gtatggaggt cgctggtcaa gctatgtgcc ttattgttta catgatggtc    2820
atggtcattg gaaacctggt ggtcctaaac ctatttctgg ccttattatt gagctcattt    2880
agttcagaca atcttacagc aattgaagaa gaccctgatg caaacaacct ccagattgca    2940
gtgactagaa ttaaaagggg aataaattat gtgaaacaaa ccttacgtga atttattcta    3000
aaagcatttt ccaaaaagcc aaagatttcc agggagataa gacaagcaga agatctgaat    3060
actaagaagg aaaactatat ttctaaccat acacttgctg aaatgagcaa aggtcacaat    3120
ttcctcaagg aaaaagataa aatcagtggt tttggaagca gcgtggacaa acacttgatg    3180
gaagacagtg atggtcaatc atttattcac aatcccagcc tcacagtgac agtgccaatt    3240
gcacctgggg aatccgattt ggaaaatatg aatgctgagg aacttagcag tgattcggat    3300
agtgaataca gcaaagtgag attaaaccgg tcaagctcct cagagtgcag cacagttgat    3360
aacccttttgc ctggagaagg agaagaagca gaggctgaac ctatgaattc cgatgagcca    3420
gaggcctgtt tcacagatgg ttgtgtacgg aggttctcat gctgccaagt taacatagag    3480
tcagggaaag gaaaaatctg gtggaacatc aggaaaacct gctacaagat tgttgaacac    3540
agttggtttg aaagcttcat tgtcctcatg atcctgctca gcagtggtgc cctggctttt    3600
gaagatattt atattgaaag gaaaaagacc attaagatta tcctggagta tgcagacaag    3660
atcttcactt acatcttcat tctggaaatg cttctaaaat ggatagcata tggttataaa    3720
acatatttca ccaatgcctg tgttggctg gatttcctaa ttgttgatgt ttctttggtt    3780
actttagtgg caaacactct tggctactca gatcttggcc ccattaaatc ccttcggaca    3840
ctgagagctt taagacctct aagagcctta tctagatttg aaggaatgag ggtcgttgtg    3900
aatgcactca taggagcaat tccttccatc atgaatgtgc tacttgtgtg tcttatattc    3960
tggctgatat tcagcatcat gggagtaaat ttgtttgctg gcaagttcta tgagtgtatt    4020
aacaccacag atgggtcacg gtttcctgca agtcaagttc caaatcgttc cgaatgtttt    4080
gcccttatga atgttagtca aatgtgcga tggaaaaacc tgaaagtgaa ctttgataat    4140
gtcggacttg gttacctatc tctgcttcaa gttgcaactt ttaagggatg gacgattatt    4200
atgtatgcag cagtggattc tgttaatgta gacaagcagc ccaaatatga atatagcctc    4260
tacatgtata tttattttgt cgtctttatc atctttgggt cattcttcac tttgaacttg    4320
ttcattggtg tcatcatag aaatttcaac caacagaaaa agaagcttgg aggtcaagac    4380
atctttatga cagaagaaca gaagaaatac tataatgcaa tgaaaagct ggggtccaag    4440
aagccacaaa agccaattcc tcgaccaggg aacaaatcc aaggatgtat atttgaccta    4500
gtgacaaatc aagcctttga tattagtatc atggttctta tctgtctcaa catggtaacc    4560
atgatggtag aaaaggaggg tcaaagtcaa catatgactg aagttttata ttggataaat    4620
gtggtttta taatccttttt cactggagaa tgtgtgctaa aactgatctc cctcagacac    4680
tactacttca ctgtaggatg gaatatttttt gattttgtgg ttgtgattat ctccattgta    4740
ggtatgtttc tagctgattt gattgaaacg tattttgtgt cccctaccct gttccgagtg    4800
atccgtcttg ccaggattgg ccgaatccta cgtctagtca aaggagcaaa ggggatccgc    4860
acgctgctct ttgctttgat gatgtcccttt cctgcgttgt ttaacatcgg cctcctgctc    4920
```

```
ttcctggtca tgttcatcta cgccatcttt ggaatgtcca actttgccta tgttaaaaag    4980
gaagatggaa ttaatgacat gttcaatttt gagacctttg caacagtat gatttgcctg    5040 ttccaaatta caacctctgc tggctgggat ggattgctag cacctattct aacagtaag    5100 ccacccgact gtgacccaaa aaagttcat cctggaagtt cagttgaagg agactgtggt    5160
aacccatctg ttggaatatt ctactttgtt agttatatca tcatatcctt cctggttgtg    5220
gtgaacatgt acattgcagt catactggag aattttagtg ttgccactga agaaagtact    5280
gaacctctga gtgaggatga ctttgagatg ttctatgagg tttgggagaa gtttgatccc    5340
gatgcgaccc agtttataga gttctctaaa ctctctgatt ttgcagctgc cctggatcct    5400
cctcttctca tagcaaaacc caacaaagtc cagctcattg ccatggatct gcccatggtt    5460
agtggtgacc ggatccattg tcttgacatc ttatttgctt ttacaaagcg tgttttgggt    5520
gagagtgggg agatggattc tcttcgttca cagatggaag aaaggttcat gtctgcaaat    5580
ccttccaaag tgtcctatga acccatcaca accacactaa acggaaaca agaggatgtg    5640 tctgctactg tcattcagcg tgcttataga cgttaccgct taaggcaaaa tgtcaaaaat    5700
atatcaagta tatacataaa agatggagac agagatgatg atttactcaa taaaaaagat    5760
atggcttttg ataatgttaa tgagaactca agtccagaaa aaacagatgc cacttcatcc    5820
accacctctc caccttcata tgatagtgta acaaagccag acaaagagaa atatgaacaa    5880
gacagaacag aaaaggaaga caagggaaa gacagcaagg aaagcaaaaa atag          5934

<210> SEQ ID NO 88
<211> LENGTH: 5934
<212> TYPE: DNA
<213> ORGANISM: Homo sapiens

<400> SEQUENCE: 88
atggcaatgt tgcctccccc aggacctcag agctttgtcc atttcacaaa acagtctctt      60
gccctcattg aacaacgcat tgctgaaaga aaatcaaagg aacccaaaga agaaaagaaa     120
gatgatgatg aagaagcccc aaagccaagc agtgacttgg aagctggcaa acaactgccc     180
ttcatctatg gggacattcc tcccggcatg gtgtcagagc ccctggagga cttggacccc     240
tactatgcag acaaaaagac tttcatagta ttgaacaaag ggaaaacaat cttccgtttc     300
aatgccacac ctgctttata tatgctttct cctttcagtc ctctaagaag aatatctatt     360
aagattttag tacactcctt attcagcatg ctcatcatgt gcactattct gacaaactgc     420
atatttatga ccatgaataa cccgccggac tggaccaaaa atgtcgagta cacttttact     480
ggaatatata cttttgaatc acttgtaaaa atccttgcaa gaggcttctg tgtaggagaa     540
ttcacttttc ttcgtgaccc gtggaactgg ctggattttg tcgtcattgt ttttgcgtat     600
ttaacagaat ttgtaaacct aggcaatgtt tcagctcttc gaactttcag agtattgaga     660
gctttgaaaa ctatttctgt aatcccaggc ctgaagacaa ttgtaggggc tttgatccag     720
tcagtgaaga agctttctga tgtcatgatc ctgactgtgt tctgtctgag tgtgtttgca     780
ctaattggac tacagctgtt catgggaaac ctgaagcata atgttttcg aaattcactt     840 gaaaataatg aaacattaga aagcataatg aatacctag agagtgaaga agactttaga     900
aaatattttt attacttgga aggatccaaa gatgctctcc tttgtggttt cagcacagat     960
tcaggtcagt gtccagaggg gtacacctgt gtgaaaattg cagaaaccc tgattatggc    1020 tacacgagct ttgacacttt cagctgggcc ttcttagcct tgtttaggct aatgacccaa    1080
```

```
gattactggg aaaacctttta ccaacagacg ctgcgtgctg ctggcaaaac ctacatgatc    1140
ttctttgtcg tagtgatttt cctgggctcc ttttatctaa taaacttgat cctggctgtg    1200
gttgccatgg catatgaaga acagaaccag gcaaacattg aagaagctaa acagaaagaa    1260
ttagaatttc aacagatgtt agaccgtctt aaaaaagagc aagaagaagc tgaggcaatt    1320
gcagcggcag cggctgaata tacaagtatt aggagaagca gaattatggg cctctcagag    1380
agttcttctg aaacatccaa actgagctct aaaagtgcta agaaagaag aaacagaaga    1440 aagaaaaaga atcaaaagaa gctctccagt ggagaggaaa agggagatgc tgagaaattg    1500
tcgaaatcag aatcagagga cagcatcaga agaaaaagtt ccaccttgg tgtcaaaggg    1560 cataggcgag cacatgaaaa gaggttgtct accccaaatc agtcaccact cagcattcgt    1620
ggctccttgt tttctgcaag gcgaagcagc agaacaagtc tttttagttt caaaggcaga    1680
ggaagagata taggatctga gactgaattt gccgatgatg agcacagcat ttttggagac    1740
aatgagagca gaaggggctc actgtttgtg ccccacagac cccaggagcg acgcagcagt    1800
aacatcagcc aagccagtag gtccccacca atgctgccgg tgaacgggaa aatgcacagt    1860
gctgtggact gcaacggtgt ggtctccctg gttgatggac gctcagccct catgctcccc    1920 aatgacagc ttctgccaga gggcacgacc aatcaaatac acaagaaaag gcgttgtagt    1980
tcctatctcc tttcagagga tatgctgaat gatcccaacc tcagacagag agcaatgagt    2040
agagcaagca tattaacaaa cactgtggaa gaacttgaag agtccagaca aaaatgtcca    2100
ccttggtggt acagatttgc acacaaattc ttgatctgga attgctctcc atattggata    2160
aaattcaaaa agtgtatcta ttttattgta atggatcctt tgtagatct tgcaattacc    2220 atttgcatag ttttaaacac attatttatg gctatggaac accacccaat gactgaggaa    2280
ttcaaaaatg tacttgctat aggaaatttg gtctttactg gaatctttgc agctgaaatg    2340
gtattaaaac tgattgccat ggatccatat gagtatttcc aagtaggctg gaatattttt    2400
gacagcctta ttgtgacttt aagtttagtg gagctctttc tagcagatgt ggaaggattg    2460
tcagttctgc gatcattcag actgctccga gtcttcaagt tggcaaaatc ctggccaaca    2520
ttgaacatgc tgattaagat cattggtaac tcagtagggg ctctaggtaa cctcacctta    2580
gtgttggcca tcatcgtctt cattttgct gtggtcggca tgcagctctt tggtaagagc    2640
tacaaagaat gtgtctgcaa gatcaatgat gactgtacgc tcccacggtg gcacatgaac    2700
gacttcttcc actccttcct gattgtgttc cgcgtgctgt gtggagagtg atagagacc    2760 atgtgggact gtatgaggt cgctggtcaa gctatgtgcc ttattgttta catgatggtc    2820
atggtcattg gaaacctggt ggtcctaaac ctatttctgg ccttattatt gagctcattt    2880
agttcagaca atcttacagc aattgaagaa gaccctgatg caaacaacct ccagattgca    2940
gtgactagaa ttaaaaaggg aataaattat gtgaaacaaa ccttacgtga atttattcta    3000 aaagcattt ccaaaaagcc aaagatttcc agggagataa gacaagcaga agatctgaat    3060
actaagaagg aaaactatat ttctaaccat acacttgctg aaatgagcaa aggtcacaat    3120
ttcctcaagg aaaagataa aatcagtggt tttggaagca gcgtggacaa acacttgatg    3180
gaagacagtg atggtcaatc atttattcac aatcccagcc tcacagtgac agtgccaatt    3240
gcacctgggg aatccgattt ggaaaatatg aatgctgagg aacttagcag tgattcggat    3300
agtgaataca gcaaagtgag attaaaccgg tcaagctcct cagagtgcag cacagttgat    3360 aacccttgc ctggagaagg agaagaagca gaggctgaac ctatgaattc cgatgagcca    3420
gaggcctgtt tcacagatgg ttgtgtacgg aggttctcat gctgccaagt taacatagag    3480
```

```
tcagggaaag gaaaaatctg gtggaacatc aggaaaacct gctacaagat tgttgaacac    3540
agttggtttg aaagcttcat tgtcctcatg atcctgctca gcagtggtgc cctggctttt    3600
gaagatattt atattgaaag gaaaaagacc attaagatta tcctggagta tgcagacaag    3660
atcttcactt acatcttcat tctggaaatg cttctaaaat ggatagcata tggttataaa    3720
acatatttca ccaatgcctg tgttggctg gatttcctaa ttgttgatgt ttctttggtt    3780
actttagtgg caaacactct tggctactca gatcttggcc ccattaaatc ccttcggaca    3840
ctgagagctt taagacctct aagagcctta tctagatttg aaggaatgag ggtcgttgtg    3900
aatgcactca taggagcaat tccttccatc atgaatgtgc tacttgtgtg tcttatattc    3960
tggctgatat tcagcatcat gggagtaaat ttgtttgctg gcaagttcta tgagtgtatt    4020
aacaccacag atgggtcacg gtttcctgca agtcaagttc caaatcgttc cgaatgtttt    4080
gcccttatga atgttagtca aaatgtgcga tggaaaaacc tgaaagtgaa ctttgataat    4140
gtcggacttg gttacctatc tctgcttcaa gttgcaactt ttaagggatg gacgattatt    4200
atgtatgcag cagtggattc tgttaatgta gacaagcagc ccaaatatga atatagcctc    4260
tacatgtata tttatttttgt cgtctttatc atctttgggt cattcttcac tttgaacttg    4320
ttcattggtg tcatcataga taatttcaac caacagaaaa agaagcttgg aggtcaagac    4380
atctttatga cagaagaaca gaagaaatac tataatgcaa tgaaaaagct ggggtccaag    4440
aagccacaaa agccaattcc tcgaccaggg aacaaaatcc aaggatgtat atttgaccta    4500
gtgacaaatc aagcctttga tattagtatc atggttctta tctgtctcaa catggtaacc    4560
atgatggtag aaaaggaggg tcaaagtcaa catatgactg aagtttttata ttggataaat    4620
gtggttttta taatccttt cactggagaa tgtgtgctaa aactgatctc cctcagacac    4680
tactacttca ctgtaggatg gaatattttt gattttgtgg ttgtgattat ctccattgta    4740
ggtatgtttc tagctgattt gattgaaacg tattttgtgt ccctaccct gttccgagtg    4800
atccgtcttg ccaggattgg ccgaatccta cgtctagtca aaggagcaaa ggggatccgc    4860
acgctgctct ttgctttgat gatgtccctt cctgcgttgt taacatcgg cctcctgctc    4920
ttcctggtca tgttcatcta cgccatcttt ggaatgtcca actttgccta tgttaaaaag    4980
gaagatggaa ttaatgacat gttcaatttt gagacctttg caacagtat gatttgcctg    5040
ttccaaatta caacctctgc tggctgggat ggattgctag cacctattct taacagtaag    5100
ccacccgact gtgacccaaa aaaagttcat cctggaagtt cagttgaagg agactgtggt    5160
aacccatctg ttgaatatt ctactttgtt agttatatca tcatatcctt cctggttgtg    5220
gtgaacatgt acattgcagt catactggag aattttagtg ttgccactga agaaagtact    5280
gaacctctga gtgaggatga ctttgagatg ttctatgagg tttgggagaa gtttgatccc    5340
gatgcgaccc agtttataga gttctctaaa ctctctgatt ttgcagctgc cctggatcct    5400
cctcttctca tagcaaaacc caacaaagtc cagctcattg ccatggatct gcccatggtt    5460
agtggtgacc ggatccattg tcttgacatc ttatttgctt ttacaaagcg tgttttgggt    5520
gagagtgggg agatggattc tcttcgttca cagatggaag aaaggttcat gtctgcaaat    5580
ccttccaaag tgtcctatga acccatcaca accacactaa aacggaaaca agaggatgtg    5640
tctgctactg tcattcagcg tgcttataga cgttaccgct taaggcaaaa tgtcaaaaat    5700
atatcaagta tatacataaa agatggagac agagatgatg atttactcaa taaaaaagat    5760
atggcttttg ataatgttaa tgagaactca agtccagaaa aaacagatgc cacttcatcc    5820
```

```
accacctctc caccttcata tgatagtgta acaaagccag acaaagagaa atatgaacaa    5880
gacagaacag aaaaggaaga caaagggaaa gacagcaagg aaagcaaaaa atag          5934

<210> SEQ ID NO 89
<211> LENGTH: 5934
<212> TYPE: DNA
<213> ORGANISM: Homo sapiens

<400> SEQUENCE: 89
atggcaatgt tgcctccccc aggacctcag agctttgtcc atttcacaaa acagtctctt      60
gccctcattg aacaacgcat tgctgaaaga aaatcaaagg aacccaaaga agaaaagaaa     120
gatgatgatg aagaagcccc aaagccaagc agtgacttgg aagctggcaa acaactgccc     180
ttcatctatg gggacattcc tcccggcatg gtgtcagagc ccctggagga cttggacccc     240
tactatgcag acaaaaagac tttcatagta ttgaacaaag ggaaaacaat cttccgtttc     300
aatgccacac ctgctttata tatgctttct cctttcagtc ctctaagaag aatatctatt     360
aagattttag tacactcctt attcagcatg ctcatcatgt gcactattct gacaaactgc     420
atatttatga ccatgaataa cccgccggac tggaccaaaa atgtcgagta cacttttact     480
ggaatatata cttttgaatc acttgtaaaa atccttgcaa gaggcttctg tgtaggagaa     540
ttcacttttc ttcgtgaccc gtggaactgg ctggattttg tcgtcattgt ttttgcgtat     600
ttaacagaat ttgtaaacct aggcaatgtt tcagctcttc gaactttcag agtattgaga     660
gctttgaaaa ctatttctgt aatcccaggc ctgaagacaa ttgtaggggc tttgatccag     720
tcagtgaaga agctttctga tgtcatgatc ctgactgtgt tctgtctgag tgtgtttgca     780
ctaattggac tacagctgtt catgggaaac ctgaagcata atgttttcg aaattcactt     840 gaaaataatg aaacattaga aagcataatg aataccctag agagtgaaga agactttaga     900
aaatattttt attacttgga aggatccaaa gatgctctcc tttgtggttt cagcacagat     960
tcaggtcagt gtccagaggg gtacacctgt gtgaaaattg cagaaaccc tgattatggc    1020 tacacgagct ttgacacttt cagctgggcc ttcttagcct tgtttaggct aatgacccaa    1080
gattactggg aaaaccttta ccaacagacg ctgcgtgctg ctggcaaaac ctacatgatc    1140
ttctttgtcg tagtgatttt cctgggctcc ttttatctaa taaacttgat cctggctgtg    1200
gttgccatgg catatgaaga acagaaccag gcaaacattg aagaagctaa acagaaagaa    1260
ttagaatttc aacagatgtt agaccgtctt aaaaaagagc aagaagaagc tgaggcaatt    1320
gcagcggcag cggctgaata tacaagtatt aggagaagca gaattatggg cctctcagag    1380
agttcttctg aaacatccaa actgagctct aaaagtgcta agaaagaag aaacagaaga    1440 aagaaaaaga tcaaaagaa gctctccagt ggagaggaaa agggagatgc tgagaaattg    1500
tcgaaatcag aatcagagga cagcatcaga agaaaaagtt ccaccttggg tgtcgaaggg    1560
cataggcgag cacatgaaaa gaggttgtct acccccaatc agtcaccact cagcattcgt    1620
ggctccttgt tttctgcaag gcgaagcagc agaacaagtc ttttttagttt caaaggcaga    1680 ggaagagata taggatctga gactgaattt gccgatgatg agcacagcat ttttggagac    1740
aatgagagca aagggggctc actgtttgtg ccccacagac cccaggagcg acgcagcagt    1800
aacatcagcc aagccagtag gtccccacca atgctgccgg tgaacgggaa aatgcacagt    1860
gctgtggact gcaacggtgt ggtctccctg gttgatggac gctcagccct catgctcccc    1920
aatggacagc ttctgccaga gggcacgacc aatcaaatac acaagaaaag gcgttgtagt    1980
tcctatctcc tttcagagga tatgctgaat gatcccaacc tcagacagag agcaatgagt    2040
```

```
agagcaagca tgttaacaaa cactgtggaa gaacttgaag agtccagaca aaaatgtcca   2100
ccttggtggt acagatttgc acacaaattc ttgatctgga attgctctcc atattggata   2160
aaattcaaaa agtgtatcta ttttattgta atggatcctt ttgtagatct tgcaattacc   2220
atttgcatag ttttaaacac attatttatg gctatggaac accacccaat gactgaggaa   2280
ttcaaaaatg tacttgctat aggaaatttg gtctttactg gaatctttgc agctgaaatg   2340
gtattaaaac tgattgccat ggatccatat gagtatttcc aagtaggctg gaatattttt   2400
gacagcctta ttgtgacttt aagtttagtg gagctctttc tagcagatgt ggaaggattg   2460
tcagttctgc gatcattcag actgctccga gtcttcaagt tggcaaaatc ctggccaaca   2520
ttgaacatgc tgattaagat cattggtaac tcagtagggg ctctaggtaa cctcacctta   2580
gtgttggcca tcatcgtctt cattttgct gtggtcggca tgcagctctt tggtaagagc   2640
tacaaagaat gtgtctgcaa gatcaatgat gactgtacgc tcccacggtg gcacatgaac   2700
gacttcttcc actccttcct gattgtgttc cgcgtgctgt gtggagagtg gatagagacc   2760
atgtgggact gtatggaggt cgctggtcaa gctatgtgcc ttattgttta catgatggtc   2820
atggtcattg gaaacctggt ggtcctaaac ctatttctgg ccttattatt gagctcattt   2880
agttcagaca atcttacagc aattgaagaa gaccctgatg caaacaacct ccagattgca   2940
gtgactagaa ttaaaagggg aataaattat gtgaaacaaa ccttacgtga atttattcta   3000
aaagcatttt ccaaaaagcc aaagatttcc agggagataa gacaagcaga agatctgaat   3060
actaagaagg aaaactatat ttctaaccat acacttgctg aaatgagcaa aggtcacaat   3120
ttcctcaagg aaaaagataa aatcagtggt tttggaagca gcgtggacaa acacttgatg   3180
gaagacagtg atggtcaatc atttattcac aatcccagcc tcacagtgac agtgccaatt   3240
gcacctgggg aatccgattt ggaaaatatg aatgctgagg aacttagcag tgattcggat   3300
agtgaataca gcaaagtgag attaaaccgg tcaagctcct cagagtgcag cacagttgat   3360 aacccttgc ctggagaagg agaagaagca gaggctgaac ctatgaattc cgatgagcca   3420
gaggcctgtt tcacagatgg ttgtgtacgg aggttctcat gctgccaagt taacatagag   3480
tcagggaaag gaaaaatctg gtggaacatc aggaaaacct gctacaagat tgttgaacac   3540
agttggtttg aaagcttcat tgtcctcatg atcctgctca gcagtggtgc cctggctttt   3600 gaagatatt atattgaaag gaaaagacc attaagatta tcctggagta tgcagacaag   3660
atcttcactt acatcttcat tctggaaatg cttctaaaat ggatagcata tggttataaa   3720
acatatttca ccaatgcctg gtgttggctg gatttcctaa ttgttgatgt ttcttttggtt   3780 actttagtgg caaacactct tggctactca gatcttggcc ccattaaatc ccttcggaca   3840
ctgagagctt taagacctct aagagcctta tctagatttg aaggaatgag ggtcgttgtg   3900
aatgcactca taggagcaat tccttccatc atgaatgtgc tacttgtgtg tcttatattc   3960
tggctgatat tcagcatcat gggagtaaat ttgtttgctg gcaagttcta tgagtgtatt   4020
aacaccacag atgggtcacg gtttcctgca agtcaagttc caatcgttc cgaatgtttt   4080 gcccttatga atgttagtca aaatgtgcga tggaaaaacc tgaaagtgaa ctttgataat   4140
gtcggacttg gttacctatc tctgcttcaa gttgcaactt taagggatg gacgattatt   4200 atgtatgcag cagtggattc tgttaatgta gacaagcagc ccaaatatga atatagcctc   4260
tacatgtata tttattttgt cgtctttatc atctttgggt cattcttcac tttgaacttg   4320
ttcattggtg tcatcataga taatttcaac caacagaaaa agaagcttgg aggtcaagac   4380
```

| | |
|---|---|
| atctttatga cagaagaaca gaagaaatac tataatgcaa tgaaaaagct ggggtccaag | 4440 |
| aagccacaaa agccaattcc tcgaccaggg aacaaaatcc aaggatgtat atttgaccta | 4500 |
| gtgacaaatc aagcctttga tattagtatc atggttctta tctgtctcaa catggtaacc | 4560 |
| atgatggtag aaaaggaggg tcaaagtcaa catatgactg aagttttata ttggataaat | 4620 |
| gtggttttta taatcctttt cactggagaa tgtgtgctaa aactgatctc cctcagacac | 4680 |
| tactacttca ctgtaggatg gaatattttt gattttgtgg ttgtgattat ctccattgta | 4740 |
| ggtatgtttc tagctgattt gattgaaacg tattttgtgt cccctaccct gttccgagtg | 4800 |
| atccgtcttg ccaggattgg ccgaatccta cgtctagtca aaggagcaaa ggggatccgc | 4860 |
| acgctgctct ttgctttgat gatgtccctt cctgcgttgt ttaacatcgg cctcctgctc | 4920 |
| ttcctggtca tgttcatcta cgccatcttt ggaatgtcca actttgccta tgttaaaaag | 4980 |
| gaagatggaa ttaatgacat gttcaatttt gagaccttgg caacagtat gatttgcctg | 5040 |
| ttccaaatta caacctctgc tggctgggat ggattgctag cacctattct taacagtaag | 5100 |
| ccacccgact gtgacccaaa aaaagttcat cctggaagtt cagttgaagg agactgtggt | 5160 |
| aacccatctg ttggaatatt ctactttgtt agttatatca tcatatccctt cctggttgtg | 5220 |
| gtgaacatgt acattgcagt catactggag aattttagtt tgccactga agaaagtact | 5280 |
| gaacctctga gtgaggatga ctttgagatg ttctatgagg tttgggagaa gtttgatccc | 5340 |
| gatgcgaccc agtttataga gttctctaaa ctctctgatt ttgcagctgc cctggatcct | 5400 |
| cctcttctca tagcaaaacc caacaaagtc cagctcattg ccatggatct gcccatggtt | 5460 |
| agtggtgacc ggatccattg tcttgacatc ttatttgctt ttacaaagcg tgttttgggt | 5520 |
| gagagtgggg agatggattc tcttcgttca cagatggaag aaaggttcat gtctgcaaat | 5580 |
| ccttccaaag tgtcctatga acccatcaca accacactaa aacggaaaca agaggatgtg | 5640 |
| tctgctactg tcattcagcg tgcttataga cgttaccgct taaggcaaaa tgtcaaaaat | 5700 |
| atatcaagta tatacataaa agatgggagac agagatgatg atttactcaa taaaaaagat | 5760 |
| atggcttttg ataatgttaa tgagaactca agtccagaaa aacagatgc cacttcatcc | 5820 |
| accacctctc caccttcata tgatagtgta acaaagccag acaaagagaa atatgaacaa | 5880 |
| gacagaacag aaaaggaaga caaagggaaa gacagcaagg aaagcaaaaa atag | 5934 |

<210> SEQ ID NO 90
<211> LENGTH: 5934
<212> TYPE: DNA
<213> ORGANISM: Homo sapiens

<400> SEQUENCE: 90

| | |
|---|---|
| atggcaatgt tgcctccccc aggacctcag agctttgtcc atttcacaaa acagtctctt | 60 |
| gccctcattg aacaacgcat tgctgaaaga aaatcaaagg aacccaaaga agaaaagaaa | 120 |
| gatgatgatg aagaagcccc aaagccaagc agtgacttgg aagctggcaa acaactgccc | 180 |
| ttcatctatg gggacattcc tcccggcatg gtgtcagagc cctggaggga cttggacccc | 240 |
| tactatgcag acaaaaagac tttcatagta ttgaacaaag ggaaaacaat cttccgtttc | 300 |
| aatgccacac tgctttata tatgctttct cctttcagtc ctctaagaag aatatctatt | 360 |
| aagatttta tacactcctt attcagcatg ctcatcatgt gcactattct gacaaactgc | 420 |
| atatttatga ccatgaataa cccgccggac tggaccaaaa atgtcgagta cactttact | 480 |
| ggaatatata cttttgaatc acttgtaaaa atccttgcaa gaggcttctg tgtaggagaa | 540 |
| ttcacttttc ttcgtgaccc gtggaactgg ctggattttg tcgtcattgt ttttgcgtat | 600 |

-continued

```
ttaacagaat tgtaaacct aggcaatgtt tcagctcttc gaactttcag agtattgaga      660
gctttgaaaa ctatttctgt aatcccaggc ctgaagacaa ttgtaggggc tttgatccag      720
tcagtgaaga agctttctga tgtcatgatc ctgactgtgt tctgtctgag tgtgtttgca      780
ctaattggac tacagctgtt catgggaaac ctgaagcata aatgttttcg aaattcactt      840
gaaaataatg aaacattaga aagcataatg aatacccag agagtgaaga agactttaga      900
aaatattttt attacttgga aggatccaaa gatgctctcc tttgtggttt cagcacagat      960
tcaggtcagt gtccagaggg gtacacctgt gtgaaaattg gcagaaaccc tgattatggc     1020
tacacgagct ttgacacttt cagctgggcc ttcttagcct tgtttaggct aatgacccaa     1080
gattactggg aaaacctta ccaacagacg ctgcgtgctg ctggcaaaac ctacatgatc     1140
ttctttgtcg tagtgatttt cctgggctcc ttttatctaa taaacttgat cctggctgtg     1200
gttgccatgg catatgaaga acagaaccag gcaaacattg aagaagctaa acagaaagaa     1260
ttagaatttc aacagatgtt agaccgtctt aaaaaagagc aagaagaagc tgaggcaatt     1320
gcagcggcag cggctgaata tacaagtatt aggagaagca gaattatggg cctctcagag     1380
agttcttctg aaacatccaa actgagctct aaaagtgcta agaaagaag aaacagaaga     1440 aagaaaaaga atcaaaagaa gctctccagt ggagaggaaa agggagatgc tgagaaattg     1500
tcgaaatcag aatcagagga cagcatcaga agaaaaagtt ccaccttggt gtcgaaggg     1560 cataggcgag cacatgaaaa gaggttgtct accccccaatc agtcaccact cagcattcgt     1620
ggctccttgt tttctgcaag gcgaagcagc agaacaagtc ttttagttt caaaggcaga     1680 ggaagagata taggatctga gactgaattt gccgatgatg agcacagcat ttttggagac     1740
aatgagagca aaggggctc actgtttgtg ccccacagac cccaggagcg acgcagcagt     1800
aacatcagcc aagccagtag gtccccacca atgctgccgg tgaacgggaa aatgcacagt     1860
gctgtggact gcaacggtgt ggtctccctg gttgatggac gctcagccct catgctcccc     1920
aatggacagc ttctgccaga gggcacgacc aatcaaatac acaagaaaag gcgttgtagt     1980
tcctatctcc tttcagagga tatgctgaat gatcccaacc tcagacagag agcaatgagt     2040
agagcaagca tattaacaaa cactgtggaa gaacttgaag agtccagaca aaaatatcca     2100
ccttggtggt acagatttgc acacaaattc ttgatctgga attgctctcc atattggata     2160
aaattcaaaa agtgtatcta ttttattgta atggatcctt ttgtagatct tgcaattacc     2220
atttgcatag ttttaaacac attatttatg gctatggaac accacccaat gactgaggaa     2280
ttcaaaaatg tacttgctat aggaaatttg gtctttactg gaatctttgc agctgaaatg     2340
gtattaaaac tgattgccat ggatccatat gagtatttcc aagtaggctg gaatattttt     2400
gacagcctta ttgtgacttt aagtttagtg gagctctttc tagcagatgt ggaaggattg     2460
tcagttctgc gatcattcag actgctccga gtcttcaagt tggcaaaatc ctggccaaca     2520
ttgaacatgt gattaagat cattggtaac tcagtagggg ctctaggtaa cctcaccttta     2580 gtgttggcca tcatcgtctt catttttgct gtggtcggca tgcagctctt tggtaagagc     2640
tacaaagaat gtgtctgcaa gatcaatgat gactgtacgc tcccacggtg gcacatgaac     2700
gacttcttcc actccttcct gattgtgttc cgcgtgctgt gtggagagtg gatagagacc     2760
atgtgggact gtatggaggt cgctggtcaa gctatgtgcc ttattgttta catgatggtc     2820
atggtcattg gaaacctggt ggtcctaaac ctatttctgg ccttattatt gagctcattt     2880
agttcagaca atcttacagc aattgaagaa gaccctgatg caaacaacct ccagattgca     2940
```

```
gtgactagaa ttaaaaaggg aataaattat gtgaaacaaa ccttacgtga atttattcta    3000
aaagcatttt ccaaaaagcc aaagatttcc agggagataa acaagcaga agatctgaat     3060 actaagaagg aaaactatat ttctaaccat acacttgctg aaatgagcaa aggtcacaat    3120
ttcctcaagg aaaagataa aatcagtggt tttggaagca gcgtggacaa acacttgatg     3180
gaagacagtg atggtcaatc atttattcac aatcccagcc tcacagtgac agtgccaatt    3240
gcacctgggg aatccgattt ggaaaatatg aatgctgagg aacttagcag tgattcggat    3300
agtgaataca gcaaagtgag attaaaccgg tcaagctcct cagagtgcag cacagttgat    3360 aacccttgc ctggagaagg agaagaagca gaggctgaac ctatgaattc cgatgagcca     3420
gaggcctgtt tcacagatgg ttgtgtacgg aggttctcat gctgccaagt taacatagag    3480
tcagggaaag gaaaaatctg gtggaacatc aggaaaacct gctacaagat tgttgaacac    3540
agttggtttg aaagcttcat tgtcctcatg atcctgctca gcagtggtgc cctggctttt    3600
gaagatattt atattgaaag gaaaaagacc attaagatta tcctggagta tgcagacaag    3660
atcttcactt acatcttcat tctggaaatg cttctaaaat ggatagcata tggttataaa    3720
acatatttca ccaatgcctg tgttggctg gatttcctaa ttgttgatgt ttctttggtt     3780
actttagtgg caaacactct tggctactca gatcttggcc ccattaaatc ccttcggaca    3840
ctgagagctt taagacctct aagagcctta tctagatttg aaggaatgag ggtcgttgtg    3900
aatgcactca taggagcaat tccttccatc atgaatgtgc tacttgtgtg tcttatattc    3960
tggctgatat tcagcatcat gggagtaaat ttgtttgctg gcaagttcta tgagtgtatt    4020
aacaccacag atgggtcacg gtttcctgca agtcaagttc caaatcgttc cgaatgtttt    4080
gcccttatga atgttagtca aaatgtgcga tggaaaaacc tgaaagtgaa ctttgataat    4140
gtcggacttg gttacctatc tctgcttcaa gttgcaactt ttaagggatg gacgattatt    4200
atgtatgcag cagtggattc tgttaatgta gacaagcagc ccaaatatga atatagcctc    4260
tacatgtata tttatttgt cgtctttatc atctttgggt cattcttcac tttgaacttg    4320
ttcattggtg tcatcataga taatttcaac caacagaaaa agaagcttgg aggtcaagac    4380
atctttatga cagaagaaca gaagaaatac tataatgcaa tgaaaagct ggggtccaag    4440 aagccacaaa agccaattcc tcgaccaggg aacaaaatcc aaggatgtat atttgaccta    4500
gtgacaaatc aagcctttga tattagtatc atggttctta tctgtctcaa catggtaacc    4560
atgatggtag aaaaggaggg tcaaagtcaa catatgactg aagttttata ttggataaat    4620
gtggttttta taatcctttt cactggagaa tgtgtgctaa aactgatctc cctcagacac    4680
tactacttca ctgtaggatg aatattttt gattttgtgg ttgtgattat ctccattgta    4740
ggtatgtttc tagctgattt gattgaaacg tattttgtgt cccctaccct gttccgagtg    4800
atccgtcttg ccaggattgg ccgaatccta cgtctagtca aaggagcaaa ggggatccgc    4860
acgctgctct ttgctttgat gatgtccctt cctgcgttgt taacatcgg cctcctgctc    4920 ttcctggtca tgttcatcta cgccatcttt ggaatgtcca actttgccta tgttaaaaag    4980
gaagatggaa ttaatgacat gttcaatttt gagacctttg gcaacagtat gatttgcctg    5040
ttccaaatta caacctctgc tggctgggat ggattgctag cacctattct taacagtaag    5100 ccaccgact gtgacccaaa aaaagttcat cctggaagtt cagttgaagg agactgtggt    5160
aacccatctg ttggaatatt ctactttgtt agtatatca tcatatcctt cctggttgtg    5220
gtgaacatgt acattgcagt catactggag aattttagtg ttgccactga agaaagtact    5280
gaacctctga gtgaggatga ctttgagatg ttctatgagg tttgggagaa gtttgatccc    5340
```

```
gatgcgaccc agtttataga gttctctaaa ctctctgatt ttgcagctgc cctggatcct    5400
cctcttctca tagcaaaacc caacaaagtc cagctcattg ccatggatct gcccatggtt    5460
agtggtgacc ggatccattg tcttgacatc ttatttgctt ttacaaagcg tgttttgggt    5520
gagagtgggg agatggattc tcttcgttca cagatggaag aaaggttcat gtctgcaaat    5580
ccttccaaag tgtcctatga acccatcaca accacactaa aacgaaaaca agaggatgtg    5640
tctgctactg tcattcagcg tgcttataga cgttaccgct taaggcaaaa tgtcaaaaat    5700
atatcaagta tatacataaa agatggagac agagatgatg atttactcaa taaaaaagat    5760
atggcttttg ataatgttaa tgagaactca agtccagaaa aaacagatgc cacttcatcc    5820
accacctctc caccttcata tgatagtgta acaaagccag acaaagagaa atatgaacaa    5880
gacagaacag aaaaggaaga caaagggaaa gacagcaagg aaagcaaaaa atag          5934
```

<210> SEQ ID NO 91  
<211> LENGTH: 5934  
<212> TYPE: DNA  
<213> ORGANISM: Homo sapiens

<400> SEQUENCE: 91

```
atggcaatgt tgcctccccc aggacctcag agctttgtcc atttcacaaa acagtctctt      60
gccctcattg aacaacgcat tgctgaaaga aaatcaaagg aacccaaaga agaaaagaaa     120
gatgatgatg aagaagcccc aaagccaagc agtgacttgg aagctggcaa acaactgccc     180
ttcatctatg gggacattcc tcccggcatg gtgtcagagc ccctggagga cttggacccc     240
tactatgcag acaaaaagac tttcatagta ttgaacaaag ggaaaacaat cttccgtttc     300
aatgccacac ctgctttata tatgctttct cctttcagtc ctctaagaag aatatctatt     360 aagatttttag tacactcctt attcagcatg ctcatcatgt gcactattct gacaaactgc     420
atatttatga ccatgaataa cccgccggac tggaccaaaa atgtcgagta cacttttact     480
ggaatatata cttttgaatc acttgtaaaa atccttgcaa gaggcttctg tgtaggagaa     540 ttcactttc ttcgtgaccc gtggaactgg ctggattttg tcgtcattgt ttttgcgtat     600
ttaacagaat ttgtaaacct aggcaatgtt tcagctcttc gaacttttcag agtattgaga     660 gctttgaaaa ctatttctgt aatcccaggc ctgaagacaa ttgtaggggc tttgatccag     720
tcagtgaaga agctttctga tgtcatgatc ctgactgtgt tctgtctgag tgtgtttgca     780
ctaattggac tacagctgtt catgggaaac ctgaagcata atgttttcg aaattcactt     840 gaaaataatg aaacattaga aagcataatg aatacctag agagtgaaga agactttaga     900
aaatattttt attacttgga aggatccaaa gatgctctcc tttgtgggtttt cagcacagat     960 tcaggtcagt gtccagaggg gtacacctgt gtgaaaattg gcagaaaccc tgattatggc    1020
tacacgagct ttgacacttt cagctgggcc ttcttagcct tgtttaggct aatgacccaa    1080
gattactggg aaaaacctttta ccaacagacg ctgcgtgctg ctggcaaaac ctacatgatc    1140
ttctttgtcg tagtgatttt cctgggctcc ttttatctaa taaacttgat cctggctgtg    1200
gttgccatgg catatgaaga acagaaccag gcaaacattg aagaagctaa acagaaagaa    1260
ttagaatttc aacagatgtt agaccgtctt aaaaaagagc aagaagaagc tgaggcaatt    1320
gcagcggcag cggctgaata tacaagtatt aggagaagca gaattatggg cctctcagag    1380
agttcttctg aaacatccaa actgagctct aaaagtgcta agaaagaag aaacagaaga    1440 aagaaaaaga atcaaaagaa gctctccagt ggagaggaaa agggagatgc tgagaaattg    1500
```

```
tcgaaatcag aatcagagga cagcatcaga agaaaaagtt tccaccttgg tgtcgaaggg    1560
cataggcgag cacatgaaaa gaggttgtct acccccaatc agtcaccact cagcattcgt    1620
ggctccttgt tttctgcaag gcgaagcagc agaacaagtc ttttttagttt caaaggcaga   1680
ggaagagata taggatctga gactgaattt gccgatgatg agcacagcat ttttggagac    1740
aatgagagca aaggggctc actgtttgtg ccccacagac cccaggagcg acgcagcagt     1800
aacatcagcc aagccagtag gtccccacca atgctgccgg tgaacgggaa aatgcacagt    1860
gctgtggact gcaacggtgt ggtctccctg gttgatggac gctcagccct catgctcccc    1920
aatggacagc ttctgccaga gggcacgacc aatcaaatac acaagaaaag gcgttgtagt    1980
tcctatctcc tttcagagga tatgctgaat gatcccaacc tcagacagag agcaatgagt    2040
agagcaagca tattaacaaa cactgtggaa gaacttgaag agtccagaca aaaatgtcca    2100
ccttggtggt acagatttgc acacaaattc ttgatctgga attgctctcc atattggata    2160
aaattcaaaa agtgtatcta ttttattgta atggatcctt ttgtagatct tgcaattacc    2220
atttgcatag ttttaaacac attatttatg gctatgaaac accacccaat gactgaggaa    2280
ttcaaaaatg tacttgctat aggaaatttg gtctttactg gaatctttgc agctgaaatg    2340
gtattaaaac tgattgccat ggatccatat gagtatttcc aagtaggctg gaatattttt    2400
gacagcctta ttgtgacttt aagtttagtg gagctctttc tagcagatgt ggaaggattg    2460
tcagttctgc gatcattcag actgctccga gtcttcaagt tggcaaaatc ctggccaaca    2520
ttgaacatgc tgattaagat cattggtaac tcagtagggg ctctaggtaa cctcacctta    2580
gtgttggcca tcatcgtctt catttttgct gtggtcggca tgcagctctt tggtaagagc    2640
tacaaagaat gtgtctgcaa gatcaatgat gactgtacgc tcccacggtg gcacatgaac    2700
gacttcttcc actccttcct gattgtgttc cgcgtgctgt gtggagagtg gatagagacc    2760
atgtgggact gtatggaggt cgctggtcaa gctatgtgcc ttattgttta catgatggtc    2820
atggtcattg gaaacctggt ggtcctaaac ctatttctgg ccttattatt gagctcattt    2880
agttcagaca atcttacagc aattgaagaa gaccctgatg caaacaacct ccagattgca    2940
gtgactagaa ttaaaaaggg aataaattat gtgaaacaaa ccttacgtga atttattcta    3000
aaagcatttt ccaaaaagcc aaagatttcc agggagataa gacaagcaga agatctgaat    3060
actaagaagg aaaactatat ttctaaccat acacttgctg aaatgagcaa aggtcacaat    3120
ttcctcaagg aaaaagataa aatcagtggt tttggaagca gcgtggacaa acacttgatg    3180
gaagacagtg atggtcaatc atttattcac aatcccagcc tcacagtgac agtgccaatt    3240
gcacctgggg aatccgattt ggaaaatatg aatgctgagg aacttagcag tgattcggat    3300
agtgaataca gcaaagtgag attaaaccgg tcaagctcct cagagtgcag cacagttgat    3360
aacccttttgc ctggagaagg agaagaagca gaggctgaac ctatgaattc cgatgagcca    3420
gaggcctgtt tcacagatgg ttgtgtacgg aggttctcat gctgccaagt aacatacag     3480
tcagggaaag gaaaaatctg gtggaacatc aggaaaacct gctacaagat tgttgaacac    3540
agttggttg aaagcttcat tgtcctcatg atcctgctca gcagtggtgc cctggctttt    3600
gaagatattt atattgaaag gaaaagacc attaagatta tcctggagta tgcagacaag    3660
atcttcactt acatcttcat tctggaaatg cttctaaaat ggatagcata tggttataaa    3720
acatatttca ccaatgcctg tgttggctg gatttcctaa ttgttgatgt ttctttggtt    3780
actttagtgg caaacactct tggctactca gatcttggcc ccattaaatc ccttcggaca    3840
ctgagagctt taagacctct aagagcctta tctagatttg aaggaatgag ggtcgttgtg    3900
```

```
aatgcactca taggagcaat tccttccatc atgaatgtgc tacttgtgtg tcttatattc    3960
tggctgatat tcagcatcat gggagtaaat ttgtttgctg gcaagttcta tgagtgtatt    4020
aacaccacag atgggtcacg gtttcctgca agtcaagttc caaatcgttc cgaatgtttt    4080
gcccttatga atgttagtca aaatgtgcga tggaaaaacc tgaaagtgaa ctttgataat    4140
gtcggacttg gttacctatc tctgcttcaa gttgcaactt ttaagggatg acgattatt    4200 atgtatgcag cagtggattc tgttaatgta gacaagcagc ccaaatatga atatagccta    4260
tacatgtata tttattttgt cgtctttatc atctttgggt cattcttcac tttgaacttg    4320
ttcattggtg tcatcataga taatttcaac caacagaaaa agaagcttgg aggtcaagac    4380
atctttatga cagaagaaca gaagaaatac tataatgcaa tgaaaaagct ggggtccaag    4440
aagccacaaa agccaattcc tcgaccaggg aacaaaatcc aaggatgtat atttgaccta    4500
gtgacaaatc aagcctttga tattagtatc atggttctta tctgtctcaa catggtaacc    4560
atgatggtag aaaaggaggg tcaaagtcaa catatgactg aagttttata ttggataaat    4620
gtggttttta aatccttttt cactggagaa tgtgtgctaa aactgatctc cctcagacac    4680
tactacttca ctgtaggatg gaatattttt gattttgtgg ttgtgattat ctccattgta    4740
ggtatgtttc tagctgattt gattgaaacg tattttgtgt ccctaccct gttccgagtg    4800 atccgtcttg ccaggattgg ccgaatccta cgtctagtca aaggagcaaa ggggatccgc    4860
acgctgctct ttgctttgat gatgtccctt cctgcgttgt ttaacatcgg cctcctgctc    4920
ttcctggtca tgttcatcta cgccatcttt ggaatgtcca actttgccta tgttaaaaag    4980
gaagatggaa ttaatgacat gttcaatttt gagacctttg gcaacagtat gatttgcctg    5040
ttccaaatta caacctctgc tggctgggat ggattgctag cacctattct taacagtaag    5100
ccacccgact gtgacccaaa aaaagttcat cctggaagtt cagttgaagg agactgtggt    5160
aacccatctg ttggaatatt ctactttgtt agttatatca tcatatcctt cctggttgtg    5220
gtgaacatgt acattgcagt catactggag aattttagtg ttgccactga agaaagtact    5280
gaacctctga gtgaggatga ctttgagatg ttctatgagg tttgggagaa gtttgatccc    5340
gatgcgaccc agtttataga gttctctaaa ctctctgatt ttgcagctgc cctggatcct    5400
cctcttctca tagcaaaacc caacaaagtc cagctcattg ccatggatct gcccatggtt    5460
agtggtgacc ggatccattg tcttgacatc ttatttgctt ttacaaagcg tgttttgggt    5520
gagagtgggg agatggattc tcttcgttca cagatggaag aaaggttcat gtctgcaaat    5580
ccttccaaag tgtcctatga acccatcaca accacactaa aacggaaaca agaggatgtg    5640
tctgctactg tcattcagcg tgcttataga cgttaccgct taaggcaaaa tgtcaaaaat    5700
atatcaagta tatacataaa agatggagac agagatgatg atttactcaa taaaaaagat    5760
atggcttttg ataatgttaa tgagaactca agtccagaaa aacagatgc cacttcatcc    5820 accacctctc caccttcata tgatagtgta acaaagccag acaaagagaa atatgaacaa    5880
gacagaacag aaaaggaaga caaagggaaa gacagcaagg aaagcaaaaa atag    5934
```

<210> SEQ ID NO 92
<211> LENGTH: 5934
<212> TYPE: DNA
<213> ORGANISM: Homo sapiens

<400> SEQUENCE: 92

```
atggcaatgt tgcctccccc aggacctcag agctttgtcc atttcacaaa acagtctctt    60
```

-continued

```
gccctcattg aacaacgcat tgctgaaaga aaatcaaagg aacccaaaga agaaaagaaa    120
gatgatgatg aagaagcccc aaagccaagc agtgacttgg aagctggcaa acaactgccc    180
ttcatctatg gggacattcc tcccggcatg gtgtcagagc cctggagga cttggacccc    240 tactatgcag acaaaaagac tttcatagta ttgaacaaag ggaaaacaat cttccgtttc    300
aatgccacac ctgctttata tatgctttct cctttcagtc ctctaagaag aatatctatt    360
aagattttag tacactcctt attcagcatg ctcatcatgt gcactattct gacaaactgc    420
atatttatga ccatgaataa cccgccggac tggaccaaaa atgtcgagta cactttttact   480 ggaatatata cttttgaatc acttgtaaaa atccttgcaa gaggcttctg tgtaggagaa    540
ttcacttttc ttcgtgaccc gtggaactgg ctggattttg tcgtcattgt ttttgcgtat    600
ttaacagaat ttgtaaacct aggcaatgtt tcagctcttc gaactttcag agtattgaga    660
gctttgaaaa ctatttctgt aatcccaggc ctgaagacaa ttgtaggggc tttgatccag    720
tcagtgaaga agctttctga tgtcatgatc ctgactgtgt tctgtctgag tgtgtttgca    780
ctaattggac tacagctgtt catgggaaac ctgaagcata aatgttttcg aaattcactt    840
gaaaataatg aaacattaga aagcataatg aatacccctag agagtgaaga agactttaga    900
aaatattttt attacttgga aggatccaaa gatgctctcc tttgtggttt cagcacagat    960
tcaggtcagt gtccagaggg gtacacctgt gtgaaaattg gcagaaaccc tgattatggc   1020
tacacgagct ttgacacttt cagctgggcc ttcttagcct tgtttaggct aatgacccaa   1080
gattactggg aaaaccttta ccaacagacg ctgcgtgctg ctggcaaaac ctacatgatc   1140
ttctttgtcg tagtgatttt cctgggctcc ttttatctaa taaacttgat cctggctgtg   1200
gttgccatgg catatgaaga acagaaccag gcaaacattg aagaagctaa acagaaagaa   1260
ttagaatttc aacagatgtt agaccgtctt aaaaaagagc aagaagaagc tgaggcaatt   1320
gcagcggcag cggctgaata tacaagtatt aggagaagca gaattatggg cctctcagag   1380
agttcttctg aaacatccaa actgagctct aaaagtgcta agaaagaag aaacagaaga   1440 aagaaaaaga atcaaaagaa gctctccagt ggagaggaaa agggagatgc tgagaaattg   1500
tcgaaatcag aatcagagga cagcatcaga agaaaaagtt ccaccttggg tgtcgaaggg   1560
cataggcgag cacatgaaaa gaggttgtct acccccaatc agtcaccact cagcattcgt   1620
ggctccttgt tttctgcaag gcgaagcagc agaacaagtc ttttttagttt caaaggcaga   1680 ggaagagata taggatctga gactgaattt gccgatgatg agcacagcat ttttggagac   1740
aatgagagca aagggggctc actgtttgtg ccccacagac cccaggagcg acgcagcagt   1800
aacatcagcc aagccagtag gtccccacca atgctgccgg tgaacgggaa aatgcacagt   1860
gctgtggact gcaacggtgt ggtctccctg gttgatggac gctcagccct catgctcccc   1920
aatggacagc ttctgccaga gggcacgacc aatcaaatac acaagaaaag gcgttgtagt   1980
tcctatctcc tttcagagga tatgctgaat gatcccaacc tcagacagag agcaatgagt   2040
agagcaagca tattaacaaa cactgtggaa gaacttgaag agtccagaca aaaatgtcca   2100
ccttggtggt acagatttgc acacaaattc ttgatctgga attgctctcc atattggata   2160
aaattcaaaa agtgtatcta ttttattgta atggatcctt ttgtagatct tgcaattacc   2220
atttgcatag ttttaaacac attatttatg gctatggaac accacccaat gactgaggaa   2280
ttcaaaaatg tacttgctat aggaaatttg gtctttactg gaatctttgc agctgaaatg   2340
gtattaaaac tgattgccat ggatccatat gagtatttcc aagtaggctg gaatattttt   2400
gacagcctta ttgtgacttt aagtttagtg gagctctttc tagcagatgt ggaaggattg   2460
```

```
tcagttctgc gatcattcag actgctccga gtcttcaagt tggcaaaatc ctggccaaca    2520
ttgaacatgc tgattaagat cattggtaac tcagtagggg ctctaggtaa cctcacctta    2580
gtgttggcca tcatcgtctt catttttgct gtggtcggca tgcagctctt tggtaagagc    2640
tacaaagaat gtgtctgcaa gatcaatgat gactgtacgc tcccacggtg gcacatgaac    2700
gacttcttcc actccttcct gattgtgttc cgcgtgctgt gtggagagtg gatagagacc    2760
atgtgggact gtatggaggt cgctggtcaa gctatgtgcc ttattgttta catgatggtc    2820
atggtcattg gaaacctggt ggtcctaaac ctatttctgg ccttattatt gagctcattt    2880
agttcagaca atcttacagc aattgaagaa gaccctgatg caaacaacct ccagattgca    2940
gtgactagaa ttaaaagggg aataaattat gtgaaacaaa ccttacgtga atttattcta    3000
aaagcatttt ccaaaaagcc aaagatttcc agggagataa acaagcaga agatctgaat    3060
actaagaagg aaaactatat ttctaaccat acacttgctg aaatgagcaa aggtcacaat    3120
ttcctcaagg aaaagataaa atcagtggt tttggaagca gcgtggacaa acacttgatg    3180
gaagacagtg atggtcaatc atttattcac aatcccagcc tcacagtgac agtgccaatt    3240
gcacctgggg aatccgattt ggaaaatatg aatgctgagg aacttagcag tgattcggat    3300
agtgaataca gcaaagtgag attaaaccgg tcaagctcct cagagtgcag cacagttgat    3360
aacccttgc ctggagaagg agaagaagca gaggctgaac ctatgaattc cgatgagcca    3420
gaggcctgtt tcacagatgg ttgtgtacgg aggttctcat gctgccaagt taacatagag    3480
tcagggaaag gaaaaatctg gtggaacatc aggaaaacct gctacaagat tgttgaacac    3540
agttggtttg aaagcttcat tgtcctcatg atcctgctca gcagtggtgc cctggctttt    3600
gaagatattt atattgaaag gaaaaagacc attaagatta tcctggagta tgcagacaag    3660
atcttcactt acatcttcat tctggaaatg cttctaaaat ggatagcata tggttataaa    3720
acatatttca ccaatgcctg gtgttggctg gatttcctaa ttgttgatgt ttctttggtt    3780
actttagtgg caaacactgt tggctactca gatcttggcc ccattaaatc ccttcggaca    3840
ctgagagctt taagacctct aagagcctta tctagatttg aaggaatgag ggtcgttgtg    3900
aatgcactca taggagcaat tccttccatc atgaatgtgc tacttgtgtg tcttatattc    3960
tggctgatat tcagcatcat gggagtaaat ttgtttgctg gcaagttcta tgagtgtatt    4020
aacaccacag atgggtcacg gtttcctgca agtcaagttc caaatcgttc cgaatgtttt    4080
gcccttatga atgttagtca aaatgtgcga tggaaaaacc tgaaagtgaa ctttgataat    4140
gtcggacttg gttacctatc tctgcttcaa gttgcaactt ttaagggatg gacgattatt    4200
atgtatgcag cagtggattc tgttaatgta gacaagcagc ccaaatatga atatagcctc    4260
tacatgtata tttattttgt cgtctttatc atctttgggt cattcttcac tttgaacttg    4320
ttcattggtg tcatcataga taatttcaac caacagaaaa agaagcttgg aggtcaagac    4380
atctttatga cagaagaaca gaagaaatac tataatgcaa tgaaaagct ggggtccaag    4440
aagccacaaa agccaattcc tcgaccaggg aacaaaatcc aaggatgtat atttgaccta    4500
gtgacaaatc aagcctttga tattagtatc atggttctta tctgtctcaa catggtaacc    4560
atgatggtag aaaaggaggg tcaaagtcaa catatgactg aagttttata ttggataaat    4620
gtggttttta taatcctttt cactggagaa tgtgtgctaa aactgatctc cctcagacac    4680
tactacttca ctgtaggatg gaatattttt gattttgtgg ttgtgattat ctccattgta    4740
ggtatgtttc tagctgattt gattgaaacg tattttgtgt cccctaccct gttccgagtg    4800
```

```
atccgtcttg ccaggattgg ccgaatccta cgtctagtca aaggagcaaa ggggatccgc    4860
acgctgctct ttgctttgat gatgtccctt cctgcgttgt ttaacatcgg cctcctgctc    4920
ttcctggtca tgttcatcta cgccatcttt ggaatgtcca actttgccta tgttaaaaag    4980
gaagatggaa ttaatgacat gttcaatttt gagacctttg caacagtat  gatttgcctg    5040 ttccaaatta caacctctgc tggctgggat ggattgctag cacctattct taacagtaag    5100
ccacccgact gtgacccaaa aaaagttcat cctggaagtt cagttgaagg agactgtggt    5160
aacccatctg ttggaatatt ctactttgtt agttatatca tcatatcctt cctggttgtg    5220
gtgaacatgt acattgcagt catactggag aattttagtg ttgccactga agaaagtact    5280
gaacctctga gtgaggatga ctttgagatg ttctatgagg tttgggagaa gtttgatccc    5340
gatgcgaccc agtttataga gttctctaaa ctctctgatt ttgcagctgc cctggatcct    5400
cctcttctca tagcaaaacc caacaaagtc cagctcattg ccatggatct gcccatggtt    5460
agtggtgacc ggatccattg tcttgacatc ttatttgctt ttacaaagcg tgtttttgggt    5520 gagagtgggg agatggattc tcttcgttca cagatggaag aaaggttcat gtctgcaaat    5580
ccttccaaag tgtcctatga acccatcaca accacactaa aacggaaaca agaggatgtg    5640
tctgctactg tcattcagcg tgcttataga cgttaccgct taaggcaaaa tgtcaaaaat    5700
atatcaagta tatacataaa agatggagac agagatgatg atttactcaa taaaaaagat    5760
atggcttttg ataatgttaa tgagaactca agtccagaaa aacagatgc  cacttcatcc    5820 accacctctc caccttcata tgatagtgta acaaagccag acaaagagaa atatgaacaa    5880
gacagaacag aaaaggaaga caaagggaaa gacagcaagg aaagcaaaaa atag          5934
```

<210> SEQ ID NO 93
<211> LENGTH: 15
<212> TYPE: DNA
<213> ORGANISM: Homo sapiens

<400> SEQUENCE: 93
ctgtaatgcc aggcc                                                        15

<210> SEQ ID NO 94
<211> LENGTH: 15
<212> TYPE: DNA
<213> ORGANISM: Artificial Sequence
<220> FEATURE:
<223> OTHER INFORMATION: Synthetic Construct

<400> SEQUENCE: 94
ctctccaatg gagag                                                        15

<210> SEQ ID NO 95
<211> LENGTH: 15
<212> TYPE: DNA
<213> ORGANISM: Homo sapiens

<400> SEQUENCE: 95
tggtgtcaaa gggca                                                        15

<210> SEQ ID NO 96
<211> LENGTH: 15
<212> TYPE: DNA
<213> ORGANISM: Homo sapiens

<400> SEQUENCE: 96
caagcatgtt aacaa                                                        15

```
<210> SEQ ID NO 97
<211> LENGTH: 15
<212> TYPE: DNA
<213> ORGANISM: Homo sapiens

<400> SEQUENCE: 97
caaaaatatc cacct                                                    15

<210> SEQ ID NO 98
<211> LENGTH: 15
<212> TYPE: DNA
<213> ORGANISM: Homo sapiens

<400> SEQUENCE: 98
taacatacag tcagg                                                    15

<210> SEQ ID NO 99
<211> LENGTH: 15
<212> TYPE: DNA
<213> ORGANISM: Homo sapiens

<400> SEQUENCE: 99
aaacactgtt ggcta                                                    15
```